US008853383B2

(12) United States Patent
Bauer et al.

(10) Patent No.: US 8,853,383 B2

(45) Date of Patent: Oct. 7, 2014

(54) **PROMOTERS FROM *BRASSICA NAPUS* FOR SEED SPECIFIC GENE EXPRESSION**

(75) Inventors: Jörg Bauer, Durham, NC (US); Toralf Senger, Durham, NC (US)

(73) Assignee: BASF Plant Science GmbH, Ludwigshafen (DE)

(*) Notice: Subject to any disclaimer, the term of this patent is extended or adjusted under 35 U.S.C. 154(b) by 548 days.

(21) Appl. No.: 13/001,742

(22) PCT Filed: Jun. 30, 2009

(86) PCT No.: PCT/EP2009/058138

§ 371 (c)(1), (2), (4) Date: Dec. 28, 2010

(87) PCT Pub. No.: WO2010/000708

PCT Pub. Date: Jan. 7, 2010

(65) Prior Publication Data

US 2011/0113510 A1 May 12, 2011

(30) Foreign Application Priority Data

Jul. 1, 2008 (EP) .................................... 08159440

(51) Int. Cl.

| | |
|---|---|
| ***C07H 21/04*** | (2006.01) |
| ***C12N 5/04*** | (2006.01) |
| ***C12N 15/00*** | (2006.01) |
| ***C12N 15/82*** | (2006.01) |
| ***A01H 5/00*** | (2006.01) |

(52) U.S. Cl.

CPC ................................. *C12N 15/8234* (2013.01)

USPC ....... 536/24.1; 800/278; 800/298; 435/320.1; 435/419

(58) Field of Classification Search

None

See application file for complete search history.

(56) References Cited

U.S. PATENT DOCUMENTS

| | | | | |
|---|---|---|---|---|
| 5,608,152 | A | 3/1997 | Kridl et al. | |
| 2003/0233671 | A1* | 12/2003 | Selvaraj et al. | 800/278 |
| 2012/0066795 | A1* | 3/2012 | Spangenberg et al. | 800/287 |

FOREIGN PATENT DOCUMENTS

| | | | |
|---|---|---|---|
| WO | WO91/13980 | * | 9/1991 |
| WO | WO-91/13980 | A1 | 9/1991 |
| WO | WO-00/07430 | A2 | 2/2000 |
| WO | WO-02/052024 | A2 | 7/2002 |
| WO | WO-2006/089911 | A2 | 8/2006 |
| WO | WO-2006/120197 | A2 | 11/2006 |
| WO | WO-2009/077478 | A2 | 6/2009 |

OTHER PUBLICATIONS

Komarnytsky and Borisjuk, Genetic Engin 25:113-41 (2003).*
Donald & Cashmore, Embo J 9:1717-26 (1990).*
Kim et al., Plant Mol Biol 24:105-17 (1994).*
Dolferus et al., Plant Physiol 105:1075-87 (1994).*
BH987704_2002.*
DU989087_2006.*
International Preliminary Report on Patentability for PCT/EP2009/058138 dated Jan. 5, 2011.

* cited by examiner

*Primary Examiner* — Medina A Ibrahim
*Assistant Examiner* — Russell Boggs
(74) *Attorney, Agent, or Firm* — Drinker Biddler & Reath LLP

(57) ABSTRACT

The present invention is concerned with means and methods for allowing tissue specific and, in particular, seed specific expression of genes. The present invention, accordingly, relates to a polynucleotide comprising an expression control sequence which allows seed specific expression of a nucleic acid of interest being operatively linked thereto. Moreover, the present invention contemplates vectors, host cells, non-human transgenic organisms comprising the aforementioned polynucleotide as well as methods and uses of such a polynucleotide.

14 Claims, 4 Drawing Sheets

| Candidate | Expression pattern* |
| --- | --- |

| | 1 | 2 | 3 | 4 | 5 | 6 | 7 | 8 | 9 | 10 | 11 | 12 | 13 | 14 |
| --- | --- | --- | --- | --- | --- | --- | --- | --- | --- | --- | --- | --- | --- | --- |
| BnSCP | | | | | | | | | | | | | | |
| BnGRPL | | | | | | | | | | | | | | |
| BnCRU4 | | | | | | | | | | | | | | |
| BnMYR | | | | | | | | | | | | | | |
| BnSETL | | | | | | | | | | | | | | |
| BnSCT2 | | | | | | | | | | | | | | |
| BnMDP | | | | | | | | | | | | | | |
| BnRTI-4 | | | | | | | | | | | | | | |
| BnMTFL | | | | | | | | | | | | | | |
| BnGSTF | | | | | | | | | | | | | | |
| BnSRP | | | | | | | | | | | | | | |
| BnPEF | | | | | | | | | | | | | | |
| BnWSP | | | | | | | | | | | | | | |
| BnLSP | | | | | | | | | | | | | | |

PROMOTERS FROM *BRASSICA NAPUS* FOR SEED SPECIFIC GENE EXPRESSION

RELATED APPLICATIONS

This application is a national stage application (under 35 U.S.C. §371) of PCT/EP2009/058138, filed Jun. 30, 2009, which claims benefit of European application 08159440.0, filed Jul. 1, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00062. The size of the text file is 416 KB, and the text file was created on Dec. 28, 2010.

FIELD OF THE INVENTION

The present invention is concerned with means and methods for allowing tissue specific and, in particular, seed specific expression of genes. The present invention, accordingly, relates to a polynucleotide comprising an expression control sequence which allows seed specific expression of a nucleic acid of interest being operatively linked thereto. Moreover, the present invention contemplates vectors, host cells, non-human transgenic organisms comprising the aforementioned polynucleotide as well as methods and uses of such a polynucleotide.

BACKGROUND OF THE INVENTION

In the field of "green" (agricultural) biotechnology, plants are genetically manipulated in order to confer beneficial traits. These beneficial traits may be yield increase, tolerance increase, reduced dependency on fertilizers, herbicidal, pesticidal- or fungicidal-resistance, or the capability of producing chemical specialties such as nutrients, drugs, oils for food and petrochemistry etc.

In many cases, it is required to express a heterologous gene in the genetically modified plants at a rather specific location in order to obtain a plant exhibiting the desired beneficial trait. One major location for gene expression is the plant seed. In the seeds, many important synthesis pathways, e.g., in fatty acid synthesis, take place. Accordingly, expression of heterologous genes in seeds allow for the manipulation of fatty acid synthesis pathways and, thus, for the provision of various fatty acid derivatives and lipid-based compounds.

However, for many heterologous genes, a seed specific expression will be required. Promoters which allow for a seed specific expression are known in the art. Such promoters include the oilseed rape napin promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley Ipt2 or Ipt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

However, there is a clear need for further expression control sequences such as promoters and terminators which allow for a reliable and efficient control of expression of foreign nucleic acids in seeds.

The technical problem underlying this invention can be seen as the provision of means and methods complying with the aforementioned needs. The technical problem is solved by the embodiments characterized in the claims and herein below.

DETAILED DESCRIPTION OF THE INVENTION

Figure 1:
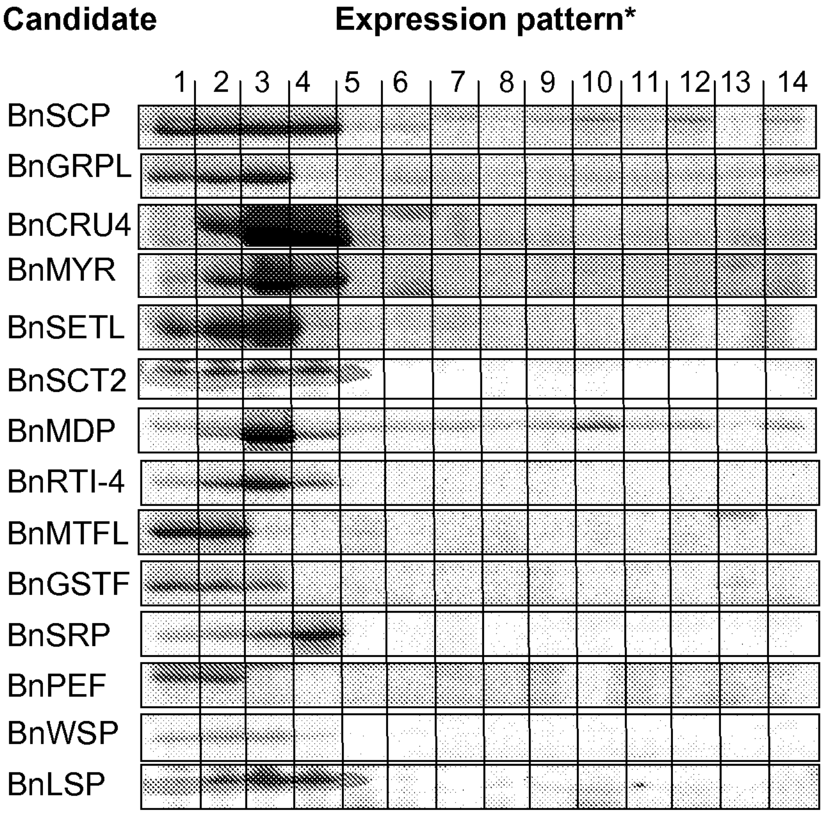
FIG. 1 shows a developmental expression analysis. Tissue types and developmental stages are given as listed in table 10. Samples 10, 11, 12 were pooled (assigned as 10), as well as samples 13, 14, 15 (assigned as 13).

Accordingly, the present invention relates to a polynucleotide comprising an expression control sequence which allows seed specific expression of a nucleic acid of interest being operatively linked thereto, said expression control sequence being selected from the group consisting of:

(a) an expression control sequence having a nucleic acid sequence as shown in any one of SEQ ID NOs: 1, 6, 9, 14, 16, 22, 25, 70, 77, 85, 95, 103, 111, 119, 124 or 131;

(b) an expression control sequence having a nucleic acid sequence which is at least 80% identical to a nucleic acid sequence shown in any one of SEQ ID NOs: 1, 6, 9, 14, 16, 22, 25, 70, 77, 85, 95, 103, 111, 119, 124 or 131;

(c) an expression control sequence having a nucleic acid sequence which hybridizes under stringent conditions to a a nucleic acid sequence as shown in any one of SEQ ID NOs: 1, 6, 9, 14, 16, 22, 25, 70, 77, 85, 95, 103, 111, 119, 124 or 131;

(d) an expression control sequence having a nucleic acid sequence which hybridizes to a nucleic acid sequences located upstream of an open reading frame sequence shown in any one of SEQ ID NOs: 5, 13, 20, 21, 27, 28, 71, 78, 86, 96, 104, 112 or 125;

(e) an expression control sequence having a nucleic acid sequence which hybridizes to a nucleic acid sequences located upstream of an open reading frame sequence being at least 80% identical to an open reading frame sequence as shown in any one of SEQ ID NOs: 5, 13, 20, 21, 27, 28, 71, 78, 86, 96, 104, 112 or 125;

(f) an expression control sequence obtainable by 5' genome walking or by thermal asymmetric interlaced polymerase chain reaction (TAIL-PCR) on genomic DNA from the first exon of an open reading frame sequence as shown in any one of SEQ ID NOs: 5, 13, 20, 21, 27, 28, 71, 78, 86, 96, 104, 112 or 125; and (g) an expression control sequence obtainable by 5' genome walking or TAIL PCR on genomic DNA from the first exon of an open reading frame sequence being at least 80% identical to an open reading frame as shown in any one of SEQ ID NOs: 5, 13, 20, 21, 27, 28, 71, 78, 86, 96, 104, 112 or 125.

The term "polynucleotide" as used herein refers to a linear or circular nucleic acid molecule. It encompasses DNA as well as RNA molecules. The polynucleotide of the present invention is characterized in that it shall comprise an expression control sequence as defined elsewhere in this specification. In addition to the expression control sequence, the polynucleotide of the present invention, preferably, further comprises at least one nucleic acid of interest being operatively linked to the expression control sequence and/or a termination sequence or transcription. Thus, the polynucleotide of the present invention, preferably, comprises an expression cassette for the expression of at least one nucleic acid of interest. Alternatively, the polynucleotide may comprise in addition to the said expression control sequence a multiple cloning site and/or a termination sequence for transcription. In such a case, the multiple cloning site is, preferably, arranged in a manner as to allow for operative linkage of a nucleic acid to be introduced in the multiple cloning site with the expression control sequence. In addition to the aforementioned components, the polynucleotide of the present invention, preferably, could comprise components required for homologous recombination, i.e. flanking genomic sequences from a target locus. However, also preferably, the polynucleotide of the present invention can essentially consist of the said expression control sequence.

The term "expression control sequence" as used herein refers to a nucleic acid which is capable of governing the expression of another nucleic acid operatively linked thereto, e.g. a nucleic acid of interest referred to elsewhere in this specification in detail. An expression control sequence as referred to in accordance with the present invention, preferably, comprises sequence motifs which are recognized and bound by polypeptides, i.e. transcription factors. The said transcription factors shall upon binding recruit RNA polymerases, preferably, RNA polymerase I, II or III, more preferably, RNA polymerase II or III, and most preferably, RNA polymerase II. Thereby the expression of a nucleic acid operatively linked to the expression control sequence will be initiated. It is to be understood that dependent on the type of nucleic acid to be expressed, i.e. the nucleic acid of interest, expression as meant herein may comprise transcription of RNA polynucleotides from the nucleic acid sequence (as suitable for, e.g., anti-sense approaches or RNAi approaches) or may comprises transcription of RNA polynucleotides followed by translation of the said RNA polynucleotides into polypeptides (as suitable for, e.g., gene expression and recombinant polypeptide production approaches). In order to govern expression of a nucleic acid, the expression control sequence may be located immediately adjacent to the nucleic acid to be expressed, i.e. physically linked to the said nucleic acid at its 5"end. Alternatively, it may be located in physical proximity. In the latter case, however, the sequence must be located so as to allow functional interaction with the nucleic acid to be expressed. An expression control sequence referred to herein, preferably, comprises between 200 and 5,000 nucleotides in length. More preferably, it comprises between 500 and 2,500 nucleotides and, more preferably, at least 1,000 nucleotides. As mentioned before, an expression control sequence, preferably, comprises a plurality of sequence motifs which are required for transcription factor binding or for conferring a certain structure to the polynucletide comprising the expression control sequence. Sequence motifs are also sometimes referred to as cis-regulatory elements and, as meant herein, include promoter elements as well as enhancer elements. Preferred expression control sequences to be included into a polynucleotide of the present invention have a nucleic acid sequence as shown in any one of SEQ ID NOs: 1, 6, 9, 14, 16, 22, 25, 70, 77, 85, 95, 103, 111, 119, 124 and 131.

Further preferably, an expression control sequence comprised by a polynucleotide of the present invention has a nucleic acid sequence which hybridizes to a nucleic acid sequences located upstream of an open reading frame sequence shown in any one of SEQ ID NOs: 5, 13, 20, 21, 27, 28, 71, 78, 86, 96, 104, 112 and 125, i.e. is a variant expression control sequence. It will be understood that expression control sequences may slightly differ in its sequences due to allelic variations. Accordingly, the present invention also contemplates an expression control sequence which can be derived from an open reading frame as shown in any one of SEQ ID NOs: 5, 13, 20, 21, 27, 28, 71, 78, 86, 96, 104, 112 and 125. Said expression control sequences are capable of hybridizing, preferably under stringent conditions, to the upstream sequences of the open reading frames shown in any one of SEQ ID NOs. 5, 13, 20, 21, 27, 28, 71, 78, 86, 96, 104, 112 and 125, i.e. the expression control sequences shown in any one of SEQ ID NOs.: 1, 6, 9, 14, 16, 22, 25, 70, 77, 85, 95, 103, 111, 119, 124 and 131. Stringent hybridization conditions as meant herein are, preferably, hybridization conditions in 6× sodium chloride/sodium citrate (=SSC) at approximately 45° C., followed by one or more wash steps in 0.2×SSC, 0.1% SDS at 53 to 65° C., preferably at 55° C., 56° C., 57° C., 58° C., 59° C., 60° C., 61° C., 62° C., 63° C., 64° C. or 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. Such hybridizing expression control sequences are, more preferably, at least 70%, at least 80%, at least 90%, at least 91%, at least 92%, at least 93%, at least 94% at least 95%, at least 96%, at least 97%, at least 98%, or at least 99% identical to the expression control sequences as shown in any one of SEQ ID NOs.: 1, 6, 9, 14, 16, 22, 25, 70, 77, 85, 95, 103, 111, 119, 124 and 131. The percent identity values are, preferably, calculated over the entire nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins 1989, CABIOS, 5: 151-153) or the programs Gap and BestFit (Needleman 1970 J. Mol. Biol. 48; 443-453 and Smith 1981, Adv. Appl. Math. 2; 482-489), which are part of the GCG software packet (Genetics Computer Group, 575 Science Drive, Madison, Wis., USA 53711 version 1991), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

Moreover, expression control sequences which allow for seed specific expression can not only be found upstream of the aforementioned open reading frames having a nucleic acid sequence as shown in any one of SEQ ID NOs. 5, 13, 20, 21, 27, 28, 71, 78, 86, 96, 104, 112 and 125. Rather, expression control sequences which allow for seed specific expression can also be found upstream of orthologous, paralogous or homologous genes (i.e. open reading frames). Thus, also preferably, an variant expression control sequence comprised by a polynucleotide of the present invention has a nucleic acid sequence which hybridizes to a nucleic acid sequences located upstream of an open reading frame sequence being at least 70%, more preferably, at least 80%, at least 90%, at least 91%, at least 92%, at least 93%, at least 94% at least 95%, at least 96%, at least 97%, at least 98%, or at least 99% identical to a sequence as shown in any one of SEQ ID NOs: 5, 13, 20, 21, 27, 28, 71, 78, 86, 96, 104, 112 and 125. The said variant open reading shall encode a polypeptide having the biological activity of the corresponding polypeptide being encoded by the open reading frame shown in any one of SEQ ID NOs.: 5, 13, 20, 21, 27, 28, 71, 78, 86, 96, 104, 112 and 125. In this context it should be mentioned that the open reading frame shown in SEQ ID NO: 5 encodes a polypeptide showing similarity to gibberlin responsive proteins, the open reading frame shown in SEQ ID NO: 13 encodes a polypeptide belonging to the pectinesterase family, the open reading frame shown in SEQ ID NO: 20 encodes "sinapoyl choline transferase 1" (SCT1), and the open reading frames shown in SEQ ID NO: 21 encodes "sinapoyl choline transferase 2" (SCT2). These biological activities can be determined by those skilled in the art without further ado. The open reading frames shown in SEQ ID NO: 27 and 28 encode polypeptides showing homology to seed proteins with yet unknown functions.

TABLE 1

Protein function of genes identified to be seed specifically expressed:

| SEQ ID | Protein function |
|---|---|
| 5 | putative gibberelin responsive protein |
| 13 | putative pectinesterase |
| 20 | Sinapoyl choline transferase |
| 21 | Sinapoyl choline transferase |
| 27 | Seed protein |
| 28 | Seed protein |
| 72 | Seed protein |
| 80 | CRU4 subunit of Cruciferin (seed storage protein) |
| 88 | Myrosinase |
| 98 | Seed protein |
| 106 | serine proteinase inhibitor |
| 114 | Transcription factor involved in embryonic development |
| 121 | Glutathione S-transferase |
| 133 | Seed protein |

Also preferably, a variant expression control sequence comprised by a polynucleotide of the present invention is (i) obtainable by 5' genome walking or TAIL PCR from an open reading frame sequence as shown in any one of SEQ ID NOs: 5, 13, 20, 21, 27, 28, 71, 78, 86, 96, 104, 112 and 125 or (ii) obtainable by 5' genome walking or TAIL PCR from a open reading frame sequence being at least 80% identical to an open reading frame as shown in any one of SEQ ID NOs: 5, 13, 20, 21, 27, 28, 71, 78, 86, 96, 104, 112 and 125. Variant expression control sequences are obtainable without further ado by the genome walking technology or by thermal asymmetric interlaced polymerase chain reaction (TAIL-PCR) which can be carried out as described in the accompanying Examples by using, e.g., commercially available kits.

Variant expression control sequences referred to in this specification for the expression control sequence shown in SEQ ID NO: 1, preferably, comprise at least 80, at least 90, at least 100, at least 110, at least 120, at least 130, at least 140 or all of the sequence motifs recited in Table 1. Variant expression control sequences referred to in this specification for the expression control sequence shown in SEQ ID NO: 6, preferably, comprise at least 80, at least 90, at least 100, at least 110 or all of the sequence motifs recited in Table 2. Variant expression control sequences referred to in this specification for the expression control sequence shown in SEQ ID NO: 9, preferably, comprise at least 40, at least 50, at least 60 or all of the sequence motifs recited in Table 3. Variant expression control sequences referred to in this specification for the expression control sequence shown in SEQ ID NO: 14, preferably, comprise at least 50, at least 60, at least 70, at least 80, at least 90 or all of the sequence motifs recited in Table 4. Variant expression control sequences referred to in this specification for the expression control sequence shown in SEQ ID NO: 16, preferably, comprise at least 50, at least 60, at least 70, at least 80, at least 90 or all of the sequence motifs recited in Table 5. Variant expression control sequences referred to in this specification for the expression control sequence shown in SEQ ID NO: 22, preferably, comprise at least 80, at least 90, at least 100, at least 110, at least 120, at least 130 or all of the sequence motifs recited in Table 6. Variant expression control sequences referred to in this specification for the expression control sequence shown in SEQ ID NO: 25, preferably, comprise at least 80, at least 100, at least 120, at least 130, at least 140, at least 150 or all of the sequence motifs recited in Table 7.

Variant expression control sequences referred to in this specification also, preferably, comprise at least the cis-regulatory elements referred to in Table 8, below. Even more preferably, the variant regulatory expression control sequences comprise said elements with the same frequency and distribution as referred to in Table 9 for the individual regulatory sequences.

The term "seed specific" as used herein means that a nucleic acid of interest being operatively linked to the expression control sequence referred to herein will be predominantly expressed in seeds when present in a plant. A predominant expression as meant herein is characterized by a statistically significantly higher amount of detectable transcription in the seeds with respect to other plant tissues. A statistically significant higher amount of transcription is, preferably, an amount being at least two-fold, three-fold, four-fold, five-fold, ten-fold, hundred-fold, five hundred-fold or thousand-fold the amount found in at least one of the other tissues with detectable transcription. Alternatively, it is an expression in seeds whereby the amount of transcription in non-seed tissues is less than 1%, 2%, 3%, 4% or most preferably 5% of the overall (whole plant) amount of expression.

The amount of transcription directly correlates to the amount of transcripts (i.e. RNA) or polypeptides encoded by the transcripts present in a cell or tissue. Suitable techniques for measuring transcription either based on RNA or polypeptides are well known in the art. Seed specific alternatively and, preferably in addition to the above, means that the expression is restricted or almost restricted to seeds, i.e. there is essentially no detectable transcription in other tissues. Almost restricted as meant herein means that unspecific expression is detectable in less than ten, less than five, less than four, less than three, less than two or one other tissue(s). Seed specific expression as used herein includes expression in seed cells or their precursors, such as cells of the endosperm and of the developing embryo.

An expression control sequences can be tested for seed specific expression by determining the expression pattern of a nucleic acid of interest, e.g., a nucleic acid encoding a reporter protein, such as GFP, in a transgenic plant. Transgenic plants can be generated by techniques well known to the person skilled in the art and as discussed elsewhere in this specification. The aforementioned amounts or expression pattern are, preferably, determined by Northern Blot or in situ hybridization techniques as described in WO 02/102970 in *Brassica napus* plants, more preferably, at 20, 25, 30, 35 or 40 days after flowering. Preferred expression pattern for the expression control sequences according to the present invention are shown in the Figure or described in the accompanying Examples, below.

The term "nucleic acid of interest" refers to a nucleic acid which shall be expressed under the control of the expression control sequence referred to herein. Preferably, a nucleic acid of interest encodes a polypeptide the presence of which is desired in a cell or non-human organism as referred to herein and, in particular, in a plant seed. Such a polypeptide may be an enzyme which is required for the synthesis of seed storage compounds or may be a seed storage protein. It is to be understood that if the nucleic acid of interest encodes a polypeptide, transcription of the nucleic acid in RNA and translation of the transcribed RNA into the polypeptide may be required. A nucleic acid of interest, also preferably, includes biologically active RNA molecules and, more preferably, antisense RNAs, ribozymes, micro RNAs or siRNAs. Said biologically active RNA molecules can be used to modify the amount of a target polypeptide present in a cell or non-human organism. For example, an undesired enzymatic activity in a seed can be reduced due to the seed specific expression of an antisense RNAs, ribozymes, micro RNAs or siRNAs. The underlying biological principles of action of the aforementioned biologically active RNA molecules are well known in the art. Moreover, the person skilled in the art is well aware of how to obtain nucleic acids which encode such biologically active RNA molecules. It is to be understood that the biologically active RNA molecules may be directly obtained by transcription of the nucleic acid of interest, i.e. without translation into a polypeptide. It is to be understood that the expression control sequence may also govern the expression of more than one nucleic acid of interest, i.e. at least one, at least two, at least three, at least four, at least five etc. nucleic acids of interest.

The term "operatively linked" as used herein means that the expression control sequence of the present invention and a nucleic acid of interest, are linked so that the expression can be governed by the said expression control sequence, i.e. the expression control sequence shall be functionally linked to said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

Advantageously, it has been found in the studies underlying the present invention that seed specific expression of a nucleic acid of interest can be achieved by expressing said nucleic acid of interest under the control of an expression control sequence from *Brassica napus* or a variant expression control sequence as specified above. The expression control sequences provided by the present invention allow for a reliable and highly specific expression of nucleic acids of interest. Thanks to the present invention, it is possible to (i) specifically manipulate biochemical processes in seeds, e.g., by expressing heterologous enzymes or biologically active RNAs, or (ii) to produce heterologous proteins in seeds. In principle, the present invention contemplates the use of the polynucleotide, the vector, the host cell or the non-human transgenic organism for the expression of a nucleic acid of interest. Preferably, the envisaged expression is seed specific. More preferably, the nucleic acid of interest to be used in the various embodiments of the present invention encodes a seed storage protein or is involved in the modulation of seed storage compounds.

As used herein, seed storage compounds include fatty acids and triacylglycerides which have a multiplicity of applications in the food industry, in animal nutrition, in cosmetics and the pharmacological sector. Depending on whether they are free saturated or unsaturated fatty acids or else triacylglycerides with an elevated content of saturated or unsaturated fatty acids, they are suitable for various different applications. More preferably, the polynucleotide of the present invention comprising the expression control sequence referred to above is applied for the manufacture of polyunsaturated fatty acids (PUFAs). For the manufacture of PUFAs in seeds, the activity of enzymes involved in their synthesis, in particular, elongases and desaturases, needs to be modulated. This will be achieved by seed specific expression of the nucleic acids of interest encoding the aforementioned enzymes or by seed specific expression of antisense, ribozyme, RNAi molecules which downregulate the activity of the enzymes by interfering with their protein synthesis. PUFAs are seed storage compounds which can be isolated by a subsequently applied purification process using the aforementioned seeds.

Particularly preferred PUFAs in accordance with the present invention are polyunsaturated long-chain ω-3-fatty acids such as eicosapentaenoic acid (=EPA, C20: $5^{\Delta 5,8,11,14,17}$), ω-3 eicostetraenic acid (=ETA, C20: $4^{\Delta 8,11,14,17}$), arachidonic acid (=ARA C20:$4^{\Delta 5,8,11,14}$) or docosahexaenoic acid (=DHA, C22:$6^{\Delta 4,7,10,13,16,19}$). They are important components of human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, $14^{\Delta 8,11,14,17}$995; Horrocks, L A and Yeo Y K Pharmacol Res 40:211-225, 1999). There is, therefore, a need for the production of polyunsaturated long-chain fatty acids.

Particular preferred enzymes involved in the synthesis of PUFAs are disclosed in WO 91/13972 (Δ9-desaturase), WO 93/11245 (Δ15-desaturase), WO 94/11516 (Δ12-desaturase), EP A 0 550 162, WO 94/18337, WO 97/30582, WO 97/21340, WO 95/18222, EP A 0 794 250, Stukey et al., J. Biol. Chem., 265, 1990: 20144-20149, Wada et al., Nature 347, 1990: 200-203 or Huang et al., Lipids 34, 1999: 649-659. Δ6-Desaturases are described in WO 93/06712, U.S. Pat. No. 5,614,393, U.S. Pat. No. 5,614,393, WO 96/21022, WO 00/21557 and WO 99/27111, and also the application for the production in transgenic organisms is described in WO 98/46763, WO 98/46764 and WO 98/46765. Here, the expression of various desaturases is also described and claimed in WO 99/64616 or WO 98/46776, as is the formation of polyunsaturated fatty acids. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Furthermore, mixtures of ω-3- and ω-6-fatty acids are usually obtained.

Furthermore, the present invention relates to a polynucleotide comprising an expression termination sequence which allows for termination of transcription of a nucleic acid of interest being operatively linked thereto, said expression termination sequence being selected from the group consisting of:

(a) a expression termination sequence having a nucleic acid sequence as shown in any one of SEQ ID NOs: 2, 7, 10, 15, 17, 23, 71, 78, 86, 96, 104, 112, or 125;

(b) a expression termination sequence having a nucleic acid sequence which is at least 80% identical to a nucleic acid sequence as shown in any one of SEQ ID NOs: which hybridizes under stringent conditions to a nucleic acid sequence as shown in any one of SEQ ID NOs: 2, 7, 10, 15, 17, 23, 71, 78, 86, 96, 104, 112, or 125;

(c) a expression termination sequence having a nucleic acid sequence which hybridizes under stringent conditions to a nucleic acid sequence as shown in any one of SEQ ID NOs: 2, 7, 10, 15, 17, 23, 71, 78, 86, 96, 104, 112, or 125;

(d) a expression termination sequence having a nucleic acid sequence which hybridizes to a nucleic acid sequences located downstream of an open reading frame sequence shown in any one of SEQ ID NOs: 5, 13, 20, 21, 27, 28, 71, 78, 86, 96, 104, 112 or 125;

(e) a expression termination sequence having a nucleic acid sequence which hybridizes to a nucleic acid sequences located downstream of an open reading frame sequence being at least 80% identical to an open reading frame sequence as shown in any one of SEQ ID NOs: 5, 13, 20, 21, 27, 28, 71, 78, 86, 96, 104, 112 or 125;

(f) a expression termination sequence obtainable by 3' genome walking or TAIL PCR on genomic DNA from the last exon of an open reading frame sequence as shown in any one of SEQ ID NOs: 5, 13, 20, 21, 27, 28, 71, 78, 86, 96, 104, 112 or 125; and (g) a expression termination sequence obtainable by 3' genome walking or TAIL PCR on genomic DNA from the last exon of an open reading frame sequence being at least 80% identical to an open reading frame as shown in any one of SEQ ID NOs: 5, 13, 20, 21, 27, 28, 71, 78, 86, 96, 104, 112 or 125.

The term "expression termination sequence" as used herein refers to a nucleic acid which is capable of governing the termination of the process of RNA transcription of a nucleic acid operatively linked thereto, e.g. a nucleic acid of interest referred to elsewhere in this specification in detail. A termination sequence as referred to in accordance with the present invention, preferably, contains a polyadenylation signal and furthermore mediates dissociation of RNA polymerases, preferably, RNA polymerase I, II or III, more preferably, RNA polymerase II or III, and most preferably, RNA polymerase II from the transcribed DNA. Thereby the elongation of a RNA transcript, transcribed from a nucleic acid operatively linked to the termination sequence will be terminated and the RNA will be released. In order to govern termination of transcription of a nucleic acid, the expression control sequence may be located immediately adjacent to the nucleic acid whose expression is to be terminated, i.e. physically linked to the said nucleic acid at its 3"end. Alternatively, it may be located in physical proximity. In the latter case, however, the sequence must be located so as to allow functional interaction with the nucleic acid whose transcription is to be terminated. A termination sequence referred to herein, preferably, comprises between 50 and 2,000 nucleotides in length. More preferably, it comprises between 100 and 800 nucleotides and, more preferably, at least 100 nucleotides. Preferred expression termination sequences are those comprised by the polynucleotide referred to above.

Furthermore, the definitions and explanations of the terms made above apply mutatis muandis except as specified herein below.

For termination sequences, the term "operatively linked" means that the termination sequence of the present invention and a nucleic acid of interest, are linked so that the termination of transcription of the mRNA can be governed by said termination sequence, i.e. the termination sequence shall be functionally linked to said nucleic acid sequence whose transcription is to be terminated. Accordingly, the expression control sequence, the nucleic acid sequence to be expressed and the termination sequence may be physically linked to each other, e.g., by inserting the expression control sequence at the 5"end of the nucleic acid sequence to be expressed and/or inserting the termination sequence at the 3' end of the nucleic acid sequence whose transcription is to be terminated. Alternatively, the expression control sequence and the nucleic acid to be expressed may be merely in physical proximity so that the expression control sequence is capable of governing the expression of at least one nucleic acid sequence of interest. The termination sequence and the nucleic acid whose transcription is to be terminated are, preferably, separated by not more than 50 bp, 40 bp, 20 bp, 10 bp or 5 bp.

Advantageously, the polynucleotide of the present invention comprising a expression termination sequence can be also applied for efficient expression control in plants and, in particular, plant seeds. Specifically, the expression termination sequence allows for accurate termination of transcription of the DNA into RNA after the nucleic acid sequence of interest has been transcribed. Thus, the transcription of undesired nucleic acid sequences is avoided.

The present invention also relates to a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride coprecipitation, DEAE-dextran-mediated transfection, lipofection, natural competence, carbon-based clusters, chemically mediated transfer, electroporation or particle bombardment (e.g., "gene-gun"). Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBUI101, pBinAR, pGPTV, pSUN and pCAMBIA. An overview of binary vectors and their use can be found in Hellens et al, Trends in Plant Science (2000) 5, 446-451. Furthermore, by using appropriate cloning vectors, the polynucleotide of the invention can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

More preferably, the vector of the present invention is an expression vector. In such an expression vector, the polynucleotide comprises an expression cassette as specified above allowing for expression in eukaryotic cells or isolated fractions thereof. An expression vector may, in addition to the polynucleotide of the invention, also comprise further regulatory elements including transcriptional as well as translational enhancers. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vector backbones are, preferably, derived from expression vectors known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the nucleic acid of interest encoding a protein to be expressed. The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. Examples of vectors for expression in the yeast *S. cerevisiae* comprise pYepSec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170: 31-39).

The polynucleotides of the present invention can be used for expression of a nucleic acid of interest in single-cell plant cells (such as algae), see Falciatore et al., 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711). Other preferred sequences for the use in functional linkage in plant gene expression cassettes are targeting sequences which are required for targeting the gene product into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, J., Fritsch, E. F., and Maniatis, T., Molecular Cloning: A Laboratory Manual, $2^{nd}$ edition, Cold Spring Harbor Laboratory, Cold Spring Harbor Laboratory Press, Cold Spring Harbor, N.Y., 1989.

The present invention also contemplates a host cell comprising the polynucleotide or the vector of the present invention.

Host cells are primary cells or cell lines derived from multicellular organisms such as plants or animals. Furthermore, host cells encompass prokaryotic or eukaryotic single cell organisms (also referred to as micro-organisms). Primary cells or cell lines to be used as host cells in accordance with the present invention may be derived from the multicellular organisms referred to below. Host cells which can be exploited are furthermore mentioned in: Goeddel, Gene Expression Technology: Methods in Enzymology 185, Academic Press, San Diego, Calif. (1990). Specific expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. Preferably, the host cells may be obtained from plants. More preferably, oil crops are envisaged which comprise large amounts of lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, Tagetes, Solanaceae plants such as potato, tobacco, eggplant and tomato, *Vicia* species, pea, alfalfa, bushy plants (coffee, cacao, tea), *Salix* species, trees (oil palm, coconut) and perennial grasses and fodder crops. Especially preferred plants according to the invention are oil crops such as soybean, peanut, oilseed rape, canola, linseed, hemp, evening primrose, sunflower, safflower, trees (oil palm, coconut). Suitable methods for obtaining host cells from the multicellular organisms referred to below as well as conditions for culturing these cells are well known in the art.

The micro-organisms are, preferably, bacteria or fungi including yeasts. Preferred fungi to be used in accordance with the present invention are selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae. Further preferred micro-organisms are selected from the group: Choanephoraceae such as the genera *Blakeslee, Choanephora*, for example the genera and species *Blakeslea trispora, Choanephora cucurbitarum, Choanephora infundibulifera* var. *cucurbitarum*, Mortierellaceae, such as the genus *Mortierella*, for example the genera and species *Mortierella isabeffina, Mortierella polycephala, Mortierella ramanniana, Mortierella vinacea, Mortierella zonata*, Pythiaceae such as the genera *Phytium, hytophthora* for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae such as the genera *Hansenula, Pichia, Saccharomyces, Saccharomycodes, Yarrowia* for example the genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceta, Saccharomyces bailii, Saccharomyces bayanus, Saccharo-*

*myces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosea, Saccharomyces rouxii, Saccharomyces uvarum, Saccharomycodes ludwigii, Yarrowia lipolytica*, Schizosacharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense*. Further preferred microorganisms are bacteria selected from the group of the families Bacillaceae, Enterobacteriacae or Rhizobiaceae. Examples of such micro-organisms may be selected from the group: Bacillaceae such as the genera *Bacillus* for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia* for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia* carotovora subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communion, Escherichia colimutabile, Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizo-biaceae such as the genera *Agrobacterium, Carbophilus, Chelatobacter, Ensifer, Rhizobium, Sinorhizobium* for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense.*

How to culture the aforementioned micro-organisms is well known to the person skilled in the art.

The present invention also relates to a non-human transgenic organism, preferably a plant or seed thereof, comprising the polynucleotide or the vector of the present invention.

The term "non-human transgenic organism", preferably, relates to a plant, a plant seed, a non-human animal or a multicellular micro-organism. The polynucleotide or vector may be present in the cytoplasm of the organism or may be incorporated into the genome either heterologous or by homologous recombination. Host cells, in particular those obtained from plants or animals, may be introduced into a developing embryo in order to obtain mosaic or chimeric organisms, i.e. non-human transgenic organisms comprising the host cells of the present invention. Suitable transgenic organisms are, preferably, all organisms which are suitable for the expression of recombinant genes. Preferred plants to be used for making non-human transgenic organisms according to the present invention are all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula offinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis [borage*], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis* sativa [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita* moschata [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta [manihot]* or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria*

*hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auriturn, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia*], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, lsochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, lsochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora* infestans, *Thallasiosira pseudonona* and *Cryptocodinium cohnii.*

Transgenic plants may be obtained by transformation techniques as published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Preferably, a multicellular micro-organism as used herein refers to protists or diatoms. More preferably, it is selected from the group of the families Dinophyceae, Turaniellidae or Oxytrichidae, such as the genera and species: *Crypthecodinium cohnii, Phaeodactylum tricornutum, Stylonychia mytilus, Stylonychia pustulate, Stylonychia putrina, Stylonychia notophora, Stylonychia* sp., *Colpidium campylum* or *Colpidium* sp.

The present invention also relates to a method for expressing a nucleic acid of interest in a host cell comprising (a) introducing the polynucleotide or the vector of the present invention into the host cell, whereby the nucleic acid sequence of interest will be operatively linked to the expression control sequence; and
(b) expressing the said nucleic acid sequence in said host cell.

The polynucleotide or vector of the present invention can be introduced into the host cell by suitable transfection or transformation techniques as specified elsewhere in this description. The nucleic acid of interest will be expressed in the host cell under suitable conditions. To this end, the host cell will be cultivated under conditions which, in principle, allow for transcription of nucleic acids. Moreover, the host cell, preferably, comprises the exogenously supplied or endogenously present transcription machinery required for expressing a nucleic acid of interest by the expression control sequence. More preferably, the host cell is a plant cell and, most preferably, a seed cell or precursor thereof.

Moreover, the present invention encompasses a method for expressing a nucleic acid of interest in a non-human organism comprising (a) introducing the polynucleotide or the vector of the present invention into the non human organism, whereby the nucleic acid sequence of interest will be operatively linked to the expression control sequence; and
(b) expressing the said nucleic acid sequence in said non-human transgenic organism.

The polynucleotide or vector of the present invention can be introduced into the non-human transgenic organism by suitable techniques as specified elsewhere in this description. The non-human transgenic organism, preferably, comprises the exogenously supplied or endogenously present transcription machinery required for expressing a nucleic acid of interest by the expression control sequence. More preferably, the non-human transgenic organism is a plant or seed thereof. It is to be understood that the nucleic acid of interest will be expressed, preferably, seed specific in the said non-human transgenic organism.

Further, the present invention relates to a method for the manufacture of stearidonic acid (SDA) in a plant seed comprising the steps of:

a) growing a transgenic plant expressing a polynucleotide encoding a delta 6 desaturase under the control of the polynucleotide of the present invention; and
b) obtaining said SDA from the harvested seeds of the said plant.

The SDA may be manufactured in the form of a triglyceride ester, a phospholipids or as Acyl-CoA bound or free fatty acid comprised by seed oil or seed fatty acid preparations obtainable from the harvested seeds of the grown transgenic plants by standard techniques such as an oil mill or chromatographic extraction and/or purification techniques.

Moreover, how to grow transgenic plants and how to harvest their seeds is well known in the art. How to make transgenic plants expressing a gene of interest such as a delta 6 desaturase under the control of the polynucleotide of the present invention is set forth elsewhere herein.

Surprisingly, the polynucleotides of the present invention were found to influence the ratio of the omega-3 fatty acid stearidonic acid (SDA) to the omega-6 fatty acid gamma linolenic acid (GLA). Accordingly, the seeds of the aforementioned transgenic plants expressing a delta 6 desaturase under the control of the promoter comprised by the polynucleotide of the invention are particularly suitable as a source for SDA or SDA enriched fatty acid preparations such as oil.

Thus, the present invention also pertains to the use of the polynucleotide of the present invention driving expression of a delta 6 desaturase in a transgenic plant for increasing (preferably to a statistically significant extent) the amount of SDA at the expense of GLA in plant seeds of said plants.

Moreover, the present invention pertains to seed oil having the said altered SDA to GLA ratio (i.e. an increased SDA amount at the expense of GLA) obtainable by an oil mill from the harvested seeds of a transgenic plant as set forth above. It will be understood that such an oil will be characterized in addition to the altered SDA to GLA ratio by the presence of remaining DNA contaminations including the polynucleotide of the present invention and/or the delta 6 desaturase encoding polynucleotide.

Nucleic acids encoding suitable delta 6 desaturases are well known in the art and are d6-Desaturases d6Des(Cp) from

*Ceratodon purpureus* (WO2000075341), d6Des(OI) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710) and, in particular, those mentioned in the accompanying Examples.

Moreover, a transgenic plant expressing a polynucleotide encoding a delta 6 desaturase under the control of the polynucleotide of the present invention may also comprise further desaturases or elongases of the omega-3 pathway which are required for the synthesis of end products such as eicosapentaenoic acid (EPA) or docosahexaenoic acid (DHA).

Thus, a method is provided for increasing stearidonic acid in a plant seed comprising the steps of growing a transgenic plant expressing a polynucleotide encoding a delta 6 desaturase under the control of the polynucleotide of the present invention.

By increasing the omega-3 pathway substrate SDA at the expense of the omega-6 pathway substrate GLA, further fatty acid products of the omega-3 pathway can be produced more efficiently in the aforementioned transgenic plants. Preferably, the desaturases and/or elongases required for the production of a desired fatty acid can also be expressed under the control of a polynucleotide of the present invention. Most preferably, however, it is envisaged that the delta 6 desaturase and the further desaturases and/or elongases are expressed under the control of polynucleotides of the present invention comprising different expression control sequences with respect to each other.

In the following tables 1 to 9, the cis-regulatory elements found in the expression control sequences of the present invention are shown.

TABLE 1 cis-regulatory elements of SEQ ID NO: 1

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_1 | P$AHBP/ATHB9.01 | HD-ZIP class III protein ATHB9 | 0.77 | 7 | 17 | (-) | 1.000 | 0.772 | ttgATGAtttc |
| SEQ_1 | P$MADS/AGL2.01 | AGL2, *Arabidopsis* MADS-domain protein AGAMOUS-like 2 | 0.82 | 57 | 77 | (+) | 1.000 | 0.897 | aaaaaCCATatcttgaaaacc |
| SEQ_1 | P$SUCB/SUCROSE.01 | Sequence motif from the promoters of different sugar-responsive genes | 0.81 | 57 | 75 | (+) | 0.750 | 0.827 | aaAAACcatatcttgaaaa |
| SEQ_1 | P$TELO/ATPURA.01 | *Arabidopsis* Telo-box interacting protein related to the conserved animal protein Pur-alpha | 0.85 | 57 | 71 | (+) | 0.750 | 0.851 | aaaaACCAtatcttg |
| SEQ_1 | P$GTBX/GT3A.01 | Trihelix DNA-binding factor GT-3a | 0.83 | 86 | 102 | (-) | 1.000 | 0.847 | accattGTTActcccct |
| SEQ_1 | P$LFYB/LFY.01 | Plant specific floral meristem identity gene LEAFY (LFY) | 0.93 | 91 | 103 | (-) | 0.914 | 0.936 | tACCAttgttact |
| SEQ_1 | P$SEF3/SEF3.01 | SEF3, Soybean embryo factor 3 | 0.87 | 147 | 161 | (+) | 1.000 | 0.875 | acccaACCCaaagag |
| SEQ_1 | P$CCAF/CCA1.01 | Circadian clock associated 1 | 0.85 | 177 | 191 | (+) | 1.000 | 0.943 | tcagctaaAATCtaa |
| SEQ_1 | P$LREM/ATCTA.01 | Motif involved in carotenoid and tocopherol biosynthesis and in the expression of photo-synthesis-related genes | 0.85 | 184 | 194 | (+) | 1.000 | 0.921 | aaATCTaagga |
| SEQ_1 | P$LEGB/RY.01 | RY and Sph motifs conserved in seed-specific promoters | 0.87 | 202 | 228 | (-) | 1.000 | 0.936 | ggctactcCATGcaatattggatgctc |
| SEQ_1 | P$CAAT/CAAT.01 | CCAAT-box in plant promoters | 0.97 | 206 | 214 | (+) | 1.000 | 0.983 | atCCAAtat |
| SEQ_1 | P$NCS1/NCS1.01 | Nodulin consensus sequence 1 | 0.85 | 230 | 240 | (+) | 0.878 | 0.865 | aAAATgatgcg |
| SEQ_1 | P$E2FF/E2F.01 | E2F class I sites | 0.82 | 234 | 248 | (-) | 0.757 | 0.833 | ttgtTTCTcgcatca |
| SEQ_1 | P$LREM/ATCTA.01 | Motif involved in carotenoid and tocopherol biosynthesis and in the expression of photo-synthesis-related genes | 0.85 | 274 | 284 | (+) | 1.000 | 0.918 | cgATCTacaat |

TABLE 1-continued cis-regulatory elements of SEQ ID NO: 1

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_1 | P$L1BX/PDF2.01 | Protodermal factor 2 | 0.85 | 278 | 294 | (+) | 1.000 | 0.899 | ctacaaTAAAtaccaga |
| SEQ_1 | P$CCAF/CCA1.01 | Circadian clock associated 1 | 0.85 | 287 | 301 | (+) | 1.000 | 0.881 | ataccagaAATCtca |
| SEQ_1 | P$GTBX/GT1.01 | GT1-Box binding factors with a trihelix DNA-binding domain | 0.85 | 330 | 346 | (+) | 0.843 | 0.903 | catgagGTGAgtctttt |
| SEQ_1 | P$OPAQ/GCN4.01 | GCN4, conserved in cereal seed storage protein gene promoters, similar to yeast GCN4 and vertebrate AP-1 | 0.81 | 332 | 348 | (+) | 1.000 | 0.830 | tgaggTGAGtcttttt |
| SEQ_1 | P$SALT/ALFIN1.02 | Zinc-finger protein in alfalfa roots, regulates salt tolerance | 0.95 | 360 | 374 | (−) | 1.000 | 0.977 | ggtatgcGGTGtttc |
| SEQ_1 | P$NACF/TANAC69.01 | Wheat NACdomain DNA binding factor | 0.68 | 367 | 389 | (+) | 0.812 | 0.736 | cgcataccagaAACGtaaagaaa |
| SEQ_1 | P$DOFF/PBOX.01 | Prolamin box, conserved in cereal seed storage protein gene promoters | 0.75 | 375 | 391 | (+) | 1.000 | 0.815 | agaaacgtAAAGaaaat |
| SEQ_1 | P$HEAT/HSE.01 | Heat shock element | 0.81 | 375 | 389 | (+) | 1.000 | 0.918 | agaaacgtaaAGAAa |
| SEQ_1 | P$MADS/MADS.01 | Binding sites for AP1, AP3-PI and AG dimers | 0.75 | 411 | 431 | (−) | 1.000 | 0.791 | ttttcCCATatttttttacatt |
| SEQ_1 | P$TBPF/TATA.01 | Plant TATA box | 0.88 | 464 | 478 | (+) | 1.000 | 0.941 | aaaaTATAaaaaaaa |
| SEQ_1 | P$GAPB/GAP.01 | Cis-element in the GAPDH promoters conferring light inducibility | 0.88 | 474 | 488 | (+) | 0.807 | 0.895 | aaaaATTAaaagaaa |
| SEQ_1 | P$PSRE/GAAA.01 | GAAA motif involved in pollen specific transcriptional activation | 0.83 | 480 | 496 | (+) | 1.000 | 0.838 | taaaaGAAAattttgac |
| SEQ_1 | P$WBXF/WRKY.01 | WRKY plant specific zinc-finger-type factor associated with pathogen defence, W box | 0.92 | 487 | 503 | (+) | 1.000 | 0.920 | aaattTTGAcgctgaaa |
| SEQ_1 | P$MYBL/MYBPH3.01 | Myb-like protein of Petunia hybrida | 0.80 | 498 | 514 | (+) | 0.750 | 0.801 | ctgaaaccGTAAatctt |
| SEQ_1 | P$TELO/ATPURA.01 | *Arabidopsis* Telo-box interacting protein related to the conserved animal protein Pur-alpha | 0.85 | 499 | 513 | (+) | 0.750 | 0.863 | tgaaACCGtaaatct |

TABLE 1-continued cis-regulatory elements of SEQ ID NO: 1

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_1 | P$CCAF/CCA1.01 | Circadian clock associated 1 | 0.85 | 501 | 515 | (+) | 1.000 | 0.889 | aaaccgtaAATCtta |
| SEQ_1 | P$L1BX/ATML1.01 | L1-specific homeodomain protein ATML1 (*A. thaliana* meristem layer 1) | 0.82 | 517 | 533 | (+) | 0.750 | 0.851 | aatcaaCAAAtgcataa |
| SEQ_1 | P$L1BX/ATML1.01 | L1-specific homeodomain protein ATML1 (*A. thaliana* meristem layer 1) | 0.82 | 525 | 541 | (+) | 1.000 | 0.954 | aatgcaTAAAtgcaaag |
| SEQ_1 | P$DOFF/PBOX.01 | Prolamin box, conserved in cereal seed storage protein gene promoters | 0.75 | 530 | 546 | (+) | 1.000 | 0.773 | ataaatgcAAAGttatt |
| SEQ_1 | P$AHBP/BLR.01 | Transcriptional repressor BELLRINGER | 0.90 | 538 | 548 | (+) | 0.826 | 0.936 | aaaGTTAttga |
| SEQ_1 | P$TBPF/TATA.01 | Plant TATA box | 0.88 | 557 | 571 | (−) | 1.000 | 0.964 | ctaaTATAaaaatat |
| SEQ_1 | P$MYBL/GAMYB.01 | GA-regulated myb gene from barley | 0.91 | 583 | 599 | (−) | 1.000 | 0.934 | tagtatttGTTAgcagt |
| SEQ_1 | P$SPF1/SP8BF.01 | DNA-binding protein of sweet potato that binds to the SP8a (ACTGTGTA) and SP8b (TACTATT) sequences of sporamin and beta-amylase genes | 0.87 | 593 | 605 | (+) | 1.000 | 0.902 | aaTACTatacaga |
| SEQ_1 | P$IDDF/ID1.01 | Maize INDETERMINATE1 zinc finger protein | 0.92 | 600 | 612 | (−) | 1.000 | 0.955 | tgttTTGTctgta |
| SEQ_1 | P$SUCB/SUCROSE.01 | Sequence motif from the promoters of different sugar-responsive genes | 0.81 | 605 | 623 | (+) | 0.750 | 0.836 | acAAAAcacattattaaaa |
| SEQ_1 | P$AHBP/HAHB4.01 | Sunflower homeodomain leucine-zipper protein Hahb-4 | 0.87 | 611 | 621 | (+) | 1.000 | 0.909 | cacattATTAa |
| SEQ_1 | P$GTBX/SBF1.01 | SBF-1 | 0.87 | 611 | 627 | (+) | 1.000 | 0.886 | cacattaTTAAaaaaac |
| SEQ_1 | P$IDDF/ID1.01 | Maize INDETERMINATE1 zinc finger protein | 0.92 | 627 | 639 | (−) | 1.000 | 0.965 | tattTTGTctttg |
| SEQ_1 | P$GTBX/GT1.01 | GT1-Box binding factors with a trihelix DNA-binding domain | 0.85 | 636 | 652 | (−) | 1.000 | 0.858 | tgatatGTTAatatatt |

TABLE 1-continued cis-regulatory elements of SEQ ID NO: 1

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_1 | P$SPF1/SP8BF.01 | DNA-binding protein of sweet potato that binds to the SP8a (ACTGTGTA) and SP8b (TAC-TATT) sequences of sporamin and beta-amylase genes | 0.87 | 649 | 661 | (+) | 0.814 | 0.901 | atCACTattacta |
| SEQ_1 | P$L1BX/ATML1.02 | *Arabidopsis thaliana* meristem layer 1 | 0.76 | 669 | 685 | (+) | 0.890 | 0.762 | acaCAATaaaaacacca |
| SEQ_1 | P$CARM/CARICH.01 | CA-rich element | 0.78 | 672 | 690 | (+) | 1.000 | 0.815 | caataaaAACAccaaataa |
| SEQ_1 | P$DOFF/PBF.01 | PBF (MPBF) | 0.97 | 698 | 714 | (+) | 1.000 | 0.990 | aacaaataAAAGtgatc |
| SEQ_1 | P$OCSE/OCSL.01 | OCS-like elements | 0.69 | 701 | 721 | (+) | 0.807 | 0.729 | aaataaaagtgatcACATaat |
| SEQ_1 | P$OCSE/OCSL.01 | OCS-like elements | 0.69 | 704 | 724 | (−) | 0.769 | 0.713 | gtaattatgtgatcACTTtta |
| SEQ_1 | P$AHBP/HAHB4.01 | Sunflower homeodomain leucine-zipper protein Hahb-4 | 0.87 | 714 | 724 | (+) | 1.000 | 0.902 | cacataATTAc |
| SEQ_1 | P$GTBX/GT1.01 | GT1-Box binding factors with a trihelix DNA-binding domain | 0.85 | 714 | 730 | (−) | 0.968 | 0.867 | gataatGTAAttatgtg |
| SEQ_1 | P$IBOX/GATA.01 | Class I GATA factors | 0.93 | 719 | 735 | (−) | 1.000 | 0.942 | ttttgGATAatgtaatt |
| SEQ_1 | P$MYBS/MYBST1.01 | MybSt1 (Myb Solanum tuberosum 1) with a single myb repeat | 0.90 | 722 | 738 | (+) | 1.000 | 0.962 | tacattATCCaaaaaat |
| SEQ_1 | P$SUCB/SUCROSE.01 | Sequence motif from the promoters of different sugar-responsive genes | 0.81 | 733 | 751 | (+) | 1.000 | 0.908 | aaAAATcatacttttaaca |
| SEQ_1 | P$GTBX/SBF1.01 | SBF-1 | 0.87 | 740 | 756 | (−) | 1.000 | 0.967 | attgttgTTAAaagtat |
| SEQ_1 | P$MYBS/TAMYB80.01 | MYB protein from wheat | 0.83 | 759 | 775 | (+) | 1.000 | 0.857 | aacaATATtccgcgcga |
| SEQ_1 | P$CGCG/OSCBT.01 | Oryza sativa CaM-binding transcription factor | 0.78 | 768 | 784 | (−) | 1.000 | 0.781 | gtcCGCGcttcgcgcgg |
| SEQ_1 | P$NCS3/NCS3.01 | Nodulin consensus sequence 3 | 0.89 | 782 | 792 | (+) | 1.000 | 0.913 | gaCACCcccct |

TABLE 1-continued

| cis-regulatory elements of SEQ ID NO: 1 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_1 | P$OPAQ/O2_GCN4.01 | Recognition site for BZIP transcription factors that belong to the group of Opaque-2 like proteins | 0.81 | 802 | 818 | (-) | 1.000 | 0.829 | catacaACATgactaca |
| SEQ_1 | P$TEFB/TEF1.01 | TEF cis acting elements in both RNA polymerase II-dependent promoters and rDNA spacer sequences | 0.76 | 842 | 862 | (-) | 0.838 | 0.843 | gcATGGgaaatcaggtccatc |
| SEQ_1 | P$EINL/TEIL.01 | TEIL (tobacco EIN3-like) | 0.92 | 843 | 851 | (+) | 0.863 | 0.966 | aTGGAcctg |
| SEQ_1 | P$LEGB/LEGB.01 | Legumin box, highly conserved sequence element about 100 bp upstream of the TSS in legumin genes | 0.59 | 847 | 873 | (-) | 0.750 | 0.592 | acgactaCTATgcatgggaaatcaggt |
| SEQ_1 | P$LEGB/RY.01 | RY and Sph motifs conserved in seed-specific promoters | 0.87 | 850 | 876 | (+) | 1.000 | 0.944 | tgatttccCATGcatagtagtcgtcat |
| SEQ_1 | P$MADS/AGL15.01 | AGL15, *Arabidopsis* MADS-domain protein AGAMOUS-like 15 | 0.79 | 851 | 871 | (-) | 1.000 | 0.850 | gacTACTatgcatgggaaatc |
| SEQ_1 | P$MADS/AGL3.01 | AGL3, MADS Box protein | 0.83 | 852 | 872 | (+) | 1.000 | 0.864 | atttcCCATgcatagtagtcg |
| SEQ_1 | P$SPF1/SP8BF.01 | DNA-binding protein of sweet potato that binds to the SP8a (ACTGTGTA) and SP8b (TAC-TATT) sequences of sporamin and beta-amylase genes | 0.87 | 858 | 870 | (-) | 1.000 | 0.922 | acTACTatgcatg |
| SEQ_1 | P$GBOX/TGA1.01 | *Arabidopsis* leucine zipper protein TGA1 | 0.90 | 861 | 881 | (-) | 1.000 | 0.900 | ccgagaTGACgactactatgc |
| SEQ_1 | P$TELO/ATPURA.01 | *Arabidopsis* Telo-box interacting protein related to the conserved animal protein Pur-alpha | 0.85 | 873 | 887 | (-) | 1.000 | 0.860 | ataaACCCgagatga |
| SEQ_1 | P$OPAQ/O2_GCN4.01 | Recognition site for BZIP transcription factors that belong to the group of Opaque-2 like proteins | 0.81 | 883 | 899 | (-) | 0.829 | 0.887 | gatataACTTgaataaa |

TABLE 1-continued cis-regulatory elements of SEQ ID NO: 1

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_1 | P$DOFF/DOF1.01 | Dof1/MNB1a - single zinc finger transcription factor | 0.98 | 912 | 928 | (−) | 1.000 | 0.993 | ttcagattAAAGaacgt |
| SEQ_1 | P$MADS/AGL15.01 | AGL15, *Arabidopsis* MADS-domain protein AGAMOUS-like 15 | 0.79 | 912 | 932 | (+) | 0.925 | 0.793 | acgTTCTttaatctgaaccct |
| SEQ_1 | P$AHBP/WUS.01 | Homeodomain protein WUSCHEL | 0.94 | 915 | 925 | (+) | 1.000 | 0.963 | ttcttTAATct |
| SEQ_1 | P$TELO/ATPURA.01 | *Arabidopsis* Telo-box interacting protein related to the conserved animal protein Pur-alpha | 0.85 | 924 | 938 | (+) | 1.000 | 0.876 | ctgaACCCtatcacc |
| SEQ_1 | P$STKM/STK.01 | Storekeeper (STK), plant specific DNA binding protein important for tuber-specific and sucrose-inducible gene expression | 0.85 | 937 | 951 | (−) | 1.000 | 0.877 | tccTAAAtaaatcgg |
| SEQ_1 | P$GTBX/GT1.01 | GT1-Box binding factors with a trihelix DNA-binding domain | 0.85 | 968 | 984 | (−) | 0.968 | 0.858 | aaagtgGTAAtttttgt |
| SEQ_1 | P$DOFF/PBF.01 | PBF (MPBF) | 0.97 | 976 | 992 | (−) | 1.000 | 0.988 | gagacagaAAAGtggta |
| SEQ_1 | P$GTBX/SBF1.01 | SBF-1 | 0.87 | 999 | 1015 | (+) | 1.000 | 0.907 | ctcgtttTTAAtttggt |
| SEQ_1 | P$MIIG/MYBC1.01 | Maize C1 myb-domain protein | 0.92 | 1009 | 1023 | (+) | 1.000 | 0.942 | atttgGTAGtttcag |
| SEQ_1 | P$SPF1/SP8BF.01 | DNA-binding protein of sweet potato that binds to the SP8a (ACTGTGTA) and SP8b (TAC-TATT) sequences of sporamin and beta-amylase genes | 0.87 | 1048 | 1060 | (−) | 0.814 | 0.872 | aaCACTatgaaaa |
| SEQ_1 | P$OPAQ/O2_GCN4.01 | Recognition site for BZIP transcription factors that belong to the group of Opaque-2 like proteins | 0.81 | 1056 | 1072 | (+) | 1.000 | 0.891 | gtgttaACATgtttaag |
| SEQ_1 | P$LREM/ATCTA.01 | Motif involved in carotenoid and tocopherol biosynthesis and in the expression of photo-synthesis-related genes | 0.85 | 1095 | 1105 | (−) | 1.000 | 0.858 | atATCTatgtt |

TABLE 1-continued

| cis-regulatory elements of SEQ ID NO: 1 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_1 | P$MYBL/NTMYBAS1.01 | Anther-specific myb gene from tobacco | 0.96 | 1125 | 1141 | (+) | 1.000 | 0.967 | tagtggtgGTTAacaaa |
| SEQ_1 | P$GTBX/SBF1.01 | SBF-1 | 0.87 | 1127 | 1143 | (+) | 1.000 | 0.894 | gtggtggTTAAcaaaag |
| SEQ_1 | P$MYBL/GAMYB.01 | GA-regulated myb gene from barley | 0.91 | 1130 | 1146 | (−) | 1.000 | 0.918 | ggccttttGTTAaccac |
| SEQ_1 | P$GBOX/BZIP911.01 | bZIP transcription factor from Antirrhinum majus | 0.77 | 1138 | 1158 | (−) | 0.750 | 0.781 | ataagtTGAAatggccttttg |
| SEQ_1 | P$OPAQ/O2.01 | Opaque-2 regulatory protein | 0.87 | 1141 | 1157 | (+) | 0.852 | 0.882 | aaggccattTCAActta |
| SEQ_1 | P$NCS1/NCS1.01 | Nodulin consensus sequence 1 | 0.85 | 1163 | 1173 | (+) | 1.000 | 0.909 | tAAAAgataga |
| SEQ_1 | P$SUCB/SUCROSE.01 | Sequence motif from the promoters of different sugar-responsive genes | 0.81 | 1176 | 1194 | (+) | 0.750 | 0.815 | gcAAAGcattgttgataaa |
| SEQ_1 | P$DOFF/DOF3.01 | Dof3 - single zinc finger transcription factor | 0.99 | 1184 | 1200 | (+) | 1.000 | 0.994 | ttgttgatAAAGcctct |
| SEQ_1 | P$GAGA/BPC.01 | Basic pentacysteine proteins | 1.00 | 1184 | 1208 | (−) | 1.000 | 1.000 | ataaagAGAGaggctttatcaacaa |
| SEQ_1 | P$IBOX/GATA.01 | Class I GATA factors | 0.93 | 1184 | 1200 | (+) | 1.000 | 0.938 | ttgttGATAaagcctct |
| SEQ_1 | P$MYBS/ZMMRP1.01 | Zea mays MYB-related protein 1 (transfer cell specific) | 0.79 | 1199 | 1215 | (+) | 0.777 | 0.841 | ctctcttTATAtaaaga |
| SEQ_1 | P$TBPF/TATA.01 | Plant TATA box | 0.88 | 1199 | 1213 | (−) | 1.000 | 0.958 | tttaTATAaagagag |
| SEQ_1 | P$TBPF/TATA.02 | Plant TATA box | 0.90 | 1201 | 1215 | (−) | 1.000 | 0.917 | tcttTATAtaaagag |
| SEQ_1 | P$TBPF/TATA.02 | Plant TATA box | 0.90 | 1202 | 1216 | (+) | 1.000 | 0.917 | tcttTATAtaaagag |
| SEQ_1 | P$TBPF/TATA.01 | Plant TATA box | 0.88 | 1204 | 1218 | (+) | 1.000 | 0.934 | tttaTATAaagaggg |
| SEQ_1 | P$DOFF/DOF3.01 | Dof3 - single zinc finger transcription factor | 0.99 | 1215 | 1231 | (−) | 1.000 | 0.995 | aaggcgctAAAGcccct |
| SEQ_1 | P$WBXF/WRKY.01 | WRKY plant specific zinc-finger-type factor associated with pathogen defence, W box | 0.92 | 1236 | 1252 | (+) | 1.000 | 0.975 | atgctTTGActttacct |

TABLE 1-continued

| cis-regulatory elements of SEQ ID NO: 1 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_1 | P$TELO/RPBX.01 | Ribosomal protein box, appears unique to plant RP genes and genes associated with gene expression | 0.84 | 1260 | 1274 | (-) | 1.000 | 0.842 | cgaaaCCCTtcactt |
| SEQ_1 | P$L1BX/ATML1.01 | L1-specific homeodomain protein ATML1 (*A. thaliana* meristem layer 1) | 0.82 | 1317 | 1333 | (+) | 0.750 | 0.830 | caagaaTCAAtgtaagc |
| SEQ_1 | P$CCAF/CCA1.01 | Circadian clock associated 1 | 0.85 | 1332 | 1346 | (-) | 1.000 | 0.879 | caaactatAATCtgc |
| SEQ_1 | P$MYBL/MYBPH3.02 | Myb-like protein of Petunia hybrida | 0.76 | 1338 | 1354 | (+) | 0.817 | 0.929 | tatagtTTGTtagtttt |
| SEQ_1 | P$MYBL/MYBPH3.02 | Myb-like protein of Petunia hybrida | 0.76 | 1342 | 1358 | (+) | 1.000 | 0.818 | gtttgtTAGTttttcag |
| SEQ_1 | P$MYBL/MYBPH3.02 | Myb-like protein of Petunia hybrida | 0.76 | 1382 | 1398 | (-) | 1.000 | 0.818 | aggcgtTAGTtcagaaa |
| SEQ_1 | P$MYBL/NTMYBAS1.01 | Anther-specific myb gene from tobacco | 0.96 | 1386 | 1402 | (-) | 1.000 | 0.967 | tcaaaggcGTTAgttca |
| SEQ_1 | P$MADS/SQUA.01 | MADS-box protein SQUAMOSA | 0.90 | 1400 | 1420 | (-) | 1.000 | 0.902 | attgaccATTTttttctttca |
| SEQ_1 | P$WBXF/ERE.01 | Elicitor response element | 0.89 | 1408 | 1424 | (-) | 1.000 | 0.973 | gtcaatTGACcattttt |
| SEQ_1 | P$GTBX/GT3A.01 | Trihelix DNA-binding factor GT-3a | 0.83 | 1425 | 1441 | (-) | 1.000 | 0.897 | ttagtgGTTAcaatggc |
| SEQ_1 | P$GTBX/GT1.01 | GT1-Box binding factors with a trihelix DNA-binding domain | 0.85 | 1432 | 1448 | (-) | 1.000 | 0.882 | catgtgGTTAgtggtta |
| SEQ_1 | P$MIIG/PALBOXP.01 | Putative cis-acting element in various PAL and 4CL gene promoters | 0.81 | 1433 | 1447 | (-) | 0.936 | 0.820 | atGTGGttagtggtt |
| SEQ_1 | P$LEGB/RY.01 | RY and Sph motifs conserved in seed-specific promoters | 0.87 | 1445 | 1471 | (-) | 1.000 | 0.944 | tgtgtttgCATGcatagccagtgcatg |
| SEQ_1 | P$LEGB/RY.01 | RY and Sph motifs conserved in seed-specific promoters | 0.87 | 1452 | 1478 | (+) | 1.000 | 0.909 | tggctatgCATGcaaacacaatgagat |
| SEQ_1 | P$SPF1/SP8BF.01 | DNA-binding protein of sweet potato that binds to the SP8a (ACTGTGTA) and SP8b (TACTATT) sequences of sporamin and beta-amylase genes | 0.87 | 1488 | 1500 | (-) | 1.000 | 0.871 | ttTACTcttaggc |
| SEQ_1 | P$MYBL/MYBPH3.02 | Myb-like protein of Petunia hybrida | 0.76 | 1493 | 1509 | (-) | 0.778 | 0.838 | caaagtTGGTttactct |
| SEQ_1 | P$MADS/AGL1.01 | AGL1, *Arabidopsis* MADS-domain protein AGAMOUS-like 1 | 0.84 | 1495 | 1515 | (-) | 0.975 | 0.840 | ggaTTCCaaagttggtttact |
| SEQ_1 | P$MADS/AGL2.01 | AGL2, *Arabidopsis* MADS-domain protein AGAMOUS-like 2 | 0.82 | 1496 | 1516 | (+) | 0.968 | 0.845 | gtaaaCCAActttggaatccc |

TABLE 1-continued

| cis-regulatory elements of SEQ ID NO: 1 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_1 | P$STKM/STK.01 | Storekeeper (STK), plant specific DNA binding protein important for tuber-specific and sucrose-inducible gene expression | 0.85 | 1513 | 1527 | (+) | 0.833 | 0.873 | tccCAAAaaattata |
| SEQ_1 | P$ERSE/ERSE_I.01 | ERSE I (ER stress-response element I)-like motif | 0.79 | 1515 | 1533 | (+) | 0.750 | 0.803 | ccaaaaaattatagcCATG |
| SEQ_1 | P$GBOX/EMBP1.01 | bZIP transcription factor implicated in ABA induced gene expression | 0.84 | 1522 | 1542 | (−) | 0.750 | 0.854 | agaacgacACATggctataat |
| SEQ_1 | P$LEGB/LEGB.01 | Legumin box, highly conserved sequence element about 100 bp upstream of the TSS in legumin genes | 0.59 | 1522 | 1548 | (+) | 1.000 | 0.609 | attatagCCATgtgtcgttcttgatga |
| SEQ_1 | P$ABRE/ABF1.01 | ABA (abscisic acid) inducible transcriptional activator | 0.79 | 1525 | 1541 | (−) | 1.000 | 0.853 | gaacgACACatggctat |
| SEQ_1 | P$OCSE/OCSL.01 | OCS-like elements | 0.69 | 1549 | 1569 | (−) | 0.807 | 0.693 | aaattttattggaaACGAatt |
| SEQ_1 | P$GTBX/SBF1.01 | SBF-1 | 0.87 | 1562 | 1578 | (−) | 0.826 | 0.872 | tttgtttCTAAatttta |
| SEQ_1 | P$MIIG/PALBOXP.01 | Putative cis-acting element in various PAL and 4CL gene promoters | 0.81 | 1570 | 1584 | (−) | 0.936 | 0.819 | ttGTGGtttgtttct |
| SEQ_1 | P$SPF1/SP8BF.01 | DNA-binding protein of sweet potato that binds to the SP8a (ACTGTGTA) and SP8b (TACTATT) sequences of sporamin and beta-amylase genes | 0.87 | 1586 | 1598 | (−) | 1.000 | 0.881 | atTACTttgtatt |
| SEQ_1 | P$OCSE/OCSL.01 | OCS-like elements | 0.69 | 1589 | 1609 | (−) | 0.769 | 0.716 | taagttaaaaaattACTTtgt |
| SEQ_1 | P$AHBP/BLR.01 | Transcriptional repressor BELLRINGER | 0.90 | 1591 | 1601 | (−) | 1.000 | 0.976 | aaaATTActtt |
| SEQ_1 | P$STKM/STK.01 | Storekeeper (STK), plant specific DNA binding protein important for tuber-specific and sucrose-inducible gene expression | 0.85 | 1593 | 1607 | (−) | 1.000 | 0.901 | agtTAAAaaattact |
| SEQ_1 | P$MADS/MADS.01 | Binding sites for AP1, AP3-PI and AG dimers | 0.75 | 1599 | 1619 | (−) | 1.000 | 0.777 | tttccCCATttaagttaaaaa |
| SEQ_1 | P$L1BX/PDF2.01 | Protodermal factor 2 | 0.85 | 1602 | 1618 | (+) | 1.000 | 0.864 | ttaactTAAAtggggaa |
| SEQ_1 | P$IBOX/IBOX.01 | I-Box in rbcS genes and other light regulated genes | 0.81 | 1640 | 1656 | (+) | 1.000 | 0.824 | aaagaGATAgggcttaa |
| SEQ_1 | P$TELO/RPBX.01 | Ribosomal protein box, appears unique to plant RP genes and genes associated with gene expression | 0.84 | 1642 | 1656 | (−) | 1.000 | 0.886 | ttaagCCCTatctct |

TABLE 1-continued

| cis-regulatory elements of SEQ ID NO: 1 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_1 | P$DOFF/DOF2.01 | Dof2 - single zinc finger transcription factor | 0.98 | 1647 | 1663 | (+) | 1.000 | 0.994 | tagggcttAAAGcagca |
| SEQ_1 | P$NACF/TANAC69.01 | Wheat NACdomain DNA binding factor | 0.68 | 1673 | 1695 | (−) | 0.812 | 0.695 | aacgaaaacgaAACGtatcacag |
| SEQ_1 | P$MYBL/GAMYB.01 | GA-regulated myb gene from barley | 0.91 | 1689 | 1705 | (+) | 1.000 | 0.963 | tttcgtttGTTAtcaca |
| SEQ_1 | P$IBOX/GATA.01 | Class I GATA factors | 0.93 | 1691 | 1707 | (−) | 1.000 | 0.931 | attgtGATAacaaacga |
| SEQ_1 | P$GTBX/S1F.01 | S1F, site 1 binding factor of spinach rps1 promoter | 0.79 | 1707 | 1723 | (+) | 1.000 | 0.851 | tttcATGGactatatac |
| SEQ_1 | P$TBPF/TATA.02 | Plant TATA box | 0.90 | 1713 | 1727 | (+) | 1.000 | 0.901 | ggacTATAtacattt |
| SEQ_1 | P$L1BX/ATML1.01 | L1-specific homeodomain protein ATML1 (*A. thaliana* meristem layer 1) | 0.82 | 1718 | 1734 | (−) | 1.000 | 0.875 | ctaagcTAAAtgtatat |
| SEQ_1 | P$PSRE/GAAA.01 | GAAA motif involved in pollen specific transcriptional activation | 0.83 | 1739 | 1755 | (+) | 1.000 | 0.847 | caaaaGAAAccatctac |
| SEQ_1 | P$LREM/ATCTA.01 | Motif involved in carotenoid and tocopherol biosynthesis and in the expression of photo-synthesis-related genes | 0.85 | 1748 | 1758 | (+) | 1.000 | 0.854 | ccATCTacttg |
| SEQ_1 | P$AHBP/ATHB1.01 | *Arabidopsis thaliana* homeo box protein 1 | 0.90 | 1768 | 1778 | (−) | 1.000 | 0.990 | ggaATTAttgt |
| SEQ_1 | P$AHBP/ATHB5.01 | HDZip class I protein ATHB5 | 0.89 | 1768 | 1778 | (+) | 0.829 | 0.940 | acaATAAttcc |

TABLE 2

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$SEF3/SEF3.01 | SEF3, Soybean embryo factor 3 | 0.87 | 5 | 19 | (+) | 1.000 | 0.921 | ctataACCCaaccca |
| SEQ_6 | P$SEF3/SEF3.01 | SEF3, Soybean embryo factor 3 | 0.87 | 10 | 24 | (+) | 1.000 | 0.891 | acccaACCCaaaaca |
| SEQ_6 | P$GTBX/SBF1.01 | SBF-1 | 0.87 | 22 | 38 | (−) | 1000 | 0.880 | aggatacTTAAacttgt |
| SEQ_6 | P$MYBL/ATMYB77.01 | R2R3-type myb-like transcription factor (I-type binding site) | 0.87 | 35 | 51 | (−) | 1000 | 0.892 | ttttgtCGGTttcagga |
| SEQ_6 | P$DREB/CRT_DRE.01 | C-repeat/dehydration response element | 0.89 | 38 | 52 | (+) | 1.000 | 0.902 | tgaaaCCGAcaaaag |
| SEQ_6 | P$DOFF/PBF.01 | PBF (MPBF) | 0.97 | 41 | 57 | (+) | 1000 | 0.986 | aaccgacaAAAGagaat |
| SEQ_6 | P$IDDF/ID1.01 | Maize INDETERMINATE1 zinc finger protein | 0.92 | 41 | 53 | (−) | 1.000 | 0.987 | tcttTTGTcggtt |
| SEQ_6 | P$EPFF/ZPT22.01 | Member of the EPF family of zinc finger transcription factors | 0.75 | 50 | 72 | (−) | 1.000 | 0.770 | agtcaaaaagaCAGTattctctt |
| SEQ_6 | P$SPF1/SP8BF.01 | DNA-binding protein of sweet potato that binds to the SP8a (ACTGTGTA) and SP8b (TACTATT) sequences of sporamin and beta-amylase genes | 0.87 | 55 | 67 | (+) | 1.000 | 0.881 | aaTACTgtctttt |
| SEQ_6 | P$NCS2/NCS2.01 | Nodulin consensus sequence 2 | 0.79 | 57 | 71 | (+) | 0.750 | 0.795 | tactgtCTTTttgac |
| SEQ_6 | P$WBXF/WRKY.01 | WRKY plant specific zinc-finger-type factor associated with pathogen defence, W box | 0.92 | 62 | 78 | (+) | 1.000 | 0.965 | tctttTTGActttcctg |
| SEQ_6 | P$HEAT/HSE.01 | Heat shock element | 0.81 | 72 | 86 | (−) | 0.826 | 0.819 | agattattcaGGAAa |
| SEQ_6 | P$AHBP/BLR.01 | Transcriptional repressor BELLRINGER | 0.90 | 77 | 87 | (−) | 1000 | 0.901 | aagATTAttca |
| SEQ_6 | P$DOFF/PBOX.01 | Prolamin box, conserved in cereal seed storage protein gene promoters | 0.75 | 80 | 96 | (−) | 1.000 | 0.769 | tatttttAAAGattat |
| SEQ_6 | P$GTBX/SBF1.01 | SBF-1 | 0.87 | 80 | 96 | (+) | 1.000 | 0.892 | ataatctTTAAaaaata |

TABLE 2-continued

| cis-regulatory elements of SEQ ID NO: 6 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$GAGA/BPC.01 | Basic pentacysteine proteins | 1.00 | 88 | 112 | (−) | 1.000 | 1000 | ttccagAGAGaactgatatttttta |
| SEQ_6 | P$PSRE/GAAA.01 | GAAA motif involved in pollen specific transcriptional activation | 0.83 | 105 | 121 | (+) | 1000 | 0.878 | ctctgGAAAtagtaaag |
| SEQ_6 | P$SPF1/SP8BF.01 | DNA-binding protein of sweet potato that binds to the SP8a (ACTGTGTA) and SP8b (TACTATT) sequences of sporamin and beta-amylase genes | 0.87 | 108 | 120 | (−) | 1.000 | 0.943 | ttTACTatttcca |
| SEQ_6 | P$OCSE/OCSL.01 | OCS-like elements | 0.69 | 116 | 136 | (−) | 0.769 | 0.700 | ttgcatcagttcttACTTtac |
| SEQ_6 | P$HOCT/HOCT.01 | Octamer motif found in plant histone H3 and H4 genes | 0.76 | 145 | 161 | (+) | 0.750 | 0.762 | atcaccgATCTacgaag |
| SEQ_6 | P$LREM/ATCTA.01 | Motif involved in carotenoid and tocopherol biosynthesis and in the expression of photosynthesis-related genes | 0.85 | 150 | 160 | (+) | 1.000 | 0.864 | cgATCTacgaa |
| SEQ_6 | P$MSAE/MSA.01 | M-phase-specific activators (NtmybA1, NtmybA2, NtmybB) | 0.80 | 174 | 188 | (−) | 1.000 | 0.834 | aaaaaAACGggtgga |
| SEQ_6 | P$AHBP/HAHB4.01 | Sunflower homeodomain leucine-zipper protein Hahb-4 | 0.87 | 187 | 197 | (+) | 1.000 | 0.934 | ttgatcATTAt |
| SEQ_6 | P$CGCG/ATSR1.01 | *Arabidopsis thaliana* signal-responsive gene1, Ca2+/calmodulin binding protein homolog to NtER1 (tobacco early ethylene-responsive gene) | 0.84 | 194 | 210 | (−) | 1.000 | 0.912 | aagCGCGtacgatataa |
| SEQ_6 | P$OCSE/OCSL.01 | OCS-like elements | 0.69 | 196 | 216 | (−) | 0.807 | 0.709 | gtttttaagcgcgtACGAtat |
| SEQ_6 | P$GTBX/SBF1.01 | SBF-1 | 0.87 | 202 | 218 | (+) | 1.000 | 0.875 | tacgcgcTTAAaaacct |
| SEQ_6 | P$MYBL/MYBPH3.02 | Myb-like protein of Petunia hybrida | 0.76 | 217 | 233 | (−) | 0.778 | 0.781 | tttagtTCGTaaaaaag |
| SEQ_6 | P$DOFF/PBOX.01 | Prolamin box, conserved in cereal seed storage protein gene promoters | 0.75 | 245 | 261 | (−) | 1000 | 0.831 | ttatctgaAAAGtaaaa |
| SEQ_6 | P$IBOX/GATA.01 | Class I GATA factors | 0.93 | 252 | 268 | (+) | 1000 | 0.933 | tttcaGATAatgttgca |

TABLE 2-continued

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$AGP1/AGP1.01 | AG-motif binding protein 1 | 0.91 | 284 | 294 | (−) | 1.000 | 0.988 | acaGATCtatc |
| SEQ_6 | P$AGP1/AGP1.01 | AG-motif binding protein 1 | 0.91 | 285 | 295 | (+) | 1000 | 0.920 | ataGATCtgtt |
| SEQ_6 | P$GARP/ARR10.01 | Type-B response regulator (ARR10), member of the GARP-family of plant myb-related DNA binding motifs | 0.97 | 287 | 295 | (+) | 1.000 | 0.970 | AGATctgtt |
| SEQ_6 | P$CAAT/CAAT.01 | CCAAT-box in plant promoters | 0.97 | 298 | 306 | (+) | 1.000 | 0.973 | ttCCAAtga |
| SEQ_6 | P$LFYB/LFY.01 | Plant specific floral meristem identity gene LEAFY (LFY) | 0.93 | 298 | 310 | (+) | 1000 | 0.930 | tTCCAatgagaat |
| SEQ_6 | P$CCAF/CCA1.01 | Circadian clock associated 1 | 0.85 | 300 | 314 | (+) | 1.000 | 0.864 | ccaatgagAATCtgt |
| SEQ_6 | P$GARP/ARR10.01 | Type-B response regulator (ARR10), member of the GARP-family of plant myb-related DNA binding motifs | 0.97 | 304 | 312 | (−) | 1.000 | 0.971 | AGATtctca |
| SEQ_6 | P$RAV5/RAV1-5.01 | 5'-part of bipartite RAV1 binding site, interacting with AP2 domain | 0.96 | 308 | 318 | (−) | 1.000 | 0.960 | aacAACAgatt |
| SEQ_6 | P$IDDF/ID1.01 | Maize INDETERMINATE1 zinc finger protein | 0.92 | 339 | 351 | (−) | 1.000 | 0.934 | tattTTGTcagat |
| SEQ_6 | P$CAAT/CAAT.02 | CCAAT-box in plant promoters | 1.00 | 400 | 408 | (−) | 1000 | 1000 | gtcCAATta |
| SEQ_6 | P$WBXF/WRKY.01 | WRKY plant specific zinc-finger-type factor associated with pathogen defence, W box | 0.92 | 405 | 421 | (−) | 1.000 | 0.957 | cacatTTGActatgtcc |
| SEQ_6 | P$MYCL/ICE.01 | ICE (inducer of CBF expression 1), AtMYC2 (rd22BP1) | 0.95 | 407 | 425 | (−) | 1.000 | 0.953 | ccaacACATttgactatgt |
| SEQ_6 | P$CARM/CARICH.01 | CA-rich element | 0.78 | 412 | 430 | (−) | 1.000 | 0.785 | aaagtccAACAcatttgac |
| SEQ_6 | P$GTBX/SBF1.01 | SBF-1 | 0.87 | 424 | 440 | (−) | 1.000 | 0.875 | tcggaaaTTAAagtcc |
| SEQ_6 | P$SUCB/SUCROSE.01 | Sequence motif from the promoters of different sugar-responsive genes | 0.81 | 439 | 457 | (+) | 1000 | 0.913 | gaAAATcattaaaaacaat |

TABLE 2-continued

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$AHBP/ATHB5.01 | HDZip class I protein ATHB5 | 0.89 | 440 | 450 | (−) | 0.829 | 0.902 | ttaATGAtttt |
| SEQ_6 | P$AHBP/HAHB4.01 | Sunflower homeodomain leucine-zipper protein Hahb-4 | 0.87 | 440 | 450 | (+) | 1.000 | 0.967 | aaaatcATTAa |
| SEQ_6 | P$GTBX/SBF1.01 | SBF-1 | 0.87 | 440 | 456 | (+) | 1.000 | 0.886 | aaaatcaTTAAaaacaa |
| SEQ_6 | P$GTBX/SBF1.01 | SBF-1 | 0.87 | 441 | 457 | (−) | 1000 | 0.888 | attgtttTTAAtgattt |
| SEQ_6 | P$L1BX/ATML1.02 | *Arabidopsis thaliana* meristem layer 1 | 0.76 | 442 | 458 | (+) | 1000 | 0.789 | aatCATTaaaaacaatt |
| SEQ_6 | P$AHBP/WUS.01 | Homeodomain protein WUSCHEL | 0.94 | 444 | 454 | (−) | 1.000 | 1000 | gttttTAATga |
| SEQ_6 | P$MYBL/MYBPH3.01 | Myb-like protein of Petunia hybrida | 0.80 | 448 | 464 | (+) | 0.750 | 0.812 | taaaaacaATTAaaaaa |
| SEQ_6 | P$TEFB/TEF1.01 | TEF cis acting elements in both RNA polymerase II-dependent promoters and rDNA spacer sequences | 0.76 | 467 | 487 | (+) | 0.838 | 0.839 | taATGGagatttttgtaatta |
| SEQ_6 | P$CCAF/CCA1.01 | Circadian clock associated 1 | 0.85 | 471 | 485 | (−) | 1.000 | 0.948 | attacaaaAATCtcc |
| SEQ_6 | P$GTBX/SBF1.01 | SBF-1 | 0.87 | 478 | 494 | (+) | 1.000 | 0.905 | tttgtaaTTAAttggaa |
| SEQ_6 | P$CAAT/CAAT.02 | CCAAT-box in plant promoters | 1.00 | 486 | 494 | (−) | 1.000 | 1000 | ttcCAATta |
| SEQ_6 | P$MADS/AGL15.01 | AGL15, *Arabidopsis* MADS-domain protein AGAMOUS-like 15 | 0.79 | 509 | 529 | (−) | 1.000 | 0.886 | ctaTACTattaaagggaaaga |
| SEQ_6 | P$MADS/AGL3.02 | AGL3, MADS Box protein | 0.80 | 510 | 530 | (+) | 0.790 | 0.859 | ctttcCCTTtaatagtataga |
| SEQ_6 | P$SPF1/SP8BF.01 | DNA-binding protein of sweet potato that binds to the SP8a (ACTGTGTA) and SP8b (TACTATT) sequences of sporamin and beta-amylase genes | 0.87 | 516 | 528 | (−) | 1.000 | 0.956 | taTACTattaaag |
| SEQ_6 | P$LREM/ATCTA.01 | Motif involved in carotenoid and tocopherol bio-synthesis and in the expression of photosynthesis-related genes | 0.85 | 523 | 533 | (−) | 1.000 | 0.902 | atATCTatact |

TABLE 2-continued

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$L1BX/ATML1.01 | L1-specific homeodomain protein ATML1 (*A. thaliana* meristem layer 1) | 0.82 | 573 | 589 | (-) | 0.750 | 0.844 | taatttTAACtgcaact |
| SEQ_6 | P$GTBX/SBF1.01 | SBF-1 | 0.87 | 574 | 590 | (+) | 1000 | 0.954 | gttgcagTTAAaattac |
| SEQ_6 | P$NACF/TANAC69.01 | Wheat NACdomain DNA binding factor | 0.68 | 577 | 599 | (+) | 1000 | 0.707 | gcagttaaaatTACGaatcatgg |
| SEQ_6 | P$MADS/AGL2.01 | AGL2, *Arabidopsis* MADS-domain protein AGA-MOUS-like 2 | 0.82 | 584 | 604 | (-) | 1.000 | 0.820 | ggagcCCATgattcgtaattt |
| SEQ_6 | P$LREM/ATCTA.01 | Motif involved in carotenoid and tocopherol bio-synthesis and in the expression of photosynthesis-related genes | 0.85 | 604 | 614 | (+) | 1.000 | 0.897 | ctATCTatatt |
| SEQ_6 | P$MYBS/ZMMRP1.01 | *Zea mays* MYB-related protein 1 (transfer cell specific) | 0.79 | 604 | 620 | (+) | 0.777 | 0.905 | ctatctaTATTttacat |
| SEQ_6 | P$DOFF/PBOX.01 | Prolamin box, conserved in cereal seed storage protein gene promoters | 0.75 | 608 | 624 | (-) | 0.761 | 0.835 | tgtgatgtAAAAtatag |
| SEQ_6 | P$DOFF/DOF2.01 | Dof2 - single zinc finger transcription factor | 0.98 | 619 | 635 | (+) | 1.000 | 0.995 | atcacaatAAAGctata |
| SEQ_6 | P$TBPF/TATA.02 | Plant TATA box | 0.90 | 628 | 642 | (+) | 1.000 | 0.903 | aagcTATAtatcatt |
| SEQ_6 | P$LFYB/LFY.01 | Plant specific floral meristem identity gene LEAFY (LFY) | 0.93 | 634 | 646 | (-) | 0.914 | 0.936 | cACCAatgatata |
| SEQ_6 | P$CAAT/CAAT.01 | CCAAT-box in plant promoters | 0.97 | 638 | 646 | (-) | 1.000 | 0.988 | caCCAAtga |
| SEQ_6 | P$IDDF/ID1.01 | Maize INDETERMINATE1 zinc finger protein | 0.92 | 657 | 669 | (-) | 1000 | 0.921 | gggtTTGTcttca |
| SEQ_6 | P$TELO/RPBX.01 | Ribosomal protein box, appears unique to plant RP genes and genes associated with gene expression | 0.84 | 662 | 676 | (+) | 1.000 | 0.981 | acaaaCCCTaaactc |
| SEQ_6 | P$AHBP/HAHB4.01 | Sunflower homeodomain leucine-zipper protein Hahb-4 | 0.87 | 684 | 694 | (-) | 1.000 | 0.923 | cttattATTAg |

TABLE 2-continued

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$MYCL/ICE.01 | ICE (inducer of CBF expression 1), AtMYC2 (rd22BP1) | 0.95 | 694 | 712 | (+) | 0.954 | 0.972 | gccaaACACttgattccaa |
| SEQ_6 | P$MADS/SQUA.01 | MADS-box protein SQUAMOSA | 0.90 | 711 | 731 | (−) | 1000 | 0.906 | ggtcgctATTTgtttctgttt |
| SEQ_6 | P$IBOX/GATA.01 | Class I GATA factors | 0.93 | 733 | 749 | (+) | 1.000 | 0.958 | tgcacGATAatagatag |
| SEQ_6 | P$LREM/ATCTA.01 | Motif involved in carotenoid and tocopherol biosynthesis and in the expression of photosynthesis-related genes | 0.85 | 739 | 749 | (−) | 1.000 | 0.853 | ctATCTattat |
| SEQ_6 | P$HMGF/HMG_IY.02 | High mobility group I/Y-like protein isolated from pea | 1.00 | 755 | 769 | (−) | 1.000 | 1000 | tattTATTtttcaaa |
| SEQ_6 | P$CCAF/CCA1.01 | Circadian clock associated 1 | 0.85 | 774 | 788 | (−) | 1000 | 0.864 | aaccaagaAATCtga |
| SEQ_6 | P$SPF1/SP8BF.01 | DNA-binding protein of sweet potato that binds to the SP8a (ACTGTGTA) and SP8b (TACTATT) sequences of sporamin and beta-amylase genes | 0.87 | 787 | 799 | (−) | 1.000 | 0.909 | ttTACTgtttaaa |
| SEQ_6 | P$DOFF/DOF2.01 | Dof2 - single zinc finger transcription factor | 0.98 | 790 | 806 | (+) | 1.000 | 0.981 | aaacagtaAAAGctaat |
| SEQ_6 | P$L1BX/ATML1.02 | *Arabidopsis thaliana* meristem layer 1 | 0.76 | 790 | 806 | (+) | 0.808 | 0.780 | aaaCAGTaaaagctaat |
| SEQ_6 | P$CARM/CARICH.01 | CA-rich element | 0.78 | 800 | 818 | (−) | 1.000 | 0.836 | tttttgaAACAcattagct |
| SEQ_6 | P$MYBL/MYBPH3.01 | Myb-like protein of Petunia hybrida | 0.80 | 823 | 839 | (+) | 0.750 | 0.818 | aaaaaacaGTAAaagct |
| SEQ_6 | P$SPF1/SP8BF.01 | DNA-binding protein of sweet potato that binds to the SP8a (ACTGTGTA) and SP8b (TACTATT) sequences of sporamin and beta-amylase genes | 0.87 | 823 | 835 | (−) | 1000 | 0.905 | ttTACTgtttttt |
| SEQ_6 | P$DOFF/DOF2.01 | Dof2 - single zinc finger transcription factor | 0.98 | 826 | 842 | (+) | 1000 | 0.981 | aaacagtaAAAGctaat |
| SEQ_6 | P$L1BX/ATML1.02 | *Arabidopsis thaliana* meristem layer 1 | 0.76 | 826 | 842 | (+) | 0.808 | 0.780 | aaaCAGTaaaagctaat |
| SEQ_6 | P$GAPB/GAP.01 | Cis-element in the GAPDH promoters conferring light inducibility | 0.88 | 843 | 857 | (+) | 1000 | 0.984 | acacATGAagacaag |

TABLE 2-continued cis-regulatory elements of SEQ ID NO: 6

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_6 | P$LREM/ATCTA.01 | Motif involved in carotenoid and tocopherol biosynthesis and in the expression of photosynthesis-related genes | 0.85 | 863 | 873 | (−) | 1.000 | 0.912 | aaATCTataag |
| SEQ_6 | P$CCAF/CCA1.01 | Circadian clock associated 1 | 0.85 | 866 | 880 | (−) | 1.000 | 0.885 | gtgggtaaAATCtat |
| SEQ_6 | P$GTBX/SBF1.01 | SBF-1 | 0.87 | 867 | 883 | (−) | 0.782 | 0.889 | tttgtggGTAAaatcta |
| SEQ_6 | P$MYBL/MYBPH3.02 | Myb-like protein of Petunia hybrida | 0.76 | 877 | 893 | (−) | 0.817 | 0.846 | acaagtTTGTtttgtgg |
| SEQ_6 | P$MADS/AGL2.01 | AGL2, *Arabidopsis* MADS-domain protein AGAMOUS-like 2 | 0.82 | 906 | 926 | (−) | 0.968 | 0.856 | agaagCCAAcattggcaacga |
| SEQ_6 | P$MADS/AG.01 | Agamous, required for normal flower development, similarity to SRF (human) and MCM (yeast) proteins | 0.80 | 907 | 927 | (+) | 0.902 | 0.806 | cgtTGCCaatgttggcttctt |
| SEQ_6 | P$LFYB/LFY.01 | Plant specific floral meristem identity gene LEAFY (LFY) | 0.93 | 910 | 922 | (+) | 0.885 | 0.938 | tGCCAatgttggc |
| SEQ_6 | P$DOFF/PBOX.01 | Prolamin box, conserved in cereal seed storage protein gene promoters | 0.75 | 920 | 936 | (−) | 1.000 | 0.801 | tgtggtggAAAGaagcc |
| SEQ_6 | P$SALT/ALFIN1.01 | Zinc-finger protein in alfalfa roots, regulates salt tolerance | 0.93 | 926 | 940 | (−) | 1.000 | 0.986 | tttgtGTGGtggaaa |
| SEQ_6 | P$TEFB/TEF1.01 | TEF cis acting elements in both RNA polymerase II-dependent promoters and rDNA spacer sequences | 0.76 | 931 | 951 | (−) | 0.838 | 0.781 | taACGGtcatatttgtgtggt |
| SEQ_6 | P$WBXF/ERE.01 | Elicitor response element | 0.89 | 937 | 953 | (+) | 1.000 | 0.897 | caaataTGACcgttaag |
| SEQ_6 | P$MYBL/ATMYB77.01 | R2R3-type myb-like transcription factor (I-type binding site) | 0.87 | 940 | 956 | (+) | 0.857 | 0.916 | atatgaCCGTtaagact |
| SEQ_6 | P$MSAE/MSA.01 | M-phase-specific activators (NtmybA1, NtmybA2, NtmybB) | 0.80 | 941 | 955 | (−) | 1.000 | 0.889 | gtcttAACGgtcata |

TABLE 2-continued

| cis-regulatory elements of SEQ ID NO: 6 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_6 | P$AHBP/HAHB4.01 | Sunflower homeodomain leucine-zipper protein Hahb-4 | 0.87 | 968 | 978 | (+) | 1000 | 0.916 | tttataATTAc |
| SEQ_6 | P$GTBX/GT1.01 | GT1-Box binding factors with a trihelix DNA-binding domain | 0.85 | 968 | 984 | (−) | 0.968 | 0.859 | catgtaGTAAttataaa |
| SEQ_6 | P$LEGB/RY.01 | RY and Sph motifs conserved in seed-specific promoters | 0.87 | 970 | 996 | (−) | 1.000 | 0.952 | attttataCATGcatgtagtaattata |
| SEQ_6 | P$L1BX/ATML1.01 | L1-specific homeodomain protein ATML1 (*A. thaliana* meristem layer 1) | 0.82 | 973 | 989 | (+) | 0.750 | 0.846 | aattacTACAtgcatgt |
| SEQ_6 | P$LEGB/RY.01 | RY and Sph motifs conserved in seed-specific promoters | 0.87 | 973 | 999 | (+) | 1.000 | 0.952 | aattactaCATGcatgtataaaatcta |
| SEQ_6 | P$L1BX/ATML1.01 | L1-specific homeodomain protein ATML1 (*A. thaliana* meristem layer 1) | 0.82 | 980 | 996 | (−) | 0.750 | 0.855 | attttaTACAtgcatgt |
| SEQ_6 | P$CCAF/CCA1.01 | Circadian clock associated 1 | 0.85 | 986 | 1000 | (+) | 1.000 | 0.922 | atgtataaAATCtat |
| SEQ_6 | P$LREM/ATCTA.01 | Motif involved in carotenoid and tocopherol bio-synthesis and in the expression of photosynthesis-related genes | 0.85 | 993 | 1003 | (+) | 1.000 | 0.897 | aaATCTataga |
| SEQ_6 | P$LREM/ATCTA.01 | Motif involved in carotenoid and tocopherol bio-synthesis and in the expression of photosynthesis-related genes | 0.85 | 996 | 1006 | (−) | 1000 | 0.877 | cgATCTataga |

TABLE 3 cis-regulatory elements of SEQ ID NO: 9

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_9 | P$SUCB/SUCROSE.01 | Sequence motif from the promoters of different sugar-responsive genes | 0.81 | 17 | 35 | (+) | 0.750 | 0.859 | caAATTcaggtagcttaag |
| SEQ_9 | P$MIIG/MYBC1.01 | Maize C1 myb-domain protein | 0.92 | 21 | 35 | (+) | 1.000 | 0.928 | ttcagGTAGcttaag |
| SEQ_9 | P$MADS/AGL3.01 | AGL3, MADS Box protein | 0.83 | 30 | 50 | (−) | 0.973 | 0.858 | agccaCCAAttagagcttaag |
| SEQ_9 | P$CAAT/CAAT.01 | CCAAT-box in plant promoters | 0.97 | 39 | 47 | (−) | 1.000 | 0.981 | caCCAAtta |
| SEQ_9 | P$DOFF/DOF3.01 | Dof3 - single zinc finger transcription factor | 0.99 | 44 | 60 | (−) | 1.000 | 0.995 | tattacctAAAGccacc |
| SEQ_9 | P$MYBL/MYBPH3.02 | Myb-like protein of Petunia hybrida | 0.76 | 69 | 85 | (+) | 0.817 | 0.794 | ctcagtTTGTaaatgta |
| SEQ_9 | P$L1BX/ATML1.01 | L1-specific homeodomain protein ATML1 (*A. thaliana* meristem layer 1) | 0.82 | 72 | 88 | (+) | 1.000 | 0.925 | agtttgTAAAtgtagtt |
| SEQ_9 | P$MYBL/MYBPH3.02 | Myb-like protein of Petunia hybrida | 0.76 | 78 | 94 | (+) | 1.000 | 0.794 | taaatgTAGTtaaaact |
| SEQ_9 | P$GTBX/SBF1.01 | SBF-1 | 0.87 | 80 | 96 | (+) | 1.000 | 0.929 | aatgtagTTAAaacttt |
| SEQ_9 | P$NCS1/NCS1.01 | Nodulin consensus sequence 1 | 0.85 | 88 | 98 | (−) | 1.000 | 0.850 | cAAAAgtttta |
| SEQ_9 | P$SALT/ALFIN1.01 | Zinc-finger protein in alfalfa roots, regulates salt tolerance | 0.93 | 93 | 107 | (+) | 1.000 | 0.948 | cttttGTGGtgtaaa |
| SEQ_9 | P$DOFF/PBOX.01 | Prolamin box, conserved in cereal seed storage protein gene promoters | 0.75 | 97 | 113 | (+) | 0.776 | 0.793 | tgtggtgtAAATcatgt |
| SEQ_9 | P$GTBX/GT1.01 | GT1-Box binding factors with a trihelix DNA-binding domain | 0.85 | 97 | 113 | (+) | 0.968 | 0.857 | tgtggtGTAAatcatgt |
| SEQ_9 | P$CAAT/CAAT.01 | CCAAT-box in plant promoters | 0.97 | 121 | 129 | (−) | 1.000 | 0.979 | aaCCAAtcg |
| SEQ_9 | P$GTBX/GT1.01 | GT1-Box binding factors with a trihelix DNA-binding domain | 0.85 | 121 | 137 | (+) | 1.000 | 0.866 | cgattgGTTAataaaaa |
| SEQ_9 | P$SEF4/SEF4.01 | Soybean embryo factor 4 | 0.98 | 129 | 139 | (−) | 1.000 | 0.985 | acTTTTtatta |
| SEQ_9 | P$OPAQ/GCN4.01 | GCN4, conserved in cereal seed storage protein gene promoters, similar to yeast GCN4 and vertebrate AP-1 | 0.81 | 141 | 157 | (+) | 1.000 | 0.813 | gttgaTGAGttaaaaaa |
| SEQ_9 | P$MYBL/MYBPH3.02 | Myb-like protein of Petunia hybrida | 0.76 | 158 | 174 | (+) | 1.000 | 0.805 | caaaatTAGTtgcagtt |
| SEQ_9 | P$AHBP/BLR.01 | Transcriptional repressor BELLRINGER | 0.90 | 159 | 169 | (+) | 1.000 | 0.981 | aaaATTAgttg |

TABLE 3-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 9 | | | | | | | | | |
| SEQ_9 | P$L1BX/ATML1.01 | L1-specific homeodomain protein ATML1 (*A. thaliana* meristem layer 1) | 0.82 | 165 | 181 | (−) | 0.750 | 0.844 | taatttTAACtgcaact |
| SEQ_9 | P$GTBX/SBF1.01 | SBF-1 | 0.87 | 166 | 182 | (+) | 1.000 | 0.954 | gttgcagTTAAaattac |
| SEQ_9 | P$NACF/TANAC69.01 | Wheat NACdomain DNA binding factor | 0.68 | 169 | 191 | (+) | 1.000 | 0.707 | gcagttaaaatTACGaatcatgg |
| SEQ_9 | P$MADS/AGL2.01 | AGL2, *Arabidopsis* MADS-domain protein AGA-MOUS-like 2 | 0.82 | 176 | 196 | (−) | 1.000 | 0.820 | ggagcCCATgattcgtaattt |
| SEQ_9 | P$LREM/ATCTA.01 | Motif involved in carotenoid and tocopherol biosynthesis and in the expression of photosynthesis-related genes | 0.85 | 196 | 206 | (+) | 1.000 | 0.897 | ctATCTatatt |
| SEQ_9 | P$MYBS/ZMMRP1.01 | *Zea mays* MYB-related protein 1 (transfer cell specific) | 0.79 | 196 | 212 | (+) | 0.777 | 0.905 | ctatctaTATTttacat |
| SEQ_9 | P$DOFF/PBOX.01 | Prolamin box, conserved in cereal seed storage protein gene promoters | 0.75 | 200 | 216 | (−) | 0.761 | 0.834 | tgtaatgtAAAAtatag |
| SEQ_9 | P$DOFF/DOF2.01 | Dof2 - single zinc finger transcription factor | 0.98 | 211 | 227 | (+) | 1.000 | 0.988 | attacaatAAAGctttt |
| SEQ_9 | P$DOFF/DOF2.01 | Dof2 - single zinc finger transcription factor | 0.98 | 242 | 258 | (+) | 1.000 | 0.995 | attacaatAAAGctata |
| SEQ_9 | P$TBPF/TATA.02 | Plant TATA box | 0.90 | 251 | 265 | (+) | 1.000 | 0.913 | aagcTATAtatcact |
| SEQ_9 | P$MYBS/ZMMRP1.01 | *Zea mays* MYB-related protein 1 (transfer cell specific) | 0.79 | 272 | 288 | (−) | 0.777 | 0.827 | ttgtcttTATTtcagat |
| SEQ_9 | P$DOFF/DOF1.01 | Dof1/MNB1a - single zinc finger transcription factor | 0.98 | 273 | 289 | (+) | 1.000 | 0.984 | tctgaaatAAAGacaaa |
| SEQ_9 | P$IDDF/ID1.01 | Maize INDETERMINATE1 zinc finger protein | 0.92 | 280 | 292 | (−) | 1.000 | 0.940 | gggtTTGTcttta |
| SEQ_9 | P$TELO/RPBX.01 | Ribosomal protein box, appears unique to plant RP genes and genes associated with gene expression | 0.84 | 285 | 299 | (+) | 1.000 | 0.864 | acaaaCCCTgaactc |
| SEQ_9 | P$AHBP/ATHB1.01 | *Arabidopsis thaliana* homeo box protein 1 | 0.90 | 307 | 317 | (−) | 1.000 | 0.989 | ctaATTAtttc |
| SEQ_9 | P$AHBP/HAHB4.01 | Sunflower homeodomain leucine-zipper protein Hahb-4 | 0.87 | 307 | 317 | (+) | 1.000 | 0.943 | gaaataATTAg |
| SEQ_9 | P$MYCL/ICE.01 | ICE (inducer of CBF expression 1), AtMYC2 (rd22BP1) | 0.95 | 317 | 335 | (+) | 0.954 | 0.972 | gccaaACACttgattccaa |
| SEQ_9 | P$MADS/SQUA.01 | MADS-box protein SQUAMOSA | 0.90 | 334 | 354 | (−) | 1.000 | 0.906 | ggtcgctATTTgtttctgttt |
| SEQ_9 | P$ERSE/ERSE_I.01 | ERSE I (ER stress-response element I)-like motif | 0.79 | 343 | 361 | (+) | 1.000 | 0.799 | caaatagcgacctaaCACG |
| SEQ_9 | P$IBOX/GATA.01 | Class I GATA factors | 0.93 | 356 | 372 | (+) | 1.000 | 0.958 | aacacGATAatagatag |

TABLE 3-continued cis-regulatory elements of SEQ ID NO: 9

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_9 | P$LREM/ATCTA.01 | Motif involved in carotenoid and tocopherol biosynthesis and in the expression of photosynthesis-related genes | 0.85 | 362 | 372 | (-) | 1.000 | 0.853 | ctATCTattat |
| SEQ_9 | P$AHBP/BLR.01 | Transcriptional repressor BELLRINGER | 0.90 | 383 | 393 | (-) | 1.000 | 0.928 | tatATTAtttt |
| SEQ_9 | P$IBOX/IBOX.01 | I-Box in rbcS genes and other light regulated genes | 0.81 | 385 | 401 | (+) | 0.750 | 0.817 | aataaTATAaggatcag |
| SEQ_9 | P$CCAF/CCA1.01 | Circadian clock associated 1 | 0.85 | 398 | 412 | (-) | 1.000 | 0.864 | aaccaagaAATCtga |
| SEQ_9 | P$SPF1/SP8BF.01 | DNA-binding protein of sweet potato that binds to the SP8a (ACTGTGTA) and SP8b (TACTATT) sequences of sporamin and beta-amylase genes | 0.87 | 411 | 423 | (-) | 1.000 | 0.909 | ttTACTgtttaaa |
| SEQ_9 | P$GAPB/GAP.01 | Cis-element in the GAPDH promoters conferring light inducibility | 0.88 | 431 | 445 | (+) | 1.000 | 0.984 | acacATGAagacaag |
| SEQ_9 | P$SUCB/SUCROSE.01 | Sequence motif from the promoters of different sugar-responsive genes | 0.81 | 448 | 466 | (+) | 1.000 | 0.815 | aaAAATtatagattttaca |
| SEQ_9 | P$LREM/ATCTA.01 | Motif involved in carotenoid and tocopherol biosynthesis and in the expression of photosynthesis-related genes | 0.85 | 452 | 462 | (-) | 1.000 | 0.912 | aaATCTataat |
| SEQ_9 | P$CCAF/CCA1.01 | Circadian clock associated 1 | 0.85 | 455 | 469 | (-) | 1.000 | 0.889 | ttttgtaaAATCtat |
| SEQ_9 | P$DOFF/PBOX.01 | Prolamin box, conserved in cereal seed storage protein gene promoters | 0.75 | 455 | 471 | (-) | 0.761 | 0.841 | tgttttgtAAAAtctat |
| SEQ_9 | P$MADS/AGL2.01 | AGL2, *Arabidopsis* MADS-domain protein AGA-MOUS-like 2 | 0.82 | 496 | 516 | (-) | 0.968 | 0.856 | agaagCCAAcattggcaacga |
| SEQ_9 | P$MADS/AG.01 | Agamous, required for normal flower development, similarity to SRF (human) and MCM (yeast) proteins | 0.80 | 497 | 517 | (+) | 0.902 | 0.806 | cgtTGCCaatgttggcttctt |
| SEQ_9 | P$LFYB/LFY.01 | Plant specific floral meristem identity gene LEAFY (LFY) | 0.93 | 500 | 512 | (+) | 0.885 | 0.938 | tGCCAatgttggc |
| SEQ_9 | P$DOFF/PBOX.01 | Prolamin box, conserved in cereal seed storage protein gene promoters | 0.75 | 510 | 526 | (-) | 1.000 | 0.801 | tgtggtggAAAGaagcc |
| SEQ_9 | P$SALT/ALFIN1.01 | Zinc-finger protein in alfalfa roots, regulates salt tolerance | 0.93 | 516 | 530 | (-) | 1.000 | 0.986 | tttgtGTGGtggaaa |
| SEQ_9 | P$TEFB/TEF1.01 | TEF cis acting elements in both RNA polymerase II-dependent promoters and rDNA spacer sequences | 0.76 | 521 | 541 | (-) | 0.838 | 0.781 | taACGGtcatatttgtgtggt |
| SEQ_9 | P$WBXF/ERE.01 | Elicitor response element | 0.89 | 527 | 543 | (+) | 1.000 | 0.897 | caaataTGACcgttaag |

TABLE 3-continued

| cis-regulatory elements of SEQ ID NO: 9 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_9 | P$MYBL/ATMYB77.01 | R2R3-type myb-like transcription factor (I-type binding site) | 0.87 | 530 | 546 | (+) | 0.857 | 0.916 | atatgaCCGTtaagact |
| SEQ_9 | P$MSAE/MSA.01 | M-phase-specific activators (NtmybA1, NtmybA2, NtmybB) | 0.80 | 531 | 545 | (−) | 1.000 | 0.889 | gtcttAACGgtcata |
| SEQ_9 | P$AHBP/HAHB4.01 | Sunflower homeodomain leucine-zipper protein Hahb-4 | 0.87 | 558 | 568 | (+) | 1.000 | 0.916 | tttataATTAc |
| SEQ_9 | P$GTBX/GT1.01 | GT1-Box binding factors with a trihelix DNA-binding domain | 0.85 | 558 | 574 | (−) | 0.968 | 0.859 | catgtaGTAAttataaa |
| SEQ_9 | P$OPAQ/O2_GCN4.01 | Recognition site for BZIP transcription factors that belong to the group of Opaque-2 like proteins | 0.81 | 564 | 580 | (+) | 1.000 | 0.823 | attactACATggatgta |
| SEQ_9 | P$HMGF/HMG_IY.01 | High mobility group I/Y-like proteins | 0.89 | 577 | 591 | (−) | 1.000 | 0.912 | tataTATTttataca |
| SEQ_9 | P$MYBS/ZMMRP1.01 | *Zea mays* MYB-related protein 1 (transfer cell specific) | 0.79 | 580 | 596 | (−) | 0.777 | 0.793 | cgatctaTATAttttat |
| SEQ_9 | P$TBPF/TATA.02 | Plant TATA box | 0.90 | 581 | 595 | (−) | 1.000 | 0.909 | gatcTATAtattta |
| SEQ_9 | P$LREM/ATCTA.01 | Motif involved in carotenoid and tocopherol biosynthesis and in the expression of photosynthesis-related genes | 0.85 | 586 | 596 | (−) | 1.000 | 0.882 | cgATCTatata |
| SEQ_9 | P$L1BX/PDF2.01 | Protodermal factor 2 | 0.85 | 617 | 633 | (−) | 1.000 | 0.891 | gagaaaTAAAtggtcga |

TABLE 4 cis-regulatory elements of SEQ ID NO: 14

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_14 | P$OCSE/OCSL.01 | OCS-like elements | 0.69 | 7 | 27 | (−) | 1.000 | 0.702 | caaagtgtgactatACGTttt |
| SEQ_14 | P$DOFF/DOF3.01 | Dof3 - single zinc finger transcription factor | 0.99 | 31 | 47 | (−) | 1.000 | 0.997 | catagtcaAAAGcacaa |
| SEQ_14 | P$WBXF/WRKY.01 | WRKY plant specific zinc-finger-type factor associated with pathogen defence, W box | 0.92 | 34 | 50 | (+) | 1.000 | 0.961 | tgcttTTGActatgtgt |
| SEQ_14 | P$MYBS/ZMMRP1.01 | *Zea mays* MYB-related protein 1 (transfer cell specific) | 0.79 | 43 | 59 | (+) | 1.000 | 0.833 | ctatgtgTATCtgttcc |
| SEQ_14 | P$LREM/ATCTA.01 | Motif involved in carotenoid and tocopherol biosynthesis and in the expression of photosynthesis-related genes | 0.85 | 59 | 69 | (−) | 1.000 | 0.892 | cgATCTataag |
| SEQ_14 | P$MADS/AG.01 | Agamous, required for normal flower development, similarity to SRF (human) and MCM (yeast) proteins | 0.80 | 92 | 112 | (−) | 0.962 | 0.820 | tagTTCCcaaaccggttccaa |
| SEQ_14 | P$MIIG/MYBC1.01 | Maize C1 myb-domain protein | 0.92 | 104 | 118 | (−) | 1.000 | 0.935 | tgttgGTAGttccca |
| SEQ_14 | P$MADS/AGL2.01 | AGL2, *Arabidopsis* MADS-domain protein AGAMOUS-like 2 | 0.82 | 108 | 128 | (+) | 0.968 | 0.828 | aactaCCAAcacaagcaatgc |
| SEQ_14 | P$NCS2/NCS2.01 | Nodulin consensus sequence 2 | 0.79 | 130 | 144 | (−) | 1.000 | 0.817 | ttttgcCTCTctaag |
| SEQ_14 | P$SPF1/SP8BF.01 | DNA-binding protein of sweet potato that binds to the SP8a (ACTGTGTA) and SP8b (TACTATT) sequences of sporamin and beta-amylase genes | 0.87 | 139 | 151 | (−) | 1.000 | 0.918 | atTACTcttttgc |
| SEQ_14 | P$DOFF/PBF.01 | PBF (MPBF) | 0.97 | 145 | 161 | (+) | 1.000 | 0.990 | gagtaataAAAGagagg |
| SEQ_14 | P$NCS1/NCS1.01 | Nodulin consensus sequence 1 | 0.85 | 163 | 173 | (+) | 1.000 | 0.862 | gAAAAgtttttg |

TABLE 4-continued

| cis-regulatory elements of SEQ ID NO: 14 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_14 | P$WBXF/WRKY.01 | WRKY plant specific zinc-finger-type factor associated with pathogen defence, W box | 0.92 | 166 | 182 | (−) | 1.000 | 0.942 | atagtTTGAcaaaactt |
| SEQ_14 | P$IDDF/ID1.01 | Maize INDETERMINATE1 zinc finger protein | 0.92 | 167 | 179 | (+) | 1.000 | 0.935 | agttTTGTcaaac |
| SEQ_14 | P$OCSE/OCSL.01 | OCS-like elements | 0.69 | 194 | 214 | (−) | 0.769 | 0.721 | aaaagttagatcttACTTtct |
| SEQ_14 | P$OCSE/OCSL.01 | OCS-like elements | 0.69 | 195 | 215 | (+) | 0.769 | 0.766 | gaaagtaagatctaACTTttt |
| SEQ_14 | P$AGP1/AGP1.01 | AG-motif binding protein 1 | 0.91 | 199 | 209 | (−) | 1.000 | 0.915 | ttaGATCttac |
| SEQ_14 | P$AGP1/AGP1.01 | AG-motif binding protein 1 | 0.91 | 200 | 210 | (+) | 1.000 | 0.983 | taaGATCtaac |
| SEQ_14 | P$LREM/ATCTA.01 | Motif involved in carotenoid and tocopherol biosynthesis and in the expression of photosynthesis-related genes | 0.85 | 202 | 212 | (+) | 1.000 | 0.910 | agATCTaactt |
| SEQ_14 | P$MYBL/MYBPH3.01 | Myb-like protein of Petunia hybrida | 0.80 | 202 | 218 | (−) | 1.000 | 0.819 | aaaaaaaaGTTAgatct |
| SEQ_14 | P$MYBL/NTMYBAS1.01 | Anther-specific myb gene from tobacco | 0.96 | 222 | 238 | (+) | 1.000 | 0.976 | tttgggatGTTAggctt |
| SEQ_14 | P$TELO/ATPURA.01 | *Arabidopsis* Telo-box interacting protein related to the conserved animal protein Pur-alpha | 0.85 | 227 | 241 | (−) | 0.750 | 0.868 | caaaAGCCtaacatc |
| SEQ_14 | P$DOFF/DOF3.01 | Dof3 - single zinc finger transcription factor | 0.99 | 231 | 247 | (−) | 1.000 | 0.997 | agccttcaAAAGcctaa |
| SEQ_14 | P$SUCB/SUCROSE.01 | Sequence motif from the promoters of different sugar-responsive genes | 0.81 | 238 | 256 | (−) | 0.750 | 0.836 | aaAAAAcatagccttcaaa |
| SEQ_14 | P$LEGB/LEGB.01 | Legumin box, highly conserved sequence element about 100 bp up-stream of the TSS in legumin genes | 0.59 | 268 | 294 | (−) | 0.750 | 0.593 | accttcgACATgatctaagaacaaaga |

TABLE 4-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 14 | | | | | | | | | |
| SEQ_14 | P$LREM/ATCTA.01 | Motif involved in carotenoid and tocopherol biosynthesis and in the expression of photosynthesis-related genes | 0.85 | 274 | 284 | (-) | 1.000 | 0.921 | tgATCTaagaa |
| SEQ_14 | P$CARM/CARICH.01 | CA-rich element | 0.78 | 286 | 304 | (-) | 1.000 | 0.816 | acatttcAACAccttcgac |
| SEQ_14 | P$L1BX/PDF2.01 | Protodermal factor 2 | 0.85 | 308 | 324 | (+) | 1.000 | 0.903 | atgtaaTAAAtgttatt |
| SEQ_14 | P$OCSE/OCSL.01 | OCS-like elements | 0.69 | 314 | 334 | (-) | 0.807 | 0.714 | gcagctgagtaataACATtta |
| SEQ_14 | P$OCSE/OCSL.01 | OCS-like elements | 0.69 | 322 | 342 | (+) | 1.000 | 0.717 | attactcagctgctACGTtta |
| SEQ_14 | P$CCAF/CCA1.01 | Circadian clock associated 1 | 0.85 | 368 | 382 | (-) | 1.000 | 0.852 | tttacataAATCtca |
| SEQ_14 | P$DOFF/PBOX.01 | Prolamin box, conserved in cereal seed storage protein gene promoters | 0.75 | 372 | 388 | (+) | 0.761 | 0.751 | atttatgtAAAAtccat |
| SEQ_14 | P$IBOX/GATA.01 | Class I GATA factors | 0.93 | 399 | 415 | (-) | 1.000 | 0.973 | aaatgGATAagattgat |
| SEQ_14 | P$MYBS/HVMCB1.01 | Hordeum vulgare Myb-related CAB-promoter-binding protein 1 | 0.93 | 402 | 418 | (+) | 1.000 | 0.963 | aatcttATCCattttct |
| SEQ_14 | P$AHBP/WUS.01 | Homeodomain protein WUSCHEL | 0.94 | 420 | 430 | (+) | 1.000 | 0.963 | ctgatTAATct |
| SEQ_14 | P$AHBP/WUS.01 | Homeodomain protein WUSCHEL | 0.94 | 421 | 431 | (-) | 1.000 | 0.963 | cagatTAATca |
| SEQ_14 | P$ABRE/ABRE.01 | ABA response elements | 0.82 | 428 | 444 | (-) | 1.000 | 0.850 | taattgcACGTtgcaga |
| SEQ_14 | P$MYBL/MYBPH3.02 | Myb-like protein of Petunia hybrida | 0.76 | 437 | 453 | (+) | 1.000 | 0.782 | tgcaatTAGTttgatca |
| SEQ_14 | P$TEFB/TEF1.01 | TEF cis acting elements in both RNA polymerase II-dependent promoters and rDNA spacer sequences | 0.76 | 450 | 470 | (-) | 0.838 | 0.779 | ccATGGctaatattgtttgat |
| SEQ_14 | P$GBOX/UPRE.01 | UPRE (unfolded protein response element) like motif | 0.86 | 493 | 513 | (-) | 0.767 | 0.862 | cttcgtCCAAgtcaacataag |

TABLE 4-continued cis-regulatory elements of SEQ ID NO: 14

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_14 | P$RAV5/RAV1-5.01 | 5'-part of bipartite RAV1 binding site, interacting with AP2 domain | 0.96 | 493 | 503 | (-) | 1.000 | 0.960 | gtcAACAtaag |
| SEQ_14 | P$GBOX/BZIP911.01 | bZIP transcription factor from Antirrhinum majus | 0.77 | 494 | 514 | (+) | 1.000 | 0.833 | ttatgtTGACttggacgaaga |
| SEQ_14 | P$OPAQ/O2.01 | Opaque-2 regulatory protein | 0.87 | 495 | 511 | (-) | 0.852 | 0.895 | tcgtccaagTCAAcata |
| SEQ_14 | P$DOFF/DOF2.01 | Dof2 - single zinc finger transcription factor | 0.98 | 544 | 560 | (-) | 1.000 | 1.000 | tatttattAAAGcaaac |
| SEQ_14 | P$L1BX/ATML1.01 | L1-specific homeodomain protein ATML1 (*A. thaliana* meristem layer 1) | 0.82 | 549 | 565 | (+) | 1.000 | 0.853 | ctttaaTAAAtataagt |
| SEQ_14 | P$SUCB/SUCROSE.01 | Sequence motif from the promoters of different sugar-responsive genes | 0.81 | 559 | 577 | (-) | 0.750 | 0.816 | caCAATcattctacttata |
| SEQ_14 | P$AHBP/ATHB5.01 | HDZip class I protein ATHB5 | 0.89 | 566 | 576 | (+) | 0.829 | 0.904 | agaATGAttgt |
| SEQ_14 | P$AHBP/ATHB5.01 | HDZip class I protein ATHB5 | 0.89 | 566 | 576 | (-) | 0.936 | 0.977 | acaATCAttct |
| SEQ_14 | P$IDDF/ID1.01 | Maize INDETERMINATE1 zinc finger protein | 0.92 | 575 | 587 | (+) | 1.000 | 0.926 | gtgtTTGTcttct |
| SEQ_14 | P$GTBX/SBF1.01 | SBF-1 | 0.87 | 581 | 597 | (-) | 1.000 | 0.885 | tctgtgaTTAAgaagac |
| SEQ_14 | P$AHBP/WUS.01 | Homeodomain protein WUSCHEL | 0.94 | 583 | 593 | (+) | 1.000 | 0.963 | cttctTAATca |
| SEQ_14 | P$SPF1/SP8BF.01 | DNA-binding protein of sweet potato that binds to the SP8a (ACTGTGTA) and SP8b (TACTATT) sequences of sporamin and beta-amylase genes | 0.87 | 590 | 602 | (-) | 1.000 | 0.876 | aaTACTctgtgat |
| SEQ_14 | P$AHBP/WUS.01 | Homeodomain protein WUSCHEL | 0.94 | 610 | 620 | (-) | 1.000 | 0.963 | aacctTAATct |

TABLE 4-continued

| cis-regulatory elements of SEQ ID NO: 14 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_14 | P$OCSE/OCSL.01 | OCS-like elements | 0.69 | 614 | 634 | (+) | 1.000 | 0.699 | taaggtttgaatgaACGTcgt |
| SEQ_14 | P$EINL/TEIL.01 | TEIL (tobacco EIN3-like) | 0.92 | 624 | 632 | (+) | 0.964 | 0.932 | aTGAAcgtc |
| SEQ_14 | P$GBOX/TGA1.01 | *Arabidopsis* leucine zipper protein TGA1 | 0.90 | 633 | 653 | (+) | 1.000 | 0.903 | gtaaaaTGACggttatgctcg |
| SEQ_14 | P$MYBL/ATMYB77.01 | R2R3-type myb-like transcription factor (I-type binding site) | 0.87 | 636 | 652 | (+) | 1.000 | 0.970 | aaatgaCGGTtatgctc |
| SEQ_14 | P$TEFB/TEF1.01 | TEF cis acting elements in both RNA polymerase II-dependent promoters and rDNA spacer sequences | 0.76 | 639 | 659 | (+) | 0.838 | 0.778 | tgACGGttatgctcgtgagag |
| SEQ_14 | P$PREM/MGPROTORE.01 | Promoter elements involved in MgProto (Mg-protoporphyrin IX) and light-mediated induction | 0.77 | 641 | 671 | (−) | 1.000 | 0.792 | taagCGACgattctctcacgagcataaccgt |
| SEQ_14 | P$IBOX/GATA.01 | Class I GATA factors | 0.93 | 668 | 684 | (+) | 1.000 | 0.982 | cttacGATAaggacgaa |
| SEQ_14 | P$MYBL/GAMYB.01 | GA-regulated myb gene from barley | 0.91 | 690 | 706 | (+) | 1.000 | 0.936 | atttgattGTTAtcagg |
| SEQ_14 | P$MYBL/NTMYBAS1.01 | Anther-specific myb gene from tobacco | 0.96 | 701 | 717 | (+) | 1.000 | 0.967 | atcaggttGTTAaaagt |
| SEQ_14 | P$GTBX/SBF1.01 | SBF-1 | 0.87 | 703 | 719 | (+) | 1.000 | 0.921 | caggttgTTAAaagttg |
| SEQ_14 | P$NCS1/NCS1.01 | Nodulin consensus sequence 1 | 0.85 | 711 | 721 | (+) | 1.000 | 0.861 | tAAAAgttgag |
| SEQ_14 | P$AREF/ARE.01 | Auxin Response Element | 0.93 | 715 | 727 | (−) | 1.000 | 0.932 | gttTGTCtcaact |
| SEQ_14 | P$IDDF/ID1.01 | Maize INDETERMINATE1 zinc finger protein | 0.92 | 717 | 729 | (−) | 1.000 | 0.927 | tcgtTTGTctcaa |
| SEQ_14 | P$MYCL/ICE.01 | ICE (inducer of CBF expression 1), AtMYC2 (rd22BP1) | 0.95 | 747 | 765 | (−) | 0.954 | 0.972 | acgtaACACctgtttagtc |

TABLE 4-continued cis-regulatory elements of SEQ ID NO: 14

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_14 | P$MYCL/ICE.01 | ICE (inducer of CBF expression 1), AtMYC2 (rd22BP1) | 0.95 | 748 | 766 | (+) | 0.863 | 0.954 | actaaACAGgtgttacgtt |
| SEQ_14 | P$GBOX/HBP1B.01 | Wheat bZIP transcription factor HBP1B (histone gene binding protein 1b) | 0.83 | 753 | 773 | (−) | 1.000 | 0.857 | aatgtgaaACGTaacacctgt |
| SEQ_14 | P$GTBX/GT3A.01 | Trihelix DNA-binding factor GT-3a | 0.83 | 753 | 769 | (+) | 1.000 | 0.858 | acaggtGTTAcgtttca |
| SEQ_14 | P$ABRE/ABRE.01 | ABA response elements | 0.82 | 755 | 771 | (+) | 1.000 | 0.820 | aggtgttACGTttcaca |
| SEQ_14 | P$NACF/TANAC69.01 | Wheat NACdomain DNA binding factor | 0.68 | 755 | 777 | (−) | 0.812 | 0.708 | aaccaatgtgaAACGtaacacct |
| SEQ_14 | P$LFYB/LFY.01 | Plant specific floral meristem identity gene LEAFY (LFY) | 0.93 | 765 | 777 | (−) | 0.914 | 0.947 | aACCAatgtgaaa |
| SEQ_14 | P$CAAT/CAAT.01 | CCAAT-box in plant promoters | 0.97 | 769 | 777 | (−) | 1.000 | 0.982 | aaCCAAtgt |
| SEQ_14 | P$GTBX/GT1.01 | GT1-Box binding factors with a trihelix DNA-binding domain | 0.85 | 790 | 806 | (+) | 1.000 | 0.906 | cttgaaGTTActctatt |
| SEQ_14 | P$AHBP/BLR.01 | Transcriptional repressor BELL-RINGER | 0.90 | 793 | 803 | (+) | 0.826 | 0.914 | gaaGTTActct |
| SEQ_14 | P$MYBL/MYBPH3.01 | Myb-like protein of Petunia hybrida | 0.80 | 802 | 818 | (−) | 1.000 | 0.828 | ttggaccgGTTAaatag |
| SEQ_14 | P$WBXF/ERE.01 | Elicitor response element | 0.89 | 824 | 840 | (−) | 1.000 | 0.894 | ttaaccTGACcggttgg |
| SEQ_14 | P$GTBX/GT1.01 | GT1-Box binding factors with a trihelix DNA-binding domain | 0.85 | 830 | 846 | (+) | 1.000 | 0.854 | ggtcagGTTAacaaaac |
| SEQ_14 | P$MYBL/GAMYB.01 | GA-regulated myb gene from barley | 0.91 | 833 | 849 | (−) | 1.000 | 0.930 | agtgttttGTTAacctg |
| SEQ_14 | P$MYBL/GAMYB.01 | GA-regulated myb gene from barley | 0.91 | 845 | 861 | (+) | 1.000 | 0.910 | acactgaaGTTAgccgc |
| SEQ_14 | P$GCCF/GCC-BOX.01 | GCC-box, ethylene-responsive element (ERE) | 0.86 | 853 | 865 | (+) | 1.000 | 1.000 | gttAGCCgccaac |

TABLE 4-continued

| cis-regulatory elements of SEQ ID NO: 14 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_14 | P$GBOX/HBP1B.01 | Wheat bZIP transcription factor HBP1B (histone gene binding protein 1b) | 0.83 | 867 | 887 | (+) | 1.000 | 0.842 | cgcttattACGTaaacggtag |
| SEQ_14 | P$NACF/TANAC69.01 | Wheat NACdomain DNA binding factor | 0.68 | 868 | 890 | (−) | 1.000 | 0.728 | tggctaccgttTACGtaataagc |
| SEQ_14 | P$OCSE/OCSL.01 | OCS-like elements | 0.69 | 872 | 892 | (−) | 1.000 | 0.710 | cgtggctaccgtttACGTaat |
| SEQ_14 | P$MSAE/MSA.01 | M-phase-specific activators (NtmybA1, NtmybA2, NtmybB) | 0.80 | 875 | 889 | (+) | 1.000 | 0.827 | acgtaAACGgtagcc |
| SEQ_14 | P$GBOX/GBF1.01 | bZIP protein G-Box binding factor 1 | 0.94 | 881 | 901 | (−) | 1.000 | 0.943 | tgctcgaaACGTggctaccgt |
| SEQ_14 | P$GBOX/HBP1A.01 | HBP-1a, suggested to be involved in the cell cycle-dependent expression | 0.88 | 882 | 902 | (+) | 1.000 | 0.943 | cggtagcCACGtttcgagcac |
| SEQ_14 | P$MYCL/MYCRS.01 | Myc recognition sequences | 0.93 | 882 | 900 | (−) | 1.000 | 0.936 | gctcgaaACGTggctaccg |
| SEQ_14 | P$NACF/TANAC69.01 | Wheat NACdomain DNA binding factor | 0.68 | 883 | 905 | (−) | 0.812 | 0.717 | gcagtgctcgaAACGtggctacc |
| SEQ_14 | P$ABRE/ABRE.01 | ABA response elements | 0.82 | 884 | 900 | (−) | 1.000 | 0.864 | gctcgaaACGTggctac |
| SEQ_14 | P$IDDF/ID1.01 | Maize INDETERMINATE1 zinc finger protein | 0.92 | 912 | 924 | (+) | 1.000 | 0.921 | taatTTGTcttca |
| SEQ_14 | P$LEGB/LEGB.01 | Legumin box, highly conserved sequence element about 100 bp up-stream of the TSS in legumin genes | 0.59 | 975 | 1001 | (−) | 0.750 | 0.657 | tcactagCCTTgcatgcgaatcagtag |
| SEQ_14 | P$LEGB/RY.01 | RY and Sph motifs conserved in seed-specific promoters | 0.87 | 978 | 1004 | (+) | 1.000 | 0.899 | ctgattcgCATGcaaggctagtgacac |

TABLE 5 cis-regulatory elements of SEQ ID NO: 16

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_16 | P$OCSE/OCSL.01 | OCS-like elements | 0.69 | 7 | 27 | (-) | 1.000 | 0.702 | caaagtgtgactatACGTttt |
| SEQ_16 | P$DOFF/DOF3.01 | Dof3 - single zinc finger transcription factor | 0.99 | 31 | 47 | (-) | 1.000 | 0.997 | catagtcaAAAGcacaa |
| SEQ_16 | P$WBXF/WRKY.01 | WRKY plant specific zinc-finger-type factor associated with pathogen defence, W box | 0.92 | 34 | 50 | (+) | 1.000 | 0.961 | tgcttTTGActatgtgt |
| SEQ_16 | P$MYBS/ZMMRP1.01 | *Zea mays* MYB-related protein 1 (transfer cell specific) | 0.79 | 43 | 59 | (+) | 1.000 | 0.833 | ctatgtgTATCtgttcc |
| SEQ_16 | P$LREM/ATCTA.01 | Motif involved in carotenoid and tocopherol biosynthesis and in the expression of photo-synthesis-related genes | 0.85 | 59 | 69 | (-) | 1.000 | 0.892 | cgATCTataag |
| SEQ_16 | P$MADS/AG.01 | Agamous, required for normal flower development, similarity to SRF (human) and MCM (yeast) proteins | 0.80 | 92 | 112 | (-) | 0.962 | 0.820 | tagTTCCcaaaccggttccaa |
| SEQ_16 | P$MIIG/MYBC1.01 | Maize C1 myb-domain protein | 0.92 | 104 | 118 | (-) | 1.000 | 0.935 | tgttgGTAGttccca |
| SEQ_16 | P$MADS/AGL2.01 | AGL2, *Arabidopsis* MADS-domain protein AGAMOUS-like 2 | 0.82 | 108 | 128 | (+) | 0.968 | 0.828 | aactaCCAAcacaagcaatgc |
| SEQ_16 | P$GAGA/BPC.01 | Basic pentacysteine proteins | 1.00 | 129 | 153 | (+) | 1.000 | 1.000 | tcttagAGAGagaaaagagtaataa |
| SEQ_16 | P$GAGA/BPC.01 | Basic pentacysteine proteins | 1.00 | 131 | 155 | (+) | 1.000 | 1.000 | ttagagAGAGaaaagagtaataaaa |
| SEQ_16 | P$DOFF/PBF.01 | PBF (MPBF) | 0.97 | 134 | 150 | (+) | 1.000 | 0.988 | gagagagaAAAGagtaa |
| SEQ_16 | P$SPF1/SP8BF.01 | DNA-binding protein of sweet potato that binds to the SP8a (ACTGTGTA) and SP8b (TACTATT) sequences of sporamin and beta-amylase genes | 0.87 | 139 | 151 | (-) | 1.000 | 0.919 | atTACTcttttct |
| SEQ_16 | P$NCS1/NCS1.01 | Nodulin consensus sequence 1 | 0.85 | 140 | 150 | (+) | 1.000 | 0.855 | gAAAAgagtaa |
| SEQ_16 | P$DOFF/PBF.01 | PBF (MPBF) | 0.97 | 145 | 161 | (+) | 1.000 | 0.990 | gagtaataAAAGagagg |
| SEQ_16 | P$NCS1/NCS1.01 | Nodulin consensus sequence 1 | 0.85 | 163 | 173 | (+) | 1.000 | 0.862 | gAAAAgttttg |
| SEQ_16 | P$WBXF/WRKY.01 | WRKY plant specific zinc-finger-type factor associated with pathogen defence, W box | 0.92 | 166 | 182 | (-) | 1.000 | 0.942 | agagtTTGAcaaaactt |
| SEQ_16 | P$IDDF/ID1.01 | Maize INDETERMINATE1 zinc finger protein | 0.92 | 167 | 179 | (+) | 1.000 | 0.935 | agttTTGTcaaac |
| SEQ_16 | P$OCSE/OCSL.01 | OCS-like elements | 0.69 | 194 | 214 | (-) | 0.769 | 0.708 | gaaagttagatcttACTTtct |

TABLE 5-continued

| cis-regulatory elements of SEQ ID NO: 16 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_16 | P$OCSE/OCSL.01 | OCS-like elements | 0.69 | 195 | 215 | (+) | 0.769 | 0.733 | gaaagtaagatctaACTTtct |
| SEQ_16 | P$AGP1/AGP1.01 | AG-motif binding protein 1 | 0.91 | 199 | 209 | (-) | 1.000 | 0.915 | ttaGATCttac |
| SEQ_16 | P$AGP1/AGP1.01 | AG-motif binding protein 1 | 0.91 | 200 | 210 | (+) | 1.000 | 0.983 | taaGATCtaac |
| SEQ_16 | P$LREM/ATCTA.01 | Motif involved in carotenoid and tocopherol biosynthesis and in the expression of photo-synthesis-related genes | 0.85 | 202 | 212 | (+) | 1.000 | 0.910 | agATCTaactt |
| SEQ_16 | P$MYBL/NTMYBAS1.01 | Anther-specific myb gene from tobacco | 0.96 | 228 | 244 | (+) | 1.000 | 0.976 | tttgggatGTTAggctt |
| SEQ_16 | P$TELO/ATPURA.01 | *Arabidopsis* Telo-box interacting protein re-lated to the conserved animal protein Pur-alpha | 0.85 | 233 | 247 | (-) | 0.750 | 0.868 | caaaAGCCtaacatc |
| SEQ_16 | P$DOFF/DOF3.01 | Dof3 - single zinc finger transcription factor | 0.99 | 237 | 253 | (-) | 1.000 | 0.997 | agccttcaAAAGcctaa |
| SEQ_16 | P$SUCB/SUCROSE.01 | Sequence motif from the promoters of different sugar-responsive genes | 0.81 | 244 | 262 | (-) | 0.750 | 0.836 | aaAAAAcatagccttcaaa |
| SEQ_16 | P$LEGB/LEGB.01 | Legumin box, highly conserved sequence element about 100 bp upstream of the TSS in legumin genes | 0.59 | 274 | 300 | (-) | 0.750 | 0.593 | accttcgACATgatctaagaacaaaga |
| SEQ_16 | P$LREM/ATCTA.01 | Motif involved in carotenoid and tocopherol biosynthesis and in the expression of photo-synthesis-related genes | 0.85 | 280 | 290 | (-) | 1.000 | 0.921 | tgATCTaagaa |
| SEQ_16 | P$CARM/CARICH.01 | CA-rich element | 0.78 | 292 | 310 | (-) | 1.000 | 0.787 | acacttcAACAccttcgac |
| SEQ_16 | P$CARM/CARICH.01 | CA-rich element | 0.78 | 300 | 318 | (-) | 1.000 | 0.829 | tacgtccAACActtcaaca |
| SEQ_16 | P$OCSE/OCSL.01 | OCS-like elements | 0.69 | 311 | 331 | (-) | 1.000 | 0.695 | taataacatttattACGTcca |
| SEQ_16 | P$L1BX/PDF2.01 | Protodermal factor 2 | 0.85 | 314 | 330 | (+) | 1.000 | 0.903 | acgtaaTAAAtgttatt |
| SEQ_16 | P$OCSE/OCSL.01 | OCS-like elements | 0.69 | 320 | 340 | (-) | 0.807 | 0.714 | gcagctgagtaataACATtta |
| SEQ_16 | P$OCSE/OCSL.01 | OCS-like elements | 0.69 | 328 | 348 | (+) | 1.000 | 0.717 | attactcagctgctACGTtta |
| SEQ_16 | P$CCAF/CCA1.01 | Circadian clock associated 1 | 0.85 | 374 | 388 | (-) | 1.000 | 0.852 | tttacataAATCtca |
| SEQ_16 | P$SUCB/SUCROSE.01 | Sequence motif from the promoters of different sugar-responsive genes | 0.81 | 386 | 404 | (+) | 1.000 | 0.818 | aaAAATccgcaatcttatc |
| SEQ_16 | P$IBOX/GATA.01 | Class I GATA factors | 0.93 | 393 | 409 | (-) | 1.000 | 0.973 | aaatgGATAagattgcg |

TABLE 5-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 16 | | | | | | | | | |
| SEQ_16 | P$MYBS/HVMCB1.01 | Hordeum vulgare Myb-related CAB-promoter-binding protein 1 | 0.93 | 396 | 412 | (+) | 1.000 | 0.963 | aatcttATCCattttct |
| SEQ_16 | P$AHBP/WUS.01 | Homeodomain protein WUSCHEL | 0.94 | 414 | 424 | (+) | 1.000 | 0.963 | ctgatTAATct |
| SEQ_16 | P$AHBP/WUS.01 | Homeodomain protein WUSCHEL | 0.94 | 415 | 425 | (-) | 1.000 | 0.963 | cagatTAATca |
| SEQ_16 | P$ABRE/ABRE.01 | ABA response elements | 0.82 | 422 | 438 | (-) | 1.000 | 0.850 | taattgcACGTtgcaga |
| SEQ_16 | P$MYBL/MYBPH3.02 | Myb-like protein of Petunia hybrida | 0.76 | 431 | 447 | (+) | 1.000 | 0.782 | tgcaatTAGTttgatca |
| SEQ_16 | P$HMGF/HMG_IY.01 | High mobility group I/Y-like proteins | 0.89 | 441 | 455 | (-) | 1.000 | 0.907 | atatTATTtgatcaa |
| SEQ_16 | P$AHBP/BLR.01 | Transcriptional repressor BELLRINGER | 0.90 | 446 | 456 | (-) | 1.000 | 0.928 | aatATTAtttg |
| SEQ_16 | P$RAV5/RAV1-5.01 | 5'-part of bipartite RAV1 binding site, interacting with AP2 domain | 0.96 | 487 | 497 | (-) | 1.000 | 0.960 | gtcAACAtaag |
| SEQ_16 | P$OPAQ/O2.01 | Opaque-2 regulatory protein | 0.87 | 489 | 505 | (-) | 0.852 | 0.895 | tcctccaagTCAAcata |
| SEQ_16 | P$DOFF/DOF3.01 | Dof3 - single zinc finger transcription factor | 0.99 | 538 | 554 | (-) | 1.000 | 0.994 | tatttataAAAGcaaac |
| SEQ_16 | P$L1BX/ATML1.01 | L1-specific homeodomain protein ATML1 (*A. thaliana* meristem layer 1) | 0.82 | 538 | 554 | (-) | 1.000 | 0.859 | tatttaTAAAagcaaac |
| SEQ_16 | P$L1BX/ATML1.01 | L1-specific homeodomain protein ATML1 (*A. thaliana* meristem layer 1) | 0.82 | 543 | 559 | (+) | 1.000 | 0.834 | cttttaTAAAtataagt |
| SEQ_16 | P$TBPF/TATA.01 | Plant TATA box | 0.88 | 543 | 557 | (+) | 1.000 | 0.971 | ctttTATAaatataa |
| SEQ_16 | P$SUCB/SUCROSE.01 | Sequence motif from the promoters of different sugar-responsive genes | 0.81 | 553 | 571 | (-) | 0.750 | 0.816 | caCAATcattctacttata |
| SEQ_16 | P$AHBP/ATHB5.01 | HDZip class I protein ATHB5 | 0.89 | 560 | 570 | (+) | 0.829 | 0.904 | agaATGAttgt |
| SEQ_16 | P$AHBP/ATHB5.01 | HDZip class I protein ATHB5 | 0.89 | 560 | 570 | (-) | 0.936 | 0.977 | acaATCAttct |
| SEQ_16 | P$IDDF/ID1.01 | Maize INDETERMINATE1 zinc finger protein | 0.92 | 569 | 581 | (+) | 1.000 | 0.926 | gtgtTTGTcttct |
| SEQ_16 | P$SPF1/SP8BF.01 | DNA-binding protein of sweet potato that binds to the SP8a (ACTGTGTA) and SP8b (TACTATT) sequences of sporamin and beta-amylase genes | 0.87 | 586 | 598 | (-) | 1.000 | 0.876 | aaTACTctgtgat |
| SEQ_16 | P$AHBP/WUS.01 | Homeodomain protein WUSCHEL | 0.94 | 606 | 616 | (-) | 1.000 | 0.963 | aacctTAATct |
| SEQ_16 | P$GBOX/TGA1.01 | *Arabidopsis* leucine zipper protein TGA1 | 0.90 | 625 | 645 | (+) | 1.000 | 0.903 | gtaaaaTGACggttatgctcg |

TABLE 5-continued

| cis-regulatory elements of SEQ ID NO: 16 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_16 | P$MYBL/ATMYB77.01 | R2R3-type myb-like transcription factor (I-type binding site) | 0.87 | 628 | 644 | (+) | 1.000 | 0.970 | aaatgaCGGTtatgctc |
| SEQ_16 | P$TEFB/TEF1.01 | TEF cis acting elements in both RNA polymerase II-dependent promoters and rDNA spacer sequences | 0.76 | 631 | 651 | (+) | 0.838 | 0.778 | tgACGGttatgctcgtgagag |
| SEQ_16 | P$IBOX/GATA.01 | Class I GATA factors | 0.93 | 660 | 676 | (+) | 1.000 | 0.950 | cttgcGATAaggacgaa |
| SEQ_16 | P$MYBL/GAMYB.01 | GA-regulated myb gene from barley | 0.91 | 682 | 698 | (+) | 1.000 | 0.986 | atttggttGTTAtcagg |
| SEQ_16 | P$MIIG/PALBOXL.01 | Cis-acting element conserved in various PAL and 4CL promoters | 0.80 | 693 | 707 | (+) | 0.750 | 0.818 | atcaggttGTTGaaa |
| SEQ_16 | P$MYBL/MYBPH3.02 | Myb-like protein of Petunia hybrida | 0.76 | 693 | 709 | (+) | 0.817 | 0.777 | atcaggTTGTtgaaaga |
| SEQ_16 | P$NCS2/NCS2.01 | Nodulin consensus sequence 2 GCN4, conserved in cereal seed storage protein gene promoters, similar to yeast | 0.79 | 705 | 719 | (-) | 0.750 | 0.801 | gtttgtCTCAtcttt |
| SEQ_16 | P$OPAQ/GCN4.01 | GCN4 and vertebrate AP-1 | 0.81 | 705 | 721 | (+) | 1.000 | 0.846 | aaagaTGAGacaaacga |
| SEQ_16 | P$AREF/ARE.01 | Auxin Response Element | 0.93 | 707 | 719 | (-) | 1.000 | 0.951 | gttTGTCtcatct |
| SEQ_16 | P$IDDF/ID1.01 | Maize INDETERMINATE1 zinc finger protein | 0.92 | 709 | 721 | (-) | 1.000 | 0.927 | tcgtTTGTctcat |
| SEQ_16 | P$MYCL/ICE.01 | ICE (inducer of CBF expression 1), AtMYC2 (rd22BP1) | 0.95 | 739 | 757 | (-) | 0.954 | 0.972 | acgtaACACctgtttagtc |
| SEQ_16 | P$MYCL/ICE.01 | ICE (inducer of CBF expression 1), AtMYC2 (rd22BP1) | 0.95 | 740 | 758 | (+) | 0.863 | 0.954 | actaaACAGgtgttacgtt |
| SEQ_16 | P$GBOX/HBP1B.01 | Wheat bZIP transcription factor HBP1B (histone gene binding protein 1b) | 0.83 | 745 | 765 | (-) | 1.000 | 0.857 | aatgtgaaACGTaacacctgt |
| SEQ_16 | P$GTBX/GT3A.01 | Trihelix DNA-binding factor GT-3a | 0.83 | 745 | 761 | (+) | 1.000 | 0.858 | acaggtGTTAcgtttca |
| SEQ_16 | P$ABRE/ABRE.01 | ABA response elements | 0.82 | 747 | 763 | (+) | 1.000 | 0.820 | aggtgttACGTttcaca |
| SEQ_16 | P$NACF/TANAC69.01 | Wheat NACdomain DNA binding factor | 0.68 | 747 | 769 | (-) | 0.812 | 0.708 | aaccaatgtgaAACGtaacacct |
| SEQ_16 | P$LFYB/LFY.01 | Plant specific floral meristem identity gene LEAFY (LFY) | 0.93 | 757 | 769 | (-) | 0.914 | 0.947 | aACCAatgtgaaa |
| SEQ_16 | P$CAAT/CAAT.01 | CCAAT-box in plant promoters | 0.97 | 761 | 769 | (-) | 1.000 | 0.982 | aaCCAAtgt |
| SEQ_16 | P$MYBL/MYBPH3.01 | Myb-like protein of Petunia hybrida | 0.80 | 794 | 810 | (-) | 1.000 | 0.818 | ccggaccgGTTAaatag |

TABLE 5-continued

| cis-regulatory elements of SEQ ID NO: 16 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_16 | P$IDDF/ID1.01 | Maize INDETERMINATE1 zinc finger protein | 0.92 | 809 | 821 | (-) | 1.000 | 0.929 | agttTTGTcaacc |
| SEQ_16 | P$GCCF/ERE_JERE.01 | Ethylene-responsive elements (ERE) and jasmonate- and elicitor-responsive elements (JERE) | 0.85 | 826 | 838 | (+) | 1.000 | 0.907 | aaaaggCGCCaac |
| SEQ_16 | P$GBOX/HBP1B.01 | Wheat bZIP transcription factor HBP1B (histone gene binding protein 1b) | 0.83 | 840 | 860 | (+) | 1.000 | 0.858 | cgcttgttACGTaaacggtag |
| SEQ_16 | P$NACF/TANAC69.01 | Wheat NACdomain DNA binding factor | 0.68 | 841 | 863 | (-) | 1.000 | 0.764 | tggctaccgttTACGtaacaagc |
| SEQ_16 | P$OCSE/OCSL.01 | OCS-like elements | 0.69 | 845 | 865 | (-) | 1.000 | 0.710 | cgtggctaccgtttACGTaac |
| SEQ_16 | P$MSAE/MSA.01 | M-phase-specific activators (NtmybA1, NtmybA2, NtmybB) | 0.80 | 848 | 862 | (+) | 1.000 | 0.827 | acgtaAACGgtagcc |
| SEQ_16 | P$GBOX/GBF1.01 | bZIP protein G-Box binding factor 1 | 0.94 | 854 | 874 | (-) | 1.000 | 0.944 | tgctcaaaACGTggctaccgt |
| SEQ_16 | P$GBOX/HBP1A.01 | HBP-1a, suggested to be involved in the cell cycle-dependent expression | 0.88 | 855 | 875 | (+) | 1.000 | 0.914 | cggtagcCACGttttgagcac |
| SEQ_16 | P$NACF/TANAC69.01 | Wheat NACdomain DNA binding factor | 0.68 | 856 | 878 | (-) | 0.812 | 0.712 | gcagtgctcaaAACGtggctacc |
| SEQ_16 | P$ABRE/ABRE.01 | ABA response elements | 0.82 | 857 | 873 | (-) | 1.000 | 0.860 | gctcaaaACGTggctac |
| SEQ_16 | P$MYCL/MYCRS.01 | Myc recognition sequences | 0.93 | 872 | 890 | (+) | 0.863 | 0.946 | gcactgcATGTgctaattt |
| SEQ_16 | P$IDDF/ID1.01 | Maize INDETERMINATE1 zinc finger protein | 0.92 | 885 | 897 | (+) | 1.000 | 0.921 | taatTTGTcttca |
| SEQ_16 | P$TCPF/ATTCP20.01 | TCP class I transcription factor (Arabidopsis) | 0.94 | 924 | 936 | (-) | 1.000 | 0.947 | ttaaGCCCaagtg |
| SEQ_16 | P$MYBL/MYBPH3.02 | Myb-like protein of Petunia hybrida | 0.76 | 940 | 956 | (-) | 1.000 | 0.781 | attaatTAGTtccacga |
| SEQ_16 | P$AHBP/WUS.01 | Homeodomain protein WUSCHEL | 0.94 | 948 | 958 | (+) | 1.000 | 1.000 | ctaatTAATga |
| SEQ_16 | P$AHBP/ATHB5.01 | HDZip class I protein ATHB5 | 0.89 | 952 | 962 | (+) | 0.829 | 0.902 | ttaATGAttcg |
| SEQ_16 | P$AHBP/HAHB4.01 | Sunflower homeodomain leucine-zipper protein Hahb-4 | 0.87 | 952 | 962 | (-) | 1.000 | 0.979 | cgaatcATTAa |
| SEQ_16 | P$LEGB/LEGB.01 | Legumin box, highly conserved sequence element about 100 by upstream of the TSS in legumin genes | 0.59 | 952 | 978 | (-) | 0.750 | 0.657 | tcactagCCTTgcatgcgaatcattaa |
| SEQ_16 | P$LEGB/RY.01 | RY and Sph motifs conserved in seed-specific promoters | 0.87 | 955 | 981 | (+) | 1.000 | 0.899 | atgattcgCATGcaaggctagtgacac |

TABLE 6 cis-regulatory elements of SEQ ID NO: 22

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_22 | P$AHBP/BLR.01 | Transcriptional repressor BELL-RINGER | 0.90 | 4 | 14 | (+) | 0.826 | 0.936 | gaaGTTAttag |
| SEQ_22 | P$MYBL/CARE.01 | CAACTC regulatory elements, GA-inducible | 0.83 | 27 | 43 | (−) | 1.000 | 0.875 | gttggctAGTTgtaagt |
| SEQ_22 | P$WBXF/WRKY.01 | WRKY plant specific zinc-finger-type factor associated with pathogen defence, W box | 0.92 | 49 | 65 | (−) | 1.000 | 0.975 | catgtTTGAcctctaca |
| SEQ_22 | P$OPAQ/O2_GCN4.01 | Recognition site for BZIP transcription factors that belong to the group of Opaque-2 like proteins | 0.81 | 56 | 72 | (−) | 1.000 | 0.853 | tttgtaACATgtttgac |
| SEQ_22 | P$GTBX/GT3A.01 | Trihelix DNA-binding factor GT-3a | 0.83 | 59 | 75 | (+) | 1.000 | 0.867 | aaacatGTTAcaaactc |
| SEQ_22 | P$MYBL/MYBPH3.02 | Myb-like protein of Petunia hybrida | 0.76 | 61 | 77 | (−) | 0.817 | 0.798 | ttgagtTTGTaacatgt |
| SEQ_22 | P$HMGF/HMG_IY.02 | High mobility group I/Y-like protein isolated from pea | 1.00 | 72 | 86 | (−) | 1.000 | 1.000 | ctttTATTtttgagt |
| SEQ_22 | P$PSRE/GAAA.01 | GAAA motif involved in pollen specific transcriptional activation | 0.83 | 81 | 97 | (+) | 1.000 | 0.879 | taaaaGAAAcagtggag |
| SEQ_22 | P$LFYB/LFY.01 | Plant specific floral meristem identity gene LEAFY (LFY) | 0.93 | 85 | 97 | (−) | 1.000 | 0.969 | cTCCActgtttct |
| SEQ_22 | P$GTBX/GT1.01 | GT1-Box binding factors with a trihelix DNA-binding domain | 0.85 | 100 | 116 | (−) | 1.000 | 0.904 | gttcagGTTActcgatt |
| SEQ_22 | P$MYCL/ICE.01 | ICE (inducer of CBF expression 1), AtMYC2 (rd22BP1) | 0.95 | 109 | 127 | (−) | 0.954 | 0.972 | atcaaACACctgttcaggt |
| SEQ_22 | P$MYCL/ICE.01 | ICE (inducer of CBF expression 1), AtMYC2 (rd22BP1) | 0.95 | 110 | 128 | (+) | 0.863 | 0.954 | cctgaACAGgtgtttgatc |
| SEQ_22 | P$CARM/CARICH.01 | CA-rich element | 0.78 | 112 | 130 | (−) | 1.000 | 0.809 | ttgatcaAACAcctgttca |
| SEQ_22 | P$MYBL/MYBPH3.02 | Myb-like protein of Petunia hybrida | 0.76 | 140 | 156 | (−) | 1.000 | 0.781 | aagagaTAGTgacacac |
| SEQ_22 | P$MYBS/ZMMRP1.01 | *Zea mays* MYB-related protein 1 (transfer cell specific) | 0.79 | 142 | 158 | (+) | 1.000 | 0.824 | gtgtcacTATCtcttgg |
| SEQ_22 | P$DOFF/DOF1.01 | Dof1/MNB1a - single zinc finger transcription factor | 0.98 | 169 | 185 | (+) | 1.000 | 0.984 | acacaaatAAAGaccct |

TABLE 6-continued

| cis-regulatory elements of SEQ ID NO: 22 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_22 | P$MIIG/PALBOXL.01 | Cis-acting element conserved in various PAL and 4CL promoters | 0.80 | 188 | 202 | (−) | 0.785 | 0.801 | agcagcttGGTTagg |
| SEQ_22 | P$CAAT/CAAT.01 | CCAAT-box in plant promoters | 0.97 | 204 | 212 | (+) | 1.000 | 0.985 | atCCAAtcc |
| SEQ_22 | P$OPAQ/O2_GCN4.01 | Recognition site for BZIP transcription factors that belong to the group of Opaque-2 like proteins | 0.81 | 206 | 222 | (−) | 0.829 | 0.819 | tgtgtgACTTggattgg |
| SEQ_22 | P$L1BX/PDF2.01 | Protodermal factor 2 | 0.85 | 229 | 245 | (+) | 1.000 | 0.921 | cagctaTAAAtgaaaca |
| SEQ_22 | P$TBPF/TATA.02 | Plant TATA box | 0.90 | 229 | 243 | (+) | 1.000 | 0.935 | cagcTATAaatgaaa |
| SEQ_22 | P$MYBL/MYBPH3.01 | Myb-like protein of Petunia hybrida | 0.80 | 250 | 266 | (−) | 1.000 | 0.808 | attcatctGTTAaagtt |
| SEQ_22 | P$GAPB/GAP.01 | Cis-element in the GAPDH promoters conferring light inducibility | 0.88 | 257 | 271 | (+) | 1.000 | 0.964 | acagATGAatactag |
| SEQ_22 | P$HEAT/HSE.01 | Heat shock element | 0.81 | 284 | 298 | (−) | 1.000 | 0.811 | aggagacactAGAAc |
| SEQ_22 | P$AREF/ARE.01 | Auxin Response Element | 0.93 | 288 | 300 | (+) | 1.000 | 0.961 | tagTGTCtcctca |
| SEQ_22 | P$NCS2/NCS2.01 | Nodulin consensus sequence 2 | 0.79 | 288 | 302 | (+) | 0.750 | 0.819 | tagtgtCTCCtcatt |
| SEQ_22 | P$ROOT/RHE.01 | Root hair-specific element with a 2-nucleotid spacer between left part (LP) and right part (RP) | 0.77 | 298 | 322 | (−) | 1.000 | 0.852 | atcgtagcttgaattCACGtaatga |
| SEQ_22 | P$MYBL/MYBPH3.02 | Myb-like protein of Petunia hybrida | 0.76 | 317 | 333 | (−) | 1.000 | 0.775 | ttgagaTAGTgatcgta |
| SEQ_22 | P$MYBL/CARE.01 | CAACTC regulatory elements, GA-inducible | 0.83 | 326 | 342 | (−) | 1.000 | 0.838 | atgtaggAGTTgagata |
| SEQ_22 | P$LEGB/LEGB.01 | Legumin box, highly conserved sequence element about 100 by up-stream of the TSS in legumin genes | 0.59 | 357 | 383 | (+) | 0.750 | 0.595 | tacaaaaCTATgcacaaaaacaaaagc |
| SEQ_22 | P$EINL/TEIL.01 | TEIL (tobacco EIN3-like) | 0.92 | 380 | 388 | (−) | 1.000 | 0.934 | aTGTAgctt |
| SEQ_22 | P$LREM/ATCTA.01 | Motif involved in carotenoid and tocopherol biosynthesis and in the expression of photosynthesis-related genes | 0.85 | 385 | 395 | (+) | 1.000 | 0.931 | acATCTaatac |
| SEQ_22 | P$CE1F/ABI4.01 | ABA insensitive protein 4 (ABI4) | 0.87 | 432 | 444 | (+) | 1.000 | 0.872 | caatCACCgtcga |
| SEQ_22 | P$MYBL/MYBPH3.01 | Myb-like protein of Petunia hybrida | 0.80 | 450 | 466 | (+) | 1.000 | 0.849 | aggattcaGTTAattga |

TABLE 6-continued

| cis-regulatory elements of SEQ ID NO: 22 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_22 | P$CGCG/OSCBT.01 | Oryza sativa CaM-binding transcription factor | 0.78 | 475 | 491 | (-) | 0.817 | 0.796 | cttCGAGtttgatcgga |
| SEQ_22 | P$ROOT/RHE.02 | Root hair-specific element with a 3-nucleotid spacer between left part (LP) and right part (RP) | 0.77 | 486 | 510 | (+) | 1.000 | 0.801 | tcgaagactggtgagCACGaggacg |
| SEQ_22 | P$NCS2/NCS2.01 | Nodulin consensus sequence 2 | 0.79 | 525 | 539 | (-) | 0.750 | 0.823 | tgttgtATCTtcgag |
| SEQ_22 | P$CCAF/CCA1.01 | Circadian clock associated 1 | 0.85 | 539 | 553 | (+) | 1.000 | 0.859 | aagcaagaAATCtac |
| SEQ_22 | P$LREM/ATCTA.01 | Motif involved in carotenoid and tocopherol biosynthesis and in the expression of photosynthesis-related genes | 0.85 | 546 | 556 | (+) | 1.000 | 0.869 | aaATCTactga |
| SEQ_22 | P$L1BX/ATML1.02 | *Arabidopsis thaliana* meristem layer 1 | 0.76 | 563 | 579 | (-) | 0.890 | 0.767 | cgcCAATaacttcagga |
| SEQ_22 | P$AHBP/BLR.01 | Transcriptional repressor BELL-RINGER | 0.90 | 567 | 577 | (+) | 0.826 | 0.936 | gaaGTTAttgg |
| SEQ_22 | P$L1BX/HDG9.01 | Homeodomain glabrous 9 | 0.77 | 595 | 611 | (-) | 0.796 | 0.777 | ccgaaaTTAAttcggat |
| SEQ_22 | P$L1BX/HDG9.01 | Homeodomain glabrous 9 | 0.77 | 597 | 613 | (+) | 0.750 | 0.796 | ccgaatTAATttcgggg |
| SEQ_22 | P$AHBP/BLR.01 | Transcriptional repressor BELL-RINGER | 0.90 | 599 | 609 | (-) | 1.000 | 1.000 | gaaATTAattc |
| SEQ_22 | P$IBOX/GATA.01 | Class I GATA factors | 0.93 | 614 | 630 | (+) | 1.000 | 0.961 | aaaaaGATAaattagat |
| SEQ_22 | P$NCS1/NCS1.01 | Nodulin consensus sequence 1 | 0.85 | 614 | 624 | (+) | 1.000 | 0.948 | aAAAAgataaa |
| SEQ_22 | P$LREM/ATCTA.01 | Motif involved in carotenoid and tocopherol biosynthesis and in the expression of photosynthesis-related genes | 0.85 | 622 | 632 | (-) | 1.000 | 0.921 | gtATCTaattt |
| SEQ_22 | P$ABRE/ABF1.01 | ABA (abscisic acid) inducible transcriptional activator | 0.79 | 657 | 673 | (+) | 0.750 | 0.797 | aagaaACAGgtggcaat |
| SEQ_22 | P$TCPF/ATTCP20.01 | TCP class I transcription factor (Arabidopsis) | 0.94 | 670 | 682 | (-) | 1.000 | 0.949 | tccaGCCCaattg |
| SEQ_22 | P$OCSE/OCSL.01 | OCS-like elements | 0.69 | 715 | 735 | (+) | 0.807 | 0.693 | aaaaaaaacggataACATatt |
| SEQ_22 | P$MSAE/MSA.01 | M-phase-specific activators (NtmybA1, NtmybA2, NtmybB) | 0.80 | 716 | 730 | (+) | 1.000 | 0.851 | aaaaaAACGgataac |

TABLE 6-continued cis-regulatory elements of SEQ ID NO: 22

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_22 | P$MYBL/MYBPH3.01 | Myb-like protein of Petunia hybrida | 0.80 | 717 | 733 | (+) | 0.750 | 0.845 | aaaaaacgGATAacata |
| SEQ_22 | P$MYBS/MYBST1.01 | MybSt1 (Myb Solanum tuberosum 1) with a single myb repeat | 0.90 | 717 | 733 | (-) | 1.000 | 0.962 | tatgttATCCgtttttt |
| SEQ_22 | P$IBOX/GATA.01 | Class I GATA factors | 0.93 | 720 | 736 | (+) | 1.000 | 0.935 | aaacgGATAacatattt |
| SEQ_22 | P$MYBL/GAMYB.01 | GA-regulated myb gene from barley | 0.91 | 722 | 738 | (-) | 1.000 | 0.920 | ataaatatGTTAtccgt |
| SEQ_22 | P$CCAF/CCA1.01 | Circadian clock associated 1 | 0.85 | 764 | 778 | (-) | 0.757 | 0.857 | aaaaagaaAATAtct |
| SEQ_22 | P$MYBL/GAMYB.01 | GA-regulated myb gene from barley | 0.91 | 771 | 787 | (+) | 1.000 | 0.914 | ttctttttGTTAggaaa |
| SEQ_22 | P$SEF4/SEF4.01 | Soybean embryo factor 4 | 0.98 | 772 | 782 | (+) | 1.000 | 0.981 | tcTTTTtgtta |
| SEQ_22 | P$HEAT/HSE.01 | Heat shock element | 0.81 | 783 | 797 | (+) | 1.000 | 0.873 | ggaaaattttAGAAa |
| SEQ_22 | P$HMGF/HMG_IY.01 | High mobility group I/Y-like proteins | 0.89 | 790 | 804 | (-) | 1.000 | 0.895 | ccatTATTttctaaa |
| SEQ_22 | P$SUCB/SUCROSE.01 | Sequence motif from the promoters of different sugar-responsive genes | 0.81 | 794 | 812 | (+) | 1.000 | 0.851 | gaAAATaatggaaattaaa |
| SEQ_22 | P$AHBP/ATHB5.01 | HDZip class I protein ATHB5 | 0.89 | 795 | 805 | (-) | 1.000 | 0.918 | tccATTAtttt |
| SEQ_22 | P$GTBX/S1F.01 | S1F, site 1 binding factor of spinach rps1 promoter | 0.79 | 797 | 813 | (+) | 1.000 | 0.841 | aataATGGaaattaaat |
| SEQ_22 | P$GTBX/SBF1.01 | SBF-1 | 0.87 | 801 | 817 | (+) | 1.000 | 0.908 | atggaaaTTAAatagcg |
| SEQ_22 | P$L1BX/HDG9.01 | Homeodomain glabrous 9 | 0.77 | 803 | 819 | (+) | 1.000 | 0.822 | ggaaatTAAAtagcgat |
| SEQ_22 | P$GTBX/GT3A.01 | Trihelix DNA-binding factor GT-3a | 0.83 | 817 | 833 | (+) | 1.000 | 0.843 | gattatGTTAcaagata |
| SEQ_22 | P$OCSE/OCSL.01 | OCS-like elements | 0.69 | 819 | 839 | (+) | 0.807 | 0.707 | ttatgttacaagatACGAtca |
| SEQ_22 | P$GARP/ARR10.01 | Type-B response regulator (ARR10), member of the GARP-family of plant myb-related DNA binding motifs | 0.97 | 829 | 837 | (+) | 1.000 | 0.985 | AGATacgat |
| SEQ_22 | P$ROOT/RHE.02 | Root hair-specific element with a 3-nucleotid spacer between left part (LP) and right part (RP) | 0.77 | 838 | 862 | (-) | 0.750 | 0.777 | tagcattttgcactgCCCGatgctg |
| SEQ_22 | P$NCS1/NCS1.01 | Nodulin consensus sequence 1 | 0.85 | 877 | 887 | (-) | 0.804 | 0.899 | aAAAGgatcaa |
| SEQ_22 | P$MYBL/GAMYB.01 | GA-regulated myb gene from barley | 0.91 | 882 | 898 | (+) | 1.000 | 0.926 | ccttttggGTTAtctcc |
| SEQ_22 | P$MYBL/MYBPH3.02 | Myb-like protein of Petunia hybrida | 0.76 | 903 | 919 | (+) | 1.000 | 0.785 | gacaatTAGTttaggat |

TABLE 6-continued cis-regulatory elements of SEQ ID NO: 22

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_22 | P$STKM/STK.01 | Storekeeper (STK), plant specific DNA binding protein important for tuber-specific and sucrose-inducible gene expression | 0.85 | 904 | 918 | (-) | 1.000 | 0.865 | tccTAAActaattgt |
| SEQ_22 | P$TELO/ATPURA.01 | *Arabidopsis* Telo-box interacting protein related to the conserved animal protein Pur-alpha | 0.85 | 909 | 923 | (-) | 0.750 | 0.867 | caaaATCCtaaacta |
| SEQ_22 | P$AHBP/BLR.01 | Transcriptional repressor BELL-RINGER | 0.90 | 929 | 939 | (+) | 1.000 | 0.930 | tatATTAatac |
| SEQ_22 | P$IBOX/GATA.01 | Class I GATA factors | 0.93 | 935 | 951 | (-) | 1.000 | 0.932 | tgtcgGATAatagtatt |
| SEQ_22 | P$SPF1/SP8BF.01 | DNA-binding protein of sweet potato that binds to the SP8a (ACTGTGTA) and SP8b (TACTATT) sequences of sporamin and beta-amylase genes | 0.87 | 935 | 947 | (+) | 1.000 | 0.995 | aaTACTattatcc |
| SEQ_22 | P$MYBS/MYBST1.01 | MybSt1 (Myb Solanum tuberosum 1) with a single myb repeat | 0.90 | 938 | 954 | (+) | 1.000 | 0.943 | actattATCCgacaaca |
| SEQ_22 | P$IDDF/ID1.01 | Maize INDETERMINATE1 zinc finger protein | 0.92 | 944 | 956 | (-) | 1.000 | 0.922 | agtgTTGTcggat |
| SEQ_22 | P$MYCL/ICE.01 | ICE (inducer of CBF expression 1), AtMYC2 (rd22BP1) | 0.95 | 946 | 964 | (-) | 0.954 | 0.972 | ctgaaACAAgtgttgtcgg |
| SEQ_22 | P$MYCL/ICE.01 | ICE (inducer of CBF expression 1), AtMYC2 (rd22BP1) | 0.95 | 947 | 965 | (+) | 0.954 | 0.984 | cgacaACACttgtttcagc |
| SEQ_22 | P$GTBX/GT3A.01 | Trihelix DNA-binding factor GT-3a | 0.83 | 968 | 984 | (-) | 1.000 | 0.839 | aaaaatGTTAaaataag |
| SEQ_22 | P$MYBL/MYBPH3.01 | Myb-like protein of Petunia hybrida | 0.80 | 970 | 986 | (-) | 1.000 | 0.807 | caaaaaatGTTAaaata |
| SEQ_22 | P$CCAF/CCA1.01 | Circadian clock associated 1 | 0.85 | 975 | 989 | (-) | 0.766 | 0.872 | aaacaaaaAATGtta |
| SEQ_22 | P$GTBX/S1F.01 | S1F, site 1 binding factor of spinach rps1 promoter | 0.79 | 997 | 1013 | (-) | 1.000 | 0.821 | gctgATGGgaagaagaa |
| SEQ_22 | P$GTBX/SBF1.01 | SBF-1 | 0.87 | 1016 | 1032 | (+) | 1.000 | 0.875 | tttctttTTAAaaaatt |
| SEQ_22 | P$STKM/STK.01 | Storekeeper (STK), plant specific DNA binding protein important for tuber-specific and sucrose-inducible gene expression | 0.85 | 1021 | 1035 | (+) | 1.000 | 0.881 | tttTAAAaaattgaa |

TABLE 6-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 22 | | | | | | | | | |
| SEQ_22 | P$NCS1/NCS1.01 | Nodulin consensus sequence 1 | 0.85 | 1039 | 1049 | (−) | 1.000 | 0.852 | aAAAGgttaaa |
| SEQ_22 | P$GTBX/SBF1.01 | SBF-1 | 0.87 | 1042 | 1058 | (−) | 1.000 | 0.874 | gaaatttTTAAaaagtt |
| SEQ_22 | P$OPAQ/O2.01 | Opaque-2 regulatory protein | 0.87 | 1066 | 1082 | (−) | 1.000 | 0.898 | tccataataTCATctga |
| SEQ_22 | P$AGP1/AGP1.01 | AG-motif binding protein 1 | 0.91 | 1080 | 1090 | (−) | 1.000 | 0.915 | tgaGATCttcc |
| SEQ_22 | P$AGP1/AGP1.01 | AG-motif binding protein 1 | 0.91 | 1081 | 1091 | (+) | 1.000 | 0.911 | gaaGATCtcaa |
| SEQ_22 | P$L1BX/PDF2.01 | Protodermal factor 2 | 0.85 | 1090 | 1106 | (+) | 1.000 | 0.897 | aagagtTAAAtgtatcc |
| SEQ_22 | P$MYBS/OSMYBS.01 | Rice MYB proteins with single DNA binding domains, binding to the amylase element (TATCCA) | 0.82 | 1097 | 1113 | (+) | 1.000 | 0.897 | aaatgTATCcatcttgg |
| SEQ_22 | P$L1BX/PDF2.01 | Protodermal factor 2 | 0.85 | 1111 | 1127 | (−) | 0.848 | 0.899 | ccggttTTAAtgcccca |
| SEQ_22 | P$L1BX/ATML1.02 | *Arabidopsis thaliana* meristem layer 1 | 0.76 | 1113 | 1129 | (+) | 1.000 | 0.854 | gggCATTaaaaccggtg |
| SEQ_22 | P$AHBP/WUS.01 | Homeodomain protein WUSCHEL | 0.94 | 1115 | 1125 | (−) | 1.000 | 1.000 | ggtttTAATgc |
| SEQ_22 | P$IBOX/GATA.01 | Class I GATA factors | 0.93 | 1133 | 1149 | (+) | 1.000 | 0.949 | gggatGATAaatacaga |
| SEQ_22 | P$L1BX/PDF2.01 | Protodermal factor 2 | 0.85 | 1134 | 1150 | (+) | 1.000 | 0.855 | ggatgaTAAAtacagac |
| SEQ_22 | P$ROOT/RHE.02 | Root hair-specific element with a 3-nucleotid spacer between left part (LP) and right part (RP) | 0.77 | 1172 | 1196 | (+) | 1.000 | 0.804 | gtaattcatatttatCACGttgcta |
| SEQ_22 | P$NACF/TANAC69.01 | Wheat NACdomain DNA binding factor | 0.68 | 1176 | 1198 | (+) | 0.895 | 0.684 | ttcatatttatCACGttgctaaa |
| SEQ_22 | P$GBOX/HBP1B.01 | Wheat bZIP transcription factor HBP1B (histone gene binding protein 1b) | 0.83 | 1179 | 1199 | (−) | 1.000 | 0.835 | ttttagcaACGTgataaatat |
| SEQ_22 | P$MYCL/MYCRS.01 | Myc recognition sequences | 0.93 | 1180 | 1198 | (−) | 1.000 | 0.967 | tttagcaACGTgataaata |
| SEQ_22 | P$ABRE/ABRE.01 | ABA response elements | 0.82 | 1181 | 1197 | (+) | 1.000 | 0.826 | atttatcACGTtgctaa |
| SEQ_22 | P$OPAQ/O2_GCN4.01 | Recognition site for BZIP transcription factors that belong to the group of Opaque-2 like proteins Storekeeper (STK), plant specific | 0.81 | 1182 | 1198 | (+) | 0.951 | 0.830 | tttatcACGTtgctaaa |

TABLE 6-continued

| cis-regulatory elements of SEQ ID NO: 22 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_22 | P$STKM/STK.01 | DNA binding protein important for tuber-specific and sucrose-inducible gene expression | 0.85 | 1192 | 1206 | (+) | 1.000 | 0.888 | tgcTAAAaaaattat |
| SEQ_22 | P$LEGB/LEGB.01 | Legumin box, highly conserved sequence element about 100 bp up-stream of the TSS in legumin genes | 0.59 | 1223 | 1249 | (+) | 0.750 | 0.609 | acaaaatCAATtaaagagaaagaaaga |
| SEQ_22 | P$DOFF/DOF1.01 | Dof1/MNB1a - single zinc finger transcription factor | 0.98 | 1227 | 1243 | (+) | 1.000 | 0.991 | aatcaattAAAGagaaa |
| SEQ_22 | P$GAGA/GAGABP.01 | (GA)n/(CT)n binding proteins (GBP, soybean; BBR, barley) | 0.75 | 1231 | 1255 | (+) | 1.000 | 0.790 | aattaaAGAGaaagaaagaaacgca |
| SEQ_22 | P$NCS2/NCS2.01 | Nodulin consensus sequence 2 | 0.79 | 1232 | 1246 | (-) | 1.000 | 0.808 | ttctttCTCTttaat |
| SEQ_22 | P$OCSE/OCSL.01 | OCS-like elements | 0.69 | 1283 | 1303 | (+) | 0.769 | 0.735 | taaaataaaaattaACGCatg |
| SEQ_22 | P$SEF4/SEF4.01 | Soybean embryo factor 4 | 0.98 | 1285 | 1295 | (-) | 1.000 | 0.983 | aaTTTTtattt |
| SEQ_22 | P$OPAQ/O2_GCN4.01 | Recognition site for BZIP transcription factors that belong to the group of Opaque-2 like proteins | 0.81 | 1294 | 1310 | (-) | 1.000 | 0.825 | cattcaACATgcgttaa |
| SEQ_22 | P$IDRE/IDE1.01 | Iron-deficiency-responsive element 1 | 0.77 | 1297 | 1311 | (+) | 1.000 | 0.773 | acGCATgttgaatgc |
| SEQ_22 | P$GBOX/BZIP910.02 | bZIP transcription factor from Antirrhinum majus | 0.84 | 1300 | 1320 | (+) | 1.000 | 0.864 | catgttgaatgcTGACatgtc |
| SEQ_22 | P$GBOX/BZIP910.01 | bZIP transcription factor from Antirrhinum majus | 0.77 | 1306 | 1326 | (+) | 1.000 | 0.784 | gaatgcTGACatgtcagtatg |
| SEQ_22 | P$ABRE/ABF1.03 | ABA (abscisic acid) inducible transcriptional activator | 0.82 | 1307 | 1323 | (+) | 0.750 | 0.829 | aatgctgaCATGtcagt |
| SEQ_22 | P$OPAQ/O2.01 | Opaque-2 regulatory protein | 0.87 | 1307 | 1323 | (-) | 0.794 | 0.901 | actgacatgTCAGcatt |
| SEQ_22 | P$GTBX/S1F.01 | S1F, site 1 binding factor of spinach rps1 promoter | 0.79 | 1319 | 1335 | (-) | 1.000 | 0.818 | attcATGGacatactga |
| SEQ_22 | P$ROOT/RHE.01 | Root hair-specific element with a 2-nucleotid spacer between left part (LP) and right part (RP) | 0.77 | 1322 | 1346 | (+) | 1.000 | 0.844 | gtatgtccatgaatcCACGtatcaa |
| SEQ_22 | P$GBOX/GBF1.01 | bZIP protein G-Box binding factor 1 | 0.94 | 1329 | 1349 | (-) | 1.000 | 0.956 | cgcttgatACGTggattcatg |

TABLE 6-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 22 | | | | | | | | | |
| SEQ_22 | P$GBOX/HBP1A.01 | HBP-1a, suggested to be involved in the cell cycle-dependent expression | 0.88 | 1330 | 1350 | (+) | 1.000 | 0.899 | atgaatcCACGtatcaagcgc |
| SEQ_22 | P$ABRE/ABRE.01 | ABA response elements | 0.82 | 1332 | 1348 | (−) | 1.000 | 0.866 | gcttgatACGTggattc |
| SEQ_22 | P$L1BX/ATML1.01 | L1-specific homeodomain protein ATML1 (*A. thaliana* meristem layer 1) | 0.82 | 1370 | 1386 | (+) | 1.000 | 0.889 | tctttcTAAAtgaaaac |
| SEQ_22 | P$GAPB/GAP.01 | Cis-element in the GAPDH promoters conferring light inducibility | 0.88 | 1375 | 1389 | (+) | 1.000 | 0.958 | ctaaATGAaaacaac |
| SEQ_22 | P$URNA/USE.01 | Upstream sequence elements in the promoters of U-snRNA genes of higher plants | 0.75 | 1387 | 1403 | (+) | 0.750 | 0.781 | aacttcACACatcacaa |
| SEQ_22 | P$MYBL/MYBPH3.02 | Myb-like protein of Petunia hybrida | 0.76 | 1396 | 1412 | (−) | 0.817 | 0.771 | tattgtTTGTtgtgatg |
| SEQ_22 | P$DPBF/DPBF.01 | bZIP factors DPBF-1 and 2 (Dc3 promoter binding factor-1 and 2) | 0.89 | 1413 | 1423 | (+) | 1.000 | 0.898 | cACACaagacc |
| SEQ_22 | P$GAGA/BPC.01 | Basic pentacysteine proteins | 1.00 | 1413 | 1437 | (−) | 1.000 | 1.000 | aacgagAGAGagggggtcttgtgtg |
| SEQ_22 | P$GAGA/GAGABP.01 | (GA)n/(CT)n binding proteins (GBP, soybean; BBR, barley) | 0.75 | 1423 | 1447 | (−) | 0.750 | 0.805 | gcagagAGACaacgagagagagggg |
| SEQ_22 | P$GAGA/BPC.01 | Basic pentacysteine proteins | 1.00 | 1425 | 1449 | (−) | 1.000 | 1.000 | tggcagAGAGacaacgagagagagg |
| SEQ_22 | P$PREM/MGPROTORE.01 | Promoter elements involved in MgProto (Mg-protoporphyrin IX) and light-mediated induction | 0.77 | 1447 | 1477 | (+) | 1.000 | 0.794 | ccagCGACcaaatcgaagcttgagaagaaca |

TABLE 7 cis-regulatory elements of SEQ ID NO: 25

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_25 | P$IBOX/GATA.01 | Class I GATA factors | 0.93 | 27 | 43 | (+) | 1.000 | 0.946 | aaaaaGATAaccacccc |
| SEQ_25 | P$NCS1/NCS1.01 | Nodulin consensus sequence 1 | 0.85 | 27 | 37 | (+) | 1.000 | 0.948 | aAAAAgataac |
| SEQ_25 | P$MYBL/GAMYB.01 | GA-regulated myb gene from barley | 0.91 | 29 | 45 | (-) | 1.000 | 0.980 | agggggtgGTTAtcttt |
| SEQ_25 | P$SALT/ALFIN1.02 | Zinc-finger protein in alfalfa roots, regulates salt tolerance | 0.95 | 34 | 48 | (-) | 1.000 | 0.977 | gctagggGGTGgtta |
| SEQ_25 | P$SUCB/SUCROSE.01 | Sequence motif from the promoters of different sugar-responsive genes | 0.81 | 57 | 75 | (+) | 1.000 | 0.852 | ccAAATcataactatcaga |
| SEQ_25 | P$AHBP/ATHB9.01 | HD-ZIP class III protein ATHB9 | 0.77 | 58 | 68 | (-) | 1.000 | 0.772 | gttATGAtttg |
| SEQ_25 | P$MYBL/MYBPH3.02 | Myb-like protein of *Petunia hybrida* | 0.76 | 60 | 76 | (-) | 1.000 | 0.808 | ttctgaTAGTtatgatt |
| SEQ_25 | P$IBOX/GATA.01 | Class I GATA factors | 0.93 | 76 | 92 | (+) | 1.000 | 0.975 | acaaaGATAaaaagccc |
| SEQ_25 | P$DOFF/DOF3.01 | Dof3 - single zinc finger transcription factor | 0.99 | 78 | 94 | (+) | 1.000 | 0.996 | aaagataaAAAGcccga |
| SEQ_25 | P$SBPD/SBP.01 | SQUA promoter binding proteins | 0.88 | 99 | 115 | (-) | 1.000 | 0.882 | ctatgGTACaacatggt |
| SEQ_25 | P$NCS3/NCS3.01 | Nodulin consensus sequence 3 | 0.89 | 119 | 129 | (+) | 1.000 | 0.893 | caCACCctcta |
| SEQ_25 | P$LEGB/LEGB.01 | Legumin box, highly conserved sequence element about 100 by up-stream of the TSS in legumin genes | 0.59 | 122 | 148 | (-) | 0.750 | 0.626 | ttcataaCTATgtatgagatagagggt |
| SEQ_25 | P$MYBL/MYBPH3.02 | Myb-like protein of *Petunia hybrida* | 0.76 | 133 | 149 | (+) | 1.000 | 0.778 | catacaTAGTtatgaat |
| SEQ_25 | P$MIIG/P_ACT.01 | Maize activator P of flavonoid bio-synthetic genes | 0.93 | 150 | 164 | (-) | 1.000 | 0.977 | ttacGGTAggtttca |
| SEQ_25 | P$MYBL/ATMYB77.01 | R2R3-type myb-like transcription factor (I-type binding site) | 0.87 | 172 | 188 | (-) | 1.000 | 0.909 | ttgtggCGGTtcctgct |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$DREB/HVDRF1.01 | *H. vulgare* dehydration-response factor 1 | 0.89 | 175 | 189 | (+) | 1.000 | 0.953 | aggaACCGccacaat |
| SEQ_25 | P$GCCF/ERE_JERE.01 | Ethylene-responsive elements (ERE) and jasmonate- and elicitor-responsive elements (JERE) | 0.85 | 175 | 187 | (+) | 1.000 | 0.865 | aggaacCGCCaca |
| SEQ_25 | P$MYBS/TAMYB80.01 | MYB protein from wheat | 0.83 | 191 | 207 | (−) | 1.000 | 0.874 | gcttATATtcccctcac |
| SEQ_25 | P$TEFB/TEF1.01 | TEF cis acting elements in both RNA polymerase II-dependent promoters and rDNA spacer sequences | 0.76 | 192 | 212 | (+) | 1.000 | 0.796 | tgAGGGgaatataagccaaag |
| SEQ_25 | P$LEGB/LEGB.01 | Legumin box, highly conserved sequence element about 100 by up-stream of the TSS in legumin genes | 0.59 | 206 | 232 | (+) | 0.750 | 0.649 | gccaaagCCCTgcaattttcagtgaga |
| SEQ_25 | P$TEFB/TEF1.01 | TEF cis acting elements in both RNA polymerase II-dependent promoters and rDNA spacer sequences | 0.76 | 230 | 250 | (+) | 0.956 | 0.795 | agAAGGgtaagattattaaag |
| SEQ_25 | P$AHBP/HAHB4.01 | Sunflower homeodomain leucine-zipper protein Hahb-4 | 0.87 | 238 | 248 | (+) | 1.000 | 0.903 | aagattATTAa |
| SEQ_25 | P$DOFF/DOF1.01 | Dof1/MNB1a - single zinc finger transcription factor | 0.98 | 239 | 255 | (+) | 1.000 | 0.980 | agattattAAAGgcagc |
| SEQ_25 | P$L1BX/ATML1.01 | L1-specific homeodomain protein ATML1 (*A. thaliana* meristem layer 1) | 0.82 | 240 | 256 | (+) | 1.000 | 0.835 | gattatTAAAggcagcc |
| SEQ_25 | P$DREB/CRT_DRE.01 | C-repeat/dehydration response element | 0.89 | 262 | 276 | (−) | 1.000 | 0.968 | ctttgCCGAcattgt |
| SEQ_25 | P$URNA/USE.01 | Upstream sequence elements in the promoters of U-snRNA genes of higher plants | 0.75 | 284 | 300 | (−) | 1.000 | 0.858 | aatgtcCCACctcgaat |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$GTBX/SBF1.01 | SBF-1 | 0.87 | 292 | 308 | (+) | 1.000 | 0.908 | tgggacaTTAAatttaa |
| SEQ_25 | P$L1BX/HDG9.01 | Homeodomain glabrous 9 | 0.77 | 292 | 308 | (-) | 0.796 | 0.792 | ttaaatTTAAtgtccca |
| SEQ_25 | P$L1BX/PDF2.01 | Protodermal factor 2 | 0.85 | 294 | 310 | (+) | 1.000 | 0.851 | ggacatTAAAtttaaaa |
| SEQ_25 | P$AHBP/WUS.01 | Homeodomain protein WUSCHEL | 0.94 | 296 | 306 | (-) | 1.000 | 1.000 | aaattTAATgt |
| SEQ_25 | P$GTBX/SBF1.01 | SBF-1 | 0.87 | 298 | 314 | (+) | 1.000 | 0.875 | attaaatTTAAaaagaa |
| SEQ_25 | P$GTBX/SBF1.01 | SBF-1 | 0.87 | 299 | 315 | (-) | 1.000 | 0.885 | cttctttTTAAatttaa |
| SEQ_25 | P$IDRE/IDE1.01 | Iron-deficiency-responsive element 1 | 0.77 | 325 | 339 | (-) | 0.809 | 0.806 | aaGCTTgctactttc |
| SEQ_25 | P$AGP1/AGP1.01 | AG-motif binding protein 1 | 0.91 | 376 | 386 | (+) | 1.000 | 0.912 | caaGATCttcc |
| SEQ_25 | P$AHBP/WUS.01 | Homeodomain protein WUSCHEL | 0.94 | 383 | 393 | (+) | 1.000 | 0.963 | ttcctTAATcc |
| SEQ_25 | P$GTBX/S1F.01 | S1F, site 1 binding factor of spinach rps1 promoter | 0.79 | 383 | 399 | (-) | 1.000 | 0.810 | tgttATGGattaaggaa |
| SEQ_25 | P$MADS/AGL2.01 | AGL2, *Arabidopsis* MADS-domain protein AGAMOUS-like 2 | 0.82 | 387 | 407 | (+) | 1.000 | 0.865 | ttaatCCATaacaagaagtcc |
| SEQ_25 | P$AHBP/ATHB5.01 | HDZip class I protein ATHB5 | 0.89 | 435 | 445 | (+) | 0.829 | 0.940 | acaATGAttct |
| SEQ_25 | P$AHBP/ATHB5.01 | HDZip class I protein ATHB5 | 0.89 | 435 | 445 | (-) | 0.936 | 0.941 | agaATCAttgt |
| SEQ_25 | P$SUCB/SUCROSE.01 | Sequence motif from the promoters of different sugar-responsive genes | 0.81 | 444 | 462 | (+) | 1.000 | 0.875 | ctAAATcatacatattacc |
| SEQ_25 | P$MADS/AGL15.01 | AGL15, *Arabidopsis* MADS-domain protein AGAMOUS-like 15 | 0.79 | 487 | 507 | (-) | 0.850 | 0.804 | tttTGCTacacctggtagtag |
| SEQ_25 | P$MYCL/ICE.01 | ICE (inducer of CBF expression 1), AtMYC2 (rd22BP1) | 0.95 | 487 | 505 | (-) | 0.954 | 0.966 | ttgctACACctggtagtag |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$MADS/AGL2.01 | AGL2, *Arabidopsis* MADS-domain protein AGAMOUS-like 2 | 0.82 | 488 | 508 | (+) | 0.869 | 0.855 | tactaCCAGgtgtagcaaaat |
| SEQ_25 | P$L1BX/PDF2.01 | Protodermal factor 2 | 0.85 | 510 | 526 | (+) | 1.000 | 0.880 | cccgatTAAAttcataa |
| SEQ_25 | P$AHBP/WUS.01 | Homeodomain protein WUSCHEL | 0.94 | 512 | 522 | (-) | 1.000 | 0.963 | gaattTAATcg |
| SEQ_25 | P$RAV5/RAV1-5.01 | 5'-part of bipartite RAV1 binding site, interacting with AP2 domain | 0.96 | 537 | 547 | (-) | 1.000 | 0.974 | agcAACAaaat |
| SEQ_25 | P$CARM/CARICH.01 | CA-rich element | 0.78 | 548 | 566 | (+) | 1.000 | 0.837 | accttcaAACAacagatgc |
| SEQ_25 | P$MYCL/ICE.01 | ICE (inducer of CBF expression 1), AtMYC2 (rd22BP1) | 0.95 | 554 | 572 | (+) | 0.863 | 0.954 | aaacaACAGatgctcgcaa |
| SEQ_25 | P$RAV5/RAV1-5.01 | 5'-part of bipartite RAV1 binding site, interacting with AP2 domain | 0.96 | 555 | 565 | (+) | 1.000 | 0.961 | aacAACAgatg |
| SEQ_25 | P$MYBL/MYBPH3.02 | Myb-like protein of *Petunia hybrida* | 0.76 | 596 | 612 | (+) | 1.000 | 0.771 | tctagcTAGTaacgacc |
| SEQ_25 | P$MYBL/NTMYBAS1.01 | Anther-specific myb gene from tobacco | 0.96 | 600 | 616 | (-) | 1.000 | 0.975 | gttaggtcGTTActagc |
| SEQ_25 | P$MYBL/GAMYB.01 | GA-regulated myb gene from barley | 0.91 | 608 | 624 | (-) | 1.000 | 0.927 | atagtgttGTTAggtcg |
| SEQ_25 | P$MIIG/PALBOXL.01 | Cis-acting element conserved in various PAL and 4CL promoters | 0.80 | 622 | 636 | (-) | 1.000 | 0.812 | atctgtttGGTGata |
| SEQ_25 | P$CARM/CARICH.01 | CA-rich element | 0.78 | 623 | 641 | (+) | 1.000 | 0.788 | atcaccaAACAgataaaca |
| SEQ_25 | P$MYBL/CARE.01 | CAACTC regulatory elements, GA-inducible | 0.83 | 646 | 662 | (+) | 1.000 | 0.834 | tctagcgAGTTccagca |
| SEQ_25 | P$CE1F/ABI4.01 | ABA insensitive protein 4 (ABI4) | 0.87 | 680 | 692 | (+) | 1.000 | 0.900 | tcgcCACCgacga |
| SEQ_25 | P$DREB/CRT_DRE.01 | C-repeat/dehydration response element | 0.89 | 681 | 695 | (+) | 1.000 | 0.914 | cgccaCCGAcgatta |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$PREM/MGPROTORE.01 | Promoter elements involved in MgProto (Mg-protoporphyrin IX) and light-mediated induction | 0.77 | 683 | 713 | (+) | 1.000 | 0.774 | ccacCGACgattatcgattcactaaagctac |
| SEQ_25 | P$DOFF/DOF1.01 | Dof1/MNB1a - single zinc finger transcription factor | 0.98 | 698 | 714 | (+) | 1.000 | 1.000 | gattcactAAAGctaca |
| SEQ_25 | P$CGCG/ATSR1.01 | *Arabidopsis thaliana* signal-responsive gene1, Ca2+/calmodulin binding protein homolog to NtER1 (tobacco early ethylene-responsive gene) | 0.84 | 714 | 730 | (−) | 1.000 | 0.865 | ccaCGCGtgtacttgtt |
| SEQ_25 | P$CE3S/CE3.01 | Coupling element 3 (CE3), non-ACGT ABRE | 0.77 | 715 | 733 | (−) | 1.000 | 0.787 | tatccaCGCGtgtacttgt |
| SEQ_25 | P$CGCG/ATSR1.01 | *Arabidopsis thaliana* signal-responsive gene1, Ca2+/calmodulin binding protein homolog to NtER1 (tobacco early ethylene-responsive gene) | 0.84 | 721 | 737 | (+) | 1.000 | 0.870 | acaCGCGtggatagtgg |
| SEQ_25 | P$MYBS/MYBST1.01 | MybSt1 (Myb *Solanum tuberosum* 1) with a single myb repeat | 0.90 | 722 | 738 | (−) | 1.000 | 0.936 | tccactATCCacgcgtg |
| SEQ_25 | P$HOCT/HOCT.01 | Octamer motif found in plant histone H3 and H4 genes | 0.76 | 723 | 739 | (−) | 1.000 | 0.768 | ttccactATCCacgcgt |
| SEQ_25 | P$MYBS/ZMMRP1.01 | *Zea mays* MYB-related protein 1 (transfer cell specific) | 0.79 | 732 | 748 | (−) | 0.777 | 0.852 | atttctcTATTccacta |
| SEQ_25 | P$NCS2/NCS2.01 | Nodulin consensus sequence 2 | 0.79 | 746 | 760 | (+) | 0.750 | 0.803 | aattgcCTGTtcaac |
| SEQ_25 | P$MSAE/MSA.01 | M-phase-specific activators (NtmybA1, NtmybA2, NtmybB) | 0.80 | 753 | 767 | (+) | 1.000 | 0.875 | tgttcAACGgggaga |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$PREM/MGPROTORE.01 | Promoter elements involved in MgProto (Mg-protoporphyrin IX) and light-mediated induction | 0.77 | 786 | 816 | (+) | 1.000 | 0.801 | atagCGACaaggaggaggagcgatattgcta |
| SEQ_25 | P$IDDF/ID1.01 | Maize INDETERMINATE1 zinc finger protein | 0.92 | 787 | 799 | (−) | 1.000 | 0.921 | ctccTTGTcgcta |
| SEQ_25 | P$MYBS/MYBST1.01 | MybSt1 (Myb *Solanum tuberosum* 1) with a single myb repeat | 0.90 | 810 | 826 | (+) | 1.000 | 0.928 | attgctATCCggaaagt |
| SEQ_25 | P$DREB/HVDRF1.01 | *H. vulgare* dehydration-response factor 1 | 0.89 | 842 | 856 | (+) | 0.826 | 0.914 | actcGCCGccatata |
| SEQ_25 | P$GARP/ARR10.01 | Type-B response regulator (ARR10), member of the GARP-family of plant myb-related DNA binding motifs | 0.97 | 857 | 865 | (−) | 1.000 | 0.970 | AGATccttg |
| SEQ_25 | P$SALT/ALFIN1.01 | Zinc-finger protein in alfalfa roots, regulates salt tolerance | 0.93 | 872 | 886 | (−) | 1.000 | 0.930 | ccttgGTGGcgccgt |
| SEQ_25 | P$PREM/MGPROTORE.01 | Promoter elements involved in MgProto (Mg-protoporphyrin IX) and light-mediated induction | 0.77 | 888 | 918 | (−) | 1.000 | 0.774 | actaCGACggcgatgagggtgaccattcgag |
| SEQ_25 | P$NCS3/NCS3.01 | Nodulin consensus sequence 3 | 0.89 | 896 | 906 | (+) | 1.000 | 0.947 | gtCACCctcat |
| SEQ_25 | P$AHBP/ATHB9.01 | HD-ZIP class III protein ATHB9 | 0.77 | 920 | 930 | (+) | 0.750 | 0.773 | gtaTTGAtctc |
| SEQ_25 | P$GARP/ARR10.01 | Type-B response regulator (ARR10), member of the GARP-family of plant myb-related DNA binding motifs | 0.97 | 941 | 949 | (+) | 1.000 | 0.973 | AGATcctgg |
| SEQ_25 | P$ABRE/ABF1.03 | ABA (abscisic acid) inducible transcriptional activator | 0.82 | 952 | 968 | (−) | 1.000 | 0.833 | ggcgaggcCGTGgctca |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$L1BX/ATML1.02 | *Arabidopsis thaliana* meristem layer 1 | 0.76 | 987 | 1003 | (-) | 1.000 | 0.791 | aggCATTcaaatctggc |
| SEQ_25 | P$L1BX/PDF2.01 | Protodermal factor 2 | 0.85 | 989 | 1005 | (+) | 0.787 | 0.854 | cagattTGAAtgcctcc |
| SEQ_25 | P$HEAT/HSE.01 | Heat shock element | 0.81 | 1015 | 1029 | (-) | 1.000 | 0.822 | gcatatctccAGAAt |
| SEQ_25 | P$MYBL/MYBPH3.02 | Myb-like protein of *Petunia hybrida* | 0.76 | 1076 | 1092 | (+) | 0.817 | 0.775 | gagagaTTGTtgctttc |
| SEQ_25 | P$CCAF/CCA1.01 | Circadian clock associated 1 | 0.85 | 1077 | 1091 | (-) | 1.000 | 0.893 | aaagcaacAATCtct |
| SEQ_25 | P$GTBX/GT3A.01 | Trihelix DNA-binding factor GT-3a | 0.83 | 1107 | 1123 | (+) | 1.000 | 0.847 | atcagtGTTActtcgat |
| SEQ_25 | P$CCAF/CCA1.01 | Circadian clock associated 1 | 0.85 | 1126 | 1140 | (-) | 1.000 | 0.898 | gcaaacagAATCtca |
| SEQ_25 | P$GAGA/BPC.01 | Basic pentacysteine proteins | 1.00 | 1128 | 1152 | (-) | 1.000 | 1.000 | cgagagAGAGaggcaaacagaatct |
| SEQ_25 | P$GAGA/BPC.01 | Basic pentacysteine proteins | 1.00 | 1130 | 1154 | (-) | 1.000 | 1.000 | aacgagAGAGagaggcaaacagaat |
| SEQ_25 | P$HEAT/HSE.01 | Heat shock element | 0.81 | 1130 | 1144 | (-) | 1.000 | 0.855 | agaggcaaacAGAAt |
| SEQ_25 | P$GAGA/GAGABP.01 | (GA)n/(CT)n binding proteins (GBP, soybean; BBR, barley) | 0.75 | 1134 | 1158 | (-) | 0.750 | 0.760 | ccagaaCGAGagagagaggcaaaca |
| SEQ_25 | P$GAGA/GAGABP.01 | (GA)n/(CT)n binding proteins (GBP, soybean; BBR, barley) | 0.75 | 1138 | 1162 | (-) | 0.750 | 0.757 | gaaaccAGAAcgagagagagaggca |
| SEQ_25 | P$PSRE/GAAA.01 | GAAA motif involved in pollen specific transcriptional activation | 0.83 | 1164 | 1180 | (+) | 1.000 | 0.843 | ctgtaGAAAaactttt |
| SEQ_25 | P$NCS1/NCS1.01 | Nodulin consensus sequence 1 | 0.85 | 1170 | 1180 | (-) | 1.000 | 0.853 | aAAAAgttttt |
| SEQ_25 | P$PSRE/GAAA.01 | GAAA motif involved in pollen specific transcriptional activation | 0.83 | 1185 | 1201 | (-) | 1.000 | 0.838 | ctaaaGAAAatgttcgc |

TABLE 7-continued cis-regulatory elements of SEQ ID NO: 25

| Seq. name | Family/matrix | Further Information | Opt. thresh. | Start pos. | End pos. | Strand | Core sim. | Matrix sim. | Sequence |
|---|---|---|---|---|---|---|---|---|---|
| SEQ_25 | P$DOFF/DOF1.01 | Dof1/MNB1a - single zinc finger transcription factor | 0.98 | 1191 | 1207 | (-) | 1.000 | 0.984 | ttgggcctAAAGaaaat |
| SEQ_25 | P$TCPF/ATTCP20.01 | TCP class I transcription factor (*Arabidopsis*) | 0.94 | 1198 | 1210 | (+) | 1.000 | 0.968 | ttagGCCCaaagt |
| SEQ_25 | P$TCPF/ATTCP20.01 | TCP class I transcription factor (*Arabidopsis*) | 0.94 | 1208 | 1220 | (-) | 1.000 | 0.943 | aaaaGCCCaaact |
| SEQ_25 | P$DOFF/DOF3.01 | Dof3 - single zinc finger transcription factor | 0.99 | 1211 | 1227 | (-) | 1.000 | 0.994 | cgttattaAAAGcccaa |
| SEQ_25 | P$L1BX/HDG9.01 | Homeodomain glabrous 9 | 0.77 | 1211 | 1227 | (-) | 1.000 | 0.818 | cgttatTAAAagcccaa |
| SEQ_25 | P$GTBX/SBF1.01 | SBF-1 | 0.87 | 1213 | 1229 | (-) | 1.000 | 0.927 | ggcgttaTTAAaagccc |
| SEQ_25 | P$DOFF/DOF3.01 | Dof3 - single zinc finger transcription factor | 0.99 | 1223 | 1239 | (+) | 1.000 | 0.995 | taacgcctAAAGcccaa |
| SEQ_25 | P$CAAT/CAAT.01 | CCAAT-box in plant promoters | 0.97 | 1250 | 1258 | (-) | 1.000 | 0.979 | acCCAAtaa |
| SEQ_25 | P$TEFB/TEF1.01 | TEF cis acting elements in both RNA polymerase II-dependent promoters and rDNA spacer sequences | 0.76 | 1288 | 1308 | (+) | 0.956 | 0.767 | atAAGGggaatctatttattt |
| SEQ_25 | P$MADS/SQUA.01 | MADS-box protein SQUAMOSA | 0.90 | 1294 | 1314 | (+) | 1.000 | 0.917 | ggaatctATTTatttaattgt |
| SEQ_25 | P$STKM/STK.01 | Storekeeper (STK), plant specific DNA binding protein important for tuber-specific and sucrose-inducible gene expression | 0.85 | 1298 | 1312 | (-) | 1.000 | 0.859 | aatTAAAtaaataga |
| SEQ_25 | P$L1BX/HDG9.01 | Homeodomain glabrous 9 | 0.77 | 1299 | 1315 | (-) | 1.000 | 0.791 | aacaatTAAAtaaatag |
| SEQ_25 | P$HMGF/HMG_IY.01 | High mobility group I/Y-like proteins | 0.89 | 1300 | 1314 | (+) | 1.000 | 0.907 | tattTATTtaattgt |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$GTBX/SBF1.01 | SBF-1 | 0.87 | 1307 | 1323 | (+) | 1.000 | 0.872 | ttaattgTTAAtcattc |
| SEQ_25 | P$AHBP/WUS.01 | Homeodomain protein WUSCHEL | 0.94 | 1310 | 1320 | (+) | 1.000 | 0.963 | attgtTAATca |
| SEQ_25 | P$OCSE/OCSL.01 | OCS-like elements | 0.69 | 1310 | 1330 | (+) | 1.000 | 0.712 | attgttaatcattcACGTtga |
| SEQ_25 | P$LEGB/LEGB.01 | Legumin box, highly conserved sequence element about 100 bp up-stream of the TSS in legumin genes | 0.59 | 1311 | 1337 | (+) | 0.750 | 0.625 | ttgttaaTCATtcacgttgaccattga |
| SEQ_25 | P$AHBP/ATHB5.01 | HDZip class I protein ATHB5 | 0.89 | 1314 | 1324 | (+) | 0.936 | 0.939 | ttaATCAttca |
| SEQ_25 | P$AHBP/HAHB4.01 | Sunflower homeodomain leucine-zipper protein Hahb-4 | 0.87 | 1314 | 1324 | (−) | 1.000 | 0.945 | tgaatgATTAa |
| SEQ_25 | P$GBOX/HBP1B.01 | Wheat bZIP transcription factor HBP1B (histone gene binding protein 1b) | 0.83 | 1315 | 1335 | (−) | 1.000 | 0.834 | aatggtcaACGTgaatgatta |
| SEQ_25 | P$OPAQ/O2_GCN4.01 | Recognition site for BZIP transcription factors that belong to the group of Opaque-2 like proteins | 0.81 | 1317 | 1333 | (−) | 0.951 | 0.842 | tggtcaACGTgaatgat |
| SEQ_25 | P$WBXF/ERE.01 | Elicitor response element | 0.89 | 1322 | 1338 | (+) | 1.000 | 0.917 | tcacgtTGACcattgaa |
| SEQ_25 | P$HEAT/HSE.01 | Heat shock element | 0.81 | 1328 | 1342 | (+) | 1.000 | 0.826 | tgaccattgaAGAAc |
| SEQ_25 | P$NCS1/NCS1.01 | Nodulin consensus sequence 1 | 0.85 | 1373 | 1383 | (−) | 0.804 | 0.896 | cAAAGgatcaa |
| SEQ_25 | P$MADS/AGL2.01 | AGL2, *Arabidopsis* MADS-domain protein AGAMOUS-like 2 | 0.82 | 1408 | 1428 | (+) | 0.869 | 0.838 | tgtctCCAGctctagtaatga |
| SEQ_25 | P$MYBL/MYBPH3.02 | Myb-like protein of *Petunia hybrida* | 0.76 | 1427 | 1443 | (+) | 1.000 | 0.785 | gacaatTAGTttagttt |

TABLE 7-continued

| Seq. name | Family/matrix | Further Information | Opt. thresh. | Start pos. | End pos. | Strand | Core sim. | Matrix sim. | Sequence |
|---|---|---|---|---|---|---|---|---|---|
| cis-regulatory elements of SEQ ID NO: 25 | | | | | | | | | |
| SEQ_25 | P$STKM/STK.01 | Storekeeper (STK), plant specific DNA binding protein important for tuber-specific and sucrose-inducible gene expression | 0.85 | 1428 | 1442 | (-) | 1.000 | 0.864 | aacTAAActaattgt |
| SEQ_25 | P$SPF1/SP8BF.01 | DNA-binding protein of sweet potato that binds to the SP8a (ACTGTGTA) and SP8b (TACTATT) sequences of sporamin and beta-amylase genes | 0.87 | 1459 | 1471 | (-) | 1.000 | 0.989 | aaTACTattacac |
| SEQ_25 | P$GTBX/SBF1.01 | SBF-1 | 0.87 | 1495 | 1511 | (-) | 1.000 | 0.886 | aaaattgTTAAataata |
| SEQ_25 | P$MYBL/MYBPH3.01 | Myb-like protein of *Petunia hybrida* | 0.80 | 1497 | 1513 | (-) | 1.000 | 0.809 | agaaaattGTTAaataa |
| SEQ_25 | P$E2FF/E2F.01 | E2F class I sites | 0.82 | 1527 | 1541 | (+) | 1.000 | 0.832 | ttttTTCCagcaacg |
| SEQ_25 | P$GTBX/SBF1.01 | SBF-1 | 0.87 | 1548 | 1564 | (+) | 1.000 | 0.874 | tgaatttTTAAaacttg |
| SEQ_25 | P$SUCB/SUCROSE.01 | Sequence motif from the promoters of different sugar-responsive genes | 0.81 | 1552 | 1570 | (-) | 0.750 | 0.832 | aaATATcaagttttaaaaa |
| SEQ_25 | P$CCAF/CCA1.01 | Circadian clock associated 1 | 0.85 | 1568 | 1582 | (-) | 1.000 | 0.854 | ttaaaaaaAATCaaa |
| SEQ_25 | P$AHBP/BLR.01 | Transcriptional repressor BELL-RINGER | 0.90 | 1581 | 1591 | (-) | 1.000 | 0.976 | taaATTActtt |
| SEQ_25 | P$GTBX/SBF1.01 | SBF-1 | 0.87 | 1583 | 1599 | (-) | 1.000 | 0.900 | tttgcatTTAAattact |
| SEQ_25 | P$L1BX/ATML1.01 | L1-specific homeodomain protein ATML1 (*A. thaliana* meristem layer 1) | 0.82 | 1584 | 1600 | (+) | 1.000 | 0.918 | gtaattTAAAtgcaaaa |
| SEQ_25 | P$NCS1/NCS1.01 | Nodulin consensus sequence 1 | 0.85 | 1606 | 1616 | (+) | 0.878 | 0.862 | cAAATgatatt |
| SEQ_25 | P$MYBL/CARE.01 | CAACTC regulatory elements, GA-inducible | 0.83 | 1625 | 1641 | (+) | 1.000 | 0.834 | actcaagAGTTgtgtga |
| SEQ_25 | P$NCS2/NCS2.01 | Nodulin consensus sequence 2 | 0.79 | 1653 | 1667 | (-) | 1.000 | 0.809 | acttgcCTCTtgccc |
| SEQ_25 | P$TEFB/TEF1.01 | TEF cis acting elements in both RNA polymerase II-dependent promoters and rDNA spacer sequences | 0.76 | 1665 | 1685 | (-) | 0.956 | 0.816 | agAAGGatacaccagtgcact |

TABLE 7-continued

| cis-regulatory elements of SEQ ID NO: 25 | | | | | | | | | | |
|---|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$MYBS/HVMCB1.01 | Hordeum vulgare Myb-related CAB-promoter-binding protein 1 | 0.93 | 1672 | 1688 | (+) | 1.000 | 0.933 | tggtgtATCCttctcgg |
| SEQ_25 | P$GTBX/SBF1.01 | SBF-1 | 0.87 | 1686 | 1702 | (+) | 1.000 | 0.878 | cggggcgTTAAaaccgt |
| SEQ_25 | P$NCS3/NCS3.01 | Nodulin consensus sequence 3 | 0.89 | 1702 | 1712 | (-) | 1.000 | 0.965 | gtCACCttcca |
| SEQ_25 | P$MYBL/MYBPH3.01 | Myb-like protein of *Petunia hybrida* | 0.80 | 1704 | 1720 | (-) | 0.750 | 0.832 | attaaacgGTCAccttc |
| SEQ_25 | P$MSAE/MSA.01 | M-phase-specific activators (NtmybA1, NtmybA2, NtmybB) | 0.80 | 1707 | 1721 | (-) | 1.000 | 0.897 | tattaAACGgtcacc |
| SEQ_25 | P$L1BX/HDG9.01 | Homeodomain glabrous 9 | 0.77 | 1708 | 1724 | (-) | 1.000 | 0.791 | atgtatTAAAcggtcac |
| SEQ_25 | P$OPAQ/O2_GCN4.01 | Recognition site for BZIP transcription factors that belong to the group of Opaque-2 like proteins | 0.81 | 1716 | 1732 | (-) | 1.000 | 0.834 | agatagACATgtattaa |
| SEQ_25 | P$LREM/ATCTA.01 | Motif involved in carotenoid and tocopherol biosynthesis and in the expression of photosynthesis-related genes | 0.85 | 1727 | 1737 | (+) | 1.000 | 0.853 | ctATCTattat |
| SEQ_25 | P$ROOT/RHE.02 | Root hair-specific element with a 3-nucleotid spacer between left part (LP) and right part (RP) | 0.77 | 1747 | 1771 | (+) | 1.000 | 0.774 | gtacttcatagctatCACGttgctc |
| SEQ_25 | P$GBOX/HBP1B.01 | Wheat bZIP transcription factor HBP1B (histone gene binding protein 1b) | 0.83 | 1754 | 1774 | (-) | 1.000 | 0.843 | gaggagcaACGTgatagctat |
| SEQ_25 | P$OCSE/OCSL.01 | OCS-like elements | 0.69 | 1760 | 1780 | (-) | 1.000 | 0.700 | atttgtgaggagcaACGTgat |
| SEQ_25 | P$SUCB/SUCROSE.01 | Sequence motif from the promoters of different sugar-responsive genes | 0.81 | 1799 | 1817 | (+) | 1.000 | 0.911 | gcAAATcaattttataaag |
| SEQ_25 | P$TBPF/TATA.01 | Plant TATA box | 0.88 | 1807 | 1821 | (+) | 1.000 | 0.910 | atttTATAaagacgc |
| SEQ_25 | P$GTBX/GT3A.01 | Trihelix DNA-binding factor GT-3a | 0.83 | 1820 | 1836 | (-) | 1.000 | 0.865 | tcagctGTTActcatgc |
| SEQ_25 | P$MYBL/MYBPH3.01 | Myb-like protein of *Petunia hybrida* | 0.80 | 1822 | 1838 | (-) | 1.000 | 0.823 | attcagctGTTActcat |

TABLE 7-continued

| cis-regulatory elements of SEQ ID NO: 25 | | | | | | | | | |
|---|---|---|---|---|---|---|---|---|---|
| Seq. name | Family/matrix | Further Information | Opt. thresh. | Start pos. | End pos. | Strand | Core sim. | Matrix sim. | Sequence |
| SEQ_25 | P$DOFF/PBF.01 | PBF (MPBF) | 0.97 | 1834 | 1850 | (+) | 1.000 | 0.988 | tgaataaaAAAGagagg |
| SEQ_25 | P$IDRE/IDE1.01 | Iron-deficiency-responsive element 1 | 0.77 | 1856 | 1870 | (+) | 1.000 | 0.777 | acGCATgttgattgc |
| SEQ_25 | P$GBOX/BZIP910.02 | bZIP transcription factor from *Antirrhinum majus* | 0.84 | 1859 | 1879 | (+) | 1.000 | 0.962 | catgttgattgcTGACgtgtc |
| SEQ_25 | P$OCSE/OCSL.01 | OCS-like elements | 0.69 | 1859 | 1879 | (+) | 1.000 | 0.751 | catgttgattgctgACGTgtc |
| SEQ_25 | P$GBOX/HBP1B.01 | Wheat bZIP transcription factor HBP1B (histone gene binding protein 1b) | 0.83 | 1864 | 1884 | (−) | 1.000 | 0.973 | ctacggacACGTcagcaatca |
| SEQ_25 | P$GBOX/GBF1.01 | bZIP protein G-Box binding factor 1 | 0.94 | 1865 | 1885 | (+) | 1.000 | 0.999 | gattgctgACGTgtccgtagg |
| SEQ_25 | P$ABRE/ABF1.03 | ABA (abscisic acid) inducible transcriptional activator | 0.82 | 1866 | 1882 | (+) | 1.000 | 0.960 | attgctgaCGTGtccgt |
| SEQ_25 | P$OPAQ/RITA1.01 | Rice transcription activator-1 (RITA), basic leucin zipper protein, highly expressed during seed development | 0.95 | 1866 | 1882 | (−) | 1.000 | 0.956 | acggacACGTcagcaat |
| SEQ_25 | P$OPAQ/RITA1.01 | Rice transcription activator-1 (RITA), basic leucin zipper protein, highly expressed during seed development | 0.95 | 1867 | 1883 | (+) | 1.000 | 0.958 | ttgctgACGTgtccgta |
| SEQ_25 | P$EINL/TEIL.01 | TEIL (tobacco EIN3-like) | 0.92 | 1882 | 1890 | (−) | 0.863 | 0.966 | aTGGAccta |
| SEQ_25 | P$GAGA/BPC.01 | Basic pentacysteine proteins | 1.00 | 1937 | 1961 | (−) | 1.000 | 1.000 | ctcgagAGAGaggggacttatgatg |

In the following table 9, cis-regulatory element families commonly found in at least 13 of the listed expression control sequences of the present invention are shown. Table 8 describes the cis-regulatory element families.

TABLE 8

Description of cis-regulatory elements families commonly found in expression control sequences of the present invention.

| TF-Family | Description |
|---|---|
| O$VTBP | Vertebrate TATA binding protein vector |
| P$AHBP | Arabidopsis homeobox protein |
| P$DOFF | DNA binding with one finger (DOF) |
| P$GTBX | GT-box elements |
| P$IBOX | Plant I-Box sites |
| P$L1BX | L1 box, motif for L1 layer-specific expression |
| P$LREM | Light responsive element motif, not modulated by different light qualities |
| P$MYBL | MYB-like proteins |
| P$MYBS | MYB proteins with single DNA binding repeat |
| P$NCS1 | Nodulin consensus sequence 1 |
| P$CCAF | Circadian control factors |
| P$GBOX | Plant G-box/C-box bZIP proteins |

TABLE 8-continued

Description of cis-regulatory elements families commonly found in expression control sequences of the present invention.

| TF-Family | Description |
|---|---|
| P$IDDF | D domain factors, the ID domain includes a cluster of three different types of zinc fingers seperated from a fourth C2H2 finger by a long spacer |
| P$MADS | floral determination |
| P$MYCL | Myc-like basic helix-loop-helix binding factors |
| P$OPAQ | Opaque-2 like transcriptional activators |
| P$SPF1 | Sweet potato DNA-binding factor with two WRKY-domains |
| P$SUCB | Sucrose box |
| P$WBXF | W Box family |
| O$INRE | Core promoter initiator elements |
| O$PTBP | Plant TATA binding protein vector |
| P$ABRE | ABA response elements |
| P$LEGB | Legumin Box family |
| P$NACF | Plant specific NAC [NAM (no apical meristem), ATAF172, CUC2 (cup-shaped cotyledons 2)] transcription factors |
| P$OCSE | Enhancer element first identified in the promoter of the octopine synthase gene (OCS) of the *Agrobacterium tumefaciens* T-DNA |

TABLE 9

Cis-regulatory elements families commonly found in expression control sequences in at least 13 of the listed expression control sequences of the present invention.

| TF-Family | No of occurences | | | | | | | | |
|---|---|---|---|---|---|---|---|---|---|
| | p-BnSCP (SEQ-ID 70) | p-BnGRPL (SEQ-ID 1) | p-BnCRU4 (SEQ-ID 77) | p-BnMYR (SEQ-ID 85) | p-BnSETL-var1 (SEQ-ID 22) | p-BnSETL-var2 (SEQ-ID 25) | p-BnSCT2-var1 (SEQ-ID 14) | p-BnSCT2-var2 (SEQ-ID 16) | p-BnMDP (SEQ-ID 95) |
| O$VTBP | 7 | 18 | 17 | 39 | 6 | 10 | 5 | 8 | 19 |
| P$AHBP | 16 | 8 | 22 | 25 | 6 | 12 | 7 | 9 | 15 |
| P$DOFF | 14 | 8 | 11 | 9 | 2 | 7 | 5 | 5 | 4 |
| P$GTBX | 12 | 13 | 10 | 16 | 10 | 12 | 5 | 1 | 7 |
| P$IBOX | 4 | 4 | 4 | 2 | 4 | 2 | 2 | 2 | 7 |
| P$L1BX | 9 | 7 | 11 | 18 | 10 | 10 | 2 | 3 | 10 |
| P$LREM | 6 | 4 | 4 | 6 | 3 | 1 | 3 | 3 | 5 |
| P$MYBL | 9 | 11 | 12 | 7 | 16 | 14 | 9 | 7 | 9 |
| P$MYBS | 9 | 3 | 8 | 2 | 4 | 5 | 2 | 2 | 10 |
| P$NCS1 | 2 | 2 | 4 | 3 | 3 | 4 | 2 | 2 | 2 |
| P$CCAF | 4 | 4 | 4 | 2 | 3 | 3 | 1 | 1 | 3 |
| P$GBOX | 9 | 3 | 12 | 2 | 5 | 5 | 7 | 5 | 3 |
| P$IDDF | 3 | 2 | 1 | 1 | 1 | 1 | 4 | 5 | 3 |
| P$MADS | 6 | 9 | 9 | 2 | 0 | 5 | 2 | 2 | 7 |
| P$MYCL | 1 | 0 | 6 | 3 | 5 | 2 | 3 | 3 | 3 |
| P$OPAQ | 9 | 5 | 7 | 3 | 6 | 4 | 1 | 2 | 4 |
| P$SPF1 | 2 | 6 | 1 | 5 | 1 | 1 | 2 | 2 | 2 |
| P$SUCB | 6 | 4 | 3 | 7 | 1 | 4 | 2 | 3 | 0 |
| P$WBXF | 2 | 3 | 1 | 0 | 1 | 1 | 3 | 2 | 1 |
| O$INRE | 5 | 1 | 1 | 2 | 1 | 4 | 0 | 0 | 1 |
| O$PTBP | 2 | 7 | 8 | 24 | 1 | 1 | 0 | 1 | 5 |
| P$ABRE | 1 | 1 | 3 | 0 | 4 | 2 | 3 | 3 | 1 |
| P$LEGB | 6 | 4 | 8 | 2 | 1 | 2 | 2 | 2 | 7 |
| P$NACF | 2 | 2 | 2 | 1 | 1 | 0 | 3 | 3 | 2 |
| P$OCSE | 3 | 4 | 3 | 5 | 3 | 3 | 7 | 7 | 3 |

| TF-Family | No of occurences | | | | | |
|---|---|---|---|---|---|---|
| | p-BnRTI-4 (SEQ-ID 103) | p-BnMTFL (SEQ-ID 111) | p-BnGSTF (SEQ-ID 119) | p-BnPEF-var1 (SEQ-ID 6) | p-BnPEF-var2 (SEQ-ID 9) | p-BnLSP (SEQ-ID 125) |
| O$VTBP | 9 | 10 | 13 | 28 | 4 | 12 |
| P$AHBP | 22 | 9 | 9 | 18 | 5 | 14 |
| P$DOFF | 8 | 6 | 4 | 10 | 8 | 5 |
| P$GTBX | 8 | 10 | 5 | 22 | 5 | 10 |
| P$IBOX | 3 | 1 | 1 | 8 | 2 | 3 |

TABLE 9-continued

Cis-regulatory elements families commonly found in expression control sequences in at least 13 of the listed expression control sequences of the present invention.

| | | | | | | |
|---|---|---|---|---|---|---|
| P$L1BX | 10 | 2 | 1 | 10 | 3 | 9 |
| P$LREM | 6 | 2 | 2 | 8 | 4 | 5 |
| P$MYBL | 10 | 9 | 15 | 18 | 5 | 6 |
| P$MYBS | 13 | 3 | 4 | 5 | 3 | 5 |
| P$NCS1 | 1 | 3 | 2 | 1 | 1 | 2 |
| P$CCAF | 4 | 3 | 3 | 9 | 2 | 0 |
| P$GBOX | 12 | 1 | 5 | 2 | 0 | 7 |
| P$IDDF | 1 | 3 | 3 | 3 | 1 | 0 |
| P$MADS | 12 | 6 | 3 | 8 | 5 | 6 |
| P$MYCL | 3 | 1 | 6 | 4 | 1 | 1 |
| P$OPAQ | 12 | 0 | 5 | 4 | 2 | 7 |
| P$SPF1 | 3 | 0 | 2 | 7 | 1 | 2 |
| P$SUCB | 1 | 2 | 1 | 7 | 2 | 3 |
| P$WBXF | 1 | 2 | 1 | 3 | 1 | 5 |
| O$INRE | 2 | 4 | 2 | 7 | 2 | 2 |
| O$PTBP | 4 | 3 | 8 | 7 | 2 | 0 |
| P$ABRE | 3 | 1 | 3 | 1 | 0 | 4 |
| P$LEGB | 3 | 0 | 1 | 2 | 0 | 2 |
| P$NACF | 3 | 1 | 0 | 1 | 1 | 1 |
| P$OCSE | 7 | 0 | 4 | 4 | 0 | 3 |

All references cited in this specification are herewith incorporated by reference with respect to their entire disclosure content and the disclosure content specifically mentioned in this specification.

The invention will now be illustrated by the following Examples which are not intended, whatsoever, to limit the scope of this application.

Example 1

General Cloning Methods

General Cloning Methods including enzymatic digestion by restriction enzymes, agarous gel electrophoresys, purification of DNA fragments, transfer of nucleic acids to nitrocellulose on nylon membranes, maligation of DNA fragments, transformation of *E. coli* bacteria as well as culture of bacteria and sequence analysis of recombinant DNA have been carried out as described in Sambrook et al. (1989, Cold Spring Harbour Laboratory Press. ISBN 0-87969-309-6).

Example 2

Cloning of Promotor Elements from *Brassica napus*

For the analysis of seed specific expressed genes in *Brassica napus*, different tissues of various developmental stages (table 10) have been investigated.

TABLE 10 tissue types used for transcript analysis
Specific developmental stages are given using the Biologische Bundesanstalt, Bundessortenamt, and Chemical Industry (BBCH) code (Meier, 1997)

| Sample Nr. | Tissue | Developmental stage | type sample |
|---|---|---|---|
| 1 | immature embryos | walking stick | purpose prio 1 |
| 2 | immature embryos | fully developped (approx 20 days) | purpose prio 1 |
| 3 | immature embryos | fully developped pre dessic. green | purpose prio 1 |
| 4 | immature embryos | fully developped. start dessic Yellow | control/purpose prio 2 |

TABLE 10-continued tissue types used for transcript analysis
Specific developmental stages are given using the Biologische Bundesanstalt, Bundessortenamt, and Chemical Industry (BBCH) code (Meier, 1997)

| Sample Nr. | Tissue | Developmental stage | type sample |
|---|---|---|---|
| 5 | embryo sac complete | heart | control/purpose prio 2 |
| 6 | immature seed coat and endosperm | weight mix sample 1-3 | control/purpose prio 2 |
| 7 | flower buds | BBCH 57 | control/purpose prio 2 |
| 8 | anthers and stigma | BBCH 68 | control/purpose prio 2 |
| 9 | flowers (exclude anthers and stigma) | BBCH 67 | control |
| 10 | leaves | BBCH 32 | control |
| 11 | leaves | BBCH 75 | control |
| 12 | leaves | BBCH 80, senescing (yellow) | control |
| 13 | stem | BBCH 32 | control |
| 14 | stem | BBCH 75 | control |
| 15 | stem | BBCH 80, senescing (yellow) | control |
| 16 | seedling: hypocotyl and cotyledons | BBCH 12 | control |
| 17 | seedling: roots (sand) | BBCH 12 | control |
| 18 | empty siliques | weight mix sample 1-3 | control |

To this end, *Brassica napus* cv. Kumily plants were raised under standard conditions (Moloney et al. 1992, Plant Cell Reports 8: 238-242). The tissues where harvested at the indicated developmental stages (table 10) and used for the preparation of RNA (RNAeasy, Qiagen) according to the manufactures manual. To identify in further experiments seed specifically expressed mRNA transcripts, three pools were created by mixing the RNA. A seed specific pool P-S was created from sample 1, 2, 3 (see table 10). A control pool P-C1 was created from sample 9, 10, 11, 12, 13, 14, 15, 16, 17, 18. A third pool P-C2 consisting of sample 4, 5, 6 7, 8 was used as a more stringent control: transcripts not expressed in control pool P-C2 are solely expressed in early seed development and in no other tissue/developmental stage. Using the amplified fragment length polymorphism (AFLP) method, known to a person skilled in the art, 384 primer combinations were used to identify 96 candidate transcript fragments being present solely in pool P-S and/or also weakly in pool P-C2 but absent on pool P-C1. A selection of 42 primer combinations that identified the 55 most promising transcript fragments were used to analyse in detail all samples listed in table 10, resulting in 26 fragment with confirmed expression solely in the developing embryo samples 1, 2, 3 and 4. Sequencing of those candidate fragments resulted in 20 unique sequences. Basic Local Alignment Search Tool (BLAST) was used to identify the putative full length transcripts corresponding to the identified transcript fragments. Surprisingly, besides genes known in the art for seed specific expression, e.g. napin and 3-ketoacyl-CoA synthase, a number of fragments listed in table 11 showed no homology to any known *Brassica* sequence, or to genes which were not known to be seed specifically expressed and/or to genes with unknown sequence upstream of the known mRNA sequence.

TABLE 11

Candidate fragments and homologue sequences identified using BLAST.

| Candidate | fragment length | SEQ-ID | *Brassica* homologue | *Arabidopsis* homologue |
|---|---|---|---|---|
| BnSCP | 157 bp | 58 | | At5g36100 (unknown protein) |
| BnGRPL | 174 bp | 4 | | At3g10185 (similar to gibberelin responsive protein) |
| BnCRU4 | 127 bp | 59 | BnCRU4rn (Cruciferin) | |
| BnMYR | 101 bp | 60 | BnMYRmc (Myrosinase) | |
| BnSETL | 120 bp | 26 | | At1g03270 (unknown protein) |
| BnSCT2 | 172 bp | 19 | BnSCT2 (Sinapoyl-cholin transferase 2) | |
| BnMDP | 273 bp | 61 | | At3g20370 (unknown, similar |
| BnRTI-4 | 237 bp | 62 | BnRTI-4 (Trypsin Inhibitor family) | |
| BnMTFL | 144 bp | 63 | | At2g21650 (put. Myb factor transcr. Factor) |
| BnGSTF | 186 bp | 64 | | At3g62760 (AtGSTF13) |
| BnSRP | 131 bp | 65 | | |
| BnPEF | 121 bp | 12 | Pectinesterase family protein | At5g47500 (pectinesterase family protein) |
| BnWSP | 83 bp | 66 | | |
| BnLSP | 164 bp | 67 | | At5g62200 (weak similarity to embryo-specific protein 3) |

From leaf material of *Brassica napus* cv. Kumily, genomic DNA has been isolated using the DNAeasy kit (Qiagen) according to the manufacturer's manual. Culture conditions for the *Brassica napus* cv. Kumily were as discussed above. Using this genomic DNA, as template, multiple rounds of thermal asymmetric interlaced polymerase chain reaction (TAIL-PCR)—a method known to a person skilled in the art—was performed to isolate sequences 5' upstream and 3' downstream of the 20 identified expressed fragments. The amplified products were either sequences directly, or sup-cloned into the pGEM-T (Promega) vector prior sequencing. Subcloning was required in some cases, as *Brassica napus* is amphidiploid, that is, *Brassica napus* contains 10 chromosomes common with *Brassica rapa* (A genome) and 9 chromosomes common with *Brassica oleracea* (C genome). Subcloning of PCR products containing a mixture of two sequences amplified from both genomes allows to separate these two sequences. Sequencing was done by standard techniques (laser fluorescent DNA-sequenceing, ABI according to the method of Sanger et al. 1977 Proc. Natl. Acad. Sci. USA 74, 5463-5467).

For candidate expressed sequences where no *Brassica* gene was known to the art, the open reading frame was identified with help of software prediction and using alignments with homologues genes from *Arabidopsis*. The following *Brassica napus* open reading frames have been identified (Table 12):

TABLE 12

Open reading frames (ORF) identified in *Brassica napus* cDNA sequences.

| *Brassica napus* Sequence | ORF in bp | SEQ ID NO: |
|---|---|---|
| BnGRPL | 360 | 5 |
| BnPEF | 1083 | 13 |
| BnSCT1 | 1401 | 20 |
| BnSCT2 | 1401 | 21 |
| BnSETL1 | 1512 | 27 |
| BnSETL2 | 1512 | 28 |
| BnSCP | 773 | 72 |
| BnCRU4 | 1107 | 80 |
| BnMYR | 1644 | 88 |
| BnMDP | 1152 | 98 |
| BnRTI-4 | 300 | 106 |
| BnMTFL | 303 | 114 |
| BnGSTF | 660 | 121 |
| BnLSP | 574 | 133 |

For the expressed sequence SEQ-ID 126, no open reading frame could be identified.

The following *Brassica napus* sequences upstream of the expressed sequence SEQ-ID 126 or the identified expressed open reading frames (ORF) have been obtained (Table 13).

TABLE 13

Genomic 5' upstream sequences from the *Brassica napus* cDNA sequences.

| *Brassica napus* Sequence | genomic 5' sequence in bp | SEQ ID NO: |
|---|---|---|
| p-BnGRPL | 1790 | 1 |
| p-BnPEF-var1 | 2027 | 6 |
| p-BnPEF-var2 | 636 | 9 |
| p-BnSCT2-var1 | 1019 | 14 |
| p-BnSCT2-var2 | 996 | 16 |
| p-BnSETL-var1 | 1490 | 22 |
| p-BnSETL-var2 | 2010 | 25 |
| p-BnSCP | 2052 | 70 |
| p-BnCRU4 | 1951 | 77 |
| p-BnMYR | 1360 | 85 |
| p-BnMDP | 1428 | 95 |
| p-BnRTI-4 | 1820 | 103 |
| p-BnMTFL | 1335 | 111 |
| p-BnGSTF | 1565 | 119 |
| p-BnSRP | 2447 | 124 |
| p-BnLSP | 1593 | 121 |

The analysis of the 5' upstream sequences using Genomatix software Gems-Launcher showed that the sequences comprised promoter elements. This was confirmed by the presence of a TATA-Box which is required for transcription by RNA-polymerases. Also in the isolated fragments elements specific for seed-transcription factors (e.g. Prolamin-box, legumin box, RITA etc.) were found.

The following *Brassica napus* sequences downstream of the identified expressed open reading frames (ORF) have been obtained (Table 14).

TABLE 14

| Genomic 3' downstream sequences from the *Brassica napus* cDNA sequences. | | |
|---|---|---|
| *Brassica napus* Sequence | genomic 3' sequence in bp | SEQ ID NO: |
| t-BnGRPL | 581 | 2 |
| t-BnPEF-var1 | 477 | 7 |
| t-BnPEF-var2 | 538 | 10 |
| t-BnSCT2-var1 | 573 | 15 |
| t-BnSCT2-var2 | 576 | 17 |
| t-BnSETL-var1 | 614 | 23 |
| t-BnSCP | 587 | 71 |
| t-BnCRU4 | 514 | 78 |
| t-BnMYR | 652 | 86 |
| t-BnMDP | 483 | 96 |
| t-BnRTI-4 | 572 | 104 |
| t-BnMTFL | 521 | 112 |
| t-BnSRP | 865 | 125 |

Example 3

Production of Test Constructs for Demonstrating Promoter Activity

For the testing of the promoter elements in a first step promoter terminator cassettes were generated. To this end, fusion PCRs have been used wherein via two PCR steps promoter elements were linked with terminator elements. At the same time, a multiple cloning site was introduced in between the promoter and terminator elements. The primers used to generate cassettes using corresponding native *Brassica* terminators are shown in Table 15, Table 16 list the generated cassettes using the OCS terminator.

TABLE 15

Primer pairs used for the generation of promoter-multiple cloning site-terminated-cassettes via Fusion-PCR using native *Brassica* terminator sequences.

| *Brassica napus* Promoter/Terminator cassette | Primer pair 1. PCR Promoter | Primer pair 1. PCR Terminator | Primer pair 2. PCR |
|---|---|---|---|
| p-BnGRP_MCS_t-BnGRP | Forw: atacccggga-tacctgcaggt-taggccggccacaa-aacgaaatcatca-aatcgtg (SEQ ID NO: 29)<br>Rev: caatcaatta-taggcctcgcatgctt-taattaacgatcgagc-catggttttagagagccg-gaattattg (SEQ ID NO: 30) | Forw: ccatggctc-gatcgttaattaaag-catgcgaggcctataatt-gattgtttctcctcttagtttg-taaataatctatc (SEQ ID NO: 31)<br>Rev: taagcggccg-caatcggaccga-taccggtaggcgccgat-tatctacctaacctaaca-aacaaaag (SEQ ID NO: 32) | Forw: atacccgggatac ctgcaggttaggccggc-cacaaaacgaaatcat-caaatcgtg (SEQ ID NO: 29)<br>Rev: 'taagcggccg-caatcggaccga-taccggtaggcgccgat-tatctacctaacctaaca-aacaaaag (SEQ ID NO: 32) |
| p-BnPEF-var1_MCS_t-BnPEF-var1 | Forw: atacccgggatacctgcaggttaggccggccaaatttattaacccatctatttgttcac (SEQ ID NO: 33)<br>Rev: caatcaattataggcctcgcatgctttaattaacgatcgagccatgggacgagaaagaaaatggtcggag (SEQ ID NO: 34) | Forw: ccatggctcgatcgttaattaaagcatgcgaggcctataattgattgtaaggaatcaacttcaaatgcttttc (SEQ ID NO: 35)<br>Rev: taagcggccgcaatcggaccgataccggtaggcgccgacgttaagcgagagtggatag (SEQ ID NO: 36) | Forw: atacccgggatacctgcaggttaggccggccaaatttattaacccatctatttgttcac (SEQ ID NO: 33)<br>Rev: taagcggccgcaatcggaccgataccggtaggcgccgacgttaagcgagagtggatag (SEQ ID NO: 36) |
| p-BnPEF-var2_MCS_t-BnPEF-var2 | Forw: atacccgggatacctgcaggttaggccggccagaattacgtttgagttcaaattcag (SEQ ID NO: 37)<br>Rev: caatcaattataggcctcgcatgctttaattaacgatcgagccatgggacgagaaataaatggtcgaag (SEQ ID NO: 38) | Forw: Ccatggctcgatcgttaattaaagcatgcgaggcctataattgattgtaggaatcaacttcaaatgctttt (SEQ ID NO: 39)<br>Rev: taagcggccgcaatcggaccgataccggtaggcgccagaggtgaggaggagttgcac (SEQ ID NO: 40) | Forw: atacccgggatacctgcaggttaggccggccagaattacgtttgagttcaaattcag (SEQ ID NO: 37)<br>Rev: taagcggccgcaatcggaccgataccggtaggcgccagaggtgaggaggagttgcac (SEQ ID NO: 40) |
| p-BnSCT2-var1_MCS_t-BnSCT2-var1 | Forw: atacccgggatacctgcaggttaggccggccagatgcaaaaacgtatagtcacac (SEQ ID NO: 41)<br>Rev: caatcaattataggcctcgcatgctttaattaacgatcgagccatggtttctctgcttct | Forw: ccatggctcgatcgttaattaaagcatgcgaggcctataattgattgAgttcctcactcacttctctc (SEQ ID NO: 43)<br>Rev: taagcggccgcaatcggaccgataccggtaggcg | Forw: atacccgggatacctgcaggttaggccggccagatgcaaaaacgtatagtcacac (SEQ ID NO: 41)<br>Rev: taagcggccgcaatcggaccgataccggtaggcgccgccttatatggattttgtg |

TABLE 15-continued

Primer pairs used for the generation of promoter-multiple cloning site-terminated-cassettes via Fusion-PCR using native *Brassica* terminator sequences.

| *Brassica napus* Promoter/Terminator cassette | Primer pair 1. PCR Promoter | Primer pair 1. PCR Terminator | Primer pair 2. PCR |
|---|---|---|---|
| | tggtgtcac (SEQ ID NO: 42) | ccgccttatatggattttgtg ttactgacc (SEQ ID NO: 44) | ttactgacc (SEQ ID NO: 44) |
| p-BnSCT2-var2_MCS_t-BnSCT2-var2 | Forw: atacccgggatacctgca ggttaggccggccagatg caaaaacgtatagtcaca c (SEQ ID NO: 45) Rev: caatcaattataggcctcg catgctttaattaacgatcg agccatggtttctctgcttct tggtgtcac (SEQ ID NO: 46) | Forw: ccatggctcgatcgttaatt aaagcatgcgaggcctat aattgattgAgttcctcact cacttctctc (SEQ ID NO: 47) Rev: taagcggccgcaatcgg accgataccggtaggcg ccgccttatatggattttgtg ttactgacc (SEQ ID NO: 48) | Forw: atacccgggatacctgca ggttaggccggccagatg caaaaacgtatagtcaca c (SEQ ID NO: 45) Rev: taagcggccgcaatcgg accgataccggtaggcg ccgccttatatggattttgtg ttactgacc (SEQ ID NO: 48) |
| p-BnSETL-var1_MCS_t-BnSETL-var1 | Forw: atacccgggatacctgca ggttaggccggccagtag aagttattagcaacttgtac acac (SEQ ID NO: 49) Rev: caatcaattataggcctcg catgctttaattaacgatcg agccatggtttgaccccttc ttgttcttc (SEQ ID NO: 50) | Forw: ccatggctcgatcgttaatt aaagcatgcgaggcctat aattgattgtacatactatat tttttgtttaccttgtg (SEQ ID NO: 51) Rev: taagcggccgcaatcgg accgataccggtaggcg cccaaacacggctcaga gaagc (SEQ ID NO: 52) | Forw: atacccgggatacctgca ggttaggccggccagtag aagttattagcaacttgtac acac (SEQ ID NO: 49) Rev: taagcggccgcaatcgg accgataccggtaggcg cccaaacacggctcaga gaagc (SEQ ID NO: 52) |
| p-BnSETL-var2_MCS_t-BnSETL-var1 | Forw: atacccgggatacctgca ggttaggccggccatcgg ctacaaatccaactgg (SEQ ID NO: 53) Rev:- caatcaattataggcctcg catgctttaattaacgatcg agccatggtttgtcgttttcc tcagcttc (SEQ ID NO: 54) | Forw: ccatggctcgatcgttaatt aaagcatgcgaggcctat aattgattgtacatactatat tttttgtttaccttgtg (SEQ ID NO: 51) Rev: taagcggccgcaatcgg accgataccggtaggcg cccaaacacggctcaga gaagc (SEQ ID NO: 52) | Forw: atacccgggatacctgca ggttaggccggccatcgg ctacaaatccaactgg (SEQ ID NO: 53) Rev: taagcggccgcaatcgg accgataccggtaggcg cccaaacacggctcaga gaagc (SEQ ID NO: 52) |
| p-BnSCP_MCS_t-BnSCP | Forw: atacccgggatacctgca ggttaggccggccaatca taagttgtatcagttcatc (SEQ-ID No: 73) Rev: caatcaattataggcctcg catgctttaattaacgatcg agccatggtgtttgactcat actggtggta (SEQ-ID No: 74) | Forw: ccatggctcgatcgttaatt aaagcatgcgaggcctat aattgattgggagaaaat atgggagaagatggaa (SEQ-ID No: 75) Rev: taagcggccgcaatcgg accgataccggtaggcg cctatagacctgccaaatc aaaccaac (SEQ-ID No: 76) | Forw: atacccgggatacctgca ggttaggccggccaatca taagttgtatcagttcatc (SEQ-ID No: 73) Rev: taagcggccgcaatcgg accgataccggtaggcg cctatagacctgccaaatc aaaccaac (SEQ-ID No: 76) |
| p-BnCRU4_MCS_t-BnCRU4 | Forw: atacccgggatacc-tgcaggttagg-ccggccaatgtacatg-gatgcgtatagatg (SEQ-ID No: 81) Rev: caatcaattatagg-cctcgcatgctttaat-taacgatcgagccatg-gtagagcatg-tccgtgaacgacg (SEQ-ID No: 82) | Forw: ccatggctcgatcgttaat-taaagcatgcgagg-cctataattgattgagcat-gagttagtgatgtaa-cagcg (SEQ-ID No: 83) Rev: taagcggccgcaatc-ggaccgatacc-ggtaggcgccggaaga-gatggaagcttaca-gaatg (SEQ-ID No: 84) | Forw: atacccgggatacc-tgcaggttagg-ccggccaatgtacatg-gatgcgtatagatg (SEQ-ID No: 81) Rev: taagcggccgcaatc-ggaccgatacc-ggtaggcgccggaaga-gatggaagcttaca-gaatg (SEQ-ID No: 84) |

TABLE 15-continued

Primer pairs used for the generation of promoter-multiple cloning site-terminated-cassettes via Fusion-PCR using native *Brassica* terminator sequences.

| *Brassica napus* Promoter/Terminator cassette | Primer pair 1. PCR Promoter | Primer pair 1. PCR Terminator | Primer pair 2. PCR |
|---|---|---|---|
| p-BnMYR_MCS_t-BnMYR | Forw: atacccgggatacctgcaggttaggccggccacataaaaatatgttgagaaaatatc (SEQ-ID No: 89) Rev: caatcaattataggcctcgcatgctttaattaacgatcgagccatggggttaatgtgtagatttgtatatatg (SEQ-ID No: 90) | Forw: ccatggctcgatcgttaattaaagcatgcgaggcctataattgattgaacactttatccacatcaagatcgc (SEQ-ID No: 91) Rev: taagcggccgcaatcggaccgataccggtaggcgccgatgtgtgctcgtaattgcactttt (SEQ-ID No: 92) | Forw: atacccgggatacctgcaggttaggccggccacataaaaatatgttgagaaaatatc (SEQ-ID No: 89) Rev: taagcggccgcaatcggaccgataccggtaggcgccgatgtgtgctcgtaattgcactttt (SEQ-ID No: 92) |
| p-BnMDP_MCS_t-BnMDP | Forw: atacccgggatacctgcaggttaggccggccatgcgagagagaagaaatgaaataag (SEQ-ID No: 99) Rev: caatcaattataggcctcgcatgctttaattaacgatcgagccatggcttttgagattgtatatatgaatg (SEQ-ID No: 100) | Forw: ccatggctcgatcgttaattaaagcatgcgaggcctataattgattgatttctctaactaagaaactttgtag (SEQ-ID No: 101) Rev: taagcggccgcaatcggaccgataccggtaggcgcccgataaagatggtctaatgtccatc (SEQ-ID No: 102) | Forw: atacccgggatacctgcaggttaggccggccatgcgagagagaagaaatgaaataag (SEQ-ID No: 99) Rev: taagcggccgcaatcggaccgataccggtaggcgcccgataaagatggtctaatgtccatc (SEQ-ID No: 102) |
| p-BnRTI-4_MCS_t-BnRTI-4 | Forw: atacccgggatacctgcaggttaggccggccacttgcgccgaagatatatccgac (SEQ-ID No: 107) Rev: caatcaattataggcctcgcatgctttaattaacgatcgagccatggcttctctctatatatctcttac (SEQ-ID No: 108) | Forw: ccatggctcgatcgttaattaaagcatgcgaggcctataattgattgatacttcacaactttgcataagcc (SEQ-ID No: 109) Rev: taagcggccgcaatcggaccgataccggtaggcgccaccaaatccgaaaccgaatccgaac (SEQ-ID No: 110) | Forw: atacccgggatacctgcaggttaggccggccacttgcgccgaagatatatccgac (SEQ-ID No: 107) Rev: taagcggccgcaatcggaccgataccggtaggcgccaccaaatccgaaaccgaatccgaac (SEQ-ID No: 110) |
| p-BnMTFL_MCS_t-BnMTFL | Forw: atacccgggatacctgcaggttaggccggccatattcactacttatagagaacac (SEQ-ID No: 115) Rev: caatcaattataggcctcgcatgctttaattaacgatcgagccatggtgtgaaaaagtttggcgtatttc (SEQ-ID No: 116) | Forw: ccatggctcgatcgttaattaaagcatgcgaggcctataattgattgaacaagaagcaacaaagcctaaactat (SEQ-ID No: 117) Rev: taagcggccgcaatcggaccgataccggtaggcgccgatttgagttttcgtgaagttcaga (SEQ-ID No: 118) | Forw: atacccgggatacctgcaggttaggccggccatattcactacttatagagaacac (SEQ-ID No: 115) Rev: taagcggccgcaatcggaccgataccggtaggcgccgatttgagttttcgtgaagttcaga (SEQ-ID No: 118) |
| p-BnSRP_MCS_t-BnSRP | Forw: atacccgggatacctgcaggttaggccggccaaacggcaattgattctcgccctg (SEQ-ID No: 127) Rev: caatcaattataggcctcgcatgctttaattaacgatcgagccatggagagaggttattgaaaccacgt (SEQ-ID No: 128) | Forw: ccatggctcgatcgttaattaaagcatgcgaggcctataattgattgtttacatattggcccaagaggcataat (SEQ-ID No: 129) Rev: taagcggccgcaatcggaccgataccggtaggcgccgttaatgaaaacggtaccgaatttc (SEQ-ID No: 130) | Forw: atacccgggatacctgcaggttaggccggccaaacggcaattgattctcgccctg (SEQ-ID No: 127) Rev: taagcggccgcaatcggaccgataccggtaggcgccgttaatgaaaacggtaccgaatttc (SEQ-ID No: 130) |

TABLE 16

Primer pairs used for the generation of promoter-multiple cloning site-terminated-cassettes via Fusion-PCR using the OCS terminator sequence.

| | | | |
|---|---|---|---|
| p-BnGRP_MCS_t-OCS | Forw: atacccggga-tacctgcaggttagg-ccggccacaaaac-gaaatcatcaaatcgtg (SEQ ID NO: 29) Rev: caatcaatta-taggcctcgcatg-ctttaattaacgatc-gagccatggttttaga-gagccggaattattg (SEQ ID NO: 30) | Forw: ccatg-gctcgatcgttaat-taaagcatgcgagg-cctataattgatt-gctgctttaatgagatatg-cgagacg (SEQ ID NO: 55) Rev: taagc-ggccgcaatcggacc-gataccggtagg-cgccacaatcag-taaattgaacggagaa-tattattc (SEQ ID NO: 56) | Forw: atacccggga-tacctgcaggttagg-ccggccacaaaac-gaaatcatcaaatcgtg (SEQ ID NO: 29) Rev: taagc-ggccgcaatcggacc-gataccggtagg-cgccacaatcag-taaattgaacggagaa-tattattc (SEQ ID NO: 56) |
| p-BnPEF-var1_MCS_t-OCS | Forw: atacccggga-tacctgcaggttagg-ccggccaaatttat-taacccatctatttgttcac (SEQ ID NO: 33) Rev: caatcaatta-taggcctcgcatg-ctttaattaacgatc-gagccatgggacga-gaaagaaaatg-gtcggag (SEQ ID NO: 34) | Forw: ccatg-gctcgatcgttaat-taaagcatgcgagg-cctataattgatt-gctgctttaatgagatatg-cgagacg (SEQ ID NO: 55) Rev: taagc-ggccgcaatcggacc-gataccggtagg-cgccacaatcag-taaattgaacggagaa-tattattc (SEQ ID NO: 56) | Forw: atacccggga-tacctgcaggttagg-ccggccaaatttat-taacccatctatttgttcac (SEQ ID NO: 33) Rev: taagc-ggccgcaatcggacc-gataccggtagg-cgccacaatcag-taaattgaacggagaa-tattattc (SEQ ID NO: 56) |
| p-BnPEF-var2_MCS_t-OCS | Forw: atacccggga-tacctgcaggttagg-ccggccagaattacg-tttgagttcaaattcag (SEQ ID NO: 37) Rev: caatcaatta-taggcctcgcatg-ctttaattaacgatc-gagccatgggacga-gaaataaatggtcgaag (SEQ ID NO: 38) | Forw: ccatg-gctcgatcgttaat-taaagcatgcgagg-cctataattgatt-gctgctttaatgagatatg-cgagacg (SEQ ID NO: 55) Rev: taagc-ggccgcaatcggacc-gataccggtagg-cgccacaatcag-taaattgaacggagaa-tattattc (SEQ ID NO: 56) | Forw: atacccggga-tacctgcaggtagg-ccggccagaattacg-tttgagttcaaattcag (SEQ ID NO: 37) Rev: taagc-ggccgcaatcggacc-gataccggtagg-cgccacaatcag-taaattgaacggagaa-tattattc (SEQ ID NO: 56) |
| p-BnSCT2-var1_MCS_t-OCS | Forw: atacccgggatacctgcaggttaggccggccagatgcaaaaacgtatagtcacac (SEQ ID NO: 41) Rev: caatcaattataggcctcgcatgctttaattaacgatcgagccatggtttctctgcttcttggtgtcac (SEQ ID NO: 42) | Forw: ccatggctcgatcgttaattaaagcatgcgaggcctataattgattgctgctttaatgagatatgcgagacg (SEQ ID NO: 55) Rev: taagcggccgcaatcggaccgataccggtaggcgccacaatcagtaaattgaacggagaatattattc (SEQ ID NO: 56) | Forw: atacccgggatacctgcaggttaggccggccagatgcaaaaacgtatagtcacac (SEQ ID NO: 41) Rev: taagcggccgcaatcggaccgataccggtaggcgccacaatcagtaaattgaacggagaatattattc (SEQ ID NO: 56) |
| p-BnSCT2-var2_MCS_t-OCS | Forw: atacccgggatacctgcaggttaggccggccagatgcaaaaacgtatagtcacac (SEQ ID NO: 45) Rev: caatcaattataggcctcgcatgctttaattaacgatcgagccatggtttctctgcttcttggtgtcac (SEQ ID NO: 46) | Forw: ccatggctcgatcgttaattaaagcatgcgaggcctataattgattgctgctttaatgagatatgcgagacg (SEQ ID NO: 55) Rev: taagcggccgcaatcggaccgataccggtaggcgccacaatcagtaaattgaacggagaatattattc (SEQ ID NO: 56) | Forw: atacccgggatacctgcaggttaggccggccagatgcaaaaacgtatagtcacac (SEQ ID NO: 45) Rev: taagcggccgcaatcggaccgataccggtaggcgccacaatcagtaaattgaacggagaatattattc (SEQ ID NO: 56) |
| p-BnSETL-var1_MCS_t-OCS | Forw: atacccgggatacctgcaggttaggccggccagtagaagttattagcaacttgtacacac (SEQ ID NO: 49) | Forw: ccatggctcgatcgttaattaaagcatgcgaggcctataattgattgctgctttaatgagatatgcgagacg (SEQ ID NO: 55) | Forw: atacccgggatacctgcaggttaggccggccagtagaagttattagcaacttgtacacac (SEQ ID NO: 49) |

TABLE 16-continued

Primer pairs used for the generation of promoter-multiple cloning site-terminated-cassettes via Fusion-PCR using the OCS terminator sequence.

| | | | |
|---|---|---|---|
| | Rev:<br>caatcaattataggcctcg<br>catgctttaattaacgatcg<br>agccatggtttgaccccttc<br>ttgttcttc (SEQ ID<br>NO: 50) | Rev:<br>taagcggccgcaatcgg<br>accgataccggtaggcg<br>ccacaatcagtaaattga<br>acggagaatattattc<br>(SEQ ID NO: 56) | Rev:<br>taagcggccgcaatcgg<br>accgataccggtaggcg<br>ccacaatcagtaaattga<br>acggagaatattattc<br>(SEQ ID NO: 56) |
| p-BnSETL-<br>var2_MCS_t-OCS | Forw:<br>atacccgggatacctgca<br>ggttaggccggccatcgg<br>ctacaaatccaactgg<br>(SEQ ID NO: 53)<br>Rev:-<br>caatcaattataggcctcg<br>catgctttaattaacgatcg<br>agccatggtttgtcgttttcc<br>tcagcttc (SEQ ID<br>NO: 54) | Forw:<br>ccatggctcgatcgttaatt<br>aaagcatgcgaggcctat<br>aattgattgctgctttaatga<br>gatatgcgagacg<br>(SEQ ID NO: 55)<br>Rev:<br>taagcggccgcaatcgg<br>accgataccggtaggcg<br>ccacaatcagtaaattga<br>acggagaatattattc<br>(SEQ ID NO: 56) | Forw:<br>atacccgggatacctgca<br>ggttaggccggccatcgg<br>ctacaaatccaactgg<br>(SEQ ID NO: 53)<br>Rev:<br>taagcggccgcaatcgg<br>accgataccggtaggcg<br>ccacaatcagtaaattga<br>acggagaatattattc<br>(SEQ ID NO: 56) |
| p-BnSCP_MCS_t-<br>OCS | Forw:<br>atacccgggatacctg-<br>caggttaggccggc-<br>caatcataagttgtat-<br>cagttcatc (SEQ ID<br>No: 73)<br>Rev:<br>caatcaatta-<br>taggcctcgcatgctt-<br>taattaacgatcgagc-<br>catggtgtttgactca-<br>tactggtggta (SEQ-ID<br>No: 74) | Forw:<br>ccatggctcgatcgttaat-<br>taaagcatgcgagcc-<br>tataattgattgctgctt-<br>taatgagatatgcga-<br>gacg (SEQ-ID<br>No: 55)<br>Rev:<br>taagcggccgcaatcg-<br>gaccgataccgg-<br>taggcgccacaatcag-<br>taaattgaacggagaa-<br>tattattc (SEQ-ID<br>No: 56) | Forw:<br>atacccgggatacctg-<br>caggttaggccggc-<br>caatcataagttgtat-<br>cagttcatc (SEQ-ID<br>No: 73)<br>Rev:<br>taagcggccgcaatcg-<br>gaccgataccgg-<br>taggcgccacaatcag-<br>taaattgaacggagaa-<br>tattattc (SEQ-ID<br>No: 56) |
| p-<br>BnCRU4_MCS_t-<br>OCS | Forw:<br>atacccgggatacc-<br>tgcaggttagg-<br>ccggccaatgtacatg-<br>gatgcgtatagatg<br>(SEQ-ID No: 81)<br>Rev:<br>caatcaattatagg-<br>cctcgcatgctttaat-<br>taacgatcgagccatg-<br>gtagagcatg-<br>tccgtgaacgacg<br>(SEQ-ID No: 82) | Forw:<br>ccatggctcgatcgttaat-<br>taaagcatgcgagg-<br>cctataattgatt-<br>cctataattgatt-<br>gctgctttaatgagatatg-<br>cgagacg (SEQ-ID<br>No: 55)<br>Rev:<br>taagccggccgcaatc-<br>ggaccgatacc-<br>ggtaggcgccacaat-<br>cagtaaattgaacgga-<br>gaatattattc (SEQ-ID<br>No: 56) | Forw:<br>atacccgggatacc-<br>tgcaggttagg-<br>ccggccaatgtacatg-<br>gatgcgtatagatg<br>(SEQ-ID No: 81)<br>Rev:<br>taagcggccgcaatc-<br>ggaccgatacc-<br>ggtaggcgccacaat-<br>cagtaaattgaacgga-<br>gaatattattc (SEQ-ID<br>No: 56) |
| p-BnMYR_MCS_t-<br>OCS | Forw:<br>atacccgggatacc-<br>tgcaggttagg-<br>ccggccacataaaaa-<br>tatgttgagaaaatatc<br>(SEQ-ID No: 89)<br>Rev:<br>caatcaattatagg-<br>cctcgcatgctttaat-<br>taacgatcgagccatg-<br>gggttaatgtgtagatt-<br>tgtatatatg (SEQ-ID<br>No: 90) | Forw:<br>ccatggctcgatcgttaat-<br>taaagcatgcgagg-<br>cctataattgatt-<br>gctgctttaatgagatatg-<br>cgagacg (SEQ-ID<br>No: 55)<br>Rev:<br>taagcggccgcaatc-<br>ggaccgatacc-<br>ggtaggcgccacaat-<br>cagtaaattgaacgga-<br>gaatattattc (SEQ-ID<br>No: 56) | Forw:<br>atacccgggatacc-<br>tgcaggttagg-<br>ccggccacataaaaa-<br>tatgttgagaaaatatc<br>(SEQ-ID No: 89)<br>Rev:<br>taagcggccgcaatc-<br>ggaccgatacc-<br>ggtaggcgccacaat-<br>cagtaaattgaacgga-<br>gaatattattc (SEQ-ID<br>No: 56) |
| p-BnMDP_MCS_t-<br>OCS | Forw:<br>atacccgggatacctg-<br>caggttaggccggc-<br>catgcgagagagaaga-<br>aatgaaataag (SEQ-<br>ID No: 99)<br>Rev:<br>caatcaatta-<br>taggcctcgcatgctt- | Forw:<br>ccatggctcgatcgttaat-<br>taaagcatgcgaggcc-<br>tataattgattgctgctt-<br>taatgagatatgcga-<br>gacg (SEQ-ID<br>No: 55)<br>Rev:<br>taagcggccgcaatcg- | Forw:<br>atacccgggatacctg-<br>caggttaggccggc-<br>catgcgagagagaaga-<br>aatgaaataag (SEQ-<br>ID No: 99)<br>Rev:<br>taagcggccgcaatcg-<br>gaccgataccgg- |

TABLE 16-continued

Primer pairs used for the generation of promoter-multiple cloning site-terminated-cassettes via Fusion-PCR using the OCS terminator sequence.

| | | | |
|---|---|---|---|
| | taattaacgatcgagc-<br>catggcttttgagattgta-<br>tatatgaatg (SEQ-ID<br>No: 100) | gaccgataccgg-<br>taggcgccacaatcag-<br>taaattgaacggagaa-<br>tattattc (SEQ-ID<br>No: 56) | taggcgccacaatcag-<br>taaattgaacggagaa-<br>tattattc (SEQ-ID<br>No: 56) |
| p-BnRTI-<br>4_MCS_t-OCS | Forw:<br>atacccgggatacc-<br>tgcaggttagg-<br>ccggccact-<br>tgcgccgaagatatatc-<br>cgac (SEQ-ID<br>No: 107)<br>Rev:<br>caatcaattatagg-<br>cctcgcatgctttaat-<br>taacgatcgagccatg-<br>gcttctctctatatatc-<br>tcttac (SEQ-ID<br>No: 108) | Forw:<br>ccatggctcgatcgttaat-<br>taaagcatgcgagg-<br>cctataattgatt-<br>gctgctttaatgagatatg-<br>cgagacg (SEQ-ID<br>No: 55)<br>Rev:<br>taagcggccgcaatc-<br>ggaccgatacc-<br>ggtaggcgccacaat-<br>cagtaaattgaacgga-<br>gaatattattc (SEQ-ID<br>No: 56) | Forw:<br>atacccgggatacc-<br>tgcaggttagg-<br>ccggccact-<br>tgcgccgaagatatatc-<br>cgac (SEQ-ID<br>No: 107)<br>Rev:<br>taagcggccgcaatc-<br>ggaccgatacc-<br>ggtaggcgccacaat-<br>cagtaaattgaacgga-<br>gaatattattc (SEQ-ID<br>No: 56) |
| p<br>BnMTFL_MCS_t-<br>OCS | Forw:<br>atacccgggatacc-<br>tgcaggttagg-<br>ccggccatattcactact-<br>tatagagaacac (SEQ-<br>ID No: 115)<br>Rev:<br>caatcaattatagg-<br>cctcgcatgctttaat-<br>taacgatcgagccatg-<br>gtgtgaaaaagt-<br>ttggcgtatttc (SEQ-ID<br>No: 116) | Forw:<br>ccatggctcgatcgttaat-<br>taaagcatgcgagg-<br>cctataattgatt-<br>gctgctttaatgagatatg-<br>cgagacg (SEQ-ID<br>No: 55)<br>Rev:<br>taagcggccgcaatc-<br>ggaccgatacc-<br>ggtaggcgccacaat-<br>cagtaaattgaacgga-<br>gaatattattc (SEQ-ID<br>No: 56) | Forw:<br>atacccgggatacc-<br>tgcaggttagg-<br>ccggccatattcactact-<br>tatagagaacac (SEQ-<br>ID No: 115)<br>Rev:<br>taagcggccgcaatc-<br>ggaccgatacc-<br>ggtaggcgccacaat-<br>cagtaaattgaacgga-<br>gaatattattc (SEQ-ID<br>No: 56) |
| p-<br>BnGSTF_MCS_t-<br>OCS | Forw:<br>atacccgggatacc-<br>tgcaggttagg-<br>ccggccagagcattatg-<br>cttccaagcggac<br>(SEQ-ID No: 122)<br>Rev:<br>caatcaattatagg-<br>cctcgcatgctttaat-<br>taacgatcgagccatg-<br>gttcactctaact-<br>tcgtaactcg (SEQ-ID<br>No: 123) | Forw:<br>ccatggctcgatcgttaat-<br>taaagcatgcgagg-<br>cctataattgatt-<br>gctgctttaatgagatatg-<br>cgagacg (SEQ-ID<br>No: 55)<br>Rev:<br>taagcggccgcaatc-<br>ggaccgatacc-<br>ggtaggcgccacaat-<br>cagtaaattgaacgga-<br>gaatattattc (SEQ-ID<br>No: 56) | Forw:<br>atacccgggatacc-<br>tgcaggttagg-<br>ccggccagagcattatg-<br>cttccaagcggac<br>(SEQ-ID No: 122)<br>Rev:<br>taagcggccgcaatc-<br>ggaccgatacc-<br>ggtaggcgccacaat-<br>cagtaaattgaacgga-<br>gaatettattc (SEQ-ID<br>No: 56) |
| p-BnSRP_MCS_t-<br>OCS | Forw:<br>atacccgggatacctg-<br>caggttaggccggcca-<br>aacggcaatt-<br>gattctcgccctg (SEQ-<br>ID No: 127)<br>Rev:<br>caatcaatta-<br>taggcctcgcatgctt-<br>taattaacgatcgagc-<br>catggagagaggttatt-<br>gaaaccacgt (SEQ-<br>ID No: 128) | Forw:<br>ccatggctcgatcgttaat-<br>taaagcatgcgaggcc-<br>tataattgattgctgctt-<br>taatgagatatgcga-<br>gacg (SEQ-ID<br>No: 55)<br>Rev:<br>taagcggccgcaatcg-<br>gaccgataccgg-<br>taggcgccacaatcag-<br>taaattgaacggagaa-<br>tattattc (SEQ-ID<br>No: 56) | Forw:<br>atacccgggatacctg-<br>caggttaggccggcca-<br>aacggcaatt-<br>gattctcgccctg (SEQ-<br>ID No: 127)<br>Rev:<br>taagcggccgcaatcg-<br>gaccgataccgg-<br>taggcgccacaatcag-<br>taaattgaacggagaa-<br>tattattc (SEQ-ID<br>No: 56) |
| p-BnLSP_MCS_t-<br>OCS | Forw:<br>atacccgggatacctg-<br>caggttaggccggcca-<br>aatagtcaagtttatgaat-<br>cacag (SEQ-ID<br>No: 134)<br>Rev:<br>caatcaatta-<br>taggcctcgcatgctt- | Forw:<br>ccatggctcgatcgttaat-<br>taaagcatgcgaggcc-<br>tataattgattgctgctt-<br>taatgagatatgcga-<br>gacg (SEQ-ID<br>No: 55)<br>Rev:<br>taagcggccgcaatcg- | Forw:<br>atacccgggatacctg-<br>caggttaggccggcca-<br>aatagtcaagtttatgaat-<br>cacag (SEQ-ID<br>No: 134)<br>Rev:<br>taagcggccgcaatcg-<br>gaccgataccgg- |

TABLE 16-continued

Primer pairs used for the generation of promoter-multiple cloning site-terminated-cassettes via Fusion-PCR using the OCS terminator sequence.

| | | | |
|---|---|---|---|
| | taattaacgatcgagc- catggtcttgaacttctt- gacattact (SEQ-ID No: 135) | gaccgataccgg- taggcgccacaatcag- taaattgaacggagaa- tattattc (SEQ-ID No: 56) | taggcgccacaatcag- taaattgaacggagaa- tattattc (SEQ-ID No: 56): |
| p-Napin_MCS_t-OCS | Forw: atacccgggatacc- tgcaggttagg- ccggccataaggat- gacctacccattcttga (SEQ-ID No: 138) Rev: caatcaattatagg- cctcgcatgctttaat- taacgatcgagccatg- gtgtttttaatcttgtttgtatt (SEQ-ID No: 139) | Forw: ccatggctcgatcgttaat- taaagcatgcgagg- cctataattgatt- gctgctttaatgagatatg- cgagacg (SEQ-ID No: 55) Rev: taagcggccgcaatc- ggaccgatacc- ggtaggcgccacaat- cagtaaattgaacgga- gaatattattc (SEQ-ID No: 56) | Forw: atacccgggatacc- tgcaggttagg- ccggccataaggat- gacctacccattcttga (SEQ-ID No: 138) Rev: taagcggccgcaatc- ggaccgatacc- ggtaggcgccacaat- cagtaaattgaacgga- gaatattattc (SEQ-ID No: 56) |
| p-LuPXR_MCS_t-OCS | Forw: atacccgggatacc- tgcaggttagg- ccggccacacgggcag- gacatagggactact (SEQ-ID No: 142) Rev: caatcaattatagg- cctcgcatgctttaat- taacgatcgagccatg- ggatttatgataaaaatg- tcggt (SEQ-ID No: 143) | Forw: ccatggctcgatcgttaat- taaagcatgcgagg- cctataattgatt- gctgctttaatgagatatg- cgagacg (SEQ-ID No: 55) Rev: taagcggccgcaatc- ggaccgatacc- ggtaggcgccacaat- cagtaaattgaacgga- gaatattattc (SEQ-ID No: 56) | Forw: atacccgggatacc- tgcaggttagg- ccggccacacgggcag- gacatagggactact (SEQ-ID No: 142) Rev: taagcggccgcaatc- ggaccgatacc- ggtaggcgccacaat- cagtaaattgaacgga- gaatattattc (SEQ-ID No: 56) |

The promoter-terminator cassettes were cloned into the pCR2.1 (Invitrogen) vector according to the manufacturer's manual and subsequently sequenced. In a further step, the delta 6 Desaturase Gene (SEQ ID NO: 68) was introduced via the NcoI, PacI restrictions site between the promoter and terminator sequence.

Using the Multisite Gateway System (Invitrogen), a multiple cloning site (SEQ ID 57) was introduced into each of the three pENTR vectors pENTR/A pENTR/B and pENTR/C via HindIII and KpnI restrictions sites. Into the first position of this MCS, the promotor-delta 6 Desaturase-terminator cassette was cloned via FseI and KasI. Similarily, the DsRed gene was introduced into pENTR/C between the Napin promotor and the OCS terminator. By performing a site specific recombination (LR-reaction), the created pENTR/B, pENTR/C and an empty pENTR/A vector were combined with the pSUN destination vector according to the manufacturers (Invitrogen) Multisite Gateway manual to generate the final binary vectors SEQ ID: 3 pSUN-p-GRPL_d6Des(Pir)_t-OCS, SEQ ID: 8 pSUN-p-PEF-var1_d6Des(Pir)_t-OCS, SEQ ID: 11 pSUN-p-PEF-var2_d6Des(Pir)_t-OCS, SEQ ID: 18 pSUN-p-SCT2-var2_d6Des(Pir)_t-OCS, SEQ ID: 24 pSUN-p-SETL-vad_t-OCS, SEQ ID: 79 pSUN-pBnCRU4_d6Des(Pir)_t-OCS, SEQ ID: 87 pSUN-pBnMYR_d6Des(Pir)_t-OCS, SEQ ID: 93 pSUN-pBnSETL-var2_d6Des(Pir)_t-OCS, SEQ ID: 94 pSUN-pBnSCT2-vad_d6Des(Pir)_t-OCS, SEQ ID: 97 pSUN-pBnMDP_d6Des(Pir)_t-OCS, SEQ ID: 105 pSUN-pBnRTI-4_d6Des(Pir)_t-OCS, SEQ ID: 113 pSUN-pBnMTFL_d6Des(Pir)_t-OCS, SEQ ID: 120 pSUN-pBnGSTF_d6Des(Pir)_t-OCS, SEQ ID: 132 pSUN-pBnLSP_d6Des(Pir)_t-OCS. Similarly, the two binary vectors SEQ ID: 137 pSUN-pNapin_d6Des(Pir)_t-OCS and SEQ ID: 141 pSUN-pLuPXR_d6Des(Pir)_t-OCS were cloned as a positive control, that is, these two vectors are known to be capable to drive seed specific expression of PUFA genes, e.g. the delta-6-desaturase SEQ ID NO: 68.

The resulting vectors were subsequently used for the production of transgenic plants. The promoter activity in the transgenic plant seeds was measured based on the expression of delta 6 Desaturase and an observed modification in the lipid pattern of the seeds as described in example 5.

Example 4

Production of Transgenic Plants a) Generation of Transgenic Rape Seed Plants (Amended Protocol According to Moloney et al. 1992, Plant Cell Reports, 8:238-242)

For the generation of transgenic rapeseed plants, the binary vectors were transformed into *Agrobacterium tumefaciens* C58C1:pGV2260 (Deblaere et al. 1984, Nucl. Acids. Res. 13: 4777-4788). For the transformation of rapeseed plants (cv. Kumily,) a 1:50 dilution of an overnight culture of positive transformed acrobacteria colonies grown in Murashige-Skoog Medium (Murashige and Skoog 1962 Physiol. Plant. 15, 473) supplemented by 3% saccharose (3MS-Medium) was used. Petiols or Hypocotyledones of sterial rapeseed plants were incubated in a petri dish with a 1:50 acrobacterial dilusion for 5-10 minutes. This was followed by a tree day co-incubation in darkness at 25° C. on 3MS-Medium with 0.8% bacto-Agar. After three days the culture was put on to 16 hours light/8 hours darkness weekly on MS-medium containing 500 mg/l Claforan (Cefotaxime-Natrium), 100 nM Imazetapyr, 20 mikroM Benzylaminopurin (BAP) and 1.6 g/l Glucose. Growing sprouts were transferred to MS-Medium containing 2% saccharose, 250 mg/l Claforan and 0.8% Bacto-Agar. Even after three weeks no root formation was observed, a growth hormone 2-Indolbutyl acid was added to the medium for enhancing root formation.

Regenerated sprouts have been obtained on 2MS-Medium with Imazetapyr and Claforan and were transferred to the green house for sprouting. After flowering, the mature seeds were harvested and analysed for expression of the Desaturase gene via lipid analysis as described in Qui et al. 2001, J. Biol. Chem. 276, 31561-31566.

b) Production of Transgenic Flax Plants

The production of transgenic flax plants can be carried out according to the method of Bell et al., 1999, In Vitro Cell. Dev. Biol. Plant 35(6):456-465 using particle bombardment. Acrobacterial transformation could be carried out according to Mlynarova et al. (1994), Plant Cell Report 13: 282-285.

Example 5

Lipid Extraction

Lipids can be extracted as described in the standard literature including Ullman, Encyclopedia of Industrial Chemistry, Bd. A2, S. 89-90 and S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Better, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; und Dechow, F. J. (1989) Separation and purification techniques in biotechnology, Noyes Publications.

Alternatively, extraction will be carried out as described in Cahoon et al. (1999) Proc. Natl. Acad. Sci. USA 96 (22): 12935-12940, und Browse et al. (1986) Analytic Biochemistry 152:141-145. Quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

Figure 2:
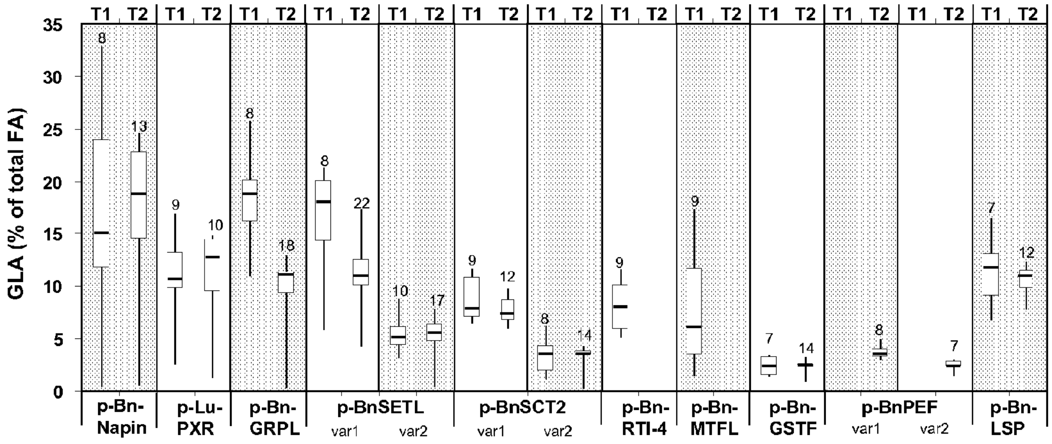
FIG. 2 shows the 18:3n-6 (GLA) content of seeds-oil of seeds harvested from transgenic plants harboring the T-DNA from vectors described in example 3. Shown are data from T1 seeds and T2 seeds as indicated on top of the figure. Measurements on T1 on seeds are on individual single seeds; measurements on T2 seeds are on seed batches. The black line indicates the minimal and the maximal observation, the box reaches from the 25% quartil to the 75 quartil; the median is indicated as black line within the box. The number of individual measurements is indicated as number above each box.
Figure 3:
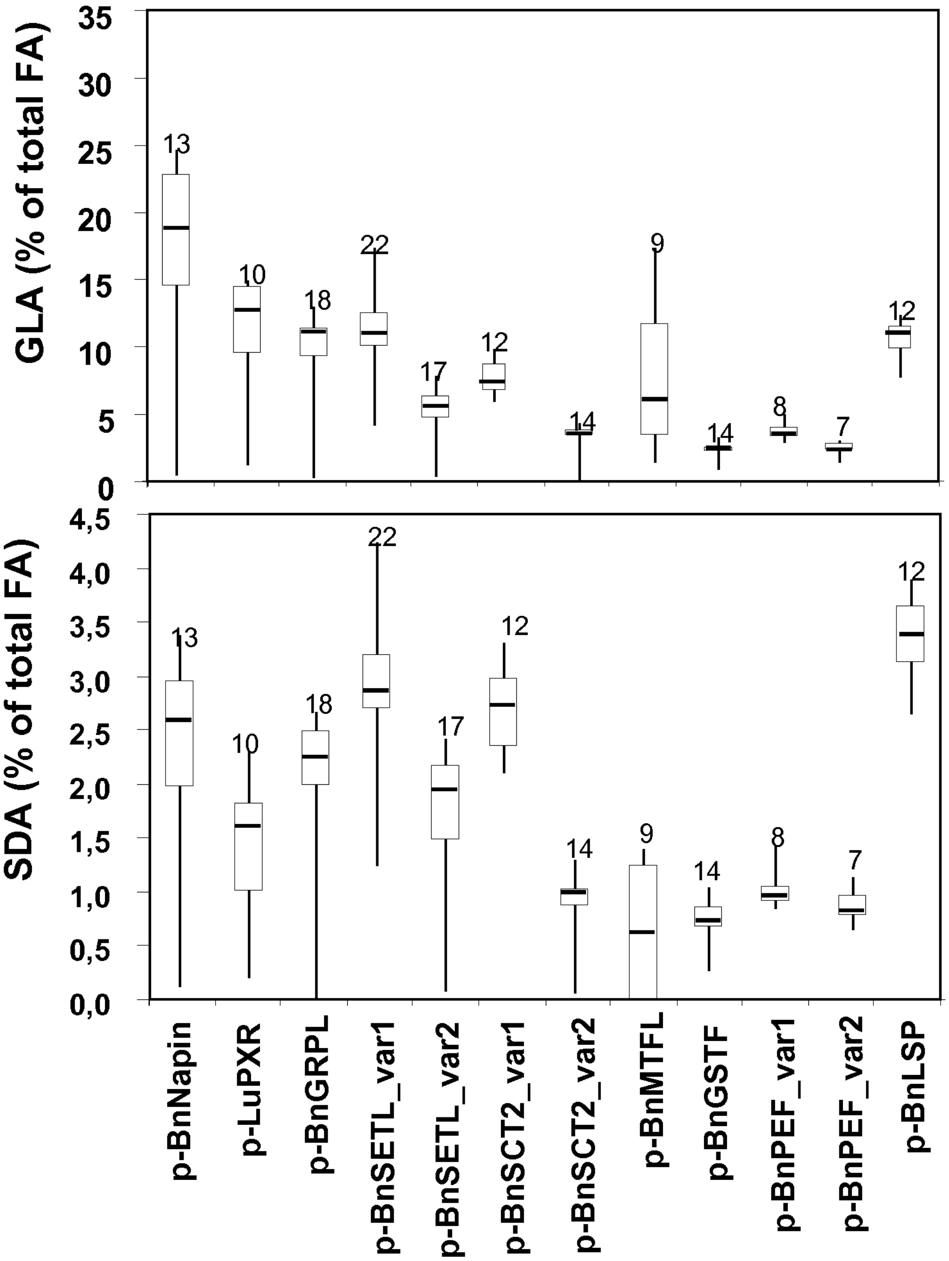
FIG. 3 shows the 18:3n-6 (GLA) and 18:4n-3 (SDA) content of seeds-oil of seeds harvested from transgenic Arabidopsis plants harboring the T-DNA from vectors described in example 3.
Figure 4:
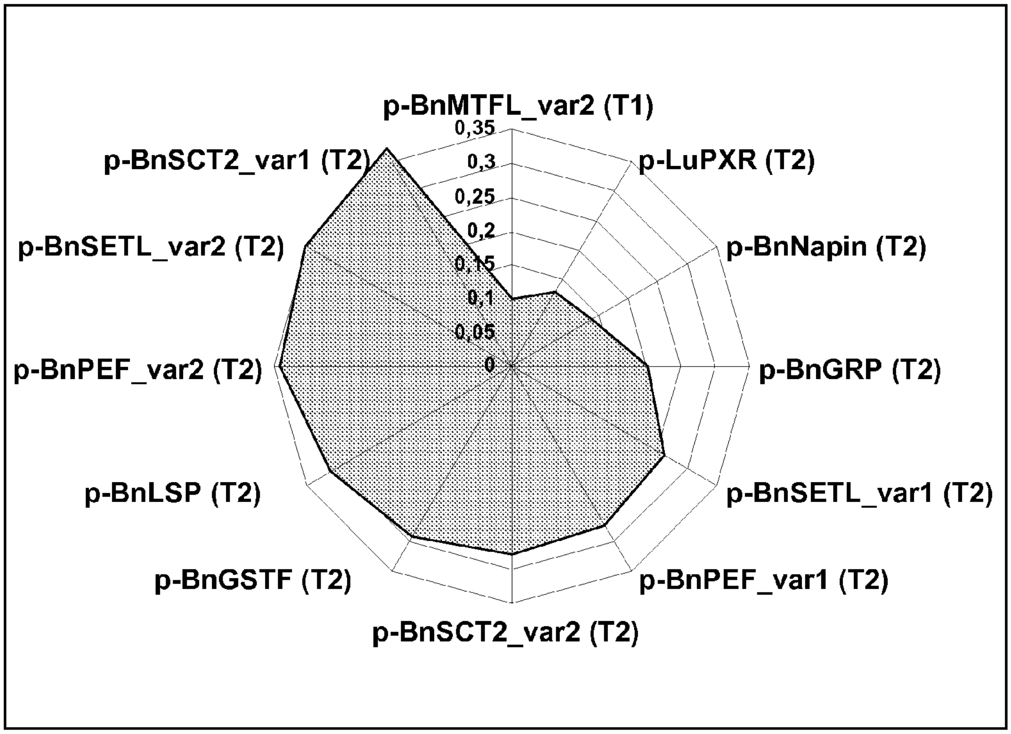
FIG. 4 illustrates for the different promoters the different ratios of the omega-3 fatty acid SDA to the omega-6 fatty acid GLA.

Based on the analysed lipids, the expression of the Desaturase can be determined since the lipid pattern of successfully transformed plant seeds will differ from the pattern of control plant seeds. Seed specific expression of a deta-6-desaturase would result in formation of 18:3n-6 (GLA) and/or 18:4n-3 (SDA), depending on whether the delta 6 desaturase uses 18:2n-6 (LA) and/or 18:3n-3 (ALA) as substrate. Surprisingly, not only the two control promotors Napin and LuPXR harbored by the vectors SEQ ID: 137 pSUN-pNapin_d6Des (Pir)_t-OCS and SEQ ID: 141 pSUN-pLuPXR_d6Des(Pir)_t-OCS were capable to drive seed specific expression of the delta-6-desaturase as indicated by the formation of GLA, but also the promotors of the present invention (FIG. 2). Interestingly, the promotors influenced the ratio of the omega-3 fatty acid SDA to the omega-6 fatty acid GLA.

The invention claimed is:

1. An expression cassette comprising an expression control sequence operatively linked to a nucleic acid of interest, wherein said expression control sequence is heterologous to and governs seed-specific expression of said nucleic acid of interest, and wherein said expression control sequence is at least 95% identical to the nucleic acid sequence SEQ ID NO: 22; wherein said expression control sequence governs seed-specific expression of said operatively linked nucleic acid of interest.

2. The expression cassette of claim 1, wherein said expression control sequence comprises the nucleic acid sequence SEQ ID NO: 22.

3. A vector comprising the expression cassette of claim 1.

4. The vector of claim 3, wherein said vector is an expression vector.

5. A non-human host cell comprising the expression cassette of claim 1 or a vector comprising said expression cassette.

6. A non-human transgenic organism comprising the expression cassette of claim 1 or a vector comprising said polynucleotide.

7. A method of expressing a nucleic acid of interest in a host cell comprising:

(a) introducing an expression cassette comprising an expression control sequence operatively inked to a nucleic acid of interest, wherein said expression control sequence is heterologous to and governs seed-specific expression of said nucleic acid of interest, and wherein said expression control sequence is at least 95% identical to the nucleic acid sequence of SEQ ID NO: 22 or 25 or a vector comprising said expression control sequence, into a host cell; and (b) expressing said nucleic acid of interest in said host cell.

8. The method of claim 7, wherein said host cell is a plant cell.

9. A method of expressing a nucleic acid of interest in a non-human organism comprising:

(a) introducing an expression cassette comprising an expression control sequence operatively inked to a nucleic acid of interest, wherein said expression control sequence is heterologous to and governs seed-specific expression of said nucleic acid of interest, and wherein said expression control sequence is at least 95% identical to the nucleic acid sequence of SEQ ID NO: 22 or 25 or a vector comprising said expression control sequence, into a non-human organism; and (b) expressing said nucleic acid of interest in said non-human transgenic organism.

10. The method of claim 9, wherein said non-human transgenic organism is a plant or seed thereof.

11. The method of claim 9, wherein said nucleic acid of interest is expressed seed-specifically.

12. The method of claim 7, wherein said nucleic acid of interest is expressed seed-specifically.

13. The expression cassette of claim 1, wherein said expression control sequence is at least 98% identical to the nucleic acid sequence SEQ ID NO: 22.

14. The expression cassette of claim 1, wherein said expression control sequence is at least 99% identical to the nucleic acid sequence SEQ ID NO: 22.

* * * * *

UNITED STATES PATENT AND TRADEMARK OFFICE

CERTIFICATE OF CORRECTION

| | |
|---|---|
| PATENT NO. | : 8,853,383 B2 |
| APPLICATION NO. | : 13/001742 |
| DATED | : October 7, 2014 |
| INVENTOR(S) | : Jörg Bauer et al. |

It is certified that error appears in the above-identified patent and that said Letters Patent is hereby corrected as shown below:

On the Title Page:

Item (75), Inventors: "Jörg Bauer, Durham, NC (US); Toralf Senger, Durham, NC (US)"

should read -- Jörg Bauer, Limburgerhof (DE); Toralf Senger, Heidelberg (DE) --

Signed and Sealed this
Twenty-seventh Day of October, 2015

Michelle K. Lee
*Director of the United States Patent and Trademark Office*

SEQUENCE LISTING

```
<160> NUMBER OF SEQ ID NOS: 143

<210> SEQ ID NO 1
<211> LENGTH: 1790
<212> TYPE: DNA
<213> ORGANISM: Brassica napus

<400> SEQUENCE: 1

caaaacgaaa tcatcaaatc gtggagccgt cctcgagcta tagaagtcag atcaccaaaa     60

accatatctt gaaaaccaag acgagagggg agtaacaatg gtaagccaac gacgaggaaa    120

acaacttcaa agacgactaa actctgaccc aacccaaaga gatgcagttc ctaacatcag    180

ctaaaatcta aggaagaaga ggagcatcca atattgcatg gagtagccta aaatgatgcg    240

agaaacaacc gcacaactgg gaactcctaa acccgatcta caataaatac cagaaatctc    300

aaggtgaaga aggcgataaa gaacaagagc atgaggtgag tcttttttgg tgatgatgag    360

aaacaccgca taccagaaac gtaaagaaaa tacatagatg ttgaaggctc aatgtaaaaa    420

atatgggaaa aaaacgaaaa catcttgaaa gttataatgt tcaaaaatat aaaaaaaatt    480

aaaagaaaat tttgacgctg aaaccgtaaa tcttagaatc aacaaatgca taaatgcaaa    540

gttattgaaa ttcaatatat ttttatatta gagactcact tcactgctaa caaatactat    600

acagacaaaa cacattatta aaaaaacaaa gacaaaatat attaacatat cactattact    660

actacataac acaataaaaa caccaaataa cattcttaac aaataaaagt gatcacataa    720

ttacattatc caaaaaatca tacttttaac aacaataaaa caatattccg cgcgaagcgc    780
```

ggacaccccc ctagtacact atgtagtcat gttgtatgaa aggccaggtt ttgcagcttt 840
cgatggacct gatttcccat gcatagtagt cgtcatctcg ggtttattca agttatatct 900
ttcttttgtt cacgttcttt aatctgaacc ctatcaccga tttatttagg aaaactcatt 960
gttatacaca aaaattacca cttttctgtc tctaatcact cgtttttaat ttggtagttt 1020
cagtggacgt atgtgtctta gtgtagcttt tcatagtgtt aacatgttta agcgtgttct 1080
tgggccatca tgaaaacata gatatggtcg aaaacaggtc taagtagtgg tggttaacaa 1140
aaggccattt caacttatgt tctaaaagat agaaagcaaa gcattgttga taaagcctct 1200
ctctttatat aaagaggggc tttagcgcct tcggcatgct ttgactttac ctcttgttca 1260
agtgaagggt ttcggcttat acgcagtatc gtagccagtt taagtgaagg cactagcaag 1320
aatcaatgta agcagattat agtttgttag tttttcagag atagctcgat gcgttctaag 1380
ctttctgaac taacgccttt gaaagaaaaa aatggtcaat tgacgccatt gtaaccacta 1440
accacatgca ctggctatgc atgcaaacac aatgagatca cgggatggcc taagagtaaa 1500
ccaactttgg aatcccaaaa aattatagcc atgtgtcgtt cttgatgaaa ttcgtttcca 1560
ataaaattta gaaacaaacc acaaaaatac aaagtaattt tttaacttaa atggggaaaa 1620
taaactttgg agtcacgaga aagagatagg gcttaaagca gcagcgatac acctgtgata 1680
cgtttcgttt tcgtttgtta tcacaatttc atggactata tacatttagc ttagcttgca 1740
aaagaaacca tctacttgag cttcaataca ataattccgg ctctctaaaa 1790

<210> SEQ ID NO 2
<211> LENGTH: 581
<212> TYPE: DNA
<213> ORGANISM: Brassica napus

<400> SEQUENCE: 2
tttctcctct tagtttgtaa ataatctatc taccataatg ttctatatag gtgttggact 60
atttggccta atcacatcaa tatatccact tcaaaattta cagcttctta aatacttact 120
aagccgtgaa ttaattacta attgagagtt attcttgtta acttacttca ttttattgtt 180
cttgaagaag cagagagcta tttcttaaaa ataccattga acaaacacag ggccggctca 240
agaaaattat gggcccctgg gcaaaataat ttttcaaaaa aaaatttaca tatactctat 300
ggataacata aaaattttgg gccccttttta aaattttttt tttgaaaatc aagtcccata 360
ttaacactaa ttatgcaaaa aaaaaaattg ggccctgggc ccacgccccc cttgccccta 420
tgcctcagcc ggccctgaac aaacaaacaa aattccgtcg acacacgaca aacttcaaac 480
tacaattaag aatgtcccta aactattgtc tgcttttcca aacctgtcaa gatcgacatt 540
gaagtttagt ctcttttgtt tgttaggtta ggtagataat c 581

<210> SEQ ID NO 3
<211> LENGTH: 16232
<212> TYPE: DNA
<213> ORGANISM: Artificial sequence
<220> FEATURE:
<223> OTHER INFORMATION: Plasmid

<400> SEQUENCE: 3
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240

-continued

```
gtgaaaaggt ttatccgttc gtccatttgt atgtcaatat ccatgataag tcgcgctgta    300
tgtgtttgtt tgaatattca tggaacgcag tggcggtttt catggcttgt tatgactgtt    360
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
```

-continued ggcaatttgc cctagcatct gctccgtaca ttaggaaccg gcggatgctt cgccctcgat 2640
caggttgcgg tagcgcatga ctaggatcgg gccagcctgc cccgcctcct ccttcaaatc 2700
gtactccggc aggtcatttg acccgatcag cttgcgcacg gtgaaacaga acttcttgaa 2760
ctctccggcg ctgccactgc gttcgtagat cgtcttgaac aaccatctgg cttctgcctt 2820
gcctgcggcg cggcgtgcca ggcggtagag aaaacggccg atgccggggt cgatcaaaaa 2880
gtaatcgggg tgaaccgtca gcacgtccgg gttcttgcct tctgtgatct cgcggtacat 2940
ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggcccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc accttttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980

-continued actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280
aaaaaaatga aatccacatc ctgccatcat aacctcatgc tggaaaaaga aatgaaaaaa 5340
tataaaaaat ttcttttgtt tattaaattt acaactttaa tactagtttc ttttctattt 5400
tttaaaagct tttgtcactt acttaaaaaa aaaaaacttt ttgaaatatt cctacttcca 5460
atgtctgatt agtgcttctg gatttccttt ttggatcatg tgaatcctaa atcagaaaaa 5520
ttcatataat acccaattca gtatattttc atacttcaat ttacaagagt tctctatgtt 5580
tttagcttct ttcttttaag ccaaatgttt taagcatctt ttatacatta aaataattta 5640
gtgttgagtt gagatttttt tttttttttt ttggatttac ttgttcaaaa tctgaaaaaa 5700
tgtttacaga aggttaaaat gaaccaaaag gcatatcaag ctagattttg aattacccta 5760
tttcatcgta tacacaaaac tgataatgtg gacacagttg attttacttc tcgatgacat 5820
cgtagtttta tttaatttgg aaaccacggc ccatatgagc acatttcaat taaaaaccaa 5880
tggtaagagc attttccatg caagattcga gagatattaa cccagtgact gttaaaacag 5940
cttagaaccc taataacgaa tttcaattac tcaatttacc attcgcattt cgcaataacc 6000
aaactgagcc agtcacaagg agtaaaccga accggattat ttatttataa aatgaaagaa 6060
aggaaaccaa acaacaacag cagtagtagt ctgacgtaaa ccaaaaagca ggcagatcaa 6120
caactaaaag aaactcaaat taccaaaaca aacaggaaat tgcaaactaa gttttttttac 6180
catatgcata caaagaccat aaaaggttct gataatcacc ggtttcatct cgtcgagatt 6240
accctgttat ccctatcagt atttaatccg gccatctcct tccgttatga catcgttgaa 6300
agtgccacca ttcgggatca tcggcaacac atgttcttgg tgcggacaaa tcacatccaa 6360
caggtaaggt cctggtgtat ccagcattgt ctgaatagct tctcggagat ctgctttctt 6420
tgtcaccctc gccgctggaa tcccgcaagc tgctgcaaac agcaacatgt tcgggaatat 6480
ctcgtcctcc tgagccggat ccccgagaaa tgtgtgagct cggttagctt tgtagaaccg 6540
atcttcccat tgcataacca tgccaagatg ctggttgttt aataaaagta ccttcactgg 6600
aagattctct acacgaatag tggctagctc ttgcacattc attataaagc ttccatctcc 6660
gtcaatatcc acaactatcg catcagggtt agcaacagac gctccaatcg cagcaggaag 6720
tccaaatccc atagctccaa ggcctcctga tgatagccac tgccttggtt tcttgtaatt 6780
gtagaactgc gccgcccaca tttgatgttg cccgacacca gtacttatta tggcttttcc 6840
atcagtcaac tcatcaagga ccttaatcgc atactgtgga ggaatagctt ccccaaacgt 6900
cttaaagctc aacggaaact tctgtttctg tacgttcaac tcattcctcc aaactccaaa 6960
atcaagctta agctcctccg ctcggttctc aagaacctta ttcatccctt gcaaagccag 7020
cttaacatca ccacacacag acacatgagg agtcttattc ttcccaatct cagccgagtc 7080
aatatcaata tgaacaatct tagccctact agcaaaagcc tcaagcttac ccgtgacacg 7140
atcatcaaac cttaccccaa acgccaacaa caaatcacta tgctccacag cgtaatttgc 7200
atacacagtc ccatgcattc caagcatatg taacgacaac tcatcatcac aaggataaga 7260
tcccagcccc atcaacgtac tcgcaacagg gatccccgta agctcaacaa acctacccaa 7320

-continued ttcatcgcta gaattcaaac aaccaccacc aacatacaac acaggcttct tagactcaga 7380
aatcaaccta acaatctgct ccaaatgaga atcttccgga ggtttaggca tcctagacat 7440
ataaccaggt aatctcatag cctgttccca attaggaatc gcaagctgtt gttgaatatc 7500
tttaggaaca tcaaccaaaa caggtccagg tctaccagaa gtagctaaaa agaaagcttc 7560
ctcaataatc ctagggatat cttcaacatc catcacaaga tagttatgct tcgtaatcga 7620
acgcgttacc tcaacaatcg gagtctcttg aaacgcatct gtaccaatca tacgacgagg 7680
gacttgtcct gtgattgcta caagaggaac actatctaac aacgcatcgg ctaatccgct 7740
aacgagattt gtagctccgg gacctgaagt ggctatacag atacctggtt tacctgagga 7800
tcgagcgtat ccttctgctg cgaatacacc tccttgttcg tgacgaggaa ggacgttacg 7860
gattgaggaa gagcgggtta aggcttggtg aatctccatt gatgtacctc cagggtaagc 7920
gaatacggtt tctacgcctt gacgttctaa agcttcgacg aggatatcag cgcctttgcg 7980
gggttgatct ggagcgaatc gggagatgaa tgtttcgggt ttggtaggtt tggttggaga 8040
gggagtggtt gtgacattgg tggttgtgtt gagcacggcg gagatggagg agggagagct 8100
ggatttgata ccgcggcggc gggaggagga ggatgatttg ttggggttta gggagaatgg 8160
gagggagaat ctggagattg gtaatggtga tttggaggag gaaggagatg gtttggtgga 8220
gaaggagatc gaagaagatg ttgttgttgt tgttgttgcc gccgccatgg ttcagctgca 8280
catacataac atatcaagat cagaacacac atatacacac acaaatacaa tcaagtcaac 8340
aactccaaaa agtccagatc tacatatata catacgtaaa taacaaaatc atgtaaataa 8400
tcacaatcat gtaatccaga tctatgcaca tatatatata cacaattaat aaaaaaaatg 8460
atataacaga tctatatcta tgtatgtaac aacacaatca gatgagagaa gtgatgtttt 8520
cagatctgta tacatacaaa cacaaacaga tgaacaattg atacgtagat ccatatgtat 8580
acgtacaatt agctacacga ttaaatgaaa aaaatcaacg atttcggatt ggtacacaca 8640
aacgcaacaa tatgaagaaa ttcatatctg attagatata aacataacca cgtgtagata 8700
cacagtcaaa tcaacaaatt tatagcttct aaacggatga gatgaacaag ataaagatat 8760
tcacataagg catacataag ataagcagat taacaaacta gcaataatac atacctaatt 8820
aaaacaagga ataacagaga gagagagaga gagagagatt taccttgaaa atgaagagga 8880
gaagagagga tttcttaaaa ttgggggtag agaaagaaag atgatgaatt gtgagaaagg 8940
agagatagaa gggggggttg tatatatagg ctgtagaaga ttatttttgt gtttgaggcg 9000
gtgaaggaag aggggatctg actatgacac gtttgcggtt acgtatttcg ataggagtct 9060
ttcaacgctt aacgccgtta ctctatatga ccgtttgggc cgtaacgggg ccgtttgtta 9120
acgctgatgt tgattctttt ctttctttct ttcttccttt tttaaagaag caattgtaca 9180
atcgttgcta gctgtcaaac ggataattcg gatacggata tgcctatatt catatccgta 9240
atttttggat tcgaattttc ccctctaggg ataacagggt aatggatcta tattgttttt 9300
gtttcacata aatgtcgttt tggattattc atgtaatatt ttaaactaaa gtacaatttt 9360
tgactacttt agtttactag ttaagctttt atttttttga ctaaccattg aatgatgaag 9420
agatcaacgc atcatattta caacttacat agtcttttgg aagtgtaaat tgctaatact 9480
acctaaaata tatctataat taactaatat tttttcgtca attataatag atcaattaaa 9540
aggctatcaa aaggaaaaaa atgaaatcca catcctgcca tcataacctc atgctggaaa 9600
aagaaatgaa aaaatataaa aaatttcttt tgtttattaa atttacaact ttaatactag 9660
tttcttttct attttttaaa agcttttgtc acttacttaa aaaaaaaaaa ctttttgaaa 9720

-continued

```
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
```

-continued

```
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc ggcctattag gccacggtcc  12480
gtacagtgtt taaacgattg acctgcagga tacaagtgcg cacagactag cggccgctaa  12540
tcccgggaat taccggtagt aggcgccaca atcagtaaat tgaacggaga atattattca  12600
taaaaatacg atagtaacgg gtgatatatt cattagaatg aaccgaaacc ggcggtaagg  12660
atctgagcta cacatgctca ggttttttac aacgtgcaca acagaattga aagcaaatat  12720
catgcgatca taggcgtctc gcatatctca ttaaagcagc aatcaattat taattaagtt  12780
aacttacatc gctgggaact cggtgataaa ttccttgctg atgtccgcca ggtggtccac  12840
gacctcgtag atgccctccc agaagccggt ctcgtggaac gggatgtcga actccttgca  12900
tagcgacttg atgagcacgt tgacctttgg caagttgtgg cgcggcacga gcgggaacag  12960
gtgatggtcg atctggtagt tcaagccacc ggtgaaccag tccatgaata ccgacgcgcg  13020
gatgttgcgc gtcgtggtca cctgcagctg ccagaagtcc ggcttggttt cgcgctcgta  13080
caccgacatg ccgttgtggc caatactgaa caccagcgcc aggagcaagc cgcaggacgc  13140
ctggcccatg aggaagtatg ccacgccctc aaacaggctc atgttgcaga agtacgggat  13200
cgcgagctgc cagatgtagt gcacgatcag acccgccttc tccggtccgt cgaactcgac  13260
cttgtcgaag atgccgaacg agaactcggt gaacacgtag aagaacgact gcgcgagcca  13320
gctcaggcgc gcgagcagca gcagcgggaa gtataggaac gcctggttgc ggatgaagaa  13380
cgggccgtgc gccgactcga acgccttgcg cgccatctcc ttagaccacg ccagcagcgg  13440
catggtgtcg atgtccgggt cgccgatgaa gccctcgtcc ttggcgctgt gcaggttcgg  13500
caccgcgtgg tgcaggttgt gcttgttctt ccaccactgc atgctgaagc cctgccaggc  13560
gttgcccacg aggcagccga taaggttgcc gagcgtgcgg ttctcgcaca cctggttgtg  13620
caagaagtcg tgcgccagcc atccggactg ctggtagaag agccccataa tcacgccggc  13680
gaccatgtac atggcgaaac tgttgaagaa gaagcagatc gccatcgaga gcaccgcgat  13740
gccgaacgtg ctcacgagct tccacgcgta gtagagcgcg ctggcgtcgt agagccccat  13800
gcccttgacc ttgacgcgca gacggcggta ggacgcgatg aactcgttga tgcgctcgcg  13860
gcgcgcgcgc tcctcgtcgc tcgccggctc cccctcgatc tcggccttgg aggtttcgtc  13920
cacgtcgccg acgtagaact gctcgagcag cttgagcgcc gaggacgggt ggaagaccgc  13980
gaaggcgtcc gtggcgtcct cgccggcctg cgtgagcatc acggagccac ccgggtgcga  14040
gtcccacttg gagatgtcgt agaccttgtg gtgaatcacg atccacgcgg tcgcgggcgt  14100
cgcgtgctcg cggatctcct tccagctcac caggcgcttc actccaggct tgaggtccac  14160
cattttgggc cccggcgcgg ttttagagag ccggaattat tgtattgaag ctcaagtaga  14220
tggtttcttt tgcaagctaa gctaaatgta tatagtccat gaaattgtga taacaaacga  14280
aaacgaaacg tatcacaggt gtatcgctgc tgctttaagc cctatctctt tctcgtgact  14340
ccaaagttta ttttccccat ttaagttaaa aaattacttt gtatttttgt ggtttgtttc  14400
taaattttat tggaaacgaa tttcatcaag aacgacacat ggctataatt ttttgggatt  14460
```

```
ccaaagttgg tttactctta ggccatcccg tgatctcatt gtgtttgcat gcatagccag  14520
tgcatgtggt tagtggttac aatggcgtca attgaccatt tttttctttc aaaggcgtta  14580
gttcagaaag cttagaacgc atcgagctat ctctgaaaaa ctaacaaact ataatctgct  14640
tacattgatt cttgctagtg ccttcactta aactggctac gatactgcgt ataagccgaa  14700
acccttcact tgaacaagag gtaaagtcaa agcatgccga aggcgctaaa gcccctcttt  14760
atataaagag agaggcttta tcaacaatgc tttgctttct atcttttaga acataagttg  14820
aaatggcctt ttgttaacca ccactactta gacctgtttt cgaccatatc tatgttttca  14880
tgatggccca agaacacgct taaacatgtt aacactatga aaagctacac taagacacat  14940
acgtccactg aaactaccaa attaaaaacg agtgattaga gacagaaaag tggtaatttt  15000
tgtgtataac aatgagtttt cctaaataaa tcggtgatag ggttcagatt aaagaacgtg  15060
aacaaaagaa agatataact tgaataaacc cgagatgacg actactatgc atgggaaatc  15120
aggtccatcg aaagctgcaa aacctggcct ttcatacaac atgactacat agtgtactag  15180
gggggtgtcc gcgcttcgcg cggaatattg ttttattgtt gttaaaagta tgatttttttg  15240
gataatgtaa ttatgtgatc acttttattt gttaagaatg ttatttggtg tttttattgt  15300
gttatgtagt agtaatagtg atatgttaat atattttgtc tttgtttttt taataatgtg  15360
ttttgtctgt atagtatttg ttagcagtga agtgagtctc taatataaaa atatattgaa  15420
tttcaataac tttgcattta tgcatttgtt gattctaaga tttacggttt cagcgtcaaa  15480
atttctttt aattttttt atatttttga acattataac tttcaagatg ttttcgtttt  15540
tttcccatat tttttacatt gagccttcaa catctatgta ttttctttac gtttctggta  15600
tgcggtgttt ctcatcatca ccaaaaaaga ctcacctcat gctcttgttc tttatcgcct  15660
tcttcacctt gagatttctg gtatttattg tagatcgggt ttaggagttc ccagttgtgc  15720
ggttgtttct cgcatcattt taggctactc catgcaatat tggatgctcc tcttcttcct  15780
tagattttag ctgatgttag gaactgcatc tctttgggtt gggtcagagt ttagtcgtct  15840
ttgaagttgt tttcctcgtc gttggcttac cattgttact cccctctcgt cttggttttc  15900
aagatatggt ttttggtgat ctgacttcta tagctcgagg acggctccac gatttgatga  15960
tttcgttttg tggccggcct agtagattta aattggcctt agtggccaag cttggcgtaa  16020
tcatggagcc tgcttttttg tacaaacttg ggtaccggcc tattaggcca cggtccgtac  16080
agtgtttaaa cgattgacct gcaggataca agtgcgcaca gactagcggc cgctaatccc  16140
gggaattacc ggtagtaggc gcctactttg gccggcctag tagatttaaa ttggccttag  16200
tggccaagct tggcgtaatc atggcaactt tt                                16232
```

```
<210> SEQ ID NO 4
<211> LENGTH: 174
<212> TYPE: DNA
<213> ORGANISM: Brassica napus

<400> SEQUENCE: 4

tcgaatacac aatacaagaa gccatgtttg ttcttctgca acaaatgttg taccaagtgt     60
ttgtgtgtgc ctccaggtac ttatggcaac aagcaagtct gtccttgcta caacaactgg    120
aagactaagc tgggtggacc aaaatgccct tgatttctcc tcttagtttg ttaa          174
```

```
<210> SEQ ID NO 5
<211> LENGTH: 360
<212> TYPE: DNA
```

<213> ORGANISM: Brassica napus

<400> SEQUENCE: 5
atggcaacca aacttaacct cattgttttc tccattgtta tgttacacca ccttatatct 60
gtccaaatgc atcccataca cgctaagtct cctgctccac aaccacatcc accacagtct 120
caaccgcatc acaatagctc tcaaaacggt actacggaag gcagtcttca gctccaagag 180
tgtgggccaa ggtgtggaca tagatgctca aatacacaat acaagaagcc atgtttgttc 240
ctctgcaaca aatgttgtac caagtgtttg tgtgtgcctc caggtactta tggcaacaag 300
caagtctgtc cttgctacaa caactggaaa actaagcttg gtggaccaaa atgcccttga 360

<210> SEQ ID NO 6
<211> LENGTH: 2027
<212> TYPE: DNA
<213> ORGANISM: Brassica napus

<400> SEQUENCE: 6
aatttattaa cccatctatt tgttcactct tatgtttagg cacgtgcgtt caattttcag 60
ttcgactgta attttttttt tttggttttc ggtgtcggtt gtgattttgt tttttttttt 120
cgaatgaaga aatataggaa ccgttcgatt atttgtgaat ttaggtttgg tttcggatta 180
attagttagc tctcagtttg attgcgataa aaatattaaa aacttagata aagtttcaaa 240
gcacggaata tttttgttg acaaatttat taatccatct atttgttcac tcttatgttt 300
aggcatgtgc gttcaatttt cagttagact gtaatttgtt tttttttgg ttttcggtgt 360 cggttgtgat tttgtttttt ttttcgaatt aagaaataaa gggaccgttc gattatttgt 420
gaatttaggt ttggtttcgg attaattagt tagctctcag tttgattgcg ataaaaaatt 480
aaaaacttat ataaagtttc gagtttaatt tggtgctggt tcggtacctg tttttggat 540 aatacggtta aaagtcacaa ttttatattt ttagaacaaa atcggctaaa tttaaatatt 600
taacatataa tattcttgtg atttctttgt attgagacat ccgtatctta catagtaata 660
tttcttatct tttataaatc tatttatatt gaagttgatt ttaataatga aaataaatta 720
tatttaaaac tcttacaatg tataataact tcccgaaaac tatcaagatt ttttatttta 780
aaattaacat ttataataca aaataagaac cattttaaaa ttaattcata aaataaccat 840
ttttaataag aacaaaaatt atccatgttt atgttaacga atataaaaaa agtaaaaact 900
gagttttaaa gcctatagga tcaaaaatta catgaagggc tactggtaag ttgggcttac 960
aaatgaacga ccaactattg ttttctataa cccaacccaa aacaagttta agtatcctga 1020
aaccgacaaa agagaatact gtctttttga ctttcctgaa taatctttaa aaaatatcag 1080
ttctctctgg aaatagtaaa gtaagaactg atgcaacatg atccatcacc gatctacgaa 1140
ggtataacac gaatccaccc gtttttttga tcattatatc gtacgcgctt aaaaaccttt 1200
tttacgaact aaaattttc tgtttttac ttttcagata atgttgcatg tgtgtgatcc 1260
gatgatagat ctgtttattc caatgagaat ctgttgtttt tgtgtgtgtc cgaagacgat 1320
ctgacaaaat aaagtatctc tcaatacaaa ccaagctatt tacattggga tgttttgttt 1380
aattggacat agtcaaatgt gttggacttt taatttccga aaatcattaa aaacaattaa 1440
aaaaggtaat ggagattttt gtaattaatt ggaaaagtga gggcataatc tttcccttta 1500
atagtataga tatggaacta tggaagctat agacactatg aattaaaatt ttagttgcag 1560
ttaaaattac gaatcatggg ctcctatcta tattttacat cacaataaag ctatatatca 1620
ttggtggaat ctgaagtgaa gacaaaccct aaactcaaaa cctctaataa taagccaaac 1680

```
acttgattcc aaacagaaac aaatagcgac cttgcacgat aatagatagg ccactttgaa   1740

aaataaataa ggatcagatt tcttggttta aacagtaaaa gctaatgtgt ttcaaaaaaa   1800

aaaaaaaaca gtaaaagcta atacacatga agacaagaaa aacttataga ttttacccac   1860

aaaacaaact tgtagactct tgtgttcgtt gccaatgttg gcttctttcc accacacaaa   1920

tatgaccgtt aagactcaaa ggaccacttt ataattacta catgcatgta taaaatctat   1980

agatcgtcca ttgtcatttg cttactccga ccattttctt tctcgtc                 2027
```

<210> SEQ ID NO 7
<211> LENGTH: 477
<212> TYPE: DNA
<213> ORGANISM: Brassica napus

<400> SEQUENCE: 7

```
taaggaatca acttcaaatg cttttccact tacctgcccc cccacactac accactgcgt     60

tctgttctca ttctttacat agcttagtta tcattagttt atttatttca ttattgtgat    120

tcatttgtaa tacatgttca agattcttgt caaaatgtgt aaactgttat gaaaataact    180

tgtgttttat tgtttcgcat gaatttagat aaaagcgaaa ttttatacca gtagaaactt    240

taacactgat agaaagattt tatcagagag agaagagaag gttgaggttt tgagatgcgt    300

aatacaacga acgtaaatgt tcgtatatat agaaagaaat tcactgtgca aatagtgtag    360

ctggccccac atcttttata tttttcaaca taaacggctg gctgctggct ttcttagctg    420

tctttcataa tactccccct tggggaccgg tgtcactatc cactctcgct taacgtc       477
```

<210> SEQ ID NO 8
<211> LENGTH: 16469
<212> TYPE: DNA
<213> ORGANISM: Artificial sequence
<220> FEATURE:
<223> OTHER INFORMATION: Plasmid

<400> SEQUENCE: 8

```
ctatacaaag ttgatagctt ggcgtaatcg atgtaccgat atcaatttaa attggccggc     60

cgagctccct gcaggggggcc cggcgcgcct ctagattaat taaaggcctt agttactaat    120

cagtgatcag attgtcgttt cccgccttca gtttaaacta tcagtgtttg acaggatata    180

ttggcgggta aacctaagag aaaagagcgt ttattagaat aatcggatat ttaaaagggc    240

gtgaaaaggt ttatccgttc gtccatttgt atgtcaatat ccatgataag tcgcgctgta    300

tgtgtttgtt tgaatattca tggaacgcag tggcggtttt catggcttgt tatgactgtt    360

tttttggggt acagtctatg cctcgggcat ccaagcagca agcgcgttac gccgtgggtc    420

gatgtttgat gttatggagc agcaacgatg ttacgcagca gggcagtcgc cctaaaacaa    480

agttaaacat catgggtgaa gcggtcatcg ccgaggtgtc cacccagctg tcggaagtcg    540

tgggtgtcat cgagcgccac ctcgaaccga ccctcctcgc cgtgcatctg tatggtagcg    600

ccgttgacgg cggccttaag ccccattcgg acatcgacct gcttgtcacc gttaccgtcc    660

gtctcgacga gaccacgcgc cgcgcgctta tcaacgacct tctggaaacg tccgcctccc    720

ccggcgagag cgaaatcctg cgcgcggttg aggtgacgat tgtggtgcac gatgacatca    780

tcccctggcg ctatccggcc aaacgcgaac tccagttcgg cgaatggcag cgtaatgata    840

ttctggcggg tatctttgaa ccggccacca tcgacattga tctggcgatc ctgctcacca    900

aggcccggga gcatagcgtg gccctcgtcg gccccgcggc cgaggaactt ttcgacccgg    960
```

-continued

```
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
```

-continued tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc accttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980
actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280
aaaaaaatga aatccacatc ctgccatcat aacctcatgc tggaaaaaga aatgaaaaaa 5340
tataaaaaat ttcttttgtt tattaaattt acaactttaa tactagtttc ttttctattt 5400
tttaaaagct tttgtcactt acttaaaaaa aaaaaacttt ttgaaatatt cctacttcca 5460
atgtctgatt agtgcttctg gatttccttt ttggatcatg tgaatcctaa atcagaaaaa 5520
ttcatataat acccaattca gtatattttc atacttcaat ttacaagagt tctctatgtt 5580
tttagcttct ttcttttaag ccaaatgttt taagcatctt ttatacatta aaataattta 5640
gtgttgagtt gagatttttt tttttttttt ttggatttac ttgttcaaaa tctgaaaaaa 5700

-continued

```
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gtttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
```

-continued

```
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa ggggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taataccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
```

-continued

```
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc ggcctattag gccacggtcc  12480
gtacagtgtt taaacgattg acctgcagga tacaagtgcg cacagactag cggccgctaa  12540
tcccgggaat taccggtagt aggcgccaca atcagtaaat tgaacggaga atattattca  12600
taaaaatacg atagtaacgg gtgatatatt cattagaatg aaccgaaacc ggcggtaagg  12660
atctgagcta cacatgctca ggttttttac aacgtgcaca acagaattga aagcaaatat  12720
catgcgatca taggcgtctc gcatatctca ttaaagcagc aatcaattat taattaagtt  12780
aacttacatc gctgggaact cggtgataaa ttccttgctg atgtccgcca ggtggtccac  12840
```

gacctcgtag atgccctccc agaagccggt ctcgtggaac gggatgtcga actccttgca 12900
tagcgacttg atgagcacgt tgacctttgg caagttgtgg cgcggcacga gcgggaacag 12960
gtgatggtcg atctggtagt tcaagccacc ggtgaaccag tccatgaata ccgacgcgcg 13020
gatgttgcgc gtcgtggtca cctgcagctg ccagaagtcc ggcttggttt cgcgctcgta 13080
caccgacatg ccgttgtggc caatactgaa caccagcgcc aggagcaagc cgcaggacgc 13140
ctggcccatg aggaagtatg ccacgccctc aaacaggctc atgttgcaga agtacgggat 13200
cgcgagctgc cagatgtagt gcacgatcag acccgccttc tccggtccgt cgaactcgac 13260
cttgtcgaag atgccgaacg agaactcggt gaacacgtag aagaacgact gcgcgagcca 13320
gctcaggcgc gcgagcagca gcagcgggaa gtataggaac gcctggttgc ggatgaagaa 13380
cgggccgtgc gccgactcga acgccttgcg cgccatctcc ttagaccacg ccagcagcgg 13440
catggtgtcg atgtccgggt cgccgatgaa gccctcgtcc ttggcgctgt gcaggttcgg 13500
caccgcgtgg tgcaggttgt gcttgttctt ccaccactgc atgctgaagc cctgccaggc 13560
gttgcccacg aggcagccga taaggttgcc gagcgtgcgg ttctcgcaca cctggttgtg 13620
caagaagtcg tgcgccagcc atccggactg ctggtagaag agccccataa tcacgccggc 13680
gaccatgtac atggcgaaac tgttgaagaa gaagcagatc gccatcgaga gcaccgcgat 13740
gccgaacgtg ctcacgagct tccacgcgta gtagagcgcg ctggcgtcgt agagccccat 13800
gcccttgacc ttgacgcgca gacggcggta ggacgcgatg aactcgttga tgcgctcgcg 13860
gcgcgcgcgc tcctcgtcgc tcgccggctc cccctcgatc tcggccttgg aggtttcgtc 13920
cacgtcgccg acgtagaact gctcgagcag cttgagcgcc gaggacgggt ggaagaccgc 13980
gaaggcgtcc gtggcgtcct cgccggcctg cgtgagcatc acggagccac ccgggtgcga 14040
gtcccacttg gagatgtcgt agaccttgtg gtgaatcacg atccacgcgg tcgcgggcgt 14100
cgcgtgctcg cggatctcct tccagctcac caggcgcttc actccaggct tgaggtccac 14160
cattttgggc cccggcgcgg tgacgagaaa gaaaatggtc ggagtaagca aatgacaatg 14220
gacgatctat agattttata catgcatgta gtaattataa agtggtcctt tgagtcttaa 14280
cggtcatatt tgtgtggtgg aaagaagcca acattggcaa cgaacacaag agtctacaag 14340
tttgttttgt gggtaaaatc tataagtttt tcttgtcttc atgtgtatta gcttttactg 14400 ttttttttt tttttgaaac acattagctt ttactgttta aaccaagaaa tctgatcctt 14460
atttattttt caaagtggcc tatctattat cgtgcaaggt cgctatttgt ttctgtttgg 14520
aatcaagtgt ttggcttatt attagaggtt ttgagtttag ggtttgtctt cacttcagat 14580
tccaccaatg atatatagct ttattgtgat gtaaaatata gataggagcc catgattcgt 14640
aattttaact gcaactaaaa ttttaattca tagtgtctat agcttccata gttccatatc 14700
tatactatta aagggaaaga ttatgccctc acttttccaa ttaattacaa aaatctccat 14760 taccttttt aattgttttt aatgattttc ggaaattaaa agtccaacac atttgactat 14820
gtccaattaa acaaaacatc ccaatgtaaa tagcttggtt tgtattgaga gatactttat 14880
tttgtcagat cgtcttcgga cacacacaaa aacaacagat tctcattgga ataaacagat 14940
ctatcatcgg atcacacaca tgcaacatta tctgaaaagt aaaaaacaga aaaattttag 15000
ttcgtaaaaa aggtttttaa gcgcgtacga tataatgatc aaaaaaacgg gtggattcgt 15060
gttatacctt cgtagatcgg tgatggatca tgttgcatca gttcttactt tactatttcc 15120
agagagaact gatattttt aaagattatt caggaaagtc aaaaagacag tattctcttt 15180

```
tgtcggtttc aggatactta aacttgtttt gggttgggtt atagaaaaca atagttggtc  15240

gttcatttgt aagcccaact taccagtagc ccttcatgta atttttgatc ctataggctt  15300

taaaactcag tttttacttt ttttatattc gttaacataa acatggataa tttttgttct  15360

tattaaaaat ggttatttta tgaattaatt ttaaaatggt tcttattttg tattataaat  15420

gttaatttta aaataaaaaa tcttgatagt tttcgggaag ttattataca ttgtaagagt  15480

tttaaatata atttatttc attattaaaa tcaacttcaa tataaataga tttataaaag  15540

ataagaaata ttactatgta agatacggat gtctcaatac aaagaaatca caagaatatt  15600

atatgttaaa tatttaaatt tagccgattt tgttctaaaa atataaaatt gtgactttta  15660

accgtattat ccaaaaaaca ggtaccgaac cagcaccaaa ttaaactcga aactttatat  15720

aagtttttaa ttttttatcg caatcaaact gagagctaac taattaatcc gaaaccaaac  15780

ctaaattcac aaataatcga acggtccctt tatttcttaa ttcgaaaaaa aaaacaaaat  15840

cacaaccgac accgaaaacc aaaaaaaaaa caaattacag tctaactgaa aattgaacgc  15900

acatgcctaa acataagagt gaacaaatag atggattaat aaatttgtca acaaaaaata  15960

ttccgtgctt tgaaacttta tctaagtttt taatattttt atcgcaatca aactgagagc  16020

taactaatta atccgaaacc aaacctaaat tcacaaataa tcgaacggtt cctatatttc  16080

ttcattcgaa aaaaaaaaac aaaatcacaa ccgacaccga aaaccaaaaa aaaaaaatta  16140

cagtcgaact gaaaattgaa cgcacgtgcc taaacataag agtgaacaaa tagatgggtt  16200

aataaattgg ccggcctagt agatttaaat tggccttagt ggccaagctt ggcgtaatca  16260

tggagcctgc ttttttgtac aaacttgggt accggcctat taggccacgg tccgtacagt  16320

gtttaaacga ttgacctgca ggatacaagt gcgcacagac tagcggccgc taatcccggg  16380

aattaccggt agtaggcgcc tactttggcc ggcctagtag atttaaattg gccttagtgg  16440

ccaagcttgg cgtaatcatg gcaactttt                                   16469
```

```
<210> SEQ ID NO 9
<211> LENGTH: 636
<212> TYPE: DNA
<213> ORGANISM: Brassica napus

<400> SEQUENCE: 9

gaattacgtt tgagttcaaa ttcaggtagc ttaagctcta attggtggct ttaggtaata     60

caagaggtct cagtttgtaa atgtagttaa aacttttgtg gtgtaaatca tgttcctctt    120

cgattggtta ataaaaagtt gttgatgagt taaaaaacaa aattagttgc agttaaaatt    180

acgaatcatg ggctcctatc tatattttac attacaataa agcttttttt ttgttcactg    240

cattacaata aagctatata tcactggtgg aatctgaaat aaagacaaac cctgaactca    300

aaacctgaaa taattagcca aacacttgat tccaaacaga aacaaatagc gacctaacac    360

gataatagat aggccacttt gaaaaataat ataaggatca gatttcttgg tttaaacagt    420

aaaaggtaaa acacatgaag acaagaaaaa aattatagat tttacaaaac aaaaaaaact    480

tgtagactct tgtgttcgtt gccaatgttg gcttctttcc accacacaaa tatgaccgtt    540

aagactcgaa ggaccacttt ataattacta catggatgta taaaatatat agatcgtcca    600

ttgtcatttg cttacttcga ccatttattt ctcgtc                              636
```

```
<210> SEQ ID NO 10
<211> LENGTH: 538
<212> TYPE: DNA
<213> ORGANISM: Brassica napus
```

<400> SEQUENCE: 10
taggaatcaa cttcaaatgc ttttccactt acttgccccc cactacacta ctgcactttg 60
ttctcattct ttatatagct tagttatcat tcttttattt atttcattat tgtgattcat 120
ttgtaataca tgtccaagat tcttgtcaaa atgtgtaaac ttatatttat aaagaaatca 180
atatatacta gcaacaatgc tggattacaa tcaattagtg aacttagctt cttggtgtat 240
ttaaatcccg tacaattaca ttgtgtaagt ggttatctct aggaatatga ctctgttttc 300
aacgtttcat agtacaatat ctcgtgaacc caagcaagtt gaaagcaaca aataaattca 360
tttacagaga aactaattta tgtatattgt tatctattat tattacagtt acatcgtcac 420
aaacatttca attatgtaaa catatattcc ataaagaaaa acaatggtca aagaatgtat 480
taaaagactg atacaagttg tgtaacataa taacattgtg caactcctcc tcacctct 538

<210> SEQ ID NO 11
<211> LENGTH: 15079
<212> TYPE: DNA
<213> ORGANISM: Artificial sequence
<220> FEATURE:
<223> OTHER INFORMATION: Plasmid

<400> SEQUENCE: 11
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540
tgggtgtcat cgagcgccac ctcgaaccga ccctcctcgc cgtgcatctg tatggtagcg 600
ccgttgacgg cggccttaag ccccattcgg acatcgacct gcttgtcacc gttaccgtcc 660
gtctcgacga gaccacgcgc cgcgcgctta tcaacgacct tctggaaacg tccgcctccc 720
ccggcgagag cgaaatcctg cgcgcggttg aggtgacgat tgtggtgcac gatgacatca 780
tcccctggcg ctatccggcc aaacgcgaac tccagttcgg cgaatggcag cgtaatgata 840
ttctggcggg tatctttgaa ccggccacca tcgacattga tctggcgatc ctgctcacca 900
aggcccggga gcatagcgtg gccctcgtcg gccccgcggc cgaggaactt ttcgacccgg 960
tgccggaaca ggatctgttc gaagcactga acgagacgct gaccctgtgg aactccccgc 1020
cggattgggc gggcgatgag cgcaatgtgg tccttacgct gagccggatt tggtactcgg 1080
cggttaccgg caagatcgcg ccgaaggatg tcgccgccga ctgggcgatg gagcgccttc 1140
cggcgcaata ccagcccgtg atcctcgaag cgcgccaagc ctatctgggc caagaagaag 1200
accgtctcgc gtcccgggcc gaccagctcg aagaatttgt ccactatgtc aagggcgaga 1260
tcacgaaggt cgttggcaaa taatgtctag ctagaaattc gttcaagccg acgccgcttc 1320
gcggcgcggc ttaactcaag cgttagatgc actaagcaca taattgctca cagccaaact 1380
atcgatgagt tgaaggaccc cgtagaaaag atcaaaggat cttcttgaga tccttttttt 1440

-continued

```
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
```

-continued gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc accttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980
actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280
aaaaaaatga aatccacatc ctgccatcat aacctcatgc tggaaaaaga aatgaaaaaa 5340
tataaaaaat ttcttttgtt tattaaattt acaactttaa tactagtttc ttttctattt 5400
tttaaaagct tttgtcactt acttaaaaaa aaaaaacttt ttgaaatatt cctacttcca 5460
atgtctgatt agtgcttctg gatttccttt ttggatcatg tgaatcctaa atcagaaaaa 5520
ttcatataat acccaattca gtatattttc atacttcaat ttacaagagt tctctatgtt 5580
tttagcttct ttcttttaag ccaaatgttt taagcatctt ttatacatta aaataattta 5640
gtgttgagtt gagattttt tttttttttt ttggatttac ttgttcaaaa tctgaaaaaa 5700
tgtttacaga aggttaaaat gaaccaaaag gcatatcaag ctagattttg aattacccta 5760
tttcatcgta tacacaaaac tgataatgtg gacacagttg attttacttc tcgatgacat 5820
cgtagtttta tttaatttgg aaaccacggc ccatatgagc acatttcaat taaaaaccaa 5880
tggtaagagc attttccatg caagattcga gagatattaa cccagtgact gttaaaacag 5940
cttagaaccc taataacgaa tttcaattac tcaatttacc attcgcattt cgcaataacc 6000
aaactgagcc agtcacaagg agtaaaccga accggattat ttatttataa aatgaaagaa 6060
aggaaaccaa acaacaacag cagtagtagt ctgacgtaaa ccaaaaagca ggcagatcaa 6120
caactaaaag aaactcaaat taccaaaaca aacaggaaat tgcaaactaa gtttttttac 6180

-continued catatgcata caaagaccat aaaaggttct gataatcacc ggtttcatct cgtcgagatt 6240
accctgttat ccctatcagt atttaatccg gccatctcct tccgttatga catcgttgaa 6300
agtgccacca ttcgggatca tcggcaacac atgttcttgg tgcggacaaa tcacatccaa 6360
caggtaaggt cctggtgtat ccagcattgt ctgaatagct tctcggagat ctgctttctt 6420
tgtcaccctc gccgctggaa tcccgcaagc tgctgcaaac agcaacatgt tcgggaatat 6480
ctcgtcctcc tgagccggat ccccgagaaa tgtgtgagct cggttagctt tgtagaaccg 6540
atcttcccat tgcataacca tgccaagatg ctggttgttt aataaaagta ccttcactgg 6600
aagattctct acacgaatag tggctagctc ttgcacattc attataaagc ttccatctcc 6660
gtcaatatcc acaactatcg catcagggtt agcaacagac gctccaatcg cagcaggaag 6720
tccaaatccc atagctccaa ggcctcctga tgatagccac tgccttggtt tcttgtaatt 6780
gtagaactgc gccgcccaca tttgatgttg cccgacacca gtacttatta tggcttttcc 6840
atcagtcaac tcatcaagga ccttaatcgc atactgtgga ggaatagctt ccccaaacgt 6900
cttaaagctc aacggaaact tctgtttctg tacgttcaac tcattcctcc aaactccaaa 6960
atcaagctta agctcctccg ctcggttctc aagaacctta ttcatccctt gcaaagccag 7020
cttaacatca ccacacacag acacatgagg agtcttattc ttcccaatct cagccgagtc 7080
aatatcaata tgaacaatct tagccctact agcaaaagcc tcaagcttac ccgtgacacg 7140
atcatcaaac cttaccccaa acgccaacaa caaatcacta tgctccacag cgtaatttgc 7200
atacacagtc ccatgcattc caagcatatg taacgacaac tcatcatcac aaggataaga 7260
tcccagcccc atcaacgtac tcgcaacagg gatccccgta agctcaacaa acctacccaa 7320
ttcatcgcta gaattcaaac aaccaccacc aacatacaac acaggcttct tagactcaga 7380
aatcaaccta acaatctgct ccaaatgaga atcttccgga ggtttaggca tcctagacat 7440
ataaccaggt aatctcatag cctgttccca attaggaatc gcaagctgtt gttgaatatc 7500
tttaggaaca tcaaccaaaa caggtccagg tctaccagaa gtagctaaaa agaaagcttc 7560
ctcaataatc ctagggatat cttcaacatc catcacaaga tagttatgct tcgtaatcga 7620
acgcgttacc tcaacaatcg gagtctcttg aaacgcatct gtaccaatca tacgacgagg 7680
gacttgtcct gtgattgcta caagaggaac actatctaac aacgcatcgg ctaatccgct 7740
aacgagattt gtagctccgg gacctgaagt ggctatacag atacctggtt tacctgagga 7800
tcgagcgtat ccttctgctg cgaatacacc tccttgttcg tgacgaggaa ggacgttacg 7860
gattgaggaa gagcgggtta aggcttggtg aatctccatt gatgtacctc cagggtaagc 7920
gaatacggtt tctacgcctt gacgttctaa agcttcgacg aggatatcag cgcctttgcg 7980
gggttgatct ggagcgaatc gggagatgaa tgtttcgggt ttggtaggtt tggttggaga 8040
gggagtggtt gtgacattgg tggttgtgtt gagcacggcg gagatggagg agggagagct 8100
ggatttgata ccgcggcggc gggaggagga ggatgatttg ttggggttta gggagaatgg 8160
gagggagaat ctggagattg gtaatggtga tttggaggag gaaggagatg gtttggtgga 8220
gaaggagatc gaagaagatg ttgttgttgt tgttgttgcc gccgccatgg ttcagctgca 8280
catacataac atatcaagat cagaacacac atatacacac acaaatacaa tcaagtcaac 8340
aactccaaaa agtccagatc tacatatata catacgtaaa taacaaaatc atgtaaataa 8400
tcacaatcat gtaatccaga tctatgcaca tatatatata cacaattaat aaaaaaaatg 8460
atataacaga tctatatcta tgtatgtaac aacacaatca gatgagagaa gtgatgtttt 8520
cagatctgta tacatacaaa cacaaacaga tgaacaattg atacgtagat ccatatgtat 8580
acgtacaatt agctacacga ttaaatgaaa aaaatcaacg atttcggatt ggtacacaca 8640
aacgcaacaa tatgaagaaa ttcatatctg attagatata aacataacca cgtgtagata 8700
cacagtcaaa tcaacaaatt tatagcttct aaacggatga gatgaacaag ataaagatat 8760
tcacataagg catacataag ataagcagat taacaaacta gcaataatac atacctaatt 8820
aaaacaagga ataacagaga gagagagaga gagagagatt taccttgaaa atgaagagga 8880
gaagagagga tttcttaaaa ttgggggtag agaaagaaag atgatgaatt gtgagaaagg 8940
agagatagaa ggggggggttg tatatatagg ctgtagaaga ttatttttgt gtttgaggcg 9000
gtgaaggaag aggggatctg actatgacac gtttgcggtt acgtatttcg ataggagtct 9060
ttcaacgctt aacgccgtta ctctatatga ccgtttgggc cgtaacgggg ccgtttgtta 9120
acgctgatgt tgattctttt ctttctttct ttcttccttt tttaaagaag caattgtaca 9180
atcgttgcta gctgtcaaac ggataattcg gatacggata tgcctatatt catatccgta 9240
atttttggat tcgaattttc ccctctaggg ataacagggt aatggatcta tattgttttt 9300
gtttcacata aatgtcgttt tggattattc atgtaatatt ttaaactaaa gtacaatttt 9360
tgactacttt agtttactag ttaagctttt atttttttga ctaaccattg aatgatgaag 9420
agatcaacgc atcatattta caacttacat agtcttttgg aagtgtaaat tgctaatact 9480
acctaaaata tatctataat taactaatat tttttcgtca attataatag atcaattaaa 9540
aggctatcaa aaggaaaaaa atgaaatcca catcctgcca tcataacctc atgctggaaa 9600
aagaaatgaa aaaatataaa aaatttcttt tgtttattaa atttacaact ttaatactag 9660
tttcttttct atttttttaaa agcttttgtc acttacttaa aaaaaaaaaa ctttttgaaa 9720
tattcctact tccaatgtct gattagtgct tctggatttc ctttttggat catgtgaatc 9780
ctaaatcaga aaaattcata taatacccaa ttcagtatat tttcatactt caatttacaa 9840
gagttctcta tgtttttagc ttctttcttt taagccaaat gttttaagca tcttttatac 9900
attaaaataa tttagtgttg agttgagatt tttttttttt ttttttggat ttacttgttc 9960
aaaatctgaa aaaatgttta cagaaggtta aaatgaacca aaaggcatat caagctagat 10020
tttgaattac cctatttcat cgtatacaca aaactgataa tgtggacaca gttgatttta 10080
cttctcgatg acatcgtagt tttatttaat ttggaaacca cggcccatat gagcacattt 10140
caattaaaaa ccaatggtaa gagcattttc catgcaagat tcgagagata ttaacccagt 10200
gactgttaaa acagcttaga accctaataa cgaatttcaa ttactcaatt taccattcgc 10260
atttcgcaat aaccaaactg agccagtcac aaggagtaaa ccgaaccgga ttatttattt 10320
ataaaatgaa agaaaggaaa ccaaacaaca acagcagtag tagtctgacg taaaccaaaa 10380
agcaggcaga tcaacaacta aaagaaactc aaattaccaa aacaaacagg aaattgcaaa 10440
ctaagttttt ttaccatatg catacaaaga ccataaaagg ttctgataat caccggtttc 10500
atctcagatc cgcgatcgcc aattgacgcg tactagtgta caagcttgcg gccgcgaatt 10560
cggtacatcc ggccagtgaa ttatcaacta tgtataataa agttgggtac ccggggatcc 10620
tctagcatat gctcgacgga caatcagtaa attgaacgga gaatattatt cataaaaata 10680
cgatagtaac gggtgatata ttcattagaa tgaaccgaaa ccggcggtaa ggatctgagc 10740
tacacatgct caggtttttt acaacgtgca caacagaatt gaaagcaaat atcatgcgat 10800
cataggcgtc tcgcatatct cattaaagca gggttaacgc tagcgggccc tctagatgca 10860
tgctcgaggc ggccttaatt aatcgatggc gccagctgca ggcggccgcc atatgcatcc 10920

-continued

```
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc ggcctattag gccacggtcc  12480
gtacagtgtt taaacgattg acctgcagga tacaagtgcg cacagactag cggccgctaa  12540
tcccgggaat taccggtagt aggcgccaca atcagtaaat tgaacggaga atattattca  12600
taaaaatacg atagtaacgg gtgatatatt cattagaatg aaccgaaacc ggcggtaagg  12660
atctgagcta cacatgctca ggttttttac aacgtgcaca acagaattga aagcaaatat  12720
catgcgatca taggcgtctc gcatatctca ttaaagcagc aatcaattat taattaagtt  12780
aacttacatc gctgggaact cggtgataaa ttccttgctg atgtccgcca ggtggtccac  12840
gacctcgtag atgccctccc agaagccggt ctcgtggaac gggatgtcga actccttgca  12900
tagcgacttg atgagcacgt tgacctttgg caagttgtgg cgcggcacga gcgggaacag  12960
gtgatggtcg atctggtagt tcaagccacc ggtgaaccag tccatgaata ccgacgcgcg  13020
gatgttgcgc gtcgtggtca cctgcagctg ccagaagtcc ggcttggttt cgcgctcgta  13080
caccgacatg ccgttgtggc caatactgaa caccagcgcc aggagcaagc cgcaggacgc  13140
ctggcccatg aggaagtatg ccacgccctc aaacaggctc atgttgcaga agtacgggat  13200
cgcgagctgc cagatgtagt gcacgatcag acccgccttc tccggtccgt cgaactcgac  13260
cttgtcgaag atgccgaacg agaactcggt gaacacgtag aagaacgact gcgcgagcca  13320
```

```
gctcaggcgc gcgagcagca gcagcgggaa gtataggaac gcctggttgc ggatgaagaa  13380

cgggccgtgc gccgactcga acgccttgcg cgccatctcc ttagaccacg ccagcagcgg  13440

catggtgtcg atgtccgggt cgccgatgaa gccctcgtcc ttggcgctgt gcaggttcgg  13500

caccgcgtgg tgcaggttgt gcttgttctt ccaccactgc atgctgaagc cctgccaggc  13560

gttgcccacg aggcagccga taaggttgcc gagcgtgcgg ttctcgcaca cctggttgtg  13620

caagaagtcg tgcgccagcc atccggactg ctggtagaag agccccataa tcacgccggc  13680

gaccatgtac atggcgaaac tgttgaagaa gaagcagatc gccatcgaga gcaccgcgat  13740

gccgaacgtg ctcacgagct tccacgcgta gtagagcgcg ctggcgtcgt agagccccat  13800

gcccttgacc ttgacgcgca gacggcggta ggacgcgatg aactcgttga tgcgctcgcg  13860

gcgcgcgcgc tcctcgtcgc tcgccggctc cccctcgatc tcggccttgg aggtttcgtc  13920

cacgtcgccg acgtagaact gctcgagcag cttgagcgcc gaggacgggt ggaagaccgc  13980

gaaggcgtcc gtggcgtcct cgccggcctg cgtgagcatc acggagccac ccgggtgcga  14040

gtcccacttg gagatgtcgt agaccttgtg gtgaatcacg atccacgcgg tcgcgggcgt  14100

cgcgtgctcg cggatctcct tccagctcac caggcgcttc actccaggct tgaggtccac  14160

cattttgggc cccggcgcgg tgacgagaaa taaatggtcg aagtaagcaa atgacaatgg  14220

acgatctata tattttatac atccatgtag taattataaa gtggtccttc gagtcttaac  14280

ggtcatattt gtgtggtgga aagaagccaa cattggcaac gaacacaaga gtctacaagt  14340

ttttttgtt ttgtaaaatc tataattttt ttcttgtctt catgtgtttt accttttact  14400

gtttaaacca agaaatctga tccttatatt atttttcaaa gtggcctatc tattatcgtg  14460

ttaggtcgct atttgtttct gtttggaatc aagtgtttgg ctaattattt caggttttga  14520

gttcagggtt tgtctttatt tcagattcca ccagtgatat atagctttat tgtaatgcag  14580

tgaacaaaaa aaaagcttta ttgtaatgta aaatatagat aggagcccat gattcgtaat  14640

tttaactgca actaattttg ttttttaact catcaacaac tttttattaa ccaatcgaag  14700

aggaacatga tttacaccac aaaagtttta actacattta caaactgaga cctcttgtat  14760

tacctaaagc caccaattag agcttaagct acctgaattt gaactcaaac gtaattctgg  14820

ccggcctagt agatttaaat tggccttagt ggccaagctt ggcgtaatca tggagcctgc  14880

ttttttgtac aaacttgggt accggcctat taggccacgg tccgtacagt gtttaaacga  14940

ttgacctgca ggatacaagt gcgcacagac tagcggccgc taatcccggg aattaccggt  15000

agtaggcgcc tactttggcc ggcctagtag atttaaattg gccttagtgg ccaagcttgg  15060

cgtaatcatg gcaactttt                                               15079
```

<210> SEQ ID NO 12
<211> LENGTH: 121
<212> TYPE: DNA
<213> ORGANISM: Brassica napus

<400> SEQUENCE: 12

```
ttaaggatct ctggcgacaa agcttacttt tccggctgcg gattttacgg tgcacaagac     60

actttatgcg acgatgcagg ccgtcactag ttcaaggagt gttacattaa ggctctatcg    120

a                                                                    121
```

<210> SEQ ID NO 13
<211> LENGTH: 1083
<212> TYPE: DNA

<213> ORGANISM: Brassica oleracea

<400> SEQUENCE: 13
atggcgcaac taagatcttt tacttattcc cttgatctct tttcagtttc tctcttaatt 60
ctcatattcc attgcttatg ttttcgtttc tcctttgttg cagcttgttc caactccacc 120
gaagatcaac accatcacca ccggaaatgg gtgggtccct caggtcacaa agtcatcacc 180
gtctcacttg acggccactc tcagtttcgc tccgtccaag acgctgtgga ctccatacca 240
aagaacaata acatgagtat cgttatcaag attgctccag gattttaccg agagaaagtg 300
gtggttccag cgacaaaacc gtacataacg tttaaaggag cgggtcggga cgtgacggtt 360
atagaatggc acgaccgtgc ctccgaccgc ggtcctgacg gtcaacagtt acgtacttac 420
caaacagctt ccgtcacagt cttcgctaat tatttctcgg ctagaaacat taccttcacg 480
aatactgcgc cggcaccaat gccgggaatg caagggtggc aggcggtggc attaaggatc 540
tctggcgaca aagcttactt ttccggctgc ggattttacg gtgcacaaga cactttatgc 600
gacgatgcag gccgtcacta cttcaaggag tgttacattg aaggctctat cgactttatc 660
ttcggtaatg gccgctccat gtataaagat tgtgagttgc attcgatagc gtcaaggttt 720
gggtcgatag cggcgcacgg gaggacatgc ccggaggaga aaacgggttt cacgttcgtg 780
ggttgtcggg taacggggac gggtccttta tacgtgggcc gggccatggg ccaatactca 840
cgcatcgtct acgcctacac ctacttcgat gctcttgttg ctcatggtgg ctgggacgat 900
tgggaccata aatccaataa aagcaagacg gcatttttcg gagtgtacaa ttgctatggg 960
ccaggagcag cagccacgac aggcgtatca tgggccagag ctttggacta tgagtcagct 1020
catcctttta tagctaagag cttcgtaaat gggagacatt ggatagctcc acgagatgct 1080
taa 1083

<210> SEQ ID NO 14
<211> LENGTH: 1019
<212> TYPE: DNA
<213> ORGANISM: Brassica napus

<400> SEQUENCE: 14
gatgcaaaaa cgtatagtca cactttgtag ttgtgctttt gactatgtgt atctgttcct 60
tatagatcga aacctggtgt gaatgacatt gttggaaccg gtttgggaac taccaacaca 120
agcaatgctc ttagagaggc aaaagagtaa taaaagagag gagaaaagtt ttgtcaaact 180
atcattgtct ttgagaaagt aagatctaac tttttttttg ttttgggatg ttaggctttt 240
gaaggctatg tttttttgc tttcttttct ttgttcttag atcatgtcga aggtgttgaa 300
atgttggatg taataaatgt tattactcag ctgctacgtt taactcttct cttacaagtg 360
tgcttcatga gatttatgta aaatccatcg ttcactgtat caatcttatc cattttcttc 420
tgattaatct gcaacgtgca attagtttga tcaaacaata ttagccatgg ggtaaaagga 480
gaaacagagt tgcttatgtt gacttggacg aagatttatc aaacactctg agctgctgag 540
agggtttgct ttaataaata taagtagaat gattgtgttt gtcttcttaa tcacagagta 600
ttgtacaaga gattaaggtt tgaatgaacg tcgtaaaatg acggttatgc tcgtgagaga 660
atcgtcgctt acgataagga cgaattgtaa tttgattgtt atcaggttgt taaaagttga 720
gacaaacgag aaaaaaacga agaacagact aaacaggtgt tacgtttcac attggtttgg 780
ttgtggagcc ttgaagttac tctatttaac cggtccaacc ggtccaaccg gtcaggttaa 840
caaaacactg aagttagccg ccaacacgct tattacgtaa acggtagcca cgtttcgagc 900
actgcgtttg ctaatttgtc ttcactcaaa ttcgcagtct tctttcttcg catttgggct 960
caagcttcgt tgagctactg attcgcatgc aaggctagtg acaccaagaa gcagagaaa 1019

<210> SEQ ID NO 15
<211> LENGTH: 573
<212> TYPE: DNA
<213> ORGANISM: Brassica napus

<400> SEQUENCE: 15
agttcctcac tcacttctct ctctctgtca aaagtttcac gagttgcttt tgttttcgtt 60
tatggttatt aagtcaaaat ttaaaaatag taataacctt ttattatttc tcagtcatca 120
atggtgaaaa acaaaatctc atttacaaga caggaaaaaa aacaagaatg atgaaaggac 180
tctagtctga taattattct gagctcataa ttgagacact gcaagatatg aatttgttaa 240
aactgttcag aaaagtgaaa ggtctccagc atcaactgat ctcttcacaa gcttagccca 300
tgattcattt gtttcatgga ttatcttcaa tgcatagtcc tgtcaaaaaa aaacaccaaa 360
caagaactgt tatagcttct ttcagtttca ttaccaaaca tgaagcagta cccacaagac 420
cttactttgt tagctggtct gtctccaaga ccgaatctgt tagcaggctt cccatctggt 480
attttatagt ctctaaacca gtctctaatg gctgtttacg taccctgata tcaccacatt 540
ttaaaggtca gtaacacaaa atccatataa ggc 573

<210> SEQ ID NO 16
<211> LENGTH: 996
<212> TYPE: DNA
<213> ORGANISM: Brassica napus

<400> SEQUENCE: 16
gatgcaaaaa cgtatagtca cactttgtag ttgtgctttt gactatgtgt atctgttcct 60
tatagatcga aacctggtgt gaatgacatt gttggaaccg gtttgggaac taccaacaca 120
agcaatgctc ttagagagag aaaagagtaa taaaagagag gagaaaagtt ttgtcaaact 180
ctcattgtct ttgagaaagt aagatctaac tttctttttt tttttttttt gggatgttag 240
gcttttgaag gctatgtttt ttttgctttc ttttctttgt tcttagatca tgtcgaaggt 300
gttgaagtgt tggacgtaat aaatgttatt actcagctgc tacgtttaac tcttctctta 360
caagtgtgct tcatgagatt tatgtaaaaa tccgcaatct tatccatttt cttctgatta 420
atctgcaacg tgcaattagt ttgatcaaat aatattagag atggggtaaa aggagaaaca 480
gagttgctta tgttgacttg gaggaagatt tatcaaacac tctgagctgc tgagagggtt 540
tgcttttata aatataagta gaatgattgt gtttgtcttc ttataatcac agagtattgt 600
acaagagatt aaggtttgaa cgttgtaaaa tgacggttat gctcgtgaga gaatcgtccc 660
ttgcgataag gacgaattgt aatttggttg ttatcaggtt gttgaaagat gagacaaacg 720
agaaaaaaac aaagaacaga ctaaacaggt gttacgtttc acattggttt ggttgtggag 780
ccttgaagtt cctctattta accggtccgg ttgacaaaac tctgaaaaag gcgccaacac 840
gcttgttacg taaacggtag ccacgttttg agcactgcat gtgctaattt gtcttcactg 900
aaattcgcag tcttctttct tcgcacttgg gcttaagctt cgtggaacta attaatgatt 960
cgcatgcaag gctagtgaca ccaagaagca gagaaa 996

<210> SEQ ID NO 17
<211> LENGTH: 576
<212> TYPE: DNA

<213> ORGANISM: Brassica napus

<400> SEQUENCE: 17
agttcctcac tcacttctct ctctctctct ctgtcaaaag tttcatgagt tgcttttgtt 60
ttcgtttatg gttattaagt caaaatttaa aaataataat aacettttat tatttctcaa 120 gtcatcaatg gtgaaaaaca aaatctcatt tacaagacgg gagaaaaaca agaatgatga 180
aaggactcta gtctgataat tattctgagc tcataattga gacaccgcaa gatatcattt 240
tgttaaaact gttcagaaaa gtgaaaggtc tccagcatca actgatctct tcacaagctt 300
agcccatgat tcatttgttt catggatgat cttcaaagca tagtcctgtt aaaaaaacac 360
caaacaagaa ctgttatagc ttctttcagt ttcattatca aacatgaagc agtacccaca 420
agaccttact ttgttagctg gtttgtctcc aagaccgaat ctgttagcag gcttcccatc 480
tgggatcttg tagtctctaa accagtctct aatggctgtt aatgtaccct ggtatcacca 540
catataaagg tcagtaacac aaaatccata taaggc 576

<210> SEQ ID NO 18
<211> LENGTH: 15433
<212> TYPE: DNA
<213> ORGANISM: Artificial sequence
<220> FEATURE:
<223> OTHER INFORMATION: Plasmid

<400> SEQUENCE: 18
ctatacaaag ttgatagctt ggcgtaatcg atgtaccgat atcaatttaa attggccggc 60
cgagctccct gcaggggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540
tgggtgtcat cgagcgccac ctcgaaccga ccctcctcgc cgtgcatctg tatggtagcg 600
ccgttgacgg cggccttaag ccccattcgg acatcgacct gcttgtcacc gttaccgtcc 660
gtctcgacga gaccacgcgc cgcgcgctta tcaacgacct tctggaaacg tccgcctccc 720
ccggcgagag cgaaatcctg cgcgcggttg aggtgacgat tgtggtgcac gatgacatca 780
tcccctggcg ctatccggcc aaacgcgaac tccagttcgg cgaatggcag cgtaatgata 840
ttctggcggg tatctttgaa ccggccacca tcgacattga tctggcgatc ctgctcacca 900
aggcccggga gcatagcgtg gccctcgtcg gccccgcggc cgaggaactt ttcgacccgg 960
tgccggaaca ggatctgttc gaagcactga acgagacgct gaccctgtgg aactccccgc 1020
cggattgggc gggcgatgag cgcaatgtgg tccttacgct gagccggatt tggtactcgg 1080
cggttaccgg caagatcgcg ccgaaggatg tcgccgccga ctgggcgatg gagcgccttc 1140
cggcgcaata ccagcccgtg atcctcgaag cgcgccaagc ctatctgggc caagaagaag 1200
accgtctcgc gtcccgggcc gaccagctcg aagaatttgt ccactatgtc aagggcgaga 1260
tcacgaaggt cgttggcaaa taatgtctag ctagaaattc gttcaagccg acgccgcttc 1320
gcggcgcggc ttaactcaag cgttagatgc actaagcaca taattgctca cagccaaact 1380

-continued atcgatgagt tgaaggaccc cgtagaaaag atcaaaggat cttcttgaga tccttttttt 1440
ctgcgcgtaa tctgctgctt gcaaacaaaa aaaccaccgc taccagcggt ggtttgtttg 1500
ccggatcaag agctaccaac tctttttccg aaggtaactg gcttcagcag agcgcagata 1560
ccaaatactg tccttctagt gtagccgtag ttaggccacc acttcaagaa ctctgtagca 1620
ccgcctacat acctcgctct gctaatcctg ttaccagtgg ctgctgccag tggcgataag 1680
tcgtgtctta ccgggttgga ctcaagacga tagttaccgg ataaggcgca gcggtcgggc 1740
tgaacggggg gttcgtgcac acagcccagc ttggagcgaa cgacctacac cgaactgaga 1800
tacctacagc gtgagctatg agaaagcgcc acgcttcccg aagggagaaa ggcggacagg 1860
tatccggtaa gcggcagggt cggaacagga gagcgcacga gggagcttcc agggggaaac 1920
gcctggtatc tttatagtcc tgtcgggttt cgccacctct gacttgagcg tcgatttttg 1980
tgatgctcgt caggggggcg gagcctatgg aaaaacgcca gcaacgcggc ctttttacgg 2040
ttcctggcct tttgctggcc ttttgctcac atgttctttc ctgcgttatc ccctgattct 2100
gtggataacc gtattaccgc ctttgagtga gctgataccg ctcgccgcag ccgaacgacc 2160
gagcgcagcg agtcagtgag cgaggaagcg gaagagcgcc tgatgcggta ttttctcctt 2220
acgcatctgt gcggtatttc acaccgcata ggccgcgata ggccgacgcg aagcggcggg 2280
gcgtagggag cgcagcgacc gaagggtagg cgctttttgc agctcttcgg ctgtgcgctg 2340
gccagacagt tatgcacagg ccaggcgggt tttaagagtt ttaataagtt ttaaagagtt 2400
ttaggcggaa aaatcgcctt ttttctcttt tatatcagtc acttacatgt gtgaccggtt 2460
cccaatgtac ggctttgggt tcccaatgta cgggttccgg ttcccaatgt acggctttgg 2520
gttcccaatg tacgtgctat ccacaggaaa gagacctttt cgaccttttt cccctgctag 2580
ggcaatttgc cctagcatct gctccgtaca ttaggaaccg gcggatgctt cgccctcgat 2640
caggttgcgg tagcgcatga ctaggatcgg gccagcctgc cccgcctcct ccttcaaatc 2700
gtactccggc aggtcatttg acccgatcag cttgcgcacg gtgaaacaga acttcttgaa 2760
ctctccggcg ctgccactgc gttcgtagat cgtcttgaac aaccatctgg cttctgcctt 2820
gcctgcggcg cggcgtgcca ggcggtagag aaaacggccg atgccggggt cgatcaaaaa 2880
gtaatcgggg tgaaccgtca gcacgtccgg gttcttgcct tctgtgatct cgcggtacat 2940
ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720

-continued

```
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
gcttttgctc attttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
agctcgtacc cggccagcgc ctcggcaacc tcaccgccga tgcgcgtgcc tttgatcgcc   4320
cgcgacacga caaaggccgc ttgtagcctt ccatccgtga cctcaatgcg ctgcttaacc   4380
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cgggcggtcg   4560
atgccgacaa cggttagcgg ttgatcttcc cgcacggccg cccaatcgcg ggcactgccc   4620
tggggatcgg aatcgactaa cagaacatcg gccccggcga gttgcagggc gcgggctaga   4680
tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc acctttttag atgatcagtg attttgtgcc   4860
gagctgccgg tcggggagct gttggctggc tggtggcagg atatattgtg gtgtaaacaa   4920
attgacgctt agacaactta ataacacatt gcggacgtct ttaatgtact gaatttagtt   4980
actgatcact gattaagtac tgcgatcgcc tcgacatatt gtttttgttt cacataaatg   5040
tcgttttgga ttattcatgt aatattttaa actaaagtac aatttttgac tactttagtt   5100
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
```

-continued

```
caactaaaag aaactcaaat taccaaaaca aacaggaaat tgcaaactaa gtttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
```

-continued

```
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa gggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
```

-continued tgctcgaggc ggccttaatt aatcgatggc gccagctgca ggcggccgcc atatgcatcc 10920
taggcctatt aatattccgg agtatacgta gccggctaac gttaacaacc ggtacctcta 10980
gactcgagca ggaacaggtg gtggcggccc tcggtgcgct cgtactgctc cacgatggtg 11040
tagtcctcgt tgtgggaggt gatgtccagc ttggagtcca cgtagtagta gccgggcagc 11100
tgcacgggct tcttggccat gtagatggac ttgaactcca ccaggtagtg gccgccgtcc 11160
ttcagcttca gggccttgtg gatctcgccc ttcagcacgc cgtcgcgggg gtacaggcgc 11220
tcggtggagg cctcccagcc catggtcttc ttctgcatta cggggccgtc ggaggggaag 11280
ttcacgccga tgaacttcac cttgtagatg aagcagccgt cctgcaggga ggagtcctgg 11340
gtcacggtca ccacgccgcc gtcctcgaag ttcatcacgc gctcccactt gaagccctcg 11400
gggaaggaca gcttcttgta gtcggggatg tcggcggggt gcttcacgta caccttggag 11460
ccgtactgga actgggggga caggatgtcc caggcgaagg gcagggggcc gcccttggtc 11520
accttcagct tcacggtgtt gtggccctcg taggggcggc cctcgccctc gccctcgatc 11580
tcgaactcgt ggccgttcac ggtgccctcc atgcgcacct tgaagcgcat gaactccttg 11640
atgacgttct tggaggagcg caccattgtt attctcctaa tcgataggcc tactagtcaa 11700
ttggcgcgcc ttatgttttt aatcttgttt gtattgatga gttttggttt gagtaaagag 11760
tgaagccgat gagttaattt ataggctata aaggagattt gcatggcgat cacgtgtaat 11820
aatgcatgca cgcatgtgat tgtatgtgtg tgctgtgaga gagaagctct taggtgtttg 11880
aagggagtga caagtggcga agaaaaacaa ttctccgcgg ctgcatgcta tgtgtaacgt 11940
gtagctaatg ttctggcatg gcatcttatg aacgattctt tttaaaaaca aggtaaaaac 12000
ttaacttcat aaaattaaaa aaaaaacgtt tactaagttg gtttaaaagg ggatgagagt 12060
ctataaattt tggaggtagt gccgttggga atataaattg ggagcttaat cagaattata 12120
gaagttaaag ttgatttagt cacggtcaat ataaattggg aatttgagtc aaaatcttcc 12180
aaattcggaa tccgtcttgt tacacccggt ggataggagc cgaacggttt gaaaatactt 12240
gaaatgtgga tgcaggtgca ggctggttta attttatgtt gaatggatac atgtcaatcg 12300
aatttgagtt ataggtacac attttactct gatactaaaa tgtaacattt gtctcaagaa 12360
tgggtaggtc atccttaaag cttgggctag agcggccgcc accgcggtgg agagcttggc 12420
gtaatcatgg ccactttgta caagaaagct gggtggtacc ggcctattag gccacggtcc 12480
gtacagtgtt taaacgattg acctgcagga tacaagtgcg cacagactag cggccgcaat 12540
cggaccgata ccggtaggcg ccacaatcag taaattgaac ggagaatatt attcataaaa 12600
atacgatagt aacgggtgat atattcatta gaatgaaccg aaaccggcgg taaggatctg 12660
agctacacat gctcaggttt tttacaacgt gcacaacaga attgaaagca aatatcatgc 12720
gatcataggc gtctcgcata tctcattaaa gcagcaatca attattaatt aagttaactt 12780
acatcgctgg gaactcggtg ataaattcct tgctgatgtc cgccaggtgg tccacgacct 12840
cgtagatgcc ctcccagaag ccggtctcgt ggaacgggat gtcgaactcc ttgcatagcg 12900
acttgatgag cacgttgacc tttggcaagt tgtggcgcgg cacgagcggg aacaggtgat 12960
ggtcgatctg gtagttcaag ccaccggtga accagtccat gaataccgac gcgcggatgt 13020
tgcgcgtcgt ggtcacctgc agctgccaga agtccggctt ggtttcgcgc tcgtacaccg 13080
acatgccgtt gtggccaata ctgaacacca gcgccaggag caagccgcag gacgcctggc 13140
ccatgaggaa gtatgccacg ccctcaaaca ggctcatgtt gcagaagtac gggatcgcga 13200

-continued gctgccagat gtagtgcacg atcagacccg ccttctccgg tccgtcgaac tcgaccttgt 13260
cgaagatgcc gaacgagaac tcggtgaaca cgtagaagaa cgactgcgcg agccagctca 13320
ggcgcgcgag cagcagcagc gggaagtata ggaacgcctg gttgcggatg aagaacgggc 13380
cgtgcgccga ctcgaacgcc ttgcgcgcca tctccttaga ccacgccagc agcggcatgg 13440
tgtcgatgtc cgggtcgccg atgaagccct cgtccttggc gctgtgcagg ttcggcaccg 13500
cgtggtgcag gttgtgcttg ttcttccacc actgcatgct gaagccctgc caggcgttgc 13560
ccacgaggca gccgataagg ttgccgagcg tgcggttctc gcacacctgg ttgtgcaaga 13620
agtcgtgcgc cagccatccg gactgctggt agaagagccc cataatcacg ccggcgacca 13680
tgtacatggc gaaactgttg aagaagaagc agatcgccat cgagagcacc gcgatgccga 13740
acgtgctcac gagcttccac gcgtagtaga gcgcgctggc gtcgtagagc cccatgccct 13800
tgaccttgac gcgcagacgg cggtaggacg cgatgaactc gttgatgcgc tcgcggcgcg 13860
cgcgctcctc gtcgctcgcc ggctccccct cgatctcggc cttggaggtt tcgtccacgt 13920
cgccgacgta gaactgctcg agcagcttga gcgccgagga cgggtggaag accgcgaagg 13980
cgtccgtggc gtcctcgccg gcctgcgtga gcatcacgga gccacccggg tgcgagtccc 14040
acttggagat gtcgtagacc ttgtggtgaa tcacgatcca cgcggtcgcg ggcgtcgcgt 14100
gctcgcggat ctccttccag ctcaccaggc gcttcactcc aggcttgagg tccaccattt 14160
tgggccccgg cgcggtttct ctgcttcttg gtgtcactag ccttgcatgc gaatcattaa 14220
ttagttccac gaagcttaag cccaagtgcg aagaaagaag actgcgaatt tcagtgaaga 14280
caaattagca catgcagtgc tcaaaacgtg gctaccgttt acgtaacaag cgtgttggcg 14340 ccttttttcag agttttgtca accggaccgg ttaaatagag gaacttcaag gctccacaac 14400
caaaccaatg tgaaacgtaa cacctgttta gtctgttctt tgtttttttc tcgtttgtct 14460
catctttcaa caacctgata acaaccaaat tacaattcgt ccttatcgca agggacgatt 14520
ctctcacgag cataaccgtc attttacaac gttcaaacct taatctcttg tacaatactc 14580
tgtgattata agaagacaaa cacaatcatt ctacttatat ttataaaagc aaaccctctc 14640
agcagctcag agtgtttgat aaatcttcct ccaagtcaac ataagcaact ctgtttctcc 14700
ttttacccca tctctaatat tatttgatca aactaattgc acgttgcaga ttaatcagaa 14760
gaaaatggat aagattgcgg atttttacat aaatctcatg aagcacactt gtaagagaag 14820
agttaaacgt agcagctgag taataacatt tattacgtcc aacacttcaa caccttcgac 14880
atgatctaag aacaaagaaa agaaagcaaa aaaaacatag ccttcaaaag cctaacatcc 14940
caaaaaaaaa aaaaaaagaa agttagatct tactttctca aagacaatga gagtttgaca 15000
aaacttttct cctctctttt attactcttt tctctctcta agagcattgc ttgtgttggt 15060
agttcccaaa ccggttccaa caatgtcatt cacaccaggt ttcgatctat aaggaacaga 15120
tacacatagt caaaagcaca actacaaagt gtgactatac gtttttgcat ctggccggcc 15180
tagtagattt aaattggcct tagtggccaa gcttggcgta atcatggagc ctgctttttt 15240
gtacaaactt gggtaccggc ctattaggcc acggtccgta cagtgtttaa acgattgacc 15300
tgcaggatac aagtgcgcac agactagcgg ccgctaatcc cgggaattac cggtagtagg 15360
cgcctacttt ggccggccta gtagatttaa attggcctta gtggccaagc ttggcgtaat 15420
catggcaact ttt 15433

<210> SEQ ID NO 19
<211> LENGTH: 172

```
<212> TYPE: DNA
<213> ORGANISM: Brassica napus
<220> FEATURE:
<221> NAME/KEY: misc_feature
<222> LOCATION: (113)..(113)
<223> OTHER INFORMATION: n is a, c, g, or t

<400> SEQUENCE: 19

tcgagactgg gtatgtgagt gttggtgaat ctggagatgt tgagctcttt tactactttg     60

tgaaatcaga gagaaatcca gataaagatc ctctcatgat ttggctaact ggngggcctg    120

gatgcagctc catttgtggt tttctgtttg caaatggtcc tttggctttt aa            172


<210> SEQ ID NO 20
<211> LENGTH: 1401
<212> TYPE: DNA
<213> ORGANISM: Brassica napus

<400> SEQUENCE: 20

atgagaaatc tttactttct agtcttattt ccgttgagca tcttgatttt ggttgatgct     60

tctttgcatg tgaagtatct tcctggtctt gaaggtcctc ttccttttga gctcgagact    120

gggtatgtga gtgttggtga atctggagat gttgagctct tttactactt tgtgaaatca    180

gagagaaatc cagataaaga tcctctcatg atttggctaa ctggtgggcc tggatgcagc    240

tccatttgtg gtttactctt tgcaaatggt cccttggctt ttaaagggga tgagtataat    300

gggacactgc ctcctttaga gctaacatct ttttcttgga caaaggtggc taacatttta    360

tatttggaat ctcctgctgg ttctggatat tcttatgcca aaactcggcg tgctgctgag    420

acgagcgaca ccaaacaaat tcaccaaatc gaccagttcc ttaggagttg gtttgtggac    480

caccctgagt ttatatccaa ttcattttac gttggtggag attcatattc cgggaagatt    540

gttccaggag ttgtgcaaca gatttcactt ggaaatgaaa aaggtctcgc accactcata    600

aatattcagg gatatgttct tggaaaccct gcagtacgta caaacttaga accaaatcat    660

agagtttcat ttgcgcatcg gatgggactt atttcagatg agctccatga gtcacttgaa    720

agaaactgtg gaggcaaatt ctttaacgta gatccaagta atgcaaaatg ttcaaatggg    780

cttctagctt atcatcggtg tatctcagag atatacatag agcagatttt gttaccaaac    840

tgcaaagtag attatgtctt atcagacata tcacaaacct taccaaatat cagaaccagt    900

cgaagaagag aactcaagga gttttcaaga aatgattcat catcgttgcc tcctcctagc    960

tgctttactt ataggtattt tctgtctgcc ttttgggcaa atgatgaaaa tgtacgcaga   1020

gctttaggcg tgaagaaggg cttcggaaaa tggagtcgat gcaacactca aaacatacca   1080

tatacatatg atattcacaa tgccattcca tatcacgtta ataatagccg taaaggcttc   1140

cgcgctctca tctacagtgg tgatcatgat atgatgatac ctttctcttc aactgaagca   1200

tggatcaaat ctctcaacta ttccattgtt gatgactgga gaccttggat gatgagtagc   1260

aatcaagtcg ctggatatac aaggacttat gcaaataaga tgacatttgc aaccatcaag   1320

ggaggaggac acacagctga gtataatcca gaccaatgct cacttatgtt caaaagatgg   1380

attgatggtg aatctctctg a                                              1401


<210> SEQ ID NO 21
<211> LENGTH: 1401
<212> TYPE: DNA
<213> ORGANISM: Brassica napus

<400> SEQUENCE: 21
```

```
atgagaaatc tttactttct agtcttattt ccgttgagca tcttgatttt ggttgatgct     60
tctttgcatg tgaagtatct tcctggtctt gaaggtcctc ttccttttga gctcgagact    120
gggtatgtga gtgttggtga atctggagat gttgagctct tttactactt tgtgaaatca    180
gagagaaatc cagataaaga tcctctcatg atttggctaa ctggtgggcc tggatgcagc    240
tccatttgtg gttttctgtt tgcaaatggt cctttggctt ttaaagggaa tgagtataat    300
gggacactgc ctcctttaga gctaacatct ttttcttgga caaaggtggc taacatttta    360
tatttggaat ctcctgctgg ttctggatat tcttatgcca aaactcggcg tgctgctgag    420
acgagcgaca ccaaacaaat tcaccaaatc gaccagttcc ttaggagttg gtttgtggac    480
caccctgagt ttatatccaa ttcattttac gttggtggag attcatattc cgggaagatt    540
gttccaggag ttgtgcaaca gatttcactt ggaaatgaaa aaggtctcac accactcata    600
aatattcagg gatatgttct tggaaaccct gcagtacgta caaacttaga accaaatcat    660
agagtttcat ttgcgcatcg gatgggactt atttcagatg agctccatga gtcacttgaa    720
agaaactgtg gaggcaaatt ctttaacgta gatccaagta atgcaaaatg ttcaaatggg    780
cttctagctt atcatcagtg catctcagag atatacatag agcagatttt gttaccaaac    840
tgcaaagtag attatgtctt agcagacata tcacaaacct taccaaatat cagaaccagt    900
cgaagaagag aactcaagga gttttcaaga aatgattcat catcgttacc tcctccaagc    960
tgctttactt ataggtattt tctgtctgcc ttttgggcaa atgatgaaaa tgtacgcaga   1020
gctttaggcg tgaagaaggg cttcggaaaa tggagtcgat gcaacactca aaacatacca   1080
tatacatatg atattcacaa tgccattcca tatcacgtca ataatagccg taaaggcttc   1140
cgcgctctca tctacagtgg tgatcatgat atgatgatac ctttctcttc aactgaagca   1200
tggatcaaat ctctcaacta ttccattgtt gatgactgga gaccttggat gatgactagc   1260
aatcaagtcg ctggatatac aaggacctat gcaaataaga tgacatttgc aaccatcaag   1320
ggaggaggac acactgctga gtataatcca gaccaatgct cacttatgtt caaaagatgg   1380
attgatggtg aatctctctg a                                              1401
```

<210> SEQ ID NO 22
<211> LENGTH: 1490
<212> TYPE: DNA
<213> ORGANISM: Brassica napus

<400> SEQUENCE: 22

```
gtagaagtta ttagcaactt gtacacactt acaactagcc aactgatatg tagaggtcaa     60
acatgttaca aactcaaaaa taaaagaaac agtggagaaa atcgagtaac ctgaacaggt    120
gtttgatcaa aagtagaatg tgtgtcacta tctcttggct gagcataaac acaaataaag    180
accctggcct aaccaagctg ctgatccaat ccaagtcaca cacaccctca gctataaatg    240
aaacaaataa actttaacag atgaatacta gctgttgttc acagttctag tgtctcctca    300
ttacgtgaat tcaagctacg atcactatct caactcctac ataaacatca gaatgctaca    360
aaactatgca caaaaacaaa agctacatct aatacgtgaa tcaattactc tcatcacaag    420
aaagaagatt tcaatcaccg tcgagaagga ggattcagtt aattgaatca aagttccgat    480
caaactcgaa gactggtgag cacgaggacg acgaagaaga gtgtctcgaa gatacaacaa    540
gcaagaaatc tactgagtga cctcctgaag ttattggcgc gattgagaga atcaatccga    600
attaatttcg gggaaaaaga taaattagat actaagcgat gggcttgggc tgggctaaga    660
aacaggtggc aattgggctg gaggaccccg cgattcatag cttccgatag cccaaaaaaa    720
```

-continued aacggataac atatttatcg ggtatttgaa tttcagtgaa ataagatatt ttctttttgt 780
taggaaaatt ttagaaaata atggaaatta aatagcgatt atgttacaag atacgatcag 840
catcgggcag tgcaaaatgc tatagcttcc caagatttga tccttttggg ttatctccta 900
atgacaatta gtttaggatt ttgaaactta tattaatact attatccgac aacacttgtt 960
tcagcttctt attttaacat tttttgtttt tttctattct tcttcccatc agcattttct 1020
ttttaaaaaa ttgaatactt taacttttta aaaatttcac aatgatcaga tgatattatg 1080
gaagatctca agagttaaat gtatccatct tggggcatta aaaccggtgt acgggatgat 1140
aaatacagac tttatatcat atgatagctc agtaattcat atttatcacg ttgctaaaaa 1200
aattataagg tactagtagt caacaaaatc aattaaagag aaagaaagaa acgcatgtga 1260
agagagttta caactggaaa agtaaaataa aaattaacgc atgttgaatg ctgacatgtc 1320
agtatgtcca tgaatccacg tatcaagcgc cattcatcga tcgtcttcct ctttctaaat 1380
gaaaacaact tcacacatca caacaaacaa tacacacaag accccctctc tctcgttgtc 1440
tctctgccag cgaccaaatc gaagcttgag aagaacaaga aggggtcaaa 1490

<210> SEQ ID NO 23
<211> LENGTH: 614
<212> TYPE: DNA
<213> ORGANISM: Brassica napus

<400> SEQUENCE: 23
tacatactat attttttgtt taccttgtgt tagtttaatg ttcagtgtcc tctctttatt 60
gtggcacgtc tctttgttgt atgttgtgtc tatacaaagt tgaaataatg gaaagaaaag 120
gaagagtgta atttgttttg ttttaagtgt ttataaatat atatatatag gtcatttaga 180
tagttctagg tttctataaa actctctctc tggaagtaga atctgttttt gagaggatcc 240
agttgcctac taatctcccc caaaaccctt caagcttaac cttcctcttc acaacaacag 300
aggaaacaca tctcttgagc tctgagttct cttctttgag catgtctatc gctaaactca 360
tctgccttat agcttccctc ttctcttcat ctctctctct caccatttcg ctgtaaaact 420
tattctcctc cctcagcctc tctatctctt ccttcagcat ctcacaattc ccaccataat 480
cgactgagga tgattcaccg tcatcaactt cagactcagc gttgtagtcg tcatgagtct 540
cacaagcctt ggaccaagaa gactcatcat cgcaagttga tgatttatca tgatgcttct 600
ctgagccgtg tttg 614

<210> SEQ ID NO 24
<211> LENGTH: 15920
<212> TYPE: DNA
<213> ORGANISM: Artificial sequence
<220> FEATURE:
<223> OTHER INFORMATION: Plasmid

<400> SEQUENCE: 24
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360

-continued

```
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
```

-continued

```
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
gcttttgctc attttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
agctcgtacc cggccagcgc ctcggcaacc tcaccgccga tgcgcgtgcc tttgatcgcc   4320
cgcgacacga caaaggccgc ttgtagcctt ccatccgtga cctcaatgcg ctgcttaacc   4380
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cgggcggtcg   4560
atgccgacaa cggttagcgg ttgatcttcc cgcacggccg cccaatcgcg ggcactgccc   4620
tggggatcgg aatcgactaa cagaacatcg gccccggcga gttgcagggc gcgggctaga   4680
tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc accttttag atgatcagtg attttgtgcc    4860
gagctgccgg tcggggagct gttggctggc tggtggcagg atatattgtg gtgtaaacaa   4920
attgacgctt agacaactta ataacacatt gcggacgtct ttaatgtact gaatttagtt   4980
actgatcact gattaagtac tgcgatcgcc tcgacatatt gtttttgttt cacataaatg   5040
tcgttttgga ttattcatgt aatattttaa actaaagtac aatttttgac tactttagtt   5100
```

-continued

```
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gtttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
```

-continued

```
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa ggggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taataccaa ttcagtatat tttcatactt caatttacaa   9840
```

-continued

```
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
```

gaaatgtgga tgcaggtgca ggctggttta attttatgtt gaatggatac atgtcaatcg 12300
aatttgagtt ataggtacac attttactct gatactaaaa tgtaacattt gtctcaagaa 12360
tgggtaggtc atccttaaag cttgggctag agcggccgcc accgcggtgg agagcttggc 12420
gtaatcatgg ccactttgta caagaaagct gggtggtacc ggcctattag gccacggtcc 12480
gtacagtgtt taaacgattg acctgcagga tacaagtgcg cacagactag cggccgctaa 12540
tcccgggaat taccggtagt aggcgccaca atcagtaaat tgaacggaga atattattca 12600
taaaaatacg atagtaacgg gtgatatatt cattagaatg aaccgaaacc ggcggtaagg 12660
atctgagcta cacatgctca ggttttttac aacgtgcaca acagaattga aagcaaatat 12720
catgcgatca taggcgtctc gcatatctca ttaaagcagc aatcaattat taattaatta 12780
catcgctggg aactcggtga taaattcctt gctgatgtcc gccaggtggt ccacgacctc 12840
gtagatgccc tcccagaagc cggtctcgtg gaacgggatg tcgaactcct tgcatagcga 12900
cttgatgagc acgttgacct ttggcaagtt gtggcgcggc acgagcggga acaggtgatg 12960
gtcgatctgg tagttcaagc caccggtgaa ccagtccatg aataccgacg cgcggatgtt 13020
gcgcgtcgtg gtcacctgca gctgccagaa gtccggcttg gtttcgcgct cgtacaccga 13080
catgccgttg tggccaatac tgaacaccag cgccaggagc aagccgcagg acgcctggcc 13140
catgaggaag tatgccacgc cctcaaacag gctcatgttg cagaagtacg ggatcgcgag 13200
ctgccagatg tagtgcacga tcagacccgc cttctccggt ccgtcgaact cgaccttgtc 13260
gaagatgccg aacgagaact cggtgaacac gtagaagaac gactgcgcga gccagctcag 13320
gcgcgcgagc agcagcagcg ggaagtatag gaacgcctgg ttgcggatga agaacgggcc 13380
gtgcgccgac tcgaacgcct tgcgcgccat ctccttagac cacgccagca gcggcatggt 13440
gtcgatgtcc gggtcgccga tgaagccctc gtccttggcg ctgtgcaggt tcggcaccgc 13500
gtggtgcagg ttgtgcttgt tcttccacca ctgcatgctg aagccctgcc aggcgttgcc 13560
cacgaggcag ccgataaggt tgccgagcgt gcggttctcg cacacctggt tgtgcaagaa 13620
gtcgtgcgcc agccatccgg actgctggta gaagagcccc ataatcacgc cggcgaccat 13680
gtacatggcg aaactgttga agaagaagca gatcgccatc gagagcaccg cgatgccgaa 13740
cgtgctcacg agcttccacg cgtagtagag cgcgctggcg tcgtagagcc ccatgccctt 13800
gaccttgacg cgcagacggc ggtaggacgc gatgaactcg ttgatgcgct cgcggcgcgc 13860
gcgctcctcg tcgctcgccg gctccccctc gatctcggcc ttggaggttt cgtccacgtc 13920
gccgacgtag aactgctcga gcagcttgag cgccgaggac gggtggaaga ccgcgaaggc 13980
gtccgtggcg tcctcgccgg cctgcgtgag catcacggag ccacccgggt gcgagtccca 14040
cttggagatg tcgtagacct tgtggtgaat cacgatccac gcggtcgcgg gcgtcgcgtg 14100
ctcgcggatc tccttccagc tcaccaggcg cttcactcca ggcttgaggt ccaccatgga 14160
aggcgcggtt tgaccccttc ttgttcttct caagcttcga tttggtcgct ggcagagaga 14220
caacgagaga gagggggtct tgtgtgtatt gtttgttgtg atgtgtgaag ttgttttcat 14280
ttagaaagag gaagacgatc gatgaatggc gcttgatacg tggattcatg gacatactga 14340
catgtcagca ttcaacatgc gttaattttt attttacttt tccagttgta aactctcttc 14400
acatgcgttt ctttctttct ctttaattga ttttgttgac tactagtacc ttataatttt 14460
tttagcaacg tgataaatat gaattactga gctatcatat gatataaagt ctgtatttat 14520
catcccgtac accggtttta atgccccaag atggatacat ttaactcttg agatcttcca 14580

-continued

```
taatatcatc tgatcattgt gaaattttta aaaagttaaa gtattcaatt ttttaaaaag  14640
aaaatgctga tgggaagaag aatagaaaaa aacaaaaaat gttaaaataa gaagctgaaa  14700
caagtgttgt cggataatag tattaatata agtttcaaaa tcctaaacta attgtcatta  14760
ggagataacc caaaaggatc aaatcttggg aagctatagc attttgcact gcccgatgct  14820
gatcgtatct tgtaacataa tcgctattta atttccatta ttttctaaaa ttttcctaac  14880
aaaaagaaaa tatcttattt cactgaaatt caaatacccg ataaatatgt tatccgtttt  14940
tttttgggct atcggaagct atgaatcgcg gggtcctcca gcccaattgc cacctgtttc  15000
ttagcccagc ccaagcccat cgcttagtat ctaatttatc tttttccccg aaattaattc  15060
ggattgattc tctcaatcgc gccaataact tcaggaggtc actcagtaga tttcttgctt  15120
gttgtatctt cgagacactc ttcttcgtcg tcctcgtgct caccagtctt cgagtttgat  15180
cggaactttg attcaattaa ctgaatcctc cttctcgacg gtgattgaaa tcttctttct  15240
tgtgatgaga gtaattgatt cacgtattag atgtagcttt tgtttttgtg catagttttg  15300
tagcattctg atgtttatgt aggagttgag atagtgatcg tagcttgaat tcacgtaatg  15360
aggagacact agaactgtga acaacagcta gtattcatct gttaaagttt atttgtttca  15420
tttatagctg agggtgtgtg tgacttggat tggatcagca gcttggttag gccagggtct  15480
ttatttgtgt ttatgctcag ccaagagata gtgacacaca ttctactttt gatcaaacac  15540
ctgttcaggt tactcgattt tctccactgt ttcttttatt tttgagtttg taacatgttt  15600
gacctctaca tatcagttgg ctagttgtaa gtgtgtacaa gttgctaata acttctactg  15660
gccggcctag tagatttaaa ttggccttag tggccaagct tggcgtaatc atggagcctg  15720
ctttttgta caaacttggg taccggccta ttaggccacg gtccgtacag tgtttaaacg  15780
attgacctgc aggatacaag tgcgcacaga ctagcggccg ctaatcccgg gaattaccgg  15840
tagtaggcgc ctactttggc cggcctagta gatttaaatt ggccttagtg gccaagcttg  15900
gcgtaatcat ggcaactttt                                              15920
```

<210> SEQ ID NO 25
<211> LENGTH: 2010
<212> TYPE: DNA
<213> ORGANISM: Brassica napus

<400> SEQUENCE: 25

```
tcggctacaa atccaactgg gaggccaaaa agataaccac cccctagctg cagaaaccaa     60
atcataacta tcagaacaaa gataaaaagc ccgagtatac catgttgtac catagaagca    120
caccctctat ctcatacata gttatgaatt gaaacctacc gtaagtacag aagcaggaac    180
cgccacaatt gtgaggggaa tataagccaa agccctgcaa ttttcagtga gaagggtaag    240
attattaaag gcagccagag aacaatgtcg gcaaagtaaa catattcgag gtgggacatt    300
aaatttaaaa agaagagaac aaaagaaagt agcaagcttg agaagaagct tacagtgcaa    360
ttggaccaaa gggtccaaga tcttccttaa tccataacaa gaagtccttc aatttctgca    420
gaaagtgaac aaaaacaatg attctaaatc atacatatta ccattcttct gatctatcac    480
tactctctac taccaggtgt agcaaaattc ccgattaaat tcataagaaa atcgaaattt    540
tgttgctacc ttcaaacaac agatgctcgc aaaatgtgat tcatagtgta aacaatctag    600
ctagtaacga cctaacaaca ctatcaccaa acagataaac agcgatctag cgagttccag    660
cagcaatact ccattctatt cgccaccgac gattatcgat tcactaaagc tacaacaagt    720
acacgcgtgg atagtggaat agagaaattg cctgttcaac ggggagaaaa atgaaagcgg    780
```

tgccgatagc gacaaggagg aggagcgata ttgctatccg gaaagtggac ggagtaaagg 840
aactcgccgc catatacaag gatctgaggc gacggcgcca ccaaggcctc gaatggtcac 900
cctcatcgcc gtcgtagtcg tattgatctc cattcgcata agatcctggc ttgagccacg 960
gcctcgccct taacccctcc actttcgcca gatttgaatg cctcctcttc cccgattctg 1020
gagatatgct tcacactgcc tcgcctctat ctccgctgaa ttgcagaaat cgaatgagag 1080
attgttgctt tcaatccttc gaattcatca gtgttacttc gatcttgaga ttctgtttgc 1140
ctctctctct cgttctggtt tcactgtaga aaaacttttt ttccgcgaac attttcttta 1200
ggcccaaagt ttgggctttt aataacgcct aaagcccaaa caaagtttat tattgggtat 1260
ttgtattttt tttgtttaat taagaaaata aggggaatct atttatttaa ttgttaatca 1320
ttcacgttga ccattgaaga acaagcacaa aatgctataa gcctcccgag atttgatcct 1380
ttgggttctc gttagagagg tgggcaatgt ctccagctct agtaatgaca attagtttag 1440
tttaggattc ttacactagt gtaatagtat tatgagagaa cactcgtttc agtttattat 1500
ttaacaattt tcttaggttt ctaatttttt ttccagcaac gttttactga atttttaaaa 1560
cttgatattt gattttttt aaagtaattt aaatgcaaaa caatccaaat gatattttgg 1620
aagaactcaa gagttgtgtg atggactgat gggggcaaga ggcaagtgca ctggtgtatc 1680
cttctcgggg cgttaaaacc gtggaaggtg accgtttaat acatgtctat ctattatgaa 1740
agctaagtac ttcatagcta tcacgttgct cctcacaaat aaactatacg agtagtcagc 1800
aaatcaattt tataaagacg catgagtaac agctgaataa aaaagagagg agaaaacgca 1860
tgttgattgc tgacgtgtcc gtaggtccat gtatccccgt atcactgtct tccttctaac 1920
caaaaaaaac atttcacatc ataagtcccc tctctctcga gctccgtcgc tgtttgtttc 1980
gaccaaatcg aagctgagga aaacgacaaa 2010

<210> SEQ ID NO 26
<211> LENGTH: 120
<212> TYPE: DNA
<213> ORGANISM: Brassica napus

<400> SEQUENCE: 26
ttaagcgaga agacagctga ggaggctatg acgccaattg aatcaacctt ttccttggat 60
gtaaccacaa agttagactg ggaaacaatt gggaaaatac tatccaaagg ccatagtcga 120

<210> SEQ ID NO 27
<211> LENGTH: 1512
<212> TYPE: DNA
<213> ORGANISM: Brassica napus

<400> SEQUENCE: 27
atggttgttc ttagcatggt ggcgttggta aaaacagctt attctttgaa cagcttcgtc 60
tttgaggcgg aagacattgt attcggttcg ccttggtggt tcgccgtcgt cggcgtggcg 120
tgtctcctcg ttctcttcgc cgggataatg tctggactca cgctcggact aatgtccctt 180
ggtctcgtcg agcttgagat tctccagcag agtggttcct ccgtggagaa aaagcaggcc 240
gctgctattt taccagtggt taagaagcag catcaacttc ttgtgactct gcttctatgc 300
aatgcagctg ccatggaggc acttcctata tgtttggata agatatttca ccccttttgtg 360 gctgttttac tctcagttac ttttgtactt gcctttggag agatcattcc acaagctata 420
tgctcgagat atggacttgc tgttggcgct aatttcttgt ggttggttcg cattttgatg 480

```
ataatctgct atcccattgc ttaccctatt ggaaaggttc ttgatgccgt gatcgggcat    540

aataacacac tgtttaggcg agctcagctg aaagctctcg tctcaattca cagccaagag    600

gctggtaagg gaggtgaact gacacacgag gaaacaatga ttataagcgg agccctggat    660

ttgagcgaga agacggctga ggaggctatg acgccaattg aatcaacttt ttccttggat    720

gtaactacaa agttagactg ggaaacaatt ggaaaaatac tatccaaagg ccatagtcga    780

atccctgtct acttagggaa tccaaaaaac atcattgggc ttttactggt gaagagtctt    840

ctaactgtac gagcggaagc agagaccccc ataagttctg tttccattag gaagatccca    900

agggttccat cagatatgcc attgtatgat attctcaacg agtttcaaaa ggggaacagt    960

cacatggccg cggttgtcaa agtcaaagat aaagataaaa agaagaacat gcagttgatg   1020

agtaatgggg aaccacccaa ggaggaatat atgaactcat actcgagtcc tcttctaaca   1080

gctcctttgc ttaagcatgt ggatgaaagg catcatgatg ttgtggtggt tgatattgat   1140

aaagcaccaa cacatgtgga aactaggggg agaaatttcc aacagaacgg ccttgtgaca   1200

aggtgggact tgccgcgttt gttggaagat aacgaggatg cagaagttat aggcatcatc   1260

acgttagaag atgtctttga agaacttcta caagcagaga tcgtggatga aaccgacgtt   1320

tacattgatg tacataaaag ggtacgcgtg gctgctgcag cagcagcggc tgtatcatcc   1380

ataacacgag cttcgccagt ggagtatcaa agcaaggtag gagtaacggt gaagaagctt   1440

gtgggtaaag aagcacgaag taccaagaaa tcaaaaacca cggagcctct tttagcagaa   1500

tcatatagat aa                                                       1512
```

<210> SEQ ID NO 28
<211> LENGTH: 1512
<212> TYPE: DNA
<213> ORGANISM: Brassica napus

<400> SEQUENCE: 28

```
atgggtgttc tgagcatggt agtcctcgta aaagcagctt attcgttgaa cagctttgtc     60

ttcgaggcgg aagacatccg attcggttcc ccgtggtggt tcgtcgtcgt cggtgtagcg    120

tgtctcctcg ttctcttcgc cgggataatg tctggcttaa cgctcggatt aatgtccctt    180

ggtctcgtcg agctcgagat tctccagcag agtggttcct cctccgagaa aaaacaagcc    240

gctgctatct taccagtggt taagaagcag catcaactgc ttgtgactct gcttctatgc    300

aatgcagctg ccatggaggc acttcctata tgtcttgata agatcttcca tccctttgtg    360

gctgttttgc tctctgttac ttttgttctt gcttttgggg agataattcc acaagcgata    420

tgctcgaggt atgggcttgc tgttggggct aactttttgt ggctggttcg cattttgatg    480

atactctgct atcctatcgc ttaccctata ggcaaggttc ttgatgcggt aattgggcat    540

aatgacacac tgtttaggcg agctcagctg aaagcacttg tctcaatgca cagccaggag    600

gctggtaagg gaggtgaact gacacacgag gaaacaatga ttataagcgg agcccttgat    660

ctgagtgaga agacagctga ggaggctatg acgccaattg aatcaacatt ttccttggat    720

gtaactacaa agctaaactg ggaaacaatt ggaaaaatac tttccagagg acatagccgg    780

atcccagtat acttagggaa tccaaaaaat atcattgggc ttctattggt taagagtctt    840

ctaactgtac gagcggaaac agaaacatca gtaagttctg tttccatcag gaagatccca    900

agggttccat cagatatgcc attgtatgat atcctcaacg agtttcaaaa ggggaacagt    960

cacatggccg cggttgtcaa ggtcaaagat aaagataaaa agaagaacat gcagttgatg   1020

agtaatgggg aaccacccaa ggaggaatat atgaactcat actcgagtcc tcttctaaca   1080
```

gctcctttgc ttaagcatgt ggatgaaagg catcatgatg ttgtggtggt tgatattgat 1140
aaagcaccaa cacatgtgga aactaggggg agaaatttcc aacagaacgg ccttgtgaca 1200
aggtgggact tgccgcgttt gttggaagat aacgaggatg cagaagttat aggcatcatc 1260
acgttagaag atgtctttga agaacttcta caagcagaga tcgtggatga aaccgacgtt 1320
tacattgatg tacataaaag ggtacgcgtg gctgctgcag cagcagcggc tgtatcatcc 1380
ataacacgag cttcgccagt ggagtatcaa agcaaggtag gagtaacggt gaagaagctt 1440
gtgggtaaag aagcacgaag taccaagaaa tcaaaaacca cggagcctct tttagcagaa 1500
tcatatagat aa 1512

<210> SEQ ID NO 29
<211> LENGTH: 55
<212> TYPE: DNA
<213> ORGANISM: Artificial sequence
<220> FEATURE:
<223> OTHER INFORMATION: Primer

<400> SEQUENCE: 29
atacccggga tacctgcagg ttaggccggc cacaaaacga aatcatcaaa tcgtg 55

<210> SEQ ID NO 30
<211> LENGTH: 69
<212> TYPE: DNA
<213> ORGANISM: Artificial sequence
<220> FEATURE:
<223> OTHER INFORMATION: Primer

<400> SEQUENCE: 30
caatcaatta taggcctcgc atgctttaat taacgatcga gccatggttt tagagagccg 60
gaattattg 69

<210> SEQ ID NO 31
<211> LENGTH: 77
<212> TYPE: DNA
<213> ORGANISM: Artificial sequence
<220> FEATURE:
<223> OTHER INFORMATION: Primer

<400> SEQUENCE: 31
ccatggctcg atcgttaatt aaagcatgcg aggcctataa ttgattgttt ctcctcttag 60
tttgtaaata atctatc 77

<210> SEQ ID NO 32
<211> LENGTH: 65
<212> TYPE: DNA
<213> ORGANISM: Artificial sequence
<220> FEATURE:
<223> OTHER INFORMATION: Primer

<400> SEQUENCE: 32
taagcggccg caatcggacc gataccggta ggcgccgatt atctacctaa cctaacaaac 60
aaaag 65

<210> SEQ ID NO 33
<211> LENGTH: 59
<212> TYPE: DNA
<213> ORGANISM: Artificial sequence
<220> FEATURE:
<223> OTHER INFORMATION: Primer

<400> SEQUENCE: 33
atacccggga tacctgcagg ttaggccggc caaatttatt aacccatcta tttgttcac 59

<210> SEQ ID NO 34
<211> LENGTH: 70
<212> TYPE: DNA
<213> ORGANISM: Artificial sequence
<220> FEATURE:
<223> OTHER INFORMATION: Primer

<400> SEQUENCE: 34
caatcaatta taggcctcgc atgctttaat taacgatcga gccatgggac gagaaagaaa 60
atggtcggag 70

<210> SEQ ID NO 35
<211> LENGTH: 73
<212> TYPE: DNA
<213> ORGANISM: Artificial sequence
<220> FEATURE:
<223> OTHER INFORMATION: Primer

<400> SEQUENCE: 35
ccatggctcg atcgttaatt aaagcatgcg aggcctataa ttgattgtaa ggaatcaact 60
tcaaatgctt ttc 73

<210> SEQ ID NO 36
<211> LENGTH: 58
<212> TYPE: DNA
<213> ORGANISM: Artificial sequence
<220> FEATURE:
<223> OTHER INFORMATION: Primer

<400> SEQUENCE: 36
taagcggccg caatcggacc gataccggta ggcgccgacg ttaagcgaga gtggatag 58

<210> SEQ ID NO 37
<211> LENGTH: 57
<212> TYPE: DNA
<213> ORGANISM: Artificial sequence
<220> FEATURE:
<223> OTHER INFORMATION: Primer

<400> SEQUENCE: 37
atacccggga tacctgcagg ttaggccggc cagaattacg tttgagttca aattcag 57

<210> SEQ ID NO 38
<211> LENGTH: 69
<212> TYPE: DNA
<213> ORGANISM: Artificial sequence
<220> FEATURE:
<223> OTHER INFORMATION: Primer

<400> SEQUENCE: 38
caatcaatta taggcctcgc atgctttaat taacgatcga gccatgggac gagaaataaa 60
tggtcgaag 69

<210> SEQ ID NO 39
<211> LENGTH: 72
<212> TYPE: DNA
<213> ORGANISM: Artificial sequence
<220> FEATURE:
<223> OTHER INFORMATION: Primer

<400> SEQUENCE: 39

```
ccatggctcg atcgttaatt aaagcatgcg aggcctataa ttgattgtag gaatcaactt     60

caaatgcttt tc                                                         72


<210> SEQ ID NO 40
<211> LENGTH: 57
<212> TYPE: DNA
<213> ORGANISM: Artificial sequence
<220> FEATURE:
<223> OTHER INFORMATION: Primer

<400> SEQUENCE: 40

taagcggccg caatcggacc gataccggta ggcgccagag gtgaggagga gttgcac        57


<210> SEQ ID NO 41
<211> LENGTH: 55
<212> TYPE: DNA
<213> ORGANISM: Artificial sequence
<220> FEATURE:
<223> OTHER INFORMATION: Primer

<400> SEQUENCE: 41

atacccggga tacctgcagg ttaggccggc cagatgcaaa aacgtatagt cacac          55


<210> SEQ ID NO 42
<211> LENGTH: 69
<212> TYPE: DNA
<213> ORGANISM: Artificial sequence
<220> FEATURE:
<223> OTHER INFORMATION: Primer

<400> SEQUENCE: 42

caatcaatta taggcctcgc atgctttaat taacgatcga gccatggttt ctctgcttct     60

tggtgtcac                                                             69


<210> SEQ ID NO 43
<211> LENGTH: 68
<212> TYPE: DNA
<213> ORGANISM: Artificial sequence
<220> FEATURE:
<223> OTHER INFORMATION: Primer

<400> SEQUENCE: 43

ccatggctcg atcgttaatt aaagcatgcg aggcctataa ttgattgagt tcctcactca     60

cttctctc                                                              68


<210> SEQ ID NO 44
<211> LENGTH: 64
<212> TYPE: DNA
<213> ORGANISM: Artificial sequence
<220> FEATURE:
<223> OTHER INFORMATION: Primer

<400> SEQUENCE: 44

taagcggccg caatcggacc gataccggta ggcgccgcct tatatggatt ttgtgttact     60

gacc                                                                  64


<210> SEQ ID NO 45
<211> LENGTH: 55
<212> TYPE: DNA
<213> ORGANISM: Artificial sequence
<220> FEATURE:
<223> OTHER INFORMATION: Primer
```

<400> SEQUENCE: 45
atacccggga tacctgcagg ttaggccggc cagatgcaaa aacgtatagt cacac      55

<210> SEQ ID NO 46
<211> LENGTH: 69
<212> TYPE: DNA
<213> ORGANISM: Artificial sequence
<220> FEATURE:
<223> OTHER INFORMATION: Primer

<400> SEQUENCE: 46
caatcaatta taggcctcgc atgctttaat taacgatcga gccatggttt ctctgcttct    60
tggtgtcac      69

<210> SEQ ID NO 47
<211> LENGTH: 68
<212> TYPE: DNA
<213> ORGANISM: Artificial sequence
<220> FEATURE:
<223> OTHER INFORMATION: Primer

<400> SEQUENCE: 47
ccatggctcg atcgttaatt aaagcatgcg aggcctataa ttgattgagt tcctcactca    60
cttctctc      68

<210> SEQ ID NO 48
<211> LENGTH: 64
<212> TYPE: DNA
<213> ORGANISM: Artificial sequence
<220> FEATURE:
<223> OTHER INFORMATION: Primer

<400> SEQUENCE: 48
taagcggccg caatcggacc gataccggta ggcgccgcct tatatggatt ttgtgttact    60
gacc      64

<210> SEQ ID NO 49
<211> LENGTH: 60
<212> TYPE: DNA
<213> ORGANISM: Artificial sequence
<220> FEATURE:
<223> OTHER INFORMATION: Primer

<400> SEQUENCE: 49
atacccggga tacctgcagg ttaggccggc cagtagaagt tattagcaac ttgtacacac    60

<210> SEQ ID NO 50
<211> LENGTH: 68
<212> TYPE: DNA
<213> ORGANISM: Artificial sequence
<220> FEATURE:
<223> OTHER INFORMATION: Primer

<400> SEQUENCE: 50
caatcaatta taggcctcgc atgctttaat taacgatcga gccatggttt gaccccttct    60
tgttcttc      68

<210> SEQ ID NO 51
<211> LENGTH: 76
<212> TYPE: DNA
<213> ORGANISM: Artificial sequence
<220> FEATURE:
<223> OTHER INFORMATION: Primer

<400> SEQUENCE: 51
ccatggctcg atcgttaatt aaagcatgcg aggcctataa ttgattgtac atactatatt 60
ttttgtttac cttgtg 76

<210> SEQ ID NO 52
<211> LENGTH: 56
<212> TYPE: DNA
<213> ORGANISM: Artificial sequence
<220> FEATURE:
<223> OTHER INFORMATION: Primer

<400> SEQUENCE: 52
taagcggccg caatcggacc gataccggta ggcgcccaaa cacggctcag agaagc 56

<210> SEQ ID NO 53
<211> LENGTH: 52
<212> TYPE: DNA
<213> ORGANISM: Artificial sequence
<220> FEATURE:
<223> OTHER INFORMATION: Primer

<400> SEQUENCE: 53
atacccggga tacctgcagg ttaggccggc catcggctac aaatccaact gg 52

<210> SEQ ID NO 54
<211> LENGTH: 68
<212> TYPE: DNA
<213> ORGANISM: Artificial sequence
<220> FEATURE:
<223> OTHER INFORMATION: Primer

<400> SEQUENCE: 54
caatcaatta taggcctcgc atgctttaat taacgatcga gccatggttt gtcgttttcc 60
tcagcttc 68

<210> SEQ ID NO 55
<211> LENGTH: 72
<212> TYPE: DNA
<213> ORGANISM: Artificial sequence
<220> FEATURE:
<223> OTHER INFORMATION: Primer

<400> SEQUENCE: 55
ccatggctcg atcgttaatt aaagcatgcg aggcctataa ttgattgctg ctttaatgag 60
atatgcgaga cg 72

<210> SEQ ID NO 56
<211> LENGTH: 68
<212> TYPE: DNA
<213> ORGANISM: Artificial sequence
<220> FEATURE:
<223> OTHER INFORMATION: Primer

<400> SEQUENCE: 56
taagcggccg caatcggacc gataccggta ggcgccacaa tcagtaaatt gaacggagaa 60
tattattc 68

<210> SEQ ID NO 57
<211> LENGTH: 161
<212> TYPE: DNA
<213> ORGANISM: Artificial sequence
<220> FEATURE:

<223> OTHER INFORMATION: Multiple cloning site assembled using long
      complementary primers

<400> SEQUENCE: 57
aagcttggcc actaaggcca atttaaatct actaggccgg ccaaagtagg cgcctactac     60
cggtaattcc cgggattagc ggccgctagt ctgtgcgcac ttgtatcctg caggtcaatc    120
gtttaaacac tgtacggacc gtggcctaat aggccggtac c                        161

<210> SEQ ID NO 58
<211> LENGTH: 157
<212> TYPE: DNA
<213> ORGANISM: Brassica napus

<400> SEQUENCE: 58
gaacagggga agagaaacga aaaaacacta ctaagaaaaa gaaaaaaacc gggcgtgcag     60
gtgtacagtg aggagaaaat atgggagaag atggaagagt tgaggaaggt agtaggatac    120
agtgttgcaa ggagtgctac gtatgcagaa gagttaa                             157

<210> SEQ ID NO 59
<211> LENGTH: 127
<212> TYPE: DNA
<213> ORGANISM: Brassica napus

<400> SEQUENCE: 59
tcgattcaag acaacgacaa cgcgcagatc atttactcgc gggacgcacc tcagtcatga     60
gaggtttacc acttgaagtt atatccaacg ggtatcagat ctcaccccaa gaagctagaa    120
gtgttaa                                                              127

<210> SEQ ID NO 60
<211> LENGTH: 101
<212> TYPE: DNA
<213> ORGANISM: Brassica napus

<400> SEQUENCE: 60
cttgatcgtt tttctattag ctgtggtaag ttgcaacgct aataaggaaa ttacttgcga     60
agagaacgag ccatttacat gtaataacac tgatcgttta a                        101

<210> SEQ ID NO 61
<211> LENGTH: 273
<212> TYPE: DNA
<213> ORGANISM: Brassica napus

<400> SEQUENCE: 61
ttaaataaag atgatctaga gatctattca cgtgattata aaggctcacc ttcaaactta     60
gtgacgggta tgagagaccg tcctccaatg tcttactctc tcagaatgga gtctttcaac    120
acgctccttc agtcaaatga gacagaaaga tacgaatctc gtccttttcc cgttggtgga    180
tacaactggt cacttattgt gtatcccaac gggaacaggc aggatagtgg ctcagggttc    240
atttcgcttt attagccata gacaactcgg tac                                 273

<210> SEQ ID NO 62
<211> LENGTH: 237
<212> TYPE: DNA
<213> ORGANISM: Brassica napus

<400> SEQUENCE: 62
ttaagtgctt atgcgacttc tgcagcgaca aagcttatga tcagattcta agtactggta     60
tttgatcaat cctgcatgtg taaaaagaaa ggcgacgatg gtccaagtaa taatgtagtt 120
gtcgtaatga atatgtgaaa taaataaaaa aagccggaag tatccaaggc tatcatcgct 180
tgatcatatt atgtggtttg tctcgtgcat ggttagaagc gaataaaata gtatcga 237

<210> SEQ ID NO 63
<211> LENGTH: 144
<212> TYPE: DNA
<213> ORGANISM: Brassica napus

<400> SEQUENCE: 63
ttaagcagaa caaagccttt gagcgtgctc tagcaaccta tgaccaagac actcctgacc 60
gttggtataa tgttgctaga gctgttggtg gaacaacacc tgatgaagct aagagacaat 120
atgaccttct cgtacggaca tcga 144

<210> SEQ ID NO 64
<211> LENGTH: 186
<212> TYPE: DNA
<213> ORGANISM: Brassica napus

<400> SEQUENCE: 64
tcgatgtgta cgaagagaag ctcgggaaga caaatacttg gccggagatt cttacacact 60
cgcggatctc caccacgttc cttacactta ctacttcatg aagacgggtc atgctggttt 120
ggtcaacgac cgtcctaatg tcaaggcgtg gtgggaagac ctttgttctc gtccggcttt 180
ccttaa 186

<210> SEQ ID NO 65
<211> LENGTH: 131
<212> TYPE: DNA
<213> ORGANISM: Brassica napus

<400> SEQUENCE: 65
ttaagcgtag agagaagaag caagctcaga ttagctggag tttctttatc agaaacgttt 60
tggcaaggcc cagctttcat ccctttgaag ctattcaccg gagttcactg taacgagcgg 120
agaagaatcg g 131

<210> SEQ ID NO 66
<211> LENGTH: 83
<212> TYPE: DNA
<213> ORGANISM: Brassica napus

<400> SEQUENCE: 66
tcgattatca tcatgttttg tgataatctt ccgtcagcaa tcgcaaggag tttcagtgac 60
ttttgcatgt tctgggtttg agg 83

<210> SEQ ID NO 67
<211> LENGTH: 164
<212> TYPE: DNA
<213> ORGANISM: Brassica napus

<400> SEQUENCE: 67
tcgagagcat ttgagcgatg ttcatcagat acatatgaga taaatggacc atgtgtacgc 60
cagatctgct atgtatatgt tcacaggtct ggtccagatg gttgggttcc agagagtgtt 120
caaatattca gtcatagctc caaagcagtc actttcactt ttaa 164

<210> SEQ ID NO 68
<211> LENGTH: 1380

<212> TYPE: DNA
<213> ORGANISM: Pythium irregulare

<400> SEQUENCE: 68
atggtggacc tcaagcctgg agtgaagcgc ctggtgagct ggaaggagat ccgcgagcac 60
gcgacgcccg cgaccgcgtg gatcgtgatt caccacaagg tctacgacat ctccaagtgg 120
gactcgcacc cgggtggctc cgtgatgctc acgcaggccg gcgaggacgc cacggacgcc 180
ttcgcggtct tccacccgtc ctcggcgctc aagctgctcg agcagttcta cgtcggcgac 240
gtggacgaaa cctccaaggc cgagatcgag ggggagccgg cgagcgacga ggagcgcgcg 300
cgccgcgagc gcatcaacga gttcatcgcg tcctaccgtc gtctgcgcgt caaggtcaag 360
ggcatggggc tctacgacgc cagcgcgctc tactacgcgt ggaagctcgt gagcacgttc 420
ggcatcgcgg tgctctcgat ggcgatctgc ttcttcttca acagtttcgc catgtacatg 480
gtcgccggcg tgattatggg gctcttctac cagcagtccg gatggctggc gcacgacttc 540
ttgcacaacc aggtgtgcga gaaccgcacg ctcggcaacc ttatcggctg cctcgtgggc 600
aacgcctggc agggcttcag catgcagtgg tggaagaaca agcacaacct gcaccacgcg 660
gtgccgaacc tgcacagcgc caaggacgag ggcttcatcg gcgacccgga catcgacacc 720
atgccgctgc tggcgtggtc taaggagatg gcgcgcaagg cgttcgagtc ggcgcacggc 780
ccgttcttca tccgcaacca ggcgttccta tacttcccgc tgctgctgct cgcgcgcctg 840
agctggctcg cgcagtcgtt cttctacgtg ttcaccgagt tctcgttcgg catcttcgac 900
aaggtcgagt tcgacggacc ggagaaggcg ggtctgatcg tgcactacat ctggcagctc 960
gcgatcccgt acttctgcaa catgagcctg tttgagggcg tggcatactt cctcatgggc 1020
caggcgtcct gcggcttgct cctggcgctg gtgttcagta ttggccacaa cggcatgtcg 1080
gtgtacgagc gcgaaaccaa gccggacttc tggcagctgc aggtgaccac gacgcgcaac 1140
atccgcgcgt cggtattcat ggactggttc accggtggct tgaactacca gatcgaccat 1200
cacctgttcc cgctcgtgcc gcgccacaac ttgccaaagg tcaacgtgct catcaagtcg 1260
ctatgcaagg agttcgacat cccgttccac gagaccggct tctgggaggg catctacgag 1320
gtcgtggacc acctggcgga catcagcaag gaattcatca ccgagttccc agcgatgtaa 1380

<210> SEQ ID NO 69
<211> LENGTH: 705
<212> TYPE: DNA
<213> ORGANISM: Discosoma

<400> SEQUENCE: 69
atggtgcgct cctccaagaa cgtcatcaag gagttcatgc gcttcaaggt gcgcatggag 60
ggcaccgtga acggccacga gttcgagatc gagggcgagg gcgagggccg cccctacgag 120
ggccacaaca ccgtgaagct gaaggtgacc aagggcggcc ccctgccctt cgcctgggac 180
atcctgtccc cccagttcca gtacggctcc aaggtgtacg tgaagcaccc cgccgacatc 240
cccgactaca agaagctgtc cttccccgag ggcttcaagt gggagcgcgt gatgaacttc 300
gaggacggcg gcgtggtgac cgtgacccag gactcctccc tgcaggacgg ctgcttcatc 360
tacaaggtga agttcatcgg cgtgaacttc ccctccgacg gccccgtaat gcagaagaag 420
accatgggct gggaggcctc caccgagcgc ctgtaccccc gcgacggcgt gctgaagggc 480
gagatccaca aggccctgaa gctgaaggac ggcggccact acctggtgga gttcaagtcc 540
atctacatgg ccaagaagcc cgtgcagctg cccggctact actacgtgga ctccaagctg 600

```
gacatcacct cccacaacga ggactacacc atcgtggagc agtacgagcg caccgagggc    660

cgccaccacc tgttcctgct cgagtctaga ggtaccggtt gttaa                    705


<210> SEQ ID NO 70
<211> LENGTH: 2052
<212> TYPE: DNA
<213> ORGANISM: Brassica napus

<400> SEQUENCE: 70

atcataagtt gtatcagttc atcaatcttg agaccctagc cctttccagt ctacaaggtc     60

catctgatat ttattcaatg attcactgcg atggattatt gctatgtaaa tttaaatctg    120

ataatataga tagaaatctc gcagtttgga atccgttttt gagcctagtc aaatggatcg    180

aactctcgat ttcttacaca gggcattggg atatctatgg ttttggatac gacaatctat    240

cccgtgagaa ctacaagatc ttgaggtttt gtaataaatt aggacatgaa gaggctgaga    300

tatatgagtt caagactaaa ctctggagaa gtgttgatta ctcttgtgcg tattcttggt    360

atgcatggta tgacgaagct gtgtctatgg atggaaacat gtattggttt gttaaaaggg    420

acatagataa ctcccaaaat gaaaacttca tcctgtgttt tgatttttcc agagagatat    480

tcaaagaaac atgctgtctt ccctttataa atcgtgatga tgtttggctt ttgccacgcc    540

tatcaggttt cagaggagat aggctttcta agttatctaa agataaatat gggaatattc    600

aggtgtggat tacaaacaag gtgactgatg aagttgtttc gtggagcaag tattttaatg    660

tgactctcca atatccctcg agattatccc gtgaatatat caataatatg acattcttca    720

tccacaagac caataggatc atgttatggc gcaaggaaga agatgtcaaa aataaagata    780

tatacgtcaa tgtttacgaa atatgtgaag gtgtggtcga gaaactagtt gagacaggac    840

gacatagacg tggtgataag ggttgcatta ctaagattgg ttatgtattt gtaccaagtc    900

tggttccggt tccagagtaa gaggaggctt ctgagggttg ctcgatctct ttcatacatg    960

tttgcttatt atgttctaac gcactatgca tttcctttgg tgttgcttta aaatactaaa   1020

ccttaaaaca aagctggaaa gattgcagtc tctgattttc ttttttaaac tttaattaaa   1080

ttagcaaaag aaaataaaag gaactggaac catgtttggt tcttgttaaa atcatttgtg   1140

accatatgag gttgtttgtg atcatactta acacacaagt gaggtattta acacacaagt   1200

gaagtatcta ctaatcttga acggtccata tcttcggcat atagtttgta tacttaaaac   1260

acaagtgaag tatctattta ctcttgcatg attcatcttc aaaattacat tttgtatttt   1320

ggtaacttaa tcttctatga gttttctgct tgaagttctt aaaacaattc ggttcacata   1380

gattctctgt tttctcttat agtagttgat aatctcatgg ttagatgatc tatgttacct   1440

gcgcatcact tagtggtgaa gttttgatcc taattaaatc aggtttcgaa cacaaccatt   1500

aattatatgc tgacaaaaaa aaaaaaaaaa gaacacaacc atttcctttt tcatgactga   1560

ggattaattg aacaagtgga tgatgagaaa gcaaagaggc acgttgcgac ataaaaccat   1620

gcaatcttca gttctcgacg tgtgtcattt gtctttcttt gtgtgttttc tccattttgt   1680

ctctctctaa agaagttttg tgcctcttat tttctccgtc tctaccaccc attgttctct   1740

cctacttgct ctactgaatc taccataaac aggtttgtgt ttttcctttt tcctgtttaa   1800

ttaaaccttt tcccatctca aattatagag ttttcatctc tttacattga ttttgttagt   1860

tgattatgga cttatactgg aagatgaaat gaacctaacc attttatcag aatttgttta   1920

tgtgctcaaa catattagaa attgtgtttg catgaagttt cttctcaaat cacttgggat   1980

taaggcaatt tgtttaaccg ctttttcatc tctctttttc tgtgtaaaga taccaccagt   2040
```

atgagtcaaa ca 2052

<210> SEQ ID NO 71
<211> LENGTH: 587
<212> TYPE: DNA
<213> ORGANISM: Brassica napus

<400> SEQUENCE: 71
ggagaaaata tgggagaaga tggaagtgtt gaggaaggta gtaggataca gtgttgcaag 60
gagtgctacg tatgcagagg agttaaaggc tctttatgtt ttcacaggcg tggttgagcc 120
tcctcagtca agtttgatga accaggatag tcatgatatt gcaaatgttt gtgttagact 180
tcgcttcctt atgtctgtta ttggaataaa ctagtttgat ggtgtgcttg tgtgctaggg 240
tcagactctt tcaagtctca aacatgtaat gtgtagtaaa tctcaacttt ctgtattttt 300
ttgtgacttt tgtcctagtt ttattgattt ggattttcaa ataatctcct tctatccctt 360
tctttaagct gttttctata gcacatttca cctttcaact ttttttgagt gtatggactt 420
gttactcttg actcttaaga aagtttgacc caaatgcata agctcctcct tcatataaac 480
tagtcctggt atttttaacc aaatcgaacc gaaattttgg tatttttaac cgaatcgaac 540
aaaaatttca gttagttttt tggttggttt gatttggcag gtctata 587

<210> SEQ ID NO 72
<211> LENGTH: 773
<212> TYPE: DNA
<213> ORGANISM: Brassica napus

<400> SEQUENCE: 72
atggaggaaa atgagtgttt agagagtgaa ggcaggataa gttggatatg gagtaaggca 60
gtaagtgttg ggaagaaggt tctgacagct ggtgttgtaa tgtcttcagc tccactcctg 120
tttcctccac ttgttgtcgc ctgtaccatc gccttcatat cctcagttcc tttttgtctc 180
ttcttggcaa actacgcttg tactcaaaag gtcatgagga ctcttcttcc tcctaatgaa 240
gaaacaagta gtggaataga gaaagatgaa tattcgtttg aggacgtcaa gcttggtcac 300
ggtgtaggca tggccgaatt tgacggggcg gaaccggttc tcatacagag tgaggaagat 360
gaggagatgg cgaaagaatc aacgaggatg atagagaaaa tcagggacga gggtatatct 420
gagaaagaag tacaagatgg tgaaaagtca ggaaatgcca agccagagaa ggttcaagat 480
cagactgcaa agcaagaagc acctaagact ggacatgaag gggagcttga gagtactaca 540
actgaagctt ctactggaaa ggaagaggaa acatcttcga acgagccgat agaccaaggt 600
gtaagtgcgc caagtggaac aggggaagag aaacgaaaaa atactactaa gaaaaagaaa 660
aaaaccgggc gtgcaggtgt acagtgagga gaaaatatgg gagaagatgg aagtgttgag 720
gaaggtagta ggatacagtg ttgcaaggag tgctacgtat gcagaggagt taa 773

<210> SEQ ID NO 73
<211> LENGTH: 55
<212> TYPE: DNA
<213> ORGANISM: Artificial sequence
<220> FEATURE:
<223> OTHER INFORMATION: Primer

<400> SEQUENCE: 73
atacccggga tacctgcagg ttaggccggc caatcataag ttgtatcagt tcatc 55

<210> SEQ ID NO 74

-continued

<211> LENGTH: 69
<212> TYPE: DNA
<213> ORGANISM: Artificial sequence
<220> FEATURE:
<223> OTHER INFORMATION: Primer

<400> SEQUENCE: 74
caatcaatta taggcctcgc atgctttaat taacgatcga gccatggtgt ttgactcata 60
ctggtggta 69

<210> SEQ ID NO 75
<211> LENGTH: 72
<212> TYPE: DNA
<213> ORGANISM: Artificial sequence
<220> FEATURE:
<223> OTHER INFORMATION: Primer

<400> SEQUENCE: 75
ccatggctcg atcgttaatt aaagcatgcg aggcctataa ttgattggga gaaaatatgg 60
gagaagatgg aa 72

<210> SEQ ID NO 76
<211> LENGTH: 61
<212> TYPE: DNA
<213> ORGANISM: Artificial sequence
<220> FEATURE:
<223> OTHER INFORMATION: Primer

<400> SEQUENCE: 76
taagcggccg caatcggacc gataccggta ggcgcctata gacctgccaa atcaaaccaa 60
c 61

<210> SEQ ID NO 77
<211> LENGTH: 1951
<212> TYPE: DNA
<213> ORGANISM: Brassica napus

<400> SEQUENCE: 77
atgtacatgg atgcgtatag atgcgtagac atgttcatat gtagaaaaga atatatgtgt 60
gttctgtttc tgtaaaaaag aacaaaatga gtggacaaac tgactaagtg acagctggga 120
agcacaaggt ggcatgtgga agattggaag aagacccata tatatattaa tattgcctca 180
tccttgcaat tatataaagt gaatacagtt tttattttag atgacggcac gcagttggaa 240
caagttagtt tccacccaga gttatattgg gcctcgaatg tgggtttagc tctggtctgt 300
gtggaatgct tataatggac tgatttataa atgtggccca gacattacca tctttaaatg 360
gatgaacaag tttcccctac taaaggagaa gaagacggaa caagttttag aaagaagcat 420
ccaagtggtg gcacctgagc aagcatgcag ccatacactc gtcacgctcg gttcgtcgcg 480
tccgccacat catcacgtgg ctctcacgtg tttacttgag taaaataaaa atgttatgac 540
atcgaagctg atgtgtaaga acatgcactt tgatgtgcca tgcaacttga aatgtgtcta 600
ctctctccat tcacaactca taagctcacc taattctcat cttcactcgt aataattatt 660
tcatatttct tcatccacga taaatgattt caaaagagag aatacataat ctgcagcgtc 720
agattttatt ttcagtgtaa gacattacat ggtgattaat cacctgattg gaataaccgt 780
aataatttcg aagttaacat aacatactaa ttaatctcaa caacgggaat tgcattactt 840
tatagaaata tgtgtgtgtg tgtgttataa aagctaattt gccagagtgt tataaggtat 900
tctactcgaa aaacaagttt aagagcattt ccaatgtaaa actccatatt ttcctttaaa 960

```
atggagtaaa aatgaaaata gagtaaaatt gctctaatcc tattccattt tccactccat   1020

tatagagtaa tgaacaaaca aaaaataaac tactccattt atgaagtaaa tttcattata   1080

gagtgagata tgaagttgag ttggagcatt ccttactcta tatccacttt tactccattt   1140

tacaggaaaa agtggagttg ggatgaagat cccctaacta atgcataaac aaaaaaacat   1200

agtgcatgtt gaatgtcatt ccgattagcg gtacctattt tcattaattc gatccgtatt   1260

aaacctaaac cttaccaaaa ctatattcta aaacctcgat agatcatata gaaatataac   1320

taagacctca ctgaaagaaa atagaaaaca catttccttg cgaaatttaa ttaatattcc   1380

ctaaaaagca agatctaaac gaaaactttt tttttgata agtatctaaa cgaaaactgt    1440

aaccaaccaa atcatattat taatttgttt tagccgaaac catttaatac ttttagaacc   1500

tcgttgattc ttctattttt aacagaatta ggataaataa attaggactg aattatgatg   1560

tcaaaggcac gctgcacaac caaaaatctc ctataaatac cgaaactcca tgcatgcaaa   1620

tgtagaagcc ttaactcaca attaaagtaa aaaaaaaaag atgggtccaa cctctcttat   1680

ctccttcttt ttcacattct tggccctttt ccatggcttc actgctcagc agtggcccaa   1740

cgagtgccag ctcgaccaac tcaatgcact cgagccgagt cagatcatca agagtgaggg   1800

tggtcgcatt gaggtctggg accaccatgc acctcagctc cgttgctctg gcttcgcctt   1860

tgagcgtttc gtcattgagc ctcagggtct ttacttgccc actttcttga acgccggcaa   1920

actcacgttc gtcgttcacg gacatgctct a                                  1951


<210> SEQ ID NO 78
<211> LENGTH: 514
<212> TYPE: DNA
<213> ORGANISM: Brassica napus

<400> SEQUENCE: 78

agcatgagtt agtgatgtaa cagcgtttga atgttcggtt ttgtacggtt tgtgataaaa     60

ataatgtaca aaagaagttc tacgctttaa ggcagctgtt ttgtttttga gtttttaagg    120

acgcctagtt tacaacaacg accgtcgtat agaagcgatc gttgacacag gcatgtaact    180

ctttgctgaa taaaatcata gttaatcttt ctcctttaat tatatatctt tgttaattag    240

aataaaatca taattagtct cttaagctta tatgcttcct atgatttagg tagatttttc    300

agagaaataa ataagaatgc aactagcaat agccaaactt tcacaaaaac attttagttt    360

atttccacca taagcgttgc gagtaaacag agacaaatgc aataaggttt cttcaggtta    420

aaatagtaaa acagaagaaa cgttttttca catgaaatcc ttcattgggt cctcatggtg    480

aactctcttc attctgtaag cttccatctc ttcc                                514


<210> SEQ ID NO 79
<211> LENGTH: 16397
<212> TYPE: DNA
<213> ORGANISM: Artificial sequence
<220> FEATURE:
<223> OTHER INFORMATION: Plasmid

<400> SEQUENCE: 79

ctatacaaag ttgatagctt ggcgtaatcg atgtaccgat atcaatttaa attggccggc     60

cgagctccct gcagggggcc cggcgcgcct ctagattaat taaaggcctt agttactaat    120

cagtgatcag attgtcgttt cccgccttca gtttaaacta tcagtgtttg acaggatata    180

ttggcgggta aacctaagag aaaagagcgt ttattagaat aatcggatat ttaaaagggc    240
```

-continued

```
gtgaaaaggt ttatccgttc gtccatttgt atgtcaatat ccatgataag tcgcgctgta    300
tgtgtttgtt tgaatattca tggaacgcag tggcggtttt catggcttgt tatgactgtt    360
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
```

caggttgcgg tagcgcatga ctaggatcgg gccagcctgc cccgcctcct ccttcaaatc 2700
gtactccggc aggtcatttg acccgatcag cttgcgcacg gtgaaacaga acttcttgaa 2760
ctctccggcg ctgccactgc gttcgtagat cgtcttgaac aaccatctgg cttctgcctt 2820
gcctgcggcg cggcgtgcca ggcggtagag aaaacggccg atgccggggt cgatcaaaaa 2880
gtaatcgggg tgaaccgtca gcacgtccgg gttcttgcct tctgtgatct cgcggtacat 2940
ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc acctttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980

-continued

```
actgatcact gattaagtac tgcgatcgcc tcgacatatt gtttttgttt cacataaatg   5040
tcgttttgga ttattcatgt aatattttaa actaaagtac aatttttgac tactttagtt   5100
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gttttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
```

-continued

```
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa ggggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt attttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
```

-continued

```
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt tttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
```

-continued

```
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc ggcctattag gccacggtcc  12480
gtacagtgtt taaacgattg acctgcagga tacaagtgcg cacagactag cggccgctaa  12540
tcccgggaat taccggtagt aggcgccaca atcagtaaat tgaacggaga atattattca  12600
taaaaatacg atagtaacgg gtgatatatt cattagaatg aaccgaaacc ggcggtaagg  12660
atctgagcta cacatgctca ggttttttac aacgtgcaca acagaattga aagcaaatat  12720
catgcgatca taggcgtctc gcatatctca ttaaagcagc aatcaattat taattaagct  12780
aaggaactta catcgctggg aactcggtga taaattcctt gctgatgtcc gccaggtggt  12840
ccacgacctc gtagatgccc tcccagaagc cggtctcgtg gaacgggatg tcgaactcct  12900
tgcatagcga cttgatgagc acgttgacct ttggcaagtt gtggcgcggc acgagcggga  12960
acaggtgatg gtcgatctgg tagttcaagc caccggtgaa ccagtccatg aataccgacg  13020
cgcggatgtt gcgcgtcgtg gtcacctgca gctgccagaa gtccggcttg gtttcgcgct  13080
cgtacaccga catgccgttg tggccaatac tgaacaccag cgccaggagc aagccgcagg  13140
acgcctggcc catgaggaag tatgccacgc cctcaaacag gctcatgttg cagaagtacg  13200
ggatcgcgag ctgccagatg tagtgcacga tcagacccgc cttctccggt ccgtcgaact  13260
cgaccttgtc gaagatgccg aacgagaact cggtgaacac gtagaagaac gactgcgcga  13320
gccagctcag gcgcgcgagc agcagcagcg ggaagtatag gaacgcctgg ttgcggatga  13380
agaacgggcc gtgcgccgac tcgaacgcct tgcgcgccat ctccttagac cacgccagca  13440
gcggcatggt gtcgatgtcc gggtcgccga tgaagccctc gtccttggcg ctgtgcaggt  13500
tcggcaccgc gtggtgcagg ttgtgcttgt tcttccacca ctgcatgctg aagccctgcc  13560
aggcgttgcc cacgaggcag ccgataaggt tgccgagcgt gcggttctcg cacacctggt  13620
tgtgcaagaa gtcgtgcgcc agccatccgg actgctggta gaagagcccc ataatcacgc  13680
cggcgaccat gtacatggcg aaactgttga agaagaagca gatcgccatc gagagcaccg  13740
cgatgccgaa cgtgctcacg agcttccacg cgtagtagag cgcgctggcg tcgtagagcc  13800
ccatgccctt gaccttgacg cgcagacggc ggtaggacgc gatgaactcg ttgatgcgct  13860
cgcggcgcgc gcgctcctcg tcgctcgccg gctccccctc gatctcggcc ttggaggttt  13920
cgtccacgtc gccgacgtag aactgctcga gcagcttgag cgccgaggac gggtggaaga  13980
ccgcgaaggc gtccgtggcg tcctcgccgg cctgcgtgag catcacggag ccacccgggt  14040
gcgagtccca cttggagatg tcgtagacct tgtggtgaat cacgatccac gcggtcgcgg  14100
gcgtcgcgtg ctcgcggatc tccttccagc tcaccaggcg cttcactcca ggcttgaggt  14160
ccaccatttt gggccccggc gcgcctagag catgtccgtg aacgacgaac gtgagtttgc  14220
cggcgttcaa gaaagtgggc aagtaaagac cctgaggctc aatgacgaaa cgctcaaagg  14280
cgaagccaga gcaacggagc tgaggtgcat ggtggtccca gacctcaatg cgaccaccct  14340
cactcttgat gatctgactc ggctcgagtg cattgagttg gtcgagctgg cactcgttgg  14400
gccactgctg agcagtgaag ccatggaaaa gggccaagaa tgtgaaaaag aaggagataa  14460
```

-continued

```
gagaggttgg acccatcttt tttttttac tttaattgtg agttaaggct tctacatttg  14520
catgcatgga gtttcggtat ttataggaga tttttggttg tgcagcgtgc ctttgacatc  14580
ataattcagt cctaatttat ttatcctaat tctgttaaaa atagaagaat caacgaggtt  14640
ctaaaagtat taaatggttt cggctaaaac aaattaataa tatgatttgg ttggttacag  14700
ttttcgttta gatacttatc aaaaaaaaaa gttttcgttt agatcttgct ttttagggaa  14760
tattaattaa atttcgcaag gaaatgtgtt ttctattttc tttcagtgag gtcttagtta  14820
tatttctata tgatctatcg aggttttaga atatagtttt ggtaaggttt aggtttaata  14880
cggatcgaat taatgaaaat aggtaccgct aatcggaatg acattcaaca tgcactatgt  14940
tttttgttt atgcattagt taggggatct tcatcccaac tccacttttt cctgtaaaat  15000
ggagtaaaag tggatataga gtaaggaatg ctccaactca acttcatatc tcactctata  15060
atgaaattta cttcataaat ggagtagttt attttttgtt tgttcattac tctataatgg  15120
agtggaaaat ggaataggat tagagcaatt ttactctatt ttcattttta ctccatttta  15180
aaggaaaata tggagtttta cattggaaat gctcttaaac ttgtttttcg agtagaatac  15240
cttataacac tctggcaaat tagcttttat aacacacaca cacacatatt tctataaagt  15300
aatgcaattc ccgttgttga gattaattag tatgttatgt taacttcgaa attattacgg  15360
ttattccaat caggtgatta atcaccatgt aatgtcttac actgaaaata aaatctgacg  15420
ctgcagatta tgtattctct cttttgaaat catttatcgt ggatgaagaa atatgaaata  15480
attattacga gtgaagatga gaattaggtg agcttatgag ttgtgaatgg agagagtaga  15540
cacatttcaa gttgcatggc acatcaaagt gcatgttctt acacatcagc ttcgatgtca  15600
taacattttt attttactca agtaaacacg tgagagccac gtgatgatgt ggcggacgcg  15660
acgaaccgag cgtgacgagt gtatggctgc atgcttgctc aggtgccacc acttggatgc  15720
ttctttctaa aacttgttcc gtcttcttct cctttagtag gggaaacttg ttcatccatt  15780
taaagatggt aatgtctggg ccacatttat aaatcagtcc attataagca ttccacacag  15840
accagagcta aacccacatt cgaggcccaa tataactctg ggtggaaact aacttgttcc  15900
aactgcgtgc cgtcatctaa aataaaaact gtattcactt tatataattg caaggatgag  15960
gcaatattaa tatatatatg ggtcttcttc caatcttcca catgccacct tgtgcttccc  16020
agctgtcact tagtcagttt gtccactcat tttgttcttt tttacagaaa cagaacacac  16080
atatattctt ttctacatat gaacatgtct acgcatctat acgcatccat gtacatggcc  16140
ggcctagtag atttaaattg gccttagtgg ccaagcttgg cgtaatcatg gagcctgctt  16200
ttttgtacaa acttgggtac cggcctatta ggccacggtc cgtacagtgt ttaaacgatt  16260
gacctgcagg atacaagtgc gcacagacta gcggccgcta atcccgggaa ttaccggtag  16320
taggcgccta ctttggccgg cctagtagat ttaaattggc cttagtggcc aagcttggcg  16380
taatcatggc aactttt                                                 16397
```

<210> SEQ ID NO 80
<211> LENGTH: 1107
<212> TYPE: DNA
<213> ORGANISM: Brassica napus

<400> SEQUENCE: 80

```
atgggaaaag tgactcctgg atgcgccgag acattcatgg actctcctgt atttggacaa     60
ggacagggcc aggaacaagg tcagggacag ggtcagggtc aaggccaggg tttccgtgac    120
atgcaccaga aagtagagca cctacggtcg ggtgacacca tagcgacacc acctggtgta    180
```

-continued

```
gctcaatggt tctacaacaa tggaaatgag cctctcattc ttgttgcagc cgctgacatc    240

gcaaataacc tgaaccagct tgaccgcaac ctcagaccgt ttttgttagc cggaaacaac    300

ccacaaggac agcaatggct acaaggccga cagcaacaga aacaaaacaa catcttcaat    360

ggcttcgcac ctcagatctt ggctcaagcc tttaaaatca gcgtcgagac agctcaaaaa    420

cttcaaaacc agcaagtcaa ccgtggcaac atcgtcaagg tccaaggtca attcggcgtc    480

attagaccac ccttgagaca aggccaaggc ggtcagcaac cacaggaaga aggtaatggt    540

ttggaggaga ctttgtgcac aatgcgatgc actgaaaacc ttgatgaccc gtcaagtgct    600

gatgtctaca agccatcgct cggatacatt agcacactca acagctacaa tctccctatc    660

ctcagattcc tccgccttag cgctcttcgt ggctccatcc ataacaacgc tatggtgcta    720

ccacaatgga acgtgaacgc aaacgcggcg ctctacgtga caaaggggaa ggctcatata    780

cagatggtga acgacaacgg acaaagagtg ttcgaccaag agatctccaa gggacagtta    840

cttgtcgtgc cacaaggctt cgcggtcgtg aaacgtgcca caagccaaca gtttcagtgg    900

atcgagttca agagcaacga caacgcacag atcaacacac tcgcgggacg cacctcagtc    960

atgagaggtt taccacttga agttatatcc aacgggtatc agatctcacc ccaagaagct   1020

agaagtgtta agttcagcac tcttgagacc acattgactc aaagcagtgg tcctatgggc   1080

tacggtatgc ctagggtcga ggcttga                                       1107
```

<210> SEQ ID NO 81
<211> LENGTH: 55
<212> TYPE: DNA
<213> ORGANISM: Artificial sequence
<220> FEATURE:
<223> OTHER INFORMATION: Primer

<400> SEQUENCE: 81

```
atacccggga tacctgcagg ttaggccggc caatgtacat ggatgcgtat agatg          55
```

<210> SEQ ID NO 82
<211> LENGTH: 69
<212> TYPE: DNA
<213> ORGANISM: Artificial sequence
<220> FEATURE:
<223> OTHER INFORMATION: Primer

<400> SEQUENCE: 82

```
caatcaatta taggcctcgc atgctttaat taacgatcga gccatggtag agcatgtccg     60

tgaacgacg                                                             69
```

<210> SEQ ID NO 83
<211> LENGTH: 72
<212> TYPE: DNA
<213> ORGANISM: Artificial sequence
<220> FEATURE:
<223> OTHER INFORMATION: Primer

<400> SEQUENCE: 83

```
ccatggctcg atcgttaatt aaagcatgcg aggcctataa ttgattgagc atgagttagt     60

gatgtaacag cg                                                         72
```

<210> SEQ ID NO 84
<211> LENGTH: 61
<212> TYPE: DNA
<213> ORGANISM: Artificial sequence
<220> FEATURE:

<223> OTHER INFORMATION: Primer

<400> SEQUENCE: 84
taagcggccg caatcggacc gataccggta ggcgccggaa gagatggaag cttacagaat 60
g 61

<210> SEQ ID NO 85
<211> LENGTH: 1360
<212> TYPE: DNA
<213> ORGANISM: Brassica napus

<400> SEQUENCE: 85
cataaaaata tgttgagaaa atatctaaca aaatcttatt taaaatttta aatattttta 60
taaaataaca cattaattga tttcgtaatt tgtaatataa tattgttata aatcaatgtt 120
aactaaaatt ttattataaa acaagaaaat taaaatcata tactattttc tataaattct 180
ataattatat tctgtgttat ataaaaataa aagtgatata taaattaaat atgacaaatt 240
atattaaata ggtaaattaa aaaaaaaatt aaaaaattat ttcatttaaa taaattatca 300
ctcatcatta acatgtgtta aaattcgtaa tctatataat atttttatga aaaaataaat 360
ttattaggtt aaactcttat atctacaact atatattatt tatttattta ttttgaaact 420
ctcaataata tattgtttaa aatatttata tacaaaaata taatagtata tataacattt 480
agttcatata ctatttaaaa aatatgttat tagtaaacta tgaaatttta gtaattcatt 540
taaaatattt aatgacaaat taaattttag ttatatattt tttaaaatta taacaaaacc 600
tgttgagaaa atttataaaa tattaccaat tttttttttt ttataaaata atgtattaat 660
gtagcaacaa aaacaaattc aaaattcatg taatcttcca aactaaaaaa tagtagcgta 720
atttttcaaa gttttcttga aaaaatataa attttttaaa ataaatattc aaactcaaaa 780
tgataaaaat aactttttga aatgcaccac gaaaaaaacaa atgatatatg ttgtaaacat 840
taaagcaatc taatgttttg aaatcgtaat taaaaataaa aataaaactt aatatcttaa 900
tatcataatt aaaaatatat gttaagatca taacatgccg agtaaaaaat gtaaacaata 960
atattataaa cttatacaat atataatact aaaatggaaa ttatatattt aaaatatttt 1020
atatcaaata catttataaa atgaaaagat atctgcatgt taaaatctag tgtaacattt 1080
taaaaaaagt tggacgatca aagagcaagc catgctaaaa agtggaagca aaacattaag 1140
ttagaaatat aaactgtatc agcgaacatc gacctaaagt acgtgaacct accacgggag 1200
tcatcccacc aaacctctcc taaaatatca aggctctaaa ccctagattg gcacaagaaa 1260
atgcatgcgt cacctcttct ttacaaaggc tatataaaca gtagattggc acaaggttcc 1320
atccaacaca aacacatata tacaaatcta cacattaacc 1360

<210> SEQ ID NO 86
<211> LENGTH: 652
<212> TYPE: DNA
<213> ORGANISM: Brassica napus

<400> SEQUENCE: 86
aacactttat ccacatcaag atcgccttca tgtcatctca ctctttctag ctatctgctc 60
catagtaaat aaaggagctt agtactgtaa ctaaataaaa catattccca gtggaaaaag 120
tcaagtatat attaatgaat aatactttta tgccaagtca agggattgag agaaaaaaaa 180
aaactcaatt taacaggtag atttacatca tccaaccaac cacactgcat atattaatga 240
agtatcctat tgtgatttta aaaaaatgaa gtatccataa taaaatatga ttcttattta 300
tgtcaactac aaatatcatt acactatatc tatttttgca tatctatttt cgcaacggaa 360
ctcttaaaat ttaaattggt taatatctat attaacctta atgaatagtt ctatacaatt 420
cattattaat tatataatta aacaatataa ttttaacaac tatgagacat tatctcgaca 480
acctcatacc aattataatt tagttatata aaatttatac tgtaaaactc gtgtatttgt 540
tatactacaa attactatct tcgtagtttt caaaattagt atttcaacta aacaacaata 600
atactttgga tagcttacta taaacgaaaa agtgcaatta cgagcacaca tc 652

<210> SEQ ID NO 87
<211> LENGTH: 14577
<212> TYPE: DNA
<213> ORGANISM: Artificial sequence
<220> FEATURE:
<223> OTHER INFORMATION: Plasmid

<400> SEQUENCE: 87
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540
tgggtgtcat cgagcgccac ctcgaaccga ccctcctcgc cgtgcatctg tatggtagcg 600
ccgttgacgg cggccttaag ccccattcgg acatcgacct gcttgtcacc gttaccgtcc 660
gtctcgacga gaccacgcgc cgcgcgctta tcaacgacct tctggaaacg tccgcctccc 720
ccggcgagag cgaaatcctg cgcgcggttg aggtgacgat tgtggtgcac gatgacatca 780
tcccctggcg ctatccggcc aaacgcgaac tccagttcgg cgaatggcag cgtaatgata 840
ttctggcggg tatctttgaa ccggccacca tcgacattga tctggcgatc ctgctcacca 900
aggcccggga gcatagcgtg gccctcgtcg gccccgcggc cgaggaactt ttcgacccgg 960
tgccggaaca ggatctgttc gaagcactga acgagacgct gaccctgtgg aactccccgc 1020
cggattgggc gggcgatgag cgcaatgtgg tccttacgct gagccggatt tggtactcgg 1080
cggttaccgg caagatcgcg ccgaaggatg tcgccgccga ctgggcgatg gagcgccttc 1140
cggcgcaata ccagcccgtg atcctcgaag cgcgccaagc ctatctgggc caagaagaag 1200
accgtctcgc gtcccgggcc gaccagctcg aagaatttgt ccactatgtc aagggcgaga 1260
tcacgaaggt cgttggcaaa taatgtctag ctagaaattc gttcaagccg acgccgcttc 1320
gcggcgcggc ttaactcaag cgttagatgc actaagcaca taattgctca cagccaaact 1380
atcgatgagt tgaaggaccc cgtagaaaag atcaaaggat cttcttgaga tccttttttt 1440
ctgcgcgtaa tctgctgctt gcaaacaaaa aaaccaccgc taccagcggt ggtttgtttg 1500
ccggatcaag agctaccaac tctttttccg aaggtaactg gcttcagcag agcgcagata 1560
ccaaatactg tccttctagt gtagccgtag ttaggccacc acttcaagaa ctctgtagca 1620
ccgcctacat acctcgctct gctaatcctg ttaccagtgg ctgctgccag tggcgataag 1680

-continued

```
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
```

```
gcttttgctc attttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
agctcgtacc cggccagcgc ctcggcaacc tcaccgccga tgcgcgtgcc tttgatcgcc   4320
cgcgacacga caaaggccgc ttgtagcctt ccatccgtga cctcaatgcg ctgcttaacc   4380
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cgggcggtcg   4560
atgccgacaa cggttagcgg ttgatcttcc cgcacggccg cccaatcgcg ggcactgccc   4620
tggggatcgg aatcgactaa cagaacatcg gccccggcga gttgcagggc gcgggctaga   4680
tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc acctttttag atgatcagtg attttgtgcc   4860
gagctgccgg tcggggagct gttggctggc tggtggcagg atatattgtg gtgtaaacaa   4920
attgacgctt agacaactta ataacacatt gcggacgtct ttaatgtact gaatttagtt   4980
actgatcact gattaagtac tgcgatcgcc tcgacatatt gtttttgttt cacataaatg   5040
tcgttttgga ttattcatgt aatattttaa actaaagtac aatttttgac tactttagtt   5100
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg atttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gtttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
```

-continued

```
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
```

```
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa ggggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct atttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt tttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac cggcctatta  10620
ggccacggtc cgtacagtgt ttaaacgatt gacctgcagg atacaagtgc gcacagacta  10680
gcggccgcta atcccgggaa ttaccggtag taggcgccta ctttggccgg cctagtagat  10740
ttaaattggc cttagtggcc aagcttggcg taatcatggc cactttgtac aagaaagctg  10800
ggtggtaccg gcctattagg ccacggtccg tacagtgttt aaacgattga cctgcaggat  10860
acaagtgcgc acagactagc ggccgctaat cccgggaatt accggtagta ggcgccgatg  10920
tgtgctcgta attgcacttt ttcgtttata gtaagctatc caaagtatta ttgttgttta  10980
gttgaaatac taattttgaa aactacgaag atagtaattt gtagtataac aaatacacga  11040
gttttacagt ataaatttta tataactaaa ttataattgg tatgaggttg tcgagataat  11100
gtctcatagt tgttaaaatt atattgttta attatataat taataatgaa ttgtatagaa  11160
```

```
ctattcatta aggttaatat agatattaac caatttaaat tttaagagtt ccgttgcgaa  11220
aatagatatg caaaaataga tatagtgtaa tgatatttgt agttgacata aataagaatc  11280
atattttatt atggatactt catttttta aaatcacaat aggatacttc attaatatat  11340
gcagtgtggt tggttggatg atgtaaatct acctgttaaa ttgagttttt ttttttctct  11400
caatcccttg acttggcata aaagtattat tcattaatat atacttgact ttttccactg  11460
ggaatatgtt ttatttagtt acagtactaa gctcctttat ttactatgga gcagatagct  11520
agaaagagtg agatgacatg aaggcgatct tgatgtggat aaagtgtttt aattaattac  11580
atcgctggga actcggtgat aaattccttg ctgatgtccg ccaggtggtc cacgacctcg  11640
tagatgccct cccagaagcc ggtctcgtgg aacgggatgt cgaactcctt gcatagcgac  11700
ttgatgagca cgttgacctt tggcaagttg tggcgcggca cgagcgggaa caggtgatgg  11760
tcgatctggt agttcaagcc accggtgaac cagtccatga ataccgacgc gcggatgttg  11820
cgcgtcgtgg tcacctgcag ctgccagaag tccggcttgg tttcgcgctc gtacaccgac  11880
atgccgttgt ggccaatact gaacaccagc gccaggagca agccgcagga cgcctggccc  11940
atgaggaagt atgccacgcc ctcaaacagg ctcatgttgc agaagtacgg gatcgcgagc  12000
tgccagatgt agtgcacgat cagacccgcc ttctccggtc cgtcgaactc gaccttgtcg  12060
aagatgccga acgagaactc ggtgaacacg tagaagaacg actgcgcgag ccagctcagg  12120
cgcgcgagca gcagcagcgg gaagtatagg aacgcctggt tgcggatgaa gaacgggccg  12180
tgcgccgact cgaacgcctt gcgcgccatc tccttagacc acgccagcag cggcatggtg  12240
tcgatgtccg ggtcgccgat gaagccctcg tccttggcgc tgtgcaggtt cggcaccgcg  12300
tggtgcaggt tgtgcttgtt cttccaccac tgcatgctga agccctgcca ggcgttgccc  12360
acgaggcagc cgataaggtt gccgagcgtg cggttctcgc acacctggtt gtgcaagaag  12420
tcgtgcgcca gccatccgga ctgctggtag aagagcccca taatcacgcc ggcgaccatg  12480
tacatggcga aactgttgaa gaagaagcag atcgccatcg agagcaccgc gatgccgaac  12540
gtgctcacga gcttccacgc gtagtagagc gcgctggcgt cgtagagccc catgcccttg  12600
accttgacgc gcagacggcg gtaggacgcg atgaactcgt tgatgcgctc gcggcgcgcg  12660
cgctcctcgt cgctcgccgg ctccccctcg atctcggcct tggaggtttc gtccacgtcg  12720
ccgacgtaga actgctcgag cagcttgagc gccgaggacg ggtggaagac cgcgaaggcg  12780
tccgtggcgt cctcgccggc ctgcgtgagc atcacggagc cacccgggtg cgagtcccac  12840
ttggagatgt cgtagacctt gtggtgaatc acgatccacg cggtcgcggg cgtcgcgtgc  12900
tcgcggatct ccttccagct caccaggcgc ttcactccag gcttgaggtc caccatggtt  12960
aatgtgtaga tttgtatata tgtgtttgtg ttggatggaa ccttgtgcca atctactgtt  13020
tatatagcct ttgtaaagaa gaggtgacgc atgcattttc ttgtgccaat ctagggttta  13080
gagccttgat attttaggag aggtttggtg ggatgactcc cgtggtaggt tcacgtactt  13140
taggtcgatg ttcgctgata cagtttatat ttctaactta atgttttgct tccacttttt  13200
agcatggctt gctctttgat cgtccaactt tttttaaaat gttacactag attttaacat  13260
gcagatatct tttcatttta taaatgtatt tgatataaaa tattttaaat atataatttc  13320
cattttagta ttatatattg tataagttta taatattatt gtttacattt tttactcggc  13380
atgttatgat cttaacatat atttttaatt atgatattaa gatattaagt tttattttta  13440
tttttaatta cgatttcaaa acattagatt gctttaatgt ttacaacata tatcatttgt  13500
tttttcgtgg tgcatttcaa aaagttattt ttatcatttt gagtttgaat atttattttta  13560
```

```
aaaaatttat atttttttcaa gaaaactttg aaaaattacg ctactatttt ttagtttgga  13620
agattacatg aattttgaat ttgtttttgt tgctacatta atacattatt ttataaaaaa  13680
aaaaaaattg gtaatatttt ataaattttc tcaacaggtt ttgttataat tttaaaaaat  13740
atataactaa aatttaattt gtcattaaat attttaaatg aattactaaa atttcatagt  13800
ttactaataa catatttttt aaatagtata tgaactaaat gttatatata ctattatatt  13860
tttgtatata aatattttaa acaatatatt attgagagtt tcaaaataaa taaataaata  13920
atatatagtt gtagatataa gagtttaacc taataaattt attttttcat aaaaatatta  13980
tatagattac gaattttaac acatgttaat gatgagtgat aatttattta aatgaaataa  14040
tttttaatt tttttttaa tttacctatt taatataatt tgtcatattt aatttatata  14100
tcacttttat ttttatataa cacagaatat aattatagaa tttatagaaa atagtatatg  14160
attttaattt tcttgtttta taataaaatt ttagttaaca ttgatttata acaatattat  14220
attacaaatt acgaaatcaa ttaatgtgtt attttataaa aatatttaaa attttaaata  14280
agattttgtt agatattttc tcaacatatt tttatgggcc ggcctagtag atttaaattg  14340
gccttagtgg ccaagcttgg cgtaatcatg gagcctgctt ttttgtacaa acttgggtac  14400
cggcctatta ggccacggtc cgtacagtgt ttaaacgatt gacctgcagg atacaagtgc  14460
gcacagacta gcggccgcta atcccgggaa ttaccggtag taggcgccta ctttggccgg  14520
cctagtagat ttaaattggc cttagtggcc aagcttggcg taatcatggc aacttttt  14577
```

<210> SEQ ID NO 88
<211> LENGTH: 1644
<212> TYPE: DNA
<213> ORGANISM: Brassica napus

<400> SEQUENCE: 88

```
atgaaatttc gtggactcga cttgatcgtt tttctattag ctgtggtaag ttgcaaagct    60
aataaggaaa ttacttgcga agagaacgag ccatttacat gtaataacac tgatcgttta   120
aacagtaaag gcttcccaaa agacttcatc ttcggtgttt catcggctgc ttaccagatt   180
gaaggtggca gaggacgtgg tcttaacatt tgggatggct tcactcaccg attcccagag   240
aaaggagggt ccgatcttgg gaatggagat actacttgcg agtcatatac gatgtggcag   300
aaagatatag acattatgga cgaaatgaat gctactggct acagattctc cttcgcgtgg   360
tcaagaatca ttccaaaagg aaaggtgagt aggggagtga acaaaggagg tcttgaatac   420
taccacagac tcatagatgg cctcatcgcg aagaatatca cgcctttcgt taccctctac   480
cattgggacc ttcctcaaac actgcaagat gagtatgaag gtttcttgaa ccgccaagtc   540
atagaggatt ttagagattt ggcggatcta tgtttcaagg aatttggtgg aaaggtgaag   600
aactggctca ctatcaacca gctgtactca gtgcctacga gaggctattc aaccggagca   660
gatgcacccg ttcgatgttc tccaaaggtc gatgcaagat gttacggcgg aaattcttca   720
acggaacctt atatagttgc acataaccag cttcttgctc ataccgctgt ggtcaatctt   780
tatagaacaa aatataggtt ccaaagaggg aggatcggac cggtgatgat aactagatgg   840
tttcttccat ttgatgagac taataaagcc agcatagatg cagctgagag gatgaaagaa   900
ttcttcttag gatggtatat ggagccgcta acaagaggta gatacccaga catcatgagg   960
cgaatggtag gtaatcggct tcccaacttc actgaagcag aagccagact tgttgcgggt  1020
tcatatgatt ttcttggtct caactattac gccactcagt tcgtacagcc aactcctaac  1080
```

-continued

```
ccactccccg ttacatcgga aagatacact gccatgatgg acccagggac aagactcaca   1140

tttgtaaatt cacgtggtga aaaaactggt ccactgtttg aagagttaaa agggggaaat   1200

agttattact acccaccagg catttattac gttatggact acttcacaac caaataccgt   1260

aacccattaa tctatatcac cgagagcgga ttcagtacct ctggtgatca aacccgccag   1320

gaagctgttg ccgattccaa gcggattgat tatctctgca gtcatctctg ttttctccgt   1380

aaggtcatca tggagaagcg tgtcaacata aaaggatact ttgcatgggc tcttggagat   1440

aattatgaat tcggtaaagg ttttaccgtc cgattcggac tcagttacgt taactggaca   1500

gacgttagtg atagaaacct caaagattct ggcaaatggt atcagaggtt cattaacgtt   1560

accaccaaga tcactgcaca ccaagatttc ctccgctcag gcctctcttt tgaggacaag   1620

atgaagacac tcacagatgc atga                                          1644


<210> SEQ ID NO 89
<211> LENGTH: 57
<212> TYPE: DNA
<213> ORGANISM: Artificial sequence
<220> FEATURE:
<223> OTHER INFORMATION: Primer

<400> SEQUENCE: 89

atacccggga tacctgcagg ttaggccggc cacataaaaa tatgttgaga aaatatc        57


<210> SEQ ID NO 90
<211> LENGTH: 73
<212> TYPE: DNA
<213> ORGANISM: Artificial sequence
<220> FEATURE:
<223> OTHER INFORMATION: Primer

<400> SEQUENCE: 90

caatcaatta taggcctcgc atgctttaat taacgatcga gccatggggt taatgtgtag     60

atttgtatat atg                                                        73


<210> SEQ ID NO 91
<211> LENGTH: 72
<212> TYPE: DNA
<213> ORGANISM: Artificial sequence
<220> FEATURE:
<223> OTHER INFORMATION: Primer

<400> SEQUENCE: 91

ccatggctcg atcgttaatt aaagcatgcg aggcctataa ttgattgaac actttatcca     60

catcaagatc gc                                                         72


<210> SEQ ID NO 92
<211> LENGTH: 61
<212> TYPE: DNA
<213> ORGANISM: Artificial sequence
<220> FEATURE:
<223> OTHER INFORMATION: Primer

<400> SEQUENCE: 92

taagcggccg caatcggacc gataccggta ggcgccgatg tgtgctcgta attgcacttt     60

t                                                                     61


<210> SEQ ID NO 93
<211> LENGTH: 16452
<212> TYPE: DNA
<213> ORGANISM: Artificial sequence
```

<220> FEATURE:
<223> OTHER INFORMATION: Plasmid

<400> SEQUENCE: 93

```
taatgtacgg agcagatgct agggcaaatt gccctagcag gggaaaaagg tcgaaaaggt     60
ctctttcctg tggatagcac gtacattggg aacccaaagc cgtacattgg gaaccggaac    120
ccgtacattg ggaacccaaa gccgtacatt gggaaccggt cacacatgta agtgactgat    180
ataaaagaga aaaaaggcga tttttccgcc taaaactctt taaaacttat taaaactctt    240
aaaacccgcc tggcctgtgc ataactgtct ggccagcgca cagccgaaga gctgcaaaaa    300
gcgcctaccc ttcggtcgct gcgctcccta cgccccgccg cttcgcgtcg gcctatcgcg    360
gcctatgcgg tgtgaaatac cgcacagatg cgtaaggaga aaataccgca tcaggcgctc    420
ttccgcttcc tcgctcactg actcgctgcg ctcggtcgtt cggctgcggc gagcggtatc    480
agctcactca aaggcggtaa tacggttatc cacagaatca ggggataacg caggaaagaa    540
catgtgagca aaaggccagc aaaaggccag gaaccgtaaa aaggccgcgt tgctggcgtt    600
tttccatagg ctccgccccc ctgacgagca tcacaaaaat cgacgctcaa gtcagaggtg    660
gcgaaacccg acaggactat aaagatacca ggcgtttccc cctggaagct ccctcgtgcg    720
ctctcctgtt ccgaccctgc cgcttaccgg atacctgtcc gcctttctcc cttcgggaag    780
cgtggcgctt tctcatagct cacgctgtag gtatctcagt tcggtgtagg tcgttcgctc    840
caagctgggc tgtgtgcacg aaccccccgt tcagcccgac cgctgcgcct tatccggtaa    900
ctatcgtctt gagtccaacc cggtaagaca cgacttatcg ccactggcag cagccactgg    960
taacaggatt agcagagcga ggtatgtagg cggtgctaca gagttcttga agtggtggcc   1020
taactacggc tacactagaa ggacagtatt tggtatctgc gctctgctga agccagttac   1080
cttcggaaaa agagttggta gctcttgatc cggcaaacaa accaccgctg gtagcggtgg   1140
tttttttgtt tgcaagcagc agattacgcg cagaaaaaaa ggatctcaag aagatccttt   1200
gatcttttct acggggtcct tcaactcatc gatagtttgg ctgtgagcaa ttatgtgctt   1260
agtgcatcta acgcttgagt taagccgcgc cgcgaagcgg cgtcggcttg aacgaatttc   1320
tagctagaca ttatttgcca acgaccttcg tgatctcgcc cttgacatag tggacaaatt   1380
cttcgagctg gtcggcccgg gacgcgagac ggtcttcttc ttggcccaga taggcttggc   1440
gcgcttcgag gatcacgggc tggtattgcg ccggaaggcg ctccatcgcc cagtcggcgg   1500
cgacatcctt cggcgcgatc ttgccggtaa ccgccgagta ccaaatccgg ctcagcgtaa   1560
ggaccacatt gcgctcatcg cccgcccaat ccggcgggga gttccacagg gtcagcgtct   1620
cgttcagtgc ttcgaacaga tcctgttccg gcaccgggtc gaaaagttcc tcggccgcgg   1680
ggccgacgag ggccacgcta tgctcccggg ccttggtgag caggatcgcc agatcaatgt   1740
cgatggtggc cggttcaaag atacccgcca gaatatcatt acgctgccat tcgccgaact   1800
ggagttcgcg tttggccgga tagcgccagg ggatgatgtc atcgtgcacc acaatcgtca   1860
cctcaaccgc gcgcaggatt tcgctctcgc cgggggaggc ggacgtttcc agaaggtcgt   1920
tgataagcgc gcggcgcgtg gtctcgtcga gacggacggt aacggtgaca agcaggtcga   1980
tgtccgaatg gggcttaagg ccgccgtcaa cggcgctacc atacagatgc acggcgagga   2040
gggtcggttc gaggtggcgc tcgatgacac ccacgacttc cgacagctgg gtggacacct   2100
cggcgatgac cgcttcaccc atgatgttta actttgtttt agggcgactg ccctgctgcg   2160
taacatcgtt gctgctccat aacatcaaac atcgacccac ggcgtaacgc gcttgctgct   2220
```

-continued

```
tggatgcccg aggcatagac tgtaccccaa aaaaacagtc ataacaagcc atgaaaaccg   2280
ccactgcgtt ccatgaatat tcaaacaaac acatacagcg cgacttatca tggatattga   2340
catacaaatg gacgaacgga taaacctttt cacgcccttt taaatatccg attattctaa   2400
taaacgctct tttctcttag gtttacccgc caatatatcc tgtcaaacac tgatagttta   2460
aactgaaggc gggaaacgac aatctgatca ctgattagta actaaggcct ttaattaatc   2520
tagaggcgcg ccgggccccc tgcagggagc tcggccggcc aatttaaatt gatatcggta   2580
catcgattac gccaagctat caactttgta tagaaaagtt gccatgatta cgccaagctt   2640
ggccactaag gccaatttaa atctactagg ccggccaaag taggcgccta ctaccggtaa   2700
ttcccgggat tagcggccgc tagtctgtgc gcacttgtat cctgcaggtc aatcgtttaa   2760
acactgtacg gaccgtggcc taataggccg gtacccaagt ttgtacaaaa aagcaggctc   2820
catgattacg ccaagcttgg ccactaaggc caatttaaat ctactaggcc ggccatcggc   2880
tacaaatcca actgggaggc caaaaagata accacccccct agctgcagaa accaaatcat   2940
aactatcaga acaaagataa aaagcccgag tataccatgt tgtaccatag aagcacaccc   3000
tctatctcat acatagttat gaattgaaac ctaccgtaag tacagaagca ggaaccgcca   3060
caattgtgag gggaatataa gccaaagccc tgcaattttc agtgagaagg gtaagattat   3120
taaaggcagc cagagaacaa tgtcggcaaa gtaaacatat tcgaggtggg acattaaatt   3180
taaaaagaag agaacaaaag aaagtagcaa gcttgagaag aagcttacag tgcaattgga   3240
ccaaagggtc caagatcttc cttaatccat aacaagaagt ccttcaattt ctgcagaaag   3300
tgaacaaaaa caatgattct aaatcataca tattaccatt cttctgatct atcactactc   3360
tctactacca ggtgtagcaa aattcccgat taaattcata agaaaatcga aattttgttg   3420
ctaccttcaa acaacagatg ctcgcaaaat gtgattcata gtgtaaacaa tctagctagt   3480
aacgacctaa caacactatc accaaacaga taaacagcga tctagcgagt tccagcagca   3540
atactccatt ctattcgcca ccgacgatta tcgattcact aaagctacaa caagtacacg   3600
cgtggatagt ggaatagaga aattgcctgt tcaacgggga gaaaaatgaa agcggtgccg   3660
atagcgacaa ggaggaggag cgatattgct atccggaaag tggacggagt aaaggaactc   3720
gccgccatat acaaggatct gaggcgacgg cgccaccaag gcctcgaatg gtcaccctca   3780
tcgccgtcgt agtcgtattg atctccattc gcataagatc ctggcttgag ccacggcctc   3840
gcccttaacc cctccacttt cgccagattt gaatgcctcc tcttccccga ttctggagat   3900
atgcttcaca ctgcctcgcc tctatctccg ctgaattgca gaaatcgaat gagagattgt   3960
tgctttcaat ccttcgaatt catcagtgtt acttcgatct tgagattctg tttgcctctc   4020
tctctcgttc tggtttcact gtagaaaaac tttttttccg cgaacatttt ctttaggccc   4080
aaagtttggg cttttaataa cgcctaaagc ccaaacaaag tttattattg ggtatttgta   4140
tttttttgt ctaattaaga aaataagggg aatctattta tttaattgtt aatcattcac   4200
gttgaccatt gaagaacaag cacaaaatgc tataagcctc ccgagatttg atcctttggg   4260
ttctcgttag agaggtgggc aatgtctcca gctctagtaa tgacaattag tttagtttag   4320
gattcttaca ctagtgtaat agtattatga gagaacactc gtttcagttt attatttaac   4380
aattttctta ggtttctaat ttttttcca gcaacgtttt actgaatttt taaaacttga   4440
tatttgattt tttttaaagt aatttaaatg caaaacaatc caaatgatat tttggaagaa   4500
ctcaagagtt gtgtgatgga ctgatggggg caagaggcaa gtgcactggt gtatccttct   4560
cggggcgtta aaaccgtgga aggtgaccgt ttaatacatg tctatctatt atgaaagcta   4620
```

```
agtacttcat agctatcacg ttgctcctca caaataaact atacgagtag tcagcaaatc   4680
aattttataa agacgcatga gtaacagctg aataaaaaag agaggagaaa acgcatgttg   4740
attgctgacg tgtccgtagg tccatgtatc cccgtatcac tgtcttcctt ctaaccaaaa   4800
aaaacatttc acatcataag tcccctctct ctcgagctcc gtcgctgttt gtttcgacca   4860
aatcgaagct gaggaaaacg acaaaccgcg ccggggccca aaatggtgga cctcaagcct   4920
ggagtgaagc gcctggtgag ctggaaggag atccgcgagc acgcgacgcc cgcgaccgcg   4980
tggatcgtga ttcaccacaa ggtctacgac atctccaagt gggactcgca cccgggtggc   5040
tccgtgatgc tcacgcaggc cggcgaggac gccacggacg ccttcgcggt cttccacccg   5100
tcctcggcgc tcaagctgct cgagcagttc tacgtcggcg acgtggacga aacctccaag   5160
gccgagatcg agggggagcc ggcgagcgac gaggagcgcg cgcgccgcga gcgcatcaac   5220
gagttcatcg cgtcctaccg ccgtctgcgc gtcaaggtca agggcatggg gctctacgac   5280
gccagcgcgc tctactacgc gtggaagctc gtgagcacgt tcggcatcgc ggtgctctcg   5340
atggcgatct gcttcttctt caacagtttc gccatgtaca tggtcgccgg cgtgattatg   5400
gggctcttct accagcagtc cggatggctg gcgcacgact tcttgcacaa ccaggtgtgc   5460
gagaaccgca cgctcggcaa ccttatcggc tgcctcgtgg gcaacgcctg gcagggcttc   5520
agcatgcagt ggtggaagaa caagcacaac ctgcaccacg cggtgccgaa cctgcacagc   5580
gccaaggacg agggcttcat cggcgacccg gacatcgaca ccatgccgct gctggcgtgg   5640
tctaaggaga tggcgcgcaa ggcgttcgag tcggcgcacg gcccgttctt catccgcaac   5700
caggcgttcc tatacttccc gctgctgctg ctcgcgcgcc tgagctggct cgcgcagtcg   5760
ttcttctacg tgttcaccga gttctcgttc ggcatcttcg acaaggtcga gttcgacgga   5820
ccggagaagg cgggtctgat cgtgcactac atctggcagc tcgcgatccc gtacttctgc   5880
aacatgagcc tgtttgaggg cgtggcatac ttcctcatgg gccaggcgtc ctgcggcttg   5940
ctcctggcgc tggtgttcag tattggccac aacggcatgt cggtgtacga gcgcgaaacc   6000
aagccggact tctggcagct gcaggtgacc acgacgcgca acatccgcgc gtcggtattc   6060
atggactggt tcaccggtgg cttgaactac cagatcgacc atcacctgtt cccgctcgtg   6120
ccgcgccaca acttgccaaa ggtcaacgtg ctcatcaagt cgctatgcaa ggagttcgac   6180
atcccgttcc acgagaccgg cttctgggag ggcatctacg aggtcgtgga ccacctggcg   6240
gacatcagca aggaatttat caccgagttc ccagcgatgt aagttaactt aattaataat   6300
tgattgctgc tttaatgaga tatgcgagac gcctatgatc gcatgatatt tgctttcaat   6360
tctgttgtgc acgttgtaaa aaacctgagc atgtgtagct cagatcctta ccgccggttt   6420
cggttcattc taatgaatat atcacccgtt actatcgtat ttttatgaat aatattctcc   6480
gttcaattta ctgattgtgg cgcctactac cggtaattcc cgggattagc ggccgctagt   6540
ctgtgcgcac ttgtatcctg caggtcaatc gtttaaacac tgtacggacc gtggcctaat   6600
aggccggtac cacccagctt tcttgtacaa agtggccatg attacgccaa gctctccacc   6660
gcggtggcgg ccgctctagc ccaagcttta aggatgacct acccattctt gagacaaatg   6720
ttacatttta gtatcagagt aaaatgtgta cctataactc aaattcgatt gacatgtatc   6780
cattcaacat aaaattaaac cagcctgcac ctgcatccac atttcaagta ttttcaaacc   6840
gttcggctcc tatccaccgg gtgtaacaag acggattccg aatttggaag attttgactc   6900
aaattcccaa tttatattga ccgtgactaa atcaacttta acttctataa ttctgattaa   6960
```

-continued

```
gctcccaatt tatattccca acggcactac ctccaaaatt tatagactct catccccttt   7020
taaaccaact tagtaaacgt ttttttttta attttatgaa gttaagtttt taccttgttt   7080
ttaaaaagaa tcgttcataa gatgccatgc cagaacatta gctacacgtt acacatagca   7140
tgcagccgcg gagaattgtt tttcttcgcc acttgtcact cccttcaaac acctaagagc   7200
ttctctctca cagcacacac atacaatcac atgcgtgcat gcattattac acgtgatcgc   7260
catgcaaatc tcctttatag cctataaatt aactcatcgg cttcactctt tactcaaacc   7320
aaaactcatc aatacaaaca agattaaaaa cataaggcgc gccaattgac tagtaggcct   7380
atcgattagg agaataacaa tggtgcgctc ctccaagaac gtcatcaagg agttcatgcg   7440
cttcaaggtg cgcatggagg gcaccgtgaa cggccacgag ttcgagatcg agggcgaggg   7500
cgagggccgc ccctacgagg gccacaacac cgtgaagctg aaggtgacca agggcggccc   7560
cctgcccttc gcctgggaca tcctgtcccc ccagttccag tacggctcca aggtgtacgt   7620
gaagcacccc gccgacatcc ccgactacaa gaagctgtcc ttccccgagg gcttcaagtg   7680
ggagcgcgtg atgaacttcg aggacggcgg cgtggtgacc gtgacccagg actcctccct   7740
gcaggacggc tgcttcatct acaaggtgaa gttcatcggc gtgaacttcc cctccgacgg   7800
ccccgtaatg cagaagaaga ccatgggctg ggaggcctcc accgagcgcc tgtacccccg   7860
cgacggcgtg ctgaagggcg agatccacaa ggccctgaag ctgaaggacg gcggccacta   7920
cctggtggag ttcaagtcca tctacatggc caagaagccc gtgcagctgc ccggctacta   7980
ctacgtggac tccaagctgg acatcacctc ccacaacgag gactacacca tcgtggagca   8040
gtacgagcgc accgagggcc gccaccacct gttcctgctc gagtctagag gtaccggttg   8100
ttaacgttag ccggctacgt atactccgga atattaatag gcctaggatg catatggcgg   8160
ccgcctgcag ctggcgccat cgattaatta aggccgcctc gagcatgcat ctagagggcc   8220
cgctagcgtt aaccctgctt taatgagata tgcgagacgc ctatgatcgc atgatatttg   8280
ctttcaattc tgttgtgcac gttgtaaaaa acctgagcat gtgtagctca gatccttacc   8340
gccggtttcg gttcattcta atgaatatat cacccgttac tatcgtattt ttatgaataa   8400
tattctccgt tcaatttact gattgtccgt cgagcatatg ctagaggatc cccgggtacc   8460
caactttatt atacatagtt gataattcac tggccggatg taccgaattc gcggccgcaa   8520
gcttgtacac tagtacgcgt caattggcga tcgcggatct gagatgaaac cggtgattat   8580
cagaaccttt tatggtcttt gtatgcatat ggtaaaaaaa cttagtttgc aatttcctgt   8640
ttgttttggt aatttgagtt tcttttagtt gttgatctgc ctgctttttg gtttacgtca   8700
gactactact gctgttgttg tttggtttcc tttctttcat tttataaata aataatccgg   8760
ttcggtttac tccttgtgac tggctcagtt tggttattgc gaaatgcgaa tggtaaattg   8820
agtaattgaa attcgttatt agggttctaa gctgttttaa cagtcactgg gttaatatct   8880
ctcgaatctt gcatggaaaa tgctcttacc attggttttt aattgaaatg tgctcatatg   8940
ggccgtggtt tccaaattaa ataaaactac gatgtcatcg agaagtaaaa tcaactgtgt   9000
ccacattatc agttttgtgt atacgatgaa atagggtaat tcaaaatcta gcttgatatg   9060
ccttttggtt cattttaacc ttctgtaaac atttttttcag attttgaaca agtaaatcca   9120
aaaaaaaaaa aaaaaaatct caactcaaca ctaaattatt ttaatgtata aaagatgctt   9180
aaaacatttg gcttaaaaga aagaagctaa aaacatagag aactcttgta aattgaagta   9240
tgaaaatata ctgaattggg tattatatga atttttctga tttaggattc acatgatcca   9300
aaaaggaaat ccagaagcac taatcagaca ttggaagtag gaatatttca aaaagttttt   9360
```

-continued

```
tttttttaag taagtgacaa aagcttttaa aaaatagaaa agaaactagt attaaagttg   9420
taaatttaat aaacaaaaga aattttttat attttttcat ttctttttcc agcatgaggt   9480
tatgatggca ggatgtggat ttcatttttt tccttttgat agccttttaa ttgatctatt   9540
ataattgacg aaaaaatatt agttaattat agatatattt taggtagtat tagcaattta   9600
cacttccaaa agactatgta agttgtaaat atgatgcgtt gatctcttca tcattcaatg   9660
gttagtcaaa aaaataaaag cttaactagt aaactaaagt agtcaaaaat tgtactttag   9720
tttaaaatat tacatgaata atccaaaacg acatttatgt gaaacaaaaa caatatagat   9780
ccattaccct gttatcccta gaggggaaaa ttcgaatcca aaaattacgg atatgaatat   9840
aggcatatcc gtatccgaat tatccgtttg acagctagca acgattgtac aattgcttct   9900
ttaaaaaagg aagaaagaaa gaaagaaaag aatcaacatc agcgttaaca aacggccccg   9960
ttacggccca aacggtcata tagagtaacg gcgttaagcg ttgaaagact cctatcgaaa  10020
tacgtaaccg caaacgtgtc atagtcagat cccctcttcc ttcaccgcct caaacacaaa  10080
aataatcttc tacagcctat atatacaacc ccccttcta tctctccttt ctcacaattc  10140
atcatctttc tttctctacc cccaatttta agaaatcctc tcttctcctc ttcattttca  10200
aggtaaatct ctctctctct ctctctctct gttattcctt gttttaatta ggtatgtatt  10260
attgctagtt tgttaatctg cttatcttat gtatgcctta tgtgaatatc tttatcttgt  10320
tcatctcatc cgtttagaag ctataaattt gttgatttga ctgtgtatct acacgtggtt  10380
atgtttatat ctaatcagat atgaatttct tcatattgtt gcgtttgtgt gtaccaatcc  10440
gaaatcgttg attttttca tttaatcgtg tagctaattg tacgtataca tatggatcta  10500
cgtatcaatt gttcatctgt ttgtgtttgt atgtatacag atctgaaaac atcacttctc  10560
tcatctgatt gtgttgttac atacatagat atagatctgt tatatcattt tttttattaa  10620
ttgtgtatat atatatgtgc atagatctgg attacatgat tgtgattatt tacatgattt  10680
tgttatttac gtatgtatat atgtagatct ggactttttg gagttgttga cttgattgta  10740
tttgtgtgtg tatatgtgtg ttctgatctt gatatgttat gtatgtgcag ctgaaccatg  10800
gcggcggcaa caacaacaac aacaacatct tcttcgatct ccttctccac caaaccatct  10860
ccttcctcct ccaaatcacc attaccaatc tccagattct ccctcccatt ctccctaaac  10920
cccaacaaat catcctcctc ctcccgccgc cgcggtatca aatccagctc tccctcctcc  10980
atctccgccg tgctcaacac aaccaccaat gtcacaacca ctccctctcc aaccaaacct  11040
accaaacccg aaacattcat ctcccgattc gctccagatc aaccccgcaa aggcgctgat  11100
atcctcgtcg aagctttaga acgtcaaggc gtagaaaccg tattcgctta ccctggaggt  11160
acatcaatgg agattcacca agccttaacc cgctcttcct caatccgtaa cgtccttcct  11220
cgtcacgaac aaggaggtgt attcgcagca gaaggatacg ctcgatcctc aggtaaacca  11280
ggtatctgta tagccacttc aggtcccgga gctacaaatc tcgttagcgg attagccgat  11340
gcgttgttag atagtgttcc tcttgtagca atcacaggac aagtccctcg tcgtatgatt  11400
ggtacagatg cgtttcaaga gactccgatt gttgaggtaa cgcgttcgat tacgaagcat  11460
aactatcttg tgatggatgt tgaagatatc cctaggatta ttgaggaagc tttcttttta  11520
gctacttctg gtagacctgg acctgttttg gttgatgttc ctaaagatat tcaacaacag  11580
cttgcgattc ctaattggga acaggctatg agattacctg gttatatgtc taggatgcct  11640
aaacctccgg aagattctca tttggagcag attgttaggt tgatttctga gtctaagaag  11700
```

-continued

```
cctgtgttgt atgttggtgg tggttgtttg aattctagcg atgaattggg taggtttgtt  11760
gagcttacgg ggatccctgt tgcgagtacg ttgatggggc tgggatctta tccttgtgat  11820
gatgagttgt cgttacatat gcttggaatg catgggactg tgtatgcaaa ttacgctgtg  11880
gagcatagtg atttgttgtt ggcgtttggg gtaaggtttg atgatcgtgt cacgggtaag  11940
cttgaggctt ttgctagtag ggctaagatt gttcatattg atattgactc ggctgagatt  12000
gggaagaata agactcctca tgtgtctgtg tgtggtgatg ttaagctggc tttgcaaggg  12060
atgaataagg ttcttgagaa ccgagcggag gagcttaagc ttgattttgg agtttggagg  12120
aatgagttga acgtacagaa acagaagttt ccgttgagct ttaagacgtt tggggaagct  12180
attcctccac agtatgcgat taaggtcctt gatgagttga ctgatggaaa agccataata  12240
agtactggtg tcgggcaaca tcaaatgtgg gcggcgcagt tctacaatta caagaaacca  12300
aggcagtggc tatcatcagg aggccttgga gctatgggat ttggacttcc tgctgcgatt  12360
ggagcgtctg ttgctaaccc tgatgcgata gttgtggata ttgacggaga tggaagcttt  12420
ataatgaatg tgcaagagct agccactatt cgtgtagaga atcttccagt gaaggtactt  12480
ttattaaaca accagcatct tggcatggtt atgcaatggg aagatcggtt ctacaaagct  12540
aaccgagctc acacatttct cggggatccg gctcaggagg acgagatatt cccgaacatg  12600
ttgctgtttg cagcagcttg cgggattcca gcggcgaggg tgacaaagaa agcagatctc  12660
cgagaagcta ttcagacaat gctggataca ccaggacctt acctgttgga tgtgatttgt  12720
ccgcaccaag aacatgtgtt gccgatgatc ccgaatggtg gcactttcaa cgatgtcata  12780
acggaaggag atggccggat taaatactga tagggataac agggtaatct cgacgagatg  12840
aaaccggtga ttatcagaac cttttatggt ctttgtatgc atatggtaaa aaaacttagt  12900
ttgcaatttc ctgtttgttt tggtaatttg agtttctttt agttgttgat ctgcctgctt  12960
tttggtttac gtcagactac tactgctgtt gttgtttggt ttcctttctt tcattttata  13020
aataaataat ccggttcggt ttactccttg tgactggctc agtttggtta ttgcgaaatg  13080
cgaatggtaa attgagtaat tgaaattcgt tattagggtt ctaagctgtt ttaacagtca  13140
ctgggttaat atctctcgaa tcttgcatgg aaaatgctct taccattggt ttttaattga  13200
aatgtgctca tatgggccgt ggtttccaaa ttaaataaaa ctacgatgtc atcgagaagt  13260
aaaatcaact gtgtccacat tatcagtttt gtgtatacga tgaaataggg taattcaaaa  13320
tctagcttga tatgcctttt ggttcatttt aaccttctgt aaacattttt tcagattttg  13380
aacaagtaaa tccaaaaaaa aaaaaaaaaa atctcaactc aacactaaat tattttaatg  13440
tataaaagat gcttaaaaca tttggcttaa aagaaagaag ctaaaaacat agagaactct  13500
tgtaaattga agtatgaaaa tatactgaat tgggtattat atgaattttt ctgatttagg  13560
attcacatga tccaaaaagg aaatccagaa gcactaatca gacattggaa gtaggaatat  13620
ttcaaaaagt tttttttttt taagtaagtg acaaaagctt ttaaaaaata gaaaagaaac  13680
tagtattaaa gttgtaaatt taataaacaa aagaaatttt ttatattttt tcatttcttt  13740
ttccagcatg aggttatgat ggcaggatgt ggatttcatt tttttccttt tgatagcctt  13800
ttaattgatc tattataatt gacgaaaaaa tattagttaa ttatagatat attttaggta  13860
gtattagcaa tttacacttc caaaagacta tgtaagttgt aaatatgatg cgttgatctc  13920
ttcatcattc aatggttagt caaaaaaata aaagcttaac tagtaaacta aagtagtcaa  13980
aaattgtact ttagtttaaa atattacatg aataatccaa aacgacattt atgtgaaaca  14040
aaaacaatat gtcgaggcga tcgcagtact taatcagtga tcagtaacta aattcagtac  14100
```

attaaagacg tccgcaatgt gttattaagt tgtctaagcg tcaatttgtt tacaccacaa 14160
tatatcctgc caccagccag ccaacagctc cccgaccggc agctcggcac aaaatcactg 14220
atcatctaaa aaggtgatgt gtatttgagt aaaacagctt gcgtcatgcg gtcgctgcgt 14280
atatgatgcg atgagtaaat aaacaaatac gcaaggggaa cgcatgaagg ttatcgctgt 14340
acttaaccag aaaggcgggt caggcaagac gaccatcgca acccatctag cccgcgccct 14400
gcaactcgcc ggggccgatg ttctgttagt cgattccgat ccccagggca gtgcccgcga 14460
ttgggcggcc gtgcgggaag atcaaccgct aaccgttgtc ggcatcgacc gcccgacgat 14520
tgaccgcgac gtgaaggcca tcggccggcg cgacttcgta gtgatcgacg gagcgcccca 14580
ggcggcggac ttggctgtgt ccgcgatcaa ggcagccgac ttcgtgctga ttccggtgca 14640
gccaagccct tacgacattt gggccaccgc cgacctggtg gagctggtta agcagcgcat 14700
tgaggtcacg gatggaaggc tacaagcggc ctttgtcgtg tcgcgggcga tcaaaggcac 14760
gcgcatcggc ggtgaggttg ccgaggcgct ggccgggtac gagctgccca ttcttgagtc 14820
ccgtatcacg cagcgcgtga gctacccagg cactgccgcc gccggcacaa ccgttcttga 14880
atcagaaccc gagggcgacg ctgcccgcga ggtccaggcg ctggccgctg aaattaaatc 14940
aaaactcatt tgagttaatg aggtaaagag aaaatgagca aaagcacaaa cacgctaagt 15000
gccggccgtc cgagcgcacg cagcagcaag gctgcaacgt tggccagcct ggcagacacg 15060
ccagccatga agcgggtcaa ctttcagttg ccggcggagg atcacaccaa gctgaagatg 15120
tacgcggtac gccaaggcaa gaccattacc gagctgctat ctgaatacat cgcgcagcta 15180
ccagagtaaa tgagcaaatg aataaatgag tagatgaatt ttagcggcta aaggaggcgg 15240
catggaaaat caagaacaac caggcaccga cgccgtggaa tgccccatgt gtggaggaac 15300
gggcggttgg ccaggcgtaa gcggctgggt tgtctgccgg ccctgcaatg gcactggaac 15360
ccccaagccc gaggaatcgg cgtgagcggt cgcaaaccat ccggcccggt acaaatcggc 15420
gcggcgctgg gtgatgacct ggtggagaag ttgaaggccg cgcaggccgc ccagcggcaa 15480
cgcatcgagg cagaagcacg ccccggtgaa tcgtggcaag gggccgctga tcgaatccgc 15540
aaagaatccc ggcaaccgcc ggcagccggt gcgccgtcga ttaggaagcc gcccaagggc 15600
gacgagcaac cagatttttt cgttccgatg ctctatgacg tgggcacccg cgatagtcgc 15660
agcatcatgg acgtggccgt tttccgtctg tcgaagcgtg accgacgagc tggcgaggtg 15720
atccgctacg agcttccaga cgggcacgta gaggtttccg caggccccgc cggcatggcc 15780
agtgtgtggg attacgacct ggtactgatg gcggtttccc atctaaccga atccatgaac 15840
cgataccggg aagggaaggg agacaagccc ggccgcgtgt tccgtccaca cgttgcggac 15900
gtactcaagt tctgccggcg agccgatggc ggaaagcaga aagacgacct ggtagaaacc 15960
tgcattcggt taaacaccac gcacgttgcc atgcagcgta ccaagaaggc caagaacggc 16020
cgcctggtga cggtatccga gggtgaagcc ttgattagcc gctacaagat cgtaaagagc 16080
gaaaccgggc ggccggagta catcgagatc gagcttgctg attggatgta ccgcgagatc 16140
acagaaggca agaacccgga cgtgctgacg gttcaccccg attacttttt gatcgacccc 16200
ggcatcggcc gttttctcta ccgcctggca cgccgcgccg caggcaaggc agaagccaga 16260
tggttgttca agacgatcta cgaacgcagt ggcagcgccg gagagttcaa gaagttctgt 16320
ttcaccgtgc gcaagctgat cgggtcaaat gacctgccgg agtacgattt gaaggaggag 16380
gcggggcagg ctggcccgat cctagtcatg cgctaccgca acctgatcga gggcgaagca 16440

-continued

```
tccgccggtt cc                                                     16452

<210> SEQ ID NO 94
<211> LENGTH: 15461
<212> TYPE: DNA
<213> ORGANISM: Artificial sequence
<220> FEATURE:
<223> OTHER INFORMATION: Plasmid

<400> SEQUENCE: 94

ctatacaaag ttgatagctt ggcgtaatcg atgtaccgat atcaatttaa attggccggc     60
cgagctccct gcagggggcc cggcgcgcct ctagattaat taaaggcctt agttactaat    120
cagtgatcag attgtcgttt cccgccttca gtttaaacta tcagtgtttg acaggatata    180
ttggcgggta aacctaagag aaaagagcgt ttattagaat aatcggatat ttaaaagggc    240
gtgaaaaggt ttatccgttc gtccatttgt atgtcaatat ccatgataag tcgcgctgta    300
tgtgtttgtt tgaatattca tggaacgcag tggcggtttt catggcttgt tatgactgtt    360
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
```

ttcctggcct tttgctggcc ttttgctcac atgttctttc ctgcgttatc ccctgattct 2100
gtggataacc gtattaccgc ctttgagtga gctgataccg ctcgccgcag ccgaacgacc 2160
gagcgcagcg agtcagtgag cgaggaagcg gaagagcgcc tgatgcggta ttttctcctt 2220
acgcatctgt gcggtatttc acaccgcata ggccgcgata ggccgacgcg aagcggcggg 2280
gcgtagggag cgcagcgacc gaagggtagg cgctttttgc agctcttcgg ctgtgcgctg 2340
gccagacagt tatgcacagg ccaggcgggt tttaagagtt ttaataagtt ttaaagagtt 2400
ttaggcggaa aaatcgcctt ttttctcttt tatatcagtc acttacatgt gtgaccggtt 2460
cccaatgtac ggctttgggt tcccaatgta cgggttccgg ttcccaatgt acggctttgg 2520
gttcccaatg tacgtgctat ccacaggaaa gagacctttt cgaccttttt cccctgctag 2580
ggcaatttgc cctagcatct gctccgtaca ttaggaaccg gcggatgctt cgccctcgat 2640
caggttgcgg tagcgcatga ctaggatcgg gccagcctgc cccgcctcct ccttcaaatc 2700
gtactccggc aggtcatttg acccgatcag cttgcgcacg gtgaaacaga acttcttgaa 2760
ctctccggcg ctgccactgc gttcgtagat cgtcttgaac aaccatctgg cttctgcctt 2820
gcctgcggcg cggcgtgcca ggcggtagag aaaacggccg atgccggggt cgatcaaaaa 2880
gtaatcgggg tgaaccgtca gcacgtccgg gttcttgcct tctgtgatct cgcggtacat 2940
ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380

-continued

```
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cgggcggtcg   4560
atgccgacaa cggttagcgg ttgatcttcc cgcacggccg cccaatcgcg ggcactgccc   4620
tggggatcgg aatcgactaa cagaacatcg gccccggcga gttgcagggc gcgggctaga   4680
tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc acctttttag atgatcagtg attttgtgcc   4860
gagctgccgg tcggggagct gttggctggc tggtggcagg atatattgtg gtgtaaacaa   4920
attgacgctt agacaactta ataacacatt gcggacgtct ttaatgtact gaatttagtt   4980
actgatcact gattaagtac tgcgatcgcc tcgacatatt gtttttgttt cacataaatg   5040
tcgttttgga ttattcatgt aatattttaa actaaagtac aatttttgac tactttagtt   5100
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatatttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg atttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gttttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
```

-continued gtagaactgc gccgcccaca tttgatgttg cccgacacca gtacttatta tggcttttcc 6840
atcagtcaac tcatcaagga ccttaatcgc atactgtgga ggaatagctt ccccaaacgt 6900
cttaaagctc aacggaaact tctgtttctg tacgttcaac tcattcctcc aaactccaaa 6960
atcaagctta agctcctccg ctcggttctc aagaacctta ttcatccctt gcaaagccag 7020
cttaacatca ccacacacag acacatgagg agtcttattc ttcccaatct cagccgagtc 7080
aatatcaata tgaacaatct tagccctact agcaaaagcc tcaagcttac ccgtgacacg 7140
atcatcaaac cttaccccaa acgccaacaa caaatcacta tgctccacag cgtaatttgc 7200
atacacagtc ccatgcattc caagcatatg taacgacaac tcatcatcac aaggataaga 7260
tcccagcccc atcaacgtac tcgcaacagg gatccccgta agctcaacaa acctacccaa 7320
ttcatcgcta gaattcaaac aaccaccacc aacatacaac acaggcttct tagactcaga 7380
aatcaaccta acaatctgct ccaaatgaga atcttccgga ggtttaggca tcctagacat 7440
ataaccaggt aatctcatag cctgttccca attaggaatc gcaagctgtt gttgaatatc 7500
tttaggaaca tcaaccaaaa caggtccagg tctaccagaa gtagctaaaa agaaagcttc 7560
ctcaataatc ctagggatat cttcaacatc catcacaaga tagttatgct tcgtaatcga 7620
acgcgttacc tcaacaatcg gagtctcttg aaacgcatct gtaccaatca tacgacgagg 7680
gacttgtcct gtgattgcta caagaggaac actatctaac aacgcatcgg ctaatccgct 7740
aacgagattt gtagctccgg gacctgaagt ggctatacag atacctggtt tacctgagga 7800
tcgagcgtat ccttctgctg cgaatacacc tccttgttcg tgacgaggaa ggacgttacg 7860
gattgaggaa gagcgggtta aggcttggtg aatctccatt gatgtacctc cagggtaagc 7920
gaatacggtt tctacgcctt gacgttctaa agcttcgacg aggatatcag cgcctttgcg 7980
gggttgatct ggagcgaatc gggagatgaa tgtttcgggt ttggtaggtt tggttggaga 8040
gggagtggtt gtgacattgg tggttgtgtt gagcacggcg gagatggagg agggagagct 8100
ggatttgata ccgcggcggc gggaggagga ggatgatttg ttggggttta gggagaatgg 8160
gagggagaat ctggagattg gtaatggtga tttggaggag gaaggagatg gtttggtgga 8220
gaaggagatc gaagaagatg ttgttgttgt tgttgttgcc gccgccatgg ttcagctgca 8280
catacataac atatcaagat cagaacacac atatacacac acaaatacaa tcaagtcaac 8340
aactccaaaa agtccagatc tacatatata catacgtaaa taacaaaatc atgtaaataa 8400
tcacaatcat gtaatccaga tctatgcaca tatatatata cacaattaat aaaaaaaatg 8460
atataacaga tctatatcta tgtatgtaac aacacaatca gatgagagaa gtgatgtttt 8520
cagatctgta tacatacaaa cacaaacaga tgaacaattg atacgtagat ccatatgtat 8580
acgtacaatt agctacacga ttaaatgaaa aaaatcaacg atttcggatt ggtacacaca 8640
aacgcaacaa tatgaagaaa ttcatatctg attagatata aacataacca cgtgtagata 8700
cacagtcaaa tcaacaaatt tatagcttct aaacggatga gatgaacaag ataaagatat 8760
tcacataagg catacataag ataagcagat taacaaacta gcaataatac atacctaatt 8820
aaaacaagga ataacagaga gagagagaga gagagagatt taccttgaaa atgaagagga 8880
gaagagagga tttcttaaaa ttgggggtag agaaagaaag atgatgaatt gtgagaaagg 8940
agagatagaa ggggggggttg tatatatagg ctgtagaaga ttatttttgt gtttgaggcg 9000
gtgaaggaag aggggatctg actatgacac gtttgcggtt acgtatttcg ataggagtct 9060
ttcaacgctt aacgccgtta ctctatatga ccgtttgggc cgtaacgggg ccgtttgtta 9120

-continued

```
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct atttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
```

accttcagct tcacggtgtt gtggccctcg taggggcggc cctcgccctc gccctcgatc 11580
tcgaactcgt ggccgttcac ggtgccctcc atgcgcacct tgaagcgcat gaactccttg 11640
atgacgttct tggaggagcg caccattgtt attctcctaa tcgataggcc tactagtcaa 11700
ttggcgcgcc ttatgttttt aatcttgttt gtattgatga gttttggttt gagtaaagag 11760
tgaagccgat gagttaattt ataggctata aaggagattt gcatggcgat cacgtgtaat 11820
aatgcatgca cgcatgtgat tgtatgtgtg tgctgtgaga gagaagctct taggtgtttg 11880
aagggagtga caagtggcga agaaaaacaa ttctccgcgg ctgcatgcta tgtgtaacgt 11940
gtagctaatg ttctggcatg gcatcttatg aacgattctt tttaaaaaca aggtaaaaac 12000
ttaacttcat aaaattaaaa aaaaaacgtt tactaagttg gtttaaaagg ggatgagagt 12060
ctataaattt tggaggtagt gccgttggga atataaattg ggagcttaat cagaattata 12120
gaagttaaag ttgatttagt cacggtcaat ataaattggg aatttgagtc aaaatcttcc 12180
aaattcggaa tccgtcttgt tacacccggt ggataggagc cgaacggttt gaaaatactt 12240
gaaatgtgga tgcaggtgca ggctggttta attttatgtt gaatggatac atgtcaatcg 12300
aatttgagtt ataggtacac attttactct gatactaaaa tgtaacattt gtctcaagaa 12360
tgggtaggtc atccttaaag cttgggctag agcggccgcc accgcggtgg agagcttggc 12420
gtaatcatgg ccactttgta caagaaagct gggtggtacc ggcctattag gccacggtcc 12480
gtacagtgtt taaacgattg acctgcagga tacaagtgcg cacagactag cggccgctaa 12540
tcccgggaat taccggtagt aggcgccaca atcagtaaat tgaacggaga atattattca 12600
taaaaatacg atagtaacgg gtgatatatt cattagaatg aaccgaaacc ggcggtaagg 12660
atctgagcta cacatgctca ggttttttac aacgtgcaca acagaattga aagcaaatat 12720
catgcgatca taggcgtctc gcatatctca ttaaagcagc aatcaattat taattaagtt 12780
aacttacatc gctgggaact cggtgataaa ttccttgctg atgtccgcca ggtggtccac 12840
gacctcgtag atgccctccc agaagccggt ctcgtggaac gggatgtcga actccttgca 12900
tagcgacttg atgagcacgt tgacctttgg caagttgtgg cgcggcacga gcgggaacag 12960
gtgatggtcg atctggtagt tcaagccacc ggtgaaccag tccatgaata ccgacgcgcg 13020
gatgttgcgc gtcgtggtca cctgcagctg ccagaagtcc ggcttggttt cgcgctcgta 13080
caccgacatg ccgttgtggc caatactgaa caccagcgcc aggagcaagc cgcaggacgc 13140
ctggcccatg aggaagtatg ccacgccctc aaacaggctc atgttgcaga agtacgggat 13200
cgcgagctgc cagatgtagt gcacgatcag acccgccttc tccggtccgt cgaactcgac 13260
cttgtcgaag atgccgaacg agaactcggt gaacacgtag aagaacgact gcgcgagcca 13320
gctcaggcgc gcgagcagca gcagcgggaa gtataggaac gcctggttgc ggatgaagaa 13380
cgggccgtgc gccgactcga acgccttgcg cgccatctcc ttagaccacg ccagcagcgg 13440
catggtgtcg atgtccgggt cgccgatgaa gccctcgtcc ttggcgctgt gcaggttcgg 13500
caccgcgtgg tgcaggttgt gcttgttctt ccaccactgc atgctgaagc cctgccaggc 13560
gttgcccacg aggcagccga taaggttgcc gagcgtgcgg ttctcgcaca cctggttgtg 13620
caagaagtcg tgcgccagcc atccggactg ctggtagaag agccccataa tcacgccggc 13680
gaccatgtac atggcgaaac tgttgaagaa gaagcagatc gccatcgaga gcaccgcgat 13740
gccgaacgtg ctcacgagct tccacgcgta gtagagcgcg ctggcgtcgt agagccccat 13800
gcccttgacc ttgacgcgca gacggcggta ggacgcgatg aactcgttga tgcgctcgcg 13860

-continued

```
gcgcgcgcgc tcctcgtcgc tcgccggctc cccctcgatc tcggccttgg aggtttcgtc  13920
cacgtcgccg acgtagaact gctcgagcag cttgagcgcc gaggacgggt ggaagaccgc  13980
gaaggcgtcc gtggcgtcct cgccggcctg cgtgagcatc acggagccac ccgggtgcga  14040
gtcccacttg gagatgtcgt agaccttgtg gtgaatcacg atccacgcgg tcgcgggcgt  14100
cgcgtgctcg cggatctcct tccagctcac caggcgcttc actccaggct tgaggtccac  14160
cattttgggc cccggcgcgg tttctctgct tcttggtgtc actagccttg catgcgaatc  14220
agtagctcaa cgaagcttga gcccaaatgc gaagaaagaa gactgcgaat ttgagtgaag  14280
acaaattagc aaacgcagtg ctcgaaacgt ggctaccgtt tacgtaataa gcgtgttggc  14340
ggctaacttc agtgttttgt taacctgacc ggttggaccg gttggaccgg ttaaatagag  14400
taacttcaag gctccacaac caaaccaatg tgaaacgtaa cacctgttta gtctgttctt  14460
cgttttttc tcgtttgtct caacttttaa caacctgata acaatcaaat tacaattcgt  14520
ccttatcgta agcgacgatt ctctcacgag cataaccgtc attttacgac gttcattcaa  14580
accttaatct cttgtacaat actctgtgat taagaagaca aacacaatca ttctacttat  14640
atttattaaa gcaaaccctc tcagcagctc agagtgtttg ataaatcttc gtccaagtca  14700
acataagcaa ctctgtttct ccttttaccc gatggctaat attgtttgat caaactaatt  14760
gcacgttgca gattaatcag aagaaaatgg ataagattga tacagtgaac gatggatttt  14820
acataaatct catgaagcac acttgtaaga gaagagttaa acgtagcagc tgagtaataa  14880
catttattac atccaacatt tcaacacctt cgacatgatc taagaacaaa gaaaagaaag  14940
caaaaaaaac atagccttca aaagcctaac atcccaaaac aaaaaaaaag ttagatctta  15000
ctttctcaaa gacaatgata gtttgacaaa actttctcc tctcttttat tactcttttg  15060
cctctctaag agcattgctt gtgttggtag ttcccaaacc ggttccaaca atgtcattca  15120
caccaggttt cgatctataa ggaacagata cacatagtca aaagcacaac tacaaagtgt  15180
gactatacgt ttttgcatct ggccggccta gtagatttaa attggcctta gtggccaagc  15240
ttggcgtaat catggagcct gcttttttgt acaaacttgg gtaccggcct attaggccac  15300
ggtccgtaca gtgtttaaac gattgacctg caggatacaa gtgcgcacag actagcggcc  15360
gctaatcccg ggaattaccg gtagtaggcg cctactttgg ccggcctagt agatttaaat  15420
tggccttagt ggccaagctt ggcgtaatca tggcaacttt t                       15461
```

<210> SEQ ID NO 95
<211> LENGTH: 1428
<212> TYPE: DNA
<213> ORGANISM: Brassica napus

<400> SEQUENCE: 95

```
tgcgagagag aagaaatgaa ataagtctgg aaaaaggtaa gaagaataaa actgaagcgt    60
gtcaattgcc acataaaaca ttaaatgcac ataaaataat ttgtgagttg atcgaactct   120
caacactgga accagacggg acacttttac caacgaagct accagaaaaa aatctaactg   180
acaaaagtta tataagtagt cgggggcatg cgcctcccct cgggacaaag ccaggttacc   240
cattatgggg gcctgtgccc ccgcaatatt aattgataat gtaattttcg tgtaaataag   300
catctgtatc aaccaaggtt cgattctact ttttgacatg tttctatttt attataaaga   360
gtgcacccag taattatata tcctggattc tcccctggcc ccccgtagct tacattgtag   420
atccgtccct ggttttatct attacatcat atattatcat atattatgaa atagagagag   480
agtaactgtt gtggcgaatc ttgtacaaaa aaaactgttg tggcgattta aacattcaga   540
```

aaactccggt aagaagttac attgtaattt tgtgcatgcg attgcatgcc cattttgtca 600
ataatataca cgcgtttgca gtaatcaacg tgagaatatt atagatgcac gcgtatgcat 660
ggatcagcaa ctgtatttta cgtgtgtatt aactgtgtgc atgatggcat tcatttttat 720
ttaataaatt aaatagataa caattatttt ccaataaata gcaacaattg gaaaacttat 780
ttagcaaaaa aaaaaacaat tggaaaactt tttttgtgta aaaaatagta tattatcata 840
tgatctctct ctttttcatg catgcattcg cgtgtatata gacacgaata tacatgcagt 900
ttcctgcttt aaaaatatta caatatattt caaaaaaaaa acgtaacaac atgtatgatg 960
taataatttc ataaatatat tagcattgac agaagcacct attgatgaag cggaaggttt 1020
atatgataga attagatatc cgttgattct aagaatacac ggaaaactat aataatataa 1080
agattttatt tagtctaaga atgcataaga tcaatatctt ctttaaattc gttgagatca 1140
ccaatgatct accgaaaaca agtaacatag aaaaaactct taacttttat taattaatca 1200
aaaacttgga tacaactcta ggcataagaa acctatatat gtgaaaacat aataactatg 1260
aaaaccctaa tcctaattaa aatagaaaaa actattaaaa taaagctaat acaaataaat 1320
ggtaattatc ctaattctaa gctgcatcac ctatccctcc tatcaactat ataagtctca 1380
cacgtctttg tactctacac ttcccattca tatatacaat ctcaaaag 1428

<210> SEQ ID NO 96
<211> LENGTH: 483
<212> TYPE: DNA
<213> ORGANISM: Brassica napus

<400> SEQUENCE: 96
atttctctaa ctaagaaact ttgtagctct aagtttgttt tattatcaac caacaataat 60
aagaaaggta tgtgtttgtg tttcaaataa atgaacaaaa ccttatctct cttcttgcat 120
aagcactgca actcaaaatc cttactggac atttggttat aaactgacta tttcaggacc 180
atattagtgt tttatctctt caccataaaa gcaaacactt caacacaaac gttgaggcaa 240
ttaaggaagc atgattttta ttttatttta cccatgaatt ggagttggtc atctgactca 300
ttatctttgc agaaaaagag catccgtaga atacgtttag tacattttta ttcagttggg 360
ttcaaattta aaacattggg aatggatgac attctataga attacgaatt tacgatttag 420
atattaatta ccacccctaa aagattaatc tagtaggtga tggacattag accatcttta 480
tcg 483

<210> SEQ ID NO 97
<211> LENGTH: 15869
<212> TYPE: DNA
<213> ORGANISM: Artificial sequence
<220> FEATURE:
<223> OTHER INFORMATION: Plasmid

<400> SEQUENCE: 97
cgtcggcttg aacgaatttc tagctagaca ttatttgcca acgaccttcg tgatctcgcc 60
cttgacatag tggacaaatt cttcgagctg gtcggcccgg gacgcgagac ggtcttcttc 120
ttggcccaga taggcttggc gcgcttcgag gatcacgggc tggtattgcg ccggaaggcg 180
ctccatcgcc cagtcggcgg cgacatcctt cggcgcgatc ttgccggtaa ccgccgagta 240
ccaaatccgg ctcagcgtaa ggaccacatt gcgctcatcg cccgcccaat ccggcgggga 300
gttccacagg gtcagcgtct cgttcagtgc ttcgaacaga tcctgttccg gcaccgggtc 360

-continued

```
gaaaagttcc tcggccgcgg ggccgacgag ggccacgcta tgctcccggg ccttggtgag    420
caggatcgcc agatcaatgt cgatggtggc cggttcaaag atacccgcca gaatatcatt    480
acgctgccat tcgccgaact ggagttcgcg tttggccgga tagcgccagg ggatgatgtc    540
atcgtgcacc acaatcgtca cctcaaccgc gcgcaggatt tcgctctcgc cgggggaggc    600
ggacgtttcc agaaggtcgt tgataagcgc gcggcgcgtg gtctcgtcga gacggacggt    660
aacggtgaca agcaggtcga tgtccgaatg gggcttaagg ccgccgtcaa cggcgctacc    720
atacagatgc acggcgagga gggtcggttc gaggtggcgc tcgatgacac ccacgacttc    780
cgacagctgg gtggacacct cggcgatgac cgcttcaccc atgatgttta actttgtttt    840
agggcgactg ccctgctgcg taacatcgtt gctgctccat aacatcaaac atcgacccac    900
ggcgtaacgc gcttgctgct tggatgcccg aggcatagac tgtaccccaa aaaaacagtc    960
ataacaagcc atgaaaaccg ccactgcgtt ccatgaatat tcaaacaaac acatacagcg   1020
cgacttatca tggatattga catacaaatg gacgaacgga taaacctttt cacgcccttt   1080
taaatatccg attattctaa taaacgctct tttctcttag gtttacccgc caatatatcc   1140
tgtcaaacac tgatagttta aactgaaggc gggaaacgac aatctgatca ctgattagta   1200
actaaggcct ttaattaatc tagaggcgcg ccgggccccc tgcagggagc tcggccggcc   1260
aatttaaatt gatatcggta catcgattac gccaagctat caactttgta tagaaaagtt   1320
gccatgatta cgccaagctt ggccactaag gccaatttaa atctactagg ccggccaaag   1380
taggcgccta ctaccggtaa ttcccgggat tagcggccgc tagtctgtgc gcacttgtat   1440
cctgcaggtc aatcgtttaa acactgtacg gaccgtggcc taataggccg gtacccaagt   1500
ttgtacaaaa aagcaggctc catgattacg ccaagcttgg ccactaaggc caatttaaat   1560
ctactaggcc ggcctgcgag agagaagaaa tgaaataagt ctggaaaaag gtaagaagaa   1620
taaaactgaa gcgtgtcaat tgccacataa aacattaaat gcacataaaa taatttgtga   1680
gttgatcgaa ctctcaacac tggaaccaga cgggacactt ttaccaacga agctaccaga   1740
aaaaaatcta actgacaaaa gttatataag tagtcggggg catgcgcctc ccctcgggac   1800
aaagccaggt tacccattat gggggcctgt gcccccgcaa tattaattga taatgtaatt   1860
ttcgtgtaaa taagcatctg tatcaaccaa ggttcgattc tactttttga catgtttcta   1920
ttttattata aagagtgcac ccagtaatta tatatcctgg attctcccct ggcccccgt   1980
agcttacatt gtagatccgt ccctggtttt atctattaca tcatatatta tcatatatta   2040
tgaaatagag agagagtaac tgttgtggcg aatcttgtac aaaaaaaact gttgtggcga   2100
tttaaacatt cagaaaactc cggtaagaag ttacattgta attttgtgca tgcgattgca   2160
tgcccatttt gtcaataata tacacgcgtt tgcagtaatc aacgtgagaa tattatagat   2220
gcacgcgtat gcatggatca gcaactgtat tttacgtgtg tattaactgt gtgcatgatg   2280
gcattcattt ttatttaata aattaaatag ataacaatta ttttccaata aatagcaaca   2340
attggaaaac ttatttagca aaaaaaaaaa caattggaaa actttttttg tgtaaaaaat   2400
agtatattat catatgatct ctctcttttt catgcatgca ttcgcgtgta tatagacacg   2460
aatatacatg cagtttcctg ctttaaaaat attacaatat atttcaaaaa aaaaacgtaa   2520
caacatgtat gatgtaataa tttcataaat atattagcat tgacagaagc acctattgat   2580
gaagcggaag gtttatatga tagaattaga tatccgttga ttctaagaat acacggaaaa   2640
ctataataat ataaagattt tatttagtct aagaatgcat aagatcaata tcttctttaa   2700
attcgttgag atcaccaatg atctaccgaa aacaagtaac atagaaaaaa ctcttaactt   2760
```

```
ttattatata atcaaaaact tggatacaac tctaggcata agaaacctat atatgtgaaa   2820
acataataac tatgaaaacc ctaatcctaa ttaaaataga aaaaactatt aaaataaagc   2880
taatacaaat aaatggtaat tatcctaatt ctaagctgca tcacctatcc ctcctatcaa   2940
ctatataagt ctcacacgtc tttgtactct acacttccca ttcatatata caatctcaaa   3000
agccgcgccg gggcccaaaa tggtggacct caagcctgga gtgaagcgcc tggtgagctg   3060
gaaggagatc cgcgagcacg cgacgcccgc gaccgcgtgg atcgtgattc accacaaggt   3120
ctacgacatc tccaagtggg actcgcaccc gggtggctcc gtgatgctca cgcaggccgg   3180
cgaggacgcc acggacgcct tcgcggtctt ccacccgtcc tcggcgctca agctgctcga   3240
gcagttctac gtcggcgacg tggacgaaac ctccaaggcc gagatcgagg gggagccggc   3300
gagcgacgag gagcgcgcgc gccgcgagcg catcaacgag ttcatcgcgt cctaccgccg   3360
tctgcgcgtc aaggtcaagg gcatggggct ctacgacgcc agcgcgctct actacgcgtg   3420
gaagctcgtg agcacgttcg gcatcgcggt gctctcgatg gcgatctgct tcttcttcaa   3480
cagtttcgcc atgtacatgg tcgccggcgt gattatgggg ctcttctacc agcagtccgg   3540
atggctggcg cacgacttct tgcacaacca ggtgtgcgag aaccgcacgc tcggcaacct   3600
tatcggctgc ctcgtgggca acgcctggca gggcttcagc atgcagtggt ggaagaacaa   3660
gcacaacctg caccacgcgg tgccgaacct gcacagcgcc aaggacgagg gcttcatcgg   3720
cgacccggac atcgacacca tgccgctgct ggcgtggtct aaggagatgg cgcgcaaggc   3780
gttcgagtcg gcgcacggcc cgttcttcat ccgcaaccag gcgttcctat acttcccgct   3840
gctgctgctc gcgcgcctga gctggctcgc gcagtcgttc ttctacgtgt tcaccgagtt   3900
ctcgttcggc atcttcgaca aggtcgagtt cgacggaccg gagaaggcgg gtctgatcgt   3960
gcactacatc tggcagctcg cgatcccgta cttctgcaac atgagcctgt ttgagggcgt   4020
ggcatacttc ctcatgggcc aggcgtcctg cggcttgctc ctggcgctgg tgttcagtat   4080
tggccacaac ggcatgtcgg tgtacgagcg cgaaaccaag ccggacttct ggcagctgca   4140
ggtgaccacg acgcgcaaca tccgcgcgtc ggtattcatg gactggttca ccggtggctt   4200
gaactaccag atcgaccatc acctgttccc gctcgtgccg cgccacaact tgccaaaggt   4260
caacgtgctc atcaagtcgc tatgcaagga gttcgacatc ccgttccacg agaccggctt   4320
ctgggagggc atctacgagg tcgtggacca cctggcggac atcagcaagg aatttatcac   4380
cgagttccca gcgatgtaag ttaacttaat taataattga ttgctgcttt aatgagatat   4440
gcgagacgcc tatgatcgca tgatatttgc tttcaattct gttgtgcacg ttgtaaaaaa   4500
cctgagcatg tgtagctcag atccttaccg ccggtttcgg ttcattctaa tgaatatatc   4560
acccgttact atcgtatttt tatgaataat attctccgtt caatttactg attgtggcgc   4620
ctactaccgg taattcccgg gattagcggc cgctagtctg tgcgcacttg tatcctgcag   4680
gtcaatcgtt taaacactgt acggaccgtg gcctaatagg ccggtaccac ccagctttct   4740
tgtacaaagt ggccatgatt acgccaagct ctccaccgcg gtggcggccg ctctagccca   4800
agctttaagg atgacctacc cattcttgag acaaatgtta cattttagta tcagagtaaa   4860
atgtgtacct ataactcaaa ttcgattgac atgtatccat tcaacataaa attaaaccag   4920
cctgcacctg catccacatt tcaagtattt tcaaaccgtt cggctcctat ccaccgggtg   4980
taacaagacg gattccgaat ttggaagatt ttgactcaaa ttcccaattt atattgaccg   5040
tgactaaatc aactttaact tctataattc tgattaagct cccaatttat attcccaacg   5100
```

-continued

```
gcactacctc caaaatttat agactctcat ccccttttaa accaacttag taaacgtttt   5160
tttttaatt ttatgaagtt aagtttttac cttgttttta aaaagaatcg ttcataagat   5220
gccatgccag aacattagct acacgttaca catagcatgc agccgcggag aattgttttt   5280
cttcgccact tgtcactccc ttcaaacacc taagagcttc tctctcacag cacacacata   5340
caatcacatg cgtgcatgca ttattacacg tgatcgccat gcaaatctcc tttatagcct   5400
ataaattaac tcatcggctt cactctttac tcaaaccaaa actcatcaat acaaacaaga   5460
ttaaaaacat aaggcgcgcc aattgactag taggcctatc gattaggaga ataacaatgg   5520
tgcgctcctc caagaacgtc atcaaggagt tcatgcgctt caaggtgcgc atggagggca   5580
ccgtgaacgg ccacgagttc gagatcgagg gcgagggcga gggccgcccc tacgagggcc   5640
acaacaccgt gaagctgaag gtgaccaagg gcggccccct gcccttcgcc tgggacatcc   5700
tgtcccccca gttccagtac ggctccaagg tgtacgtgaa gcaccccgcc gacatccccg   5760
actacaagaa gctgtccttc cccgagggct tcaagtggga gcgcgtgatg aacttcgagg   5820
acggcggcgt ggtgaccgtg acccaggact cctccctgca ggacggctgc ttcatctaca   5880
aggtgaagtt catcggcgtg aacttcccct ccgacggccc cgtaatgcag aagaagacca   5940
tgggctggga ggcctccacc gagcgcctgt accccccgcga cggcgtgctg aagggcgaga   6000
tccacaaggc cctgaagctg aaggacggcg gccactacct ggtggagttc aagtccatct   6060
acatggccaa gaagcccgtg cagctgcccg gctactacta cgtggactcc aagctggaca   6120
tcacctccca caacgaggac tacaccatcg tggagcagta cgagcgcacc gagggccgcc   6180
accacctgtt cctgctcgag tctagaggta ccggttgtta acgttagccg gctacgtata   6240
ctccggaata ttaataggcc taggatgcat atggcggccg cctgcagctg gcgccatcga   6300
ttaattaagg ccgcctcgag catgcatcta gagggcccgc tagcgttaac cctgctttaa   6360
tgagatatgc gagacgccta tgatcgcatg atatttgctt tcaattctgt tgtgcacgtt   6420
gtaaaaaacc tgagcatgtg tagctcagat ccttaccgcc ggtttcggtt cattctaatg   6480
aatatatcac ccgttactat cgtattttta tgaataatat tctccgttca atttactgat   6540
tgtccgtcga gcatatgcta gaggatcccc gggtacccaa ctttattata catagttgat   6600
aattcactgg ccggatgtac cgaattcgcg gccgcaagct tgtacactag tacgcgtcaa   6660
ttggcgatcg cggatctgag atgaaaccgg tgattatcag aacctttat ggtctttgta   6720
tgcatatggt aaaaaaactt agtttgcaat ttcctgtttg ttttggtaat ttgagtttct   6780
tttagttgtt gatctgcctg ctttttggtt tacgtcagac tactactgct gttgttgttt   6840
ggtttccttt ctttcatttt ataaataaat aatccggttc ggtttactcc ttgtgactgg   6900
ctcagtttgg ttattgcgaa atgcgaatgg taaattgagt aattgaaatt cgttattagg   6960
gttctaagct gttttaacag tcactgggtt aatatctctc gaatcttgca tggaaaatgc   7020
tcttaccatt ggtttttaat tgaaatgtgc tcatatgggc cgtggtttcc aaattaaata   7080
aaactacgat gtcatcgaga agtaaaatca actgtgtcca cattatcagt tttgtgtata   7140
cgatgaaata gggtaattca aaatctagct tgatatgcct tttggttcat tttaaccttc   7200
tgtaaacatt ttttcagatt ttgaacaagt aaatccaaaa aaaaaaaaaa aaaatctcaa   7260
ctcaacacta aattatttta atgtataaaa gatgcttaaa acatttggct taaaagaaag   7320
aagctaaaaa catagagaac tcttgtaaat tgaagtatga aaatatactg aattgggtat   7380
tatatgaatt tttctgattt aggattcaca tgatccaaaa aggaaatcca gaagcactaa   7440
tcagacattg gaagtaggaa tatttcaaaa agtttttttt ttttaagtaa gtgacaaaag   7500
```

-continued

```
cttttaaaaa atagaaaaga aactagtatt aaagttgtaa atttaataaa caaaagaaat   7560
tttttatatt ttttcatttc tttttccagc atgaggttat gatggcagga tgtggatttc   7620
atttttttcc ttttgatagc cttttaattg atctattata attgacgaaa aaatattagt   7680
taattataga tatattttag gtagtattag caatttacac ttccaaaaga ctatgtaagt   7740
tgtaaatatg atgcgttgat ctcttcatca ttcaatggtt agtcaaaaaa ataaaagctt   7800
aactagtaaa ctaaagtagt caaaaattgt actttagttt aaaatattac atgaataatc   7860
caaaacgaca tttatgtgaa acaaaaacaa tatagatcca ttaccctgtt atccctagag   7920
gggaaaattc gaatccaaaa attacggata tgaatatagg catatccgta tccgaattat   7980
ccgtttgaca gctagcaacg attgtacaat tgcttcttta aaaaaggaag aaagaaagaa   8040
agaaaagaat caacatcagc gttaacaaac ggccccgtta cggcccaaac ggtcatatag   8100
agtaacggcg ttaagcgttg aaagactcct atcgaaatac gtaaccgcaa acgtgtcata   8160
gtcagatccc ctcttccttc accgcctcaa acacaaaaat aatcttctac agcctatata   8220
tacaaccccc ccttctatct ctcctttctc acaattcatc atctttcttt ctctaccccc   8280
aattttaaga aatcctctct tctcctcttc attttcaagg taaatctctc tctctctctc   8340
tctctctgtt attccttgtt ttaattaggt atgtattatt gctagtttgt taatctgctt   8400
atcttatgta tgccttatgt gaatatcttt atcttgttca tctcatccgt ttagaagcta   8460
taaatttgtt gatttgactg tgtatctaca cgtggttatg tttatatcta atcagatatg   8520
aatttcttca tattgttgcg tttgtgtgta ccaatccgaa atcgttgatt tttttcattt   8580
aatcgtgtag ctaattgtac gtatacatat ggatctacgt atcaattgtt catctgtttg   8640
tgtttgtatg tatacagatc tgaaaacatc acttctctca tctgattgtg ttgttacata   8700
catagatata gatctgttat atcatttttt ttattaattg tgtatatata tatgtgcata   8760
gatctggatt acatgattgt gattatttac atgattttgt tatttacgta tgtatatatg   8820
tagatctgga ctttttggag ttgttgactt gattgtattt gtgtgtgtat atgtgtgttc   8880
tgatcttgat atgttatgta tgtgcagctg aaccatggcg gcggcaacaa caacaacaac   8940
aacatcttct tcgatctcct tctccaccaa accatctcct tcctcctcca aatcaccatt   9000
accaatctcc agattctccc tcccattctc cctaaacccc aacaaatcat cctcctcctc   9060
ccgccgccgc ggtatcaaat ccagctctcc ctcctccatc tccgccgtgc tcaacacaac   9120
caccaatgtc acaaccactc cctctccaac caaacctacc aaacccgaaa cattcatctc   9180
ccgattcgct ccagatcaac cccgcaaagg cgctgatatc ctcgtcgaag ctttagaacg   9240
tcaaggcgta gaaaccgtat tcgcttaccc tggaggtaca tcaatggaga ttcaccaagc   9300
cttaacccgc tcttcctcaa tccgtaacgt ccttcctcgt cacgaacaag gaggtgtatt   9360
cgcagcagaa ggatacgctc gatcctcagg taaaccaggt atctgtatag ccacttcagg   9420
tcccggagct acaaatctcg ttagcggatt agccgatgcg ttgttagata gtgttcctct   9480
tgtagcaatc acaggacaag tccctcgtcg tatgattggt acagatgcgt ttcaagagac   9540
tccgattgtt gaggtaacgc gttcgattac gaagcataac tatcttgtga tggatgttga   9600
agatatccct aggattattg aggaagcttt ctttttagct acttctggta gacctggacc   9660
tgttttggtt gatgttccta aagatattca acaacagctt gcgattccta attgggaaca   9720
ggctatgaga ttacctggtt atatgtctag gatgcctaaa cctccggaag attctcattt   9780
ggagcagatt gttaggttga tttctgagtc taagaagcct gtgttgtatg ttggtggtgg   9840
```

-continued

```
ttgtttgaat tctagcgatg aattgggtag gtttgttgag cttacgggga tccctgttgc   9900
gagtacgttg atggggctgg gatcttatcc ttgtgatgat gagttgtcgt tacatatgct   9960
tggaatgcat gggactgtgt atgcaaatta cgctgtggag catagtgatt tgttgttggc  10020
gtttggggta aggtttgatg atcgtgtcac gggtaagctt gaggcttttg ctagtagggc  10080
taagattgtt catattgata ttgactcggc tgagattggg aagaataaga ctcctcatgt  10140
gtctgtgtgt ggtgatgtta agctggcttt gcaagggatg aataaggttc ttgagaaccg  10200
agcggaggag cttaagcttg attttggagt ttggaggaat gagttgaacg tacagaaaca  10260
gaagtttccg ttgagcttta agacgtttgg ggaagctatt cctccacagt atgcgattaa  10320
ggtccttgat gagttgactg atggaaaagc cataataagt actggtgtcg ggcaacatca  10380
aatgtgggcg gcgcagttct acaattacaa gaaaccaagg cagtggctat catcaggagg  10440
ccttggagct atgggatttg gacttcctgc tgcgattgga gcgtctgttg ctaaccctga  10500
tgcgatagtt gtggatattg acggagatgg aagctttata atgaatgtgc aagagctagc  10560
cactattcgt gtagagaatc ttccagtgaa ggtactttta ttaaacaacc agcatcttgg  10620
catggttatg caatgggaag atcggttcta caaagctaac cgagctcaca catttctcgg  10680
ggatccggct caggaggacg agatattccc gaacatgttg ctgtttgcag cagcttgcgg  10740
gattccagcg gcgagggtga caaagaaagc agatctccga gaagctattc agacaatgct  10800
ggatacacca ggaccttacc tgttggatgt gatttgtccg caccaagaac atgtgttgcc  10860
gatgatcccg aatggtggca ctttcaacga tgtcataacg gaaggagatg gccggattaa  10920
atactgatag ggataacagg gtaatctcga cgagatgaaa ccggtgatta tcagaacctt  10980
ttatggtctt tgtatgcata tggtaaaaaa acttagtttg caatttcctg tttgttttgg  11040
taatttgagt ttcttttagt tgttgatctg cctgcttttt ggtttacgtc agactactac  11100
tgctgttgtt gtttggtttc ctttctttca ttttataaat aaataatccg gttcggttta  11160
ctccttgtga ctggctcagt ttggttattg cgaaatgcga atggtaaatt gagtaattga  11220
aattcgttat tagggttcta agctgtttta acagtcactg ggttaatatc tctcgaatct  11280
tgcatggaaa atgctcttac cattggtttt taattgaaat gtgctcatat gggccgtggt  11340
ttccaaatta aataaaacta cgatgtcatc gagaagtaaa atcaactgtg tccacattat  11400
cagttttgtg tatacgatga aatagggtaa ttcaaaatct agcttgatat gccttttggt  11460
tcattttaac cttctgtaaa catttttttca gattttgaac aagtaaatcc aaaaaaaaaa  11520
aaaaaaaatc tcaactcaac actaaattat tttaatgtat aaaagatgct taaaacattt  11580
ggcttaaaag aaagaagcta aaaacataga gaactcttgt aaattgaagt atgaaaatat  11640
actgaattgg gtattatatg aatttttctg atttaggatt cacatgatcc aaaaaggaaa  11700
tccagaagca ctaatcagac attggaagta ggaatatttc aaaaagtttt ttttttttaa  11760
gtaagtgaca aaagctttta aaaaatagaa aagaaactag tattaaagtt gtaaatttaa  11820
taaacaaaag aaatttttta tatttttca tttcttttc cagcatgagg ttatgatggc  11880
aggatgtgga tttcattttt ttccttttga tagcctttta attgatctat tataattgac  11940
gaaaaaatat tagttaatta tagatatatt ttaggtagta ttagcaattt acacttccaa  12000
aagactatgt aagttgtaaa tatgatgcgt tgatctcttc atcattcaat ggttagtcaa  12060
aaaaataaaa gcttaactag taaactaaag tagtcaaaaa ttgtacttta gtttaaaata  12120
ttacatgaat aatccaaaac gacatttatg tgaaacaaaa acaatatgtc gaggcgatcg  12180
cagtacttaa tcagtgatca gtaactaaat tcagtacatt aaagacgtcc gcaatgtgtt  12240
```

attaagttgt ctaagcgtca atttgtttac accacaatat atcctgccac cagccagcca 12300
acagctcccc gaccggcagc tcggcacaaa atcactgatc atctaaaaag gtgatgtgta 12360
tttgagtaaa acagcttgcg tcatgcggtc gctgcgtata tgatgcgatg agtaaataaa 12420
caaatacgca aggggaacgc atgaaggtta tcgctgtact taaccagaaa ggcgggtcag 12480
gcaagacgac catcgcaacc catctagccc gcgccctgca actcgccggg gccgatgttc 12540
tgttagtcga ttccgatccc cagggcagtg cccgcgattg ggcggccgtg cgggaagatc 12600
aaccgctaac cgttgtcggc atcgaccgcc cgacgattga ccgcgacgtg aaggccatcg 12660
gccggcgcga cttcgtagtg atcgacggag cgccccaggc ggcggacttg gctgtgtccg 12720
cgatcaaggc agccgacttc gtgctgattc cggtgcagcc aagcccttac gacatttggg 12780
ccaccgccga cctggtggag ctggttaagc agcgcattga ggtcacggat ggaaggctac 12840
aagcggcctt tgtcgtgtcg cgggcgatca aaggcacgcg catcggcggt gaggttgccg 12900
aggcgctggc cgggtacgag ctgcccattc ttgagtcccg tatcacgcag cgcgtgagct 12960
acccaggcac tgccgccgcc ggcacaaccg ttcttgaatc agaacccgag ggcgacgctg 13020
cccgcgaggt ccaggcgctg gccgctgaaa ttaaatcaaa actcatttga gttaatgagg 13080
taaagagaaa atgagcaaaa gcacaaacac gctaagtgcc ggccgtccga gcgcacgcag 13140
cagcaaggct gcaacgttgg ccagcctggc agacacgcca gccatgaagc gggtcaactt 13200
tcagttgccg gcggaggatc acaccaagct gaagatgtac gcggtacgcc aaggcaagac 13260
cattaccgag ctgctatctg aatacatcgc gcagctacca gagtaaatga gcaaatgaat 13320
aaatgagtag atgaatttta gcggctaaag gaggcggcat ggaaaatcaa gaacaaccag 13380
gcaccgacgc cgtggaatgc cccatgtgtg gaggaacggg cggttggcca ggcgtaagcg 13440
gctgggttgt ctgccggccc tgcaatggca ctggaacccc caagcccgag gaatcggcgt 13500
gagcggtcgc aaaccatccg gcccggtaca aatcggcgcg gcgctgggtg atgacctggt 13560
ggagaagttg aaggccgcgc aggccgccca gcggcaacgc atcgaggcag aagcacgccc 13620
cggtgaatcg tggcaagggg ccgctgatcg aatccgcaaa gaatcccggc aaccgccggc 13680
agccggtgcg ccgtcgatta ggaagccgcc caagggcgac gagcaaccag atttttcgt 13740
tccgatgctc tatgacgtgg gcacccgcga tagtcgcagc atcatggacg tggccgtttt 13800
ccgtctgtcg aagcgtgacc gacgagctgg cgaggtgatc cgctacgagc ttccagacgg 13860
gcacgtagag gtttccgcag gccccgccgg catggccagt gtgtgggatt acgacctggt 13920
actgatggcg gtttcccatc taaccgaatc catgaaccga taccgggaag ggaagggaga 13980
caagcccggc cgcgtgttcc gtccacacgt tgcggacgta ctcaagttct gccggcgagc 14040
cgatggcgga aagcagaaag acgacctggt agaaacctgc attcggttaa acaccacgca 14100
cgttgccatg cagcgtacca agaaggccaa gaacggccgc ctggtgacgg tatccgaggg 14160
tgaagccttg attagccgct acaagatcgt aaagagcgaa accgggcggc cggagtacat 14220
cgagatcgag cttgctgatt ggatgtaccg cgagatcaca gaaggcaaga acccggacgt 14280
gctgacggtt caccccgatt actttttgat cgaccccggc atcggccgtt ttctctaccg 14340
cctggcacgc cgcgccgcag gcaaggcaga agccagatgg ttgttcaaga cgatctacga 14400
acgcagtggc agcgccggag agttcaagaa gttctgtttc accgtgcgca agctgatcgg 14460
gtcaaatgac ctgccggagt acgatttgaa ggaggaggcg gggcaggctg gcccgatcct 14520
agtcatgcgc taccgcaacc tgatcgaggg cgaagcatcc gccggttcct aatgtacgga 14580

```
gcagatgcta gggcaaattg ccctagcagg ggaaaaaggt cgaaaaggtc tctttcctgt  14640

ggatagcacg tacattggga acccaaagcc gtacattggg aaccggaacc cgtacattgg  14700

gaacccaaag ccgtacattg ggaaccggtc acacatgtaa gtgactgata taaaagagaa  14760

aaaaggcgat tttccgcct aaaactcttt aaaacttatt aaaactctta aaacccgcct  14820

ggcctgtgca taactgtctg gccagcgcac agccgaagag ctgcaaaaag cgcctaccct  14880

tcggtcgctg cgctccctac gccccgccgc ttcgcgtcgg cctatcgcgg cctatgcggt  14940

gtgaaatacc gcacagatgc gtaaggagaa aataccgcat caggcgctct tccgcttcct  15000

cgctcactga ctcgctgcgc tcggtcgttc ggctgcggcg agcggtatca gctcactcaa  15060

aggcggtaat acggttatcc acagaatcag gggataacgc aggaaagaac atgtgagcaa  15120

aaggccagca aaaggccagg aaccgtaaaa aggccgcgtt gctggcgttt ttccataggc  15180

tccgcccccc tgacgagcat cacaaaaatc gacgctcaag tcagaggtgg cgaaacccga  15240

caggactata aagataccag gcgtttcccc ctggaagctc cctcgtgcgc tctcctgttc  15300

cgaccctgcc gcttaccgga tacctgtccg cctttctccc ttcgggaagc gtggcgcttt  15360

ctcatagctc acgctgtagg tatctcagtt cggtgtaggt cgttcgctcc aagctgggct  15420

gtgtgcacga accccccgtt cagcccgacc gctgcgcctt atccggtaac tatcgtcttg  15480

agtccaaccc ggtaagacac gacttatcgc cactggcagc agccactggt aacaggatta  15540

gcagagcgag gtatgtaggc ggtgctacag agttcttgaa gtggtggcct aactacggct  15600

acactagaag gacagtattt ggtatctgcg ctctgctgaa gccagttacc ttcggaaaaa  15660

gagttggtag ctcttgatcc ggcaaacaaa ccaccgctgg tagcggtggt ttttttgttt  15720

gcaagcagca gattacgcgc agaaaaaaag gatctcaaga agatcctttg atcttttcta  15780

cggggtcctt caactcatcg atagtttggc tgtgagcaat tatgtgctta gtgcatctaa  15840

cgcttgagtt aagccgcgcc gcgaagcgg                                    15869
```

<210> SEQ ID NO 98
<211> LENGTH: 1152
<212> TYPE: DNA
<213> ORGANISM: Brassica napus

<400> SEQUENCE: 98

```
atgaagagtc actacacaaa catcatttat gttgtttttc tcttattttg tcttttgatc     60

acatcttcct ctgcacaatc cctcatacga caacccactg atgacctaag cacaattcta    120

cagcagaaga atggagcgca accaaactca atcctgggag aagcgcatta cttaaataaa    180

gatgatctag agatctattc acgtgattat aaaggctcac cttcaaattt agtgacgggt    240

atgagagacc gtcctccaat gtcttactct ctcagaatgg agtctttcaa cacgctcctt    300

cagtcaaatg agacagagag atacgaatct cgtccttttc ccgttggtgg atacaactgg    360

tcacttattg tgtatcccaa cgggaacagg caggatagtg gctcagggtt catttcgctt    420

tatttagcca tagacaactc gactctcgtt tcttcgcatc aagaggtttt cgcagatctc    480

aggttttacg tattcaaaag gaccgagagg aatttcttca ccgtccaaga tacagatgta    540

tggcgatata atattttcaa aacgatgtgg ggattccctc gggtcctccc tcttgatacc    600

ttcagaaacc cgagcaacgg atacctcttc aatggagata actgcgagtt tggtgttgat    660

gtgactgttc attctccctt tgaaagttca gaacttttca ctgtcgctag gaatttccct    720

aacccgaggt tcacctggac tattcagagg ttctccacgc tggtcggaga tacgcatctc    780

tctaatacgt tctcggtcgg aggaaggaat tggaatatac aagtgaatcc acgtggccgt    840
```

tcaacggggg cgggaagagc catgtcgatg tatcttatcc ttaatgcgaa cgagaaagtt 900
agacccaatg agaagattta tgttcgagca aggcttagag ttattaacca aaggatattc 960
tcgctcttgt ggacaaccat cgaaaggcca atcgatcatt ggttcactac tccgggatta 1020
ggttggggat acgatgagtt tatctctcta gatgatctca gagatttttg gaaaggttat 1080
gtcatgggtg atgtgttgat agttgaagtc gaaatggagg caatttcttc aaccaagtat 1140
ttccctagtt ag 1152

<210> SEQ ID NO 99
<211> LENGTH: 57
<212> TYPE: DNA
<213> ORGANISM: Artificial sequence
<220> FEATURE:
<223> OTHER INFORMATION: Primer

<400> SEQUENCE: 99
atacccggga tacctgcagg ttaggccggc catgcgagag agaagaaatg aaataag 57

<210> SEQ ID NO 100
<211> LENGTH: 71
<212> TYPE: DNA
<213> ORGANISM: Artificial sequence
<220> FEATURE:
<223> OTHER INFORMATION: Primer

<400> SEQUENCE: 100
caatcaatta taggcctcgc atgctttaat taacgatcga gccatggctt ttgagattgt 60
atatatgaat g 71

<210> SEQ ID NO 101
<211> LENGTH: 73
<212> TYPE: DNA
<213> ORGANISM: Artificial sequence
<220> FEATURE:
<223> OTHER INFORMATION: Primer

<400> SEQUENCE: 101
ccatggctcg atcgttaatt aaagcatgcg aggcctataa ttgattgatt tctctaacta 60
agaaactttg tag 73

<210> SEQ ID NO 102
<211> LENGTH: 61
<212> TYPE: DNA
<213> ORGANISM: Artificial sequence
<220> FEATURE:
<223> OTHER INFORMATION: Primer

<400> SEQUENCE: 102
taagcggccg caatcggacc gataccggta ggcgcccgat aaagatggtc taatgtccat 60
c 61

<210> SEQ ID NO 103
<211> LENGTH: 1820
<212> TYPE: DNA
<213> ORGANISM: Brassica napus

<400> SEQUENCE: 103
cttgcgccga agatatatcc gacgcgttgt gtcagaaaat gccgtgcgga caagggagct 60
ctaggtggaa aatgcacttg ggaacatggc attaatgtaa agtgcctatg cgacttttgc 120

```
aggcacgaat ctggtcagat tctaagtggc atttgatcaa tcctgcatgt gtgatgatgg    180
cttctgaaat aaaaatggtg aaaatggtcc aagtataatg tagtaatgag tatgaaaaat    240
aaaaacgccg gaagcatcta aaatattgta tggtttgtat cgtggtagag gtgactaaaa    300
taagtatcaa ctttcatatt tcacaacttt gcataagcca aagaacccga gcaaatgaaa    360
tctaaaatcc tgcatttagc atccacgtga agatatatga ctgtgcttgg tgaagatata    420
tgactgtgct tgattgtcgg tcgactaatt tatgggtaat caaccgtcag aaatcgaatg    480
taactgtgac gtgttaacaa gagatttaaa tagatttttc catctctaga aagtgcgtat    540
gcgacttctg cagcaacaaa ctttgtgcag caacaaactt tgtgatcagt ttactaagtg    600
tcggttgaat cctgcaacaa tatttatagt actgatgaca gctaaatgat tcttcaacaa    660
taatttattg ccccaacgat agagataaat aaacatagta cgagttcgtt tacacatacg    720
ttaactccaa agtaaaacaa agagagattg acaaaaaaaa acaaagagag tagtagagag    780
agaaagattg gccatggcaa cgaagccagt tttttcattc gtcgtgttat tcattctctt    840
tttggctacc tttggtaatt aactaactcc atatttattc acatatattt gttcaaaaat    900
aattgtgaat cataattaac tctgtattta ttcacatatc tttgttgaaa gttttatgat    960
tcacaattaa aatgactcag aaggtatttc tcaccgtgat cttgtaaatt tcattataaa   1020
tgtgatttct attttctcaa acgttatcta tatatcataa tagcgagtgc cggaaagaat   1080
atacagtgtt gatgagtctg gtgatgatgt tggcttccat ttctatgcgc ctctaatatt   1140
tccatcggtt tgctatatga gatgccgtca ggacaaggga gctaaaggtg gaaaatgcct   1200
ttggggagat gtctttagtg ctgagtgctt atgcgacttc tgcagcgacg tacctataat   1260
gatcagactc gaagtggtat ttgaataatc ctgcatgtgt catggtttgc agaataataa   1320
aggtgaatat ggttcaacta ataatgtagt aatgaatgtg tgaaacaaaa caaaaagccg   1380
gaagtatcca aggctcacat ggtttgatca tattgtaact tgtaaggttg gtactgactg   1440
acctgtcgac gtgtagatat ctgaggcaaa gaaataaatt aatactaact tacatatata   1500
cttcacaact ttgcaaaagc caaaaaaaaa atcagaggca aagaaaatat ctacttgttt   1560
aagaatcttt cactttgcat cgacgtgtag atatctgact gtcgttcgtt taatttatgt   1620
ttaattaacg gtcagaattt acatgtcact gacgtgtgaa caatgtagtt gtgtcttgac   1680
agctacatga gtctttcaaa ataatttgtt tccccaacgt cgccaatgat aaagataaat   1740
aacatacata gtacgagttc atttacacct acgttgactc caaagtgaaa caaagagagt   1800
aagagatata tagagagaag                                                1820
```

<210> SEQ ID NO 104
<211> LENGTH: 572
<212> TYPE: DNA
<213> ORGANISM: Brassica napus

<400> SEQUENCE: 104

```
atacttcaca actttgcata agccaaaaga atcctaggtg aaaaatatat acttggtttt     60
aaacttttaa gaaattcatt agcatccacg tgagatttca gctctatttg ggtatttcta    120
aattttattc atgtttagat ttttgtaggt tcggataacc catttagtta ttttaaaaat    180
tttaaaattt attatatatt ttaaaattct caaaatctat aaataaaata aaatattaca    240
tataaatcta actaacatat gtcaaaatac ataaatttaa catataaatt gatttggttc    300
agatatttgg atagagaatc aataaatatt tcaagtagtt ttagcgttct gagtatattt    360
taactatttt agataaatta aaggcatctt atatattttg gatgtttcta atatacagta    420
```

aatctaaaaa ttatataata tatttcggta catttaggta cccaaaatat tttggttcga 480
gtcgaattcg gttttagttt tgtaggtacc aaaattttga acccgtttga atatttaatc 540
aattttggtt cggattcggt ttcggatttg gt 572

<210> SEQ ID NO 105
<211> LENGTH: 16266
<212> TYPE: DNA
<213> ORGANISM: Artificial sequence
<220> FEATURE:
<223> OTHER INFORMATION: Plasmid

<400> SEQUENCE: 105
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540
tgggtgtcat cgagcgccac ctcgaaccga ccctcctcgc cgtgcatctg tatggtagcg 600
ccgttgacgg cggccttaag ccccattcgg acatcgacct gcttgtcacc gttaccgtcc 660
gtctcgacga gaccacgcgc cgcgcgctta tcaacgacct tctggaaacg tccgcctccc 720
ccggcgagag cgaaatcctg cgcgcggttg aggtgacgat tgtggtgcac gatgacatca 780
tcccctggcg ctatccggcc aaacgcgaac tccagttcgg cgaatggcag cgtaatgata 840
ttctggcggg tatctttgaa ccggccacca tcgacattga tctggcgatc ctgctcacca 900
aggcccggga gcatagcgtg gccctcgtcg gccccgcggc cgaggaactt ttcgacccgg 960
tgccggaaca ggatctgttc gaagcactga acgagacgct gaccctgtgg aactccccgc 1020
cggattgggc gggcgatgag cgcaatgtgg tccttacgct gagccggatt tggtactcgg 1080
cggttaccgg caagatcgcg ccgaaggatg tcgccgccga ctgggcgatg gagcgccttc 1140
cggcgcaata ccagcccgtg atcctcgaag cgcgccaagc ctatctgggc caagaagaag 1200
accgtctcgc gtcccgggcc gaccagctcg aagaatttgt ccactatgtc aagggcgaga 1260
tcacgaaggt cgttggcaaa taatgtctag ctagaaattc gttcaagccg acgccgcttc 1320
gcggcgcggc ttaactcaag cgttagatgc actaagcaca taattgctca cagccaaact 1380
atcgatgagt tgaaggaccc cgtagaaaag atcaaaggat cttcttgaga tccttttttt 1440
ctgcgcgtaa tctgctgctt gcaaacaaaa aaaccaccgc taccagcggt ggtttgtttg 1500
ccggatcaag agctaccaac tctttttccg aaggtaactg gcttcagcag agcgcagata 1560
ccaaatactg tccttctagt gtagccgtag ttaggccacc acttcaagaa ctctgtagca 1620
ccgcctacat acctcgctct gctaatcctg ttaccagtgg ctgctgccag tggcgataag 1680
tcgtgtctta ccgggttgga ctcaagacga tagttaccgg ataaggcgca gcggtcgggc 1740
tgaacggggg gttcgtgcac acagcccagc ttggagcgaa cgacctacac cgaactgaga 1800
tacctacagc gtgagctatg agaaagcgcc acgcttcccg aagggagaaa ggcggacagg 1860

-continued

```
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
gcttttgctc attttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
```

agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc acctttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980
actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280
aaaaaaatga aatccacatc ctgccatcat aacctcatgc tggaaaaaga aatgaaaaaa 5340
tataaaaaat ttcttttgtt tattaaattt acaactttaa tactagtttc ttttctattt 5400
tttaaaagct tttgtcactt acttaaaaaa aaaaaacttt ttgaaatatt cctacttcca 5460
atgtctgatt agtgcttctg gatttccttt ttggatcatg tgaatcctaa atcagaaaaa 5520
ttcatataat acccaattca gtatattttc atacttcaat ttacaagagt tctctatgtt 5580
tttagcttct ttcttttaag ccaaatgttt taagcatctt ttatacatta aaataattta 5640
gtgttgagtt gagatttttt tttttttttt ttggatttac ttgttcaaaa tctgaaaaaa 5700
tgtttacaga aggttaaaat gaaccaaaag gcatatcaag ctagattttg aattacccta 5760
tttcatcgta tacacaaaac tgataatgtg gacacagttg attttacttc tcgatgacat 5820
cgtagtttta tttaatttgg aaaccacggc ccatatgagc acatttcaat taaaaaccaa 5880
tggtaagagc attttccatg caagattcga gagatattaa cccagtgact gttaaaacag 5940
cttagaaccc taataacgaa tttcaattac tcaatttacc attcgcattt cgcaataacc 6000
aaactgagcc agtcacaagg agtaaaccga accggattat ttatttataa aatgaaagaa 6060
aggaaaccaa acaacaacag cagtagtagt ctgacgtaaa ccaaaaagca ggcagatcaa 6120
caactaaaag aaactcaaat taccaaaaca aacaggaaat tgcaaactaa gtttttttac 6180
catatgcata caaagaccat aaaaggttct gataatcacc ggtttcatct cgtcgagatt 6240
accctgttat ccctatcagt atttaatccg gccatctcct tccgttatga catcgttgaa 6300
agtgccacca ttcgggatca tcggcaacac atgttcttgg tgcggacaaa tcacatccaa 6360
caggtaaggt cctggtgtat ccagcattgt ctgaatagct tctcggagat ctgctttctt 6420
tgtcaccctc gccgctggaa tcccgcaagc tgctgcaaac agcaacatgt tcgggaatat 6480
ctcgtcctcc tgagccggat ccccgagaaa tgtgtgagct cggttagctt tgtagaaccg 6540
atcttcccat tgcataacca tgccaagatg ctggttgttt aataaaagta ccttcactgg 6600

-continued aagattctct acacgaatag tggctagctc ttgcacattc attataaagc ttccatctcc 6660
gtcaatatcc acaactatcg catcagggtt agcaacagac gctccaatcg cagcaggaag 6720
tccaaatccc atagctccaa ggcctcctga tgatagccac tgccttggtt tcttgtaatt 6780
gtagaactgc gccgcccaca tttgatgttg cccgacacca gtacttatta tggcttttcc 6840
atcagtcaac tcatcaagga ccttaatcgc atactgtgga ggaatagctt ccccaaacgt 6900
cttaaagctc aacggaaact tctgtttctg tacgttcaac tcattcctcc aaactccaaa 6960
atcaagctta agctcctccg ctcggttctc aagaacctta ttcatccctt gcaaagccag 7020
cttaacatca ccacacacag acacatgagg agtcttattc ttcccaatct cagccgagtc 7080
aatatcaata tgaacaatct tagccctact agcaaaagcc tcaagcttac ccgtgacacg 7140
atcatcaaac cttaccccaa acgccaacaa caaatcacta tgctccacag cgtaatttgc 7200
atacacagtc ccatgcattc caagcatatg taacgacaac tcatcatcac aaggataaga 7260
tcccagcccc atcaacgtac tcgcaacagg gatccccgta agctcaacaa acctacccaa 7320
ttcatcgcta gaattcaaac aaccaccacc aacatacaac acaggcttct tagactcaga 7380
aatcaaccta acaatctgct ccaaatgaga atcttccgga ggtttaggca tcctagacat 7440
ataaccaggt aatctcatag cctgttccca attaggaatc gcaagctgtt gttgaatatc 7500
tttaggaaca tcaaccaaaa caggtccagg tctaccagaa gtagctaaaa agaaagcttc 7560
ctcaataatc ctagggatat cttcaacatc catcacaaga tagttatgct tcgtaatcga 7620
acgcgttacc tcaacaatcg gagtctcttg aaacgcatct gtaccaatca tacgacgagg 7680
gacttgtcct gtgattgcta caagaggaac actatctaac aacgcatcgg ctaatccgct 7740
aacgagattt gtagctccgg gacctgaagt ggctatacag atacctggtt tacctgagga 7800
tcgagcgtat ccttctgctg cgaatacacc tccttgttcg tgacgaggaa ggacgttacg 7860
gattgaggaa gagcgggtta aggcttggtg aatctccatt gatgtacctc cagggtaagc 7920
gaatacggtt tctacgcctt gacgttctaa agcttcgacg aggatatcag cgcctttgcg 7980
gggttgatct ggagcgaatc gggagatgaa tgtttcgggt ttggtaggtt tggttggaga 8040
gggagtggtt gtgacattgg tggttgtgtt gagcacggcg gagatggagg agggagagct 8100
ggatttgata ccgcggcggc gggaggagga ggatgatttg ttggggttta gggagaatgg 8160
gagggagaat ctggagattg gtaatggtga tttggaggag gaaggagatg gtttggtgga 8220
gaaggagatc gaagaagatg ttgttgttgt tgttgttgcc gccgccatgg ttcagctgca 8280
catacataac atatcaagat cagaacacac atatacacac acaaatacaa tcaagtcaac 8340
aactccaaaa agtccagatc tacatatata catacgtaaa taacaaaatc atgtaaataa 8400
tcacaatcat gtaatccaga tctatgcaca tatatatata cacaattaat aaaaaaaatg 8460
atataacaga tctatatcta tgtatgtaac aacacaatca gatgagagaa gtgatgtttt 8520
cagatctgta tacatacaaa cacaaacaga tgaacaattg atacgtagat ccatatgtat 8580
acgtacaatt agctacacga ttaaatgaaa aaaatcaacg atttcggatt ggtacacaca 8640
aacgcaacaa tatgaagaaa ttcatatctg attagatata aacataacca cgtgtagata 8700
cacagtcaaa tcaacaaatt tatagcttct aaacggatga gatgaacaag ataaagatat 8760
tcacataagg catacataag ataagcagat taacaaacta gcaataatac atacctaatt 8820
aaaacaagga ataacagaga gagagagaga gagagagatt taccttgaaa atgaagagga 8880
gaagagagga tttcttaaaa ttgggggtag agaaagaaag atgatgaatt gtgagaaagg 8940
agagatagaa ggggggttg tatatatagg ctgtagaaga ttatttttgt gtttgaggcg 9000
gtgaaggaag aggggatctg actatgacac gtttgcggtt acgtatttcg ataggagtct 9060
ttcaacgctt aacgccgtta ctctatatga ccgtttgggc cgtaacgggg ccgtttgtta 9120
acgctgatgt tgattctttt ctttctttct ttcttccttt tttaaagaag caattgtaca 9180
atcgttgcta gctgtcaaac ggataattcg gatacggata tgcctatatt catatccgta 9240
atttttggat tcgaattttc ccctctaggg ataacagggt aatggatcta tattgttttt 9300
gtttcacata aatgtcgttt tggattattc atgtaatatt ttaaactaaa gtacaatttt 9360
tgactacttt agtttactag ttaagctttt atttttttga ctaaccattg aatgatgaag 9420
agatcaacgc atcatattta caacttacat agtcttttgg aagtgtaaat tgctaatact 9480
acctaaaata tatctataat taactaatat tttttcgtca attataatag atcaattaaa 9540
aggctatcaa aaggaaaaaa atgaaatcca catcctgcca tcataacctc atgctggaaa 9600
aagaaatgaa aaaatataaa aaatttcttt tgtttattaa atttacaact ttaatactag 9660
tttcttttct atttttaaa agcttttgtc acttacttaa aaaaaaaaaa ctttttgaaa 9720
tattcctact tccaatgtct gattagtgct tctggatttc ctttttggat catgtgaatc 9780
ctaaatcaga aaaattcata taatacccaa ttcagtatat tttcatactt caatttacaa 9840
gagttctcta tgtttttagc ttctttcttt taagccaaat gttttaagca tcttttatac 9900
attaaaataa tttagtgttg agttgagatt tttttttttt ttttttggat ttacttgttc 9960
aaaatctgaa aaaatgttta cagaaggtta aaatgaacca aaaggcatat caagctagat 10020
tttgaattac cctatttcat cgtatacaca aaactgataa tgtggacaca gttgatttta 10080
cttctcgatg acatcgtagt tttatttaat ttggaaacca cggcccatat gagcacattt 10140
caattaaaaa ccaatggtaa gagcattttc catgcaagat tcgagagata ttaacccagt 10200
gactgttaaa acagcttaga accctaataa cgaatttcaa ttactcaatt taccattcgc 10260
atttcgcaat aaccaaactg agccagtcac aaggagtaaa ccgaaccgga ttatttattt 10320
ataaaatgaa agaaaggaaa ccaaacaaca acagcagtag tagtctgacg taaaccaaaa 10380
agcaggcaga tcaacaacta aaagaaactc aaattaccaa aacaaacagg aaattgcaaa 10440
ctaagttttt ttaccatatg catacaaaga ccataaaagg ttctgataat caccggtttc 10500
atctcagatc cgcgatcgcc aattgacgcg tactagtgta caagcttgcg gccgcgaatt 10560
cggtacatcc ggccagtgaa ttatcaacta tgtataataa agttgggtac ccggggatcc 10620
tctagcatat gctcgacgga caatcagtaa attgaacgga gaatattatt cataaaaata 10680
cgatagtaac gggtgatata ttcattagaa tgaaccgaaa ccggcggtaa ggatctgagc 10740
tacacatgct caggtttttt acaacgtgca caacagaatt gaaagcaaat atcatgcgat 10800
cataggcgtc tcgcatatct cattaaagca gggttaacgc tagcgggccc tctagatgca 10860
tgctcgaggc ggccttaatt aatcgatggc gccagctgca ggcggccgcc atatgcatcc 10920
taggcctatt aatattccgg agtatacgta gccggctaac gttaacaacc ggtacctcta 10980
gactcgagca ggaacaggtg gtggcggccc tcggtgcgct cgtactgctc cacgatggtg 11040
tagtcctcgt tgtgggaggt gatgtccagc ttggagtcca cgtagtagta gccgggcagc 11100
tgcacgggct tcttggccat gtagatggac ttgaactcca ccaggtagtg gccgccgtcc 11160
ttcagcttca gggccttgtg gatctcgccc ttcagcacgc cgtcgcgggg gtacaggcgc 11220
tcggtggagg cctcccagcc catggtcttc ttctgcatta cggggccgtc ggaggggaag 11280
ttcacgccga tgaacttcac cttgtagatg aagcagccgt cctgcaggga ggagtcctgg 11340

-continued

```
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc ggcctattag gccacggtcc  12480
gtacagtgtt taaacgattg acctgcagga tacaagtgcg cacagactag cggccgctaa  12540
tcccgggaat taccggtagt aggcgccaca atcagtaaat tgaacggaga atattattca  12600
taaaaatacg atagtaacgg gtgatatatt cattagaatg aaccgaaacc ggcggtaagg  12660
atctgagcta cacatgctca ggttttttac aacgtgcaca acagaattga aagcaaatat  12720
catgcgatca taggcgtctc gcatatctca ttaaagcagc aatcaattat taattaagct  12780
aaggaactta catcgctggg aactcggtga taaattcctt gctgatgtcc gccaggtggt  12840
ccacgacctc gtagatgccc tcccagaagc cggtctcgtg gaacgggatg tcgaactcct  12900
tgcatagcga cttgatgagc acgttgacct ttggcaagtt gtggcgcggc acgagcggga  12960
acaggtgatg gtcgatctgg tagttcaagc caccggtgaa ccagtccatg aataccgacg  13020
cgcggatgtt gcgcgtcgtg gtcacctgca gctgccagaa gtccggcttg gtttcgcgct  13080
cgtacaccga catgccgttg tggccaatac tgaacaccag cgccaggagc aagccgcagg  13140
acgcctggcc catgaggaag tatgccacgc cctcaaacag gctcatgttg cagaagtacg  13200
ggatcgcgag ctgccagatg tagtgcacga tcagacccgc cttctccggt ccgtcgaact  13260
cgaccttgtc gaagatgccg aacgagaact cggtgaacac gtagaagaac gactgcgcga  13320
gccagctcag gcgcgcgagc agcagcagcg ggaagtatag gaacgcctgg ttgcggatga  13380
agaacgggcc gtgcgccgac tcgaacgcct tgcgcgccat ctccttagac cacgccagca  13440
gcggcatggt gtcgatgtcc gggtcgccga tgaagccctc gtccttggcg ctgtgcaggt  13500
tcggcaccgc gtggtgcagg ttgtgcttgt tcttccacca ctgcatgctg aagccctgcc  13560
aggcgttgcc cacgaggcag ccgataaggt tgccgagcgt gcggttctcg cacacctggt  13620
tgtgcaagaa gtcgtgcgcc agccatccgg actgctggta gaagagcccc ataatcacgc  13680
cggcgaccat gtacatggcg aaactgttga agaagaagca gatcgccatc gagagcaccg  13740
```

cgatgccgaa cgtgctcacg agcttccacg cgtagtagag cgcgctggcg tcgtagagcc 13800
ccatgccctt gaccttgacg cgcagacggc ggtaggacgc gatgaactcg ttgatgcgct 13860
cgcggcgcgc gcgctcctcg tcgctcgccg gctccccctc gatctcggcc ttggaggttt 13920
cgtccacgtc gccgacgtag aactgctcga gcagcttgag cgccgaggac gggtggaaga 13980
ccgcgaaggc gtccgtggcg tcctcgccgg cctgcgtgag catcacggag ccacccgggt 14040
gcgagtccca cttggagatg tcgtagacct tgtggtgaat cacgatccac gcggtcgcgg 14100
gcgtcgcgtg ctcgcggatc tccttccagc tcaccaggcg cttcactcca ggcttgaggt 14160
ccaccatttt gggccccggc gcgcccttct ctctatatat ctcttactct ctttgtttca 14220
ctttggagtc aacgtaggtg taaatgaact cgtactatgt atgttattta tctttatcat 14280
tggcgacgtt ggggaaacaa attattttga aagactcatg tagctgtcaa gacacaacta 14340
cattgttcac acgtcagtga catgtaaatt ctgaccgtta attaaacata aattaaacga 14400
acgacagtca gatatctaca cgtcgatgca aagtgaaaga ttcttaaaca agtagatatt 14460
ttctttgcct ctgatttttt ttttggcttt tgcaaagttg tgaagtatat atgtaagtta 14520
gtattaattt atttctttgc ctcagatatc tacacgtcga caggtcagtc agtaccaacc 14580
ttacaagtta caatatgatc aaaccatgtg agccttggat acttccggct ttttgttttg 14640
tttcacacat tcattactac attattagtt gaaccatatt cacctttatt attctgcaaa 14700
ccatgacaca tgcaggatta ttcaaatacc acttcgagtc tgatcattat aggtacgtcg 14760
ctgcagaagt cgcataagca ctcagcacta aagacatctc cccaaaggca ttttccacct 14820
ttagctccct tgtcctgacg gcatctcata tagcaaaccg atggaaatat tagaggcgca 14880
tagaaatgga agccaacatc atcaccagac tcatcaacac tgtatattct ttccggcact 14940
cgctattatg atatatagat aacgtttgag aaaatagaaa tcacatttat aatgaaattt 15000
acaagatcac ggtgagaaat accttctgag tcattttaat tgtgaatcat aaaactttca 15060
acaaagatat gtgaataaat acagagttaa ttatgattca caattatttt tgaacaaata 15120
tatgtgaata aatatggagt tagttaatta ccaaaggtag ccaaaaagag aatgaataac 15180
acgacgaatg aaaaaactgg cttcgttgcc atggccaatc tttctctctc tactactctc 15240
tttgtttttt tttgtcaatc tctctttgtt ttactttgga gttaacgtat gtgtaaacga 15300
actcgtacta tgtttattta tctctatcgt tggggcaata aattattgtt gaagaatcat 15360
ttagctgtca tcagtactat aaatattgtt gcaggattca accgacactt agtaaactga 15420
tcacaaagtt tgttgctgca caaagtttgt tgctgcagaa gtcgcatacg cactttctag 15480
agatggaaaa atctatttaa atctcttgtt aacacgtcac agttacattc gatttctgac 15540
ggttgattac ccataaatta gtcgaccgac aatcaagcac agtcatatat cttcaccaag 15600
cacagtcata tatcttcacg tggatgctaa atgcaggatt ttagatttca tttgctcggg 15660
ttctttggct tatgcaaagt tgtgaaatat gaaagttgat acttatttta gtcacctcta 15720
ccacgataca aaccatacaa tattttagat gcttccggcg tttttatttt tcatactcat 15780
tactacatta tacttggacc attttcacca tttttatttc agaagccatc atcacacatg 15840
caggattgat caaatgccac ttagaatctg accagattcg tgcctgcaaa agtcgcatag 15900
gcactttaca ttaatgccat gttcccaagt gcattttcca cctagagctc ccttgtccgc 15960
acggcatttt ctgacacaac gcgtcggata tatcttcggc gcaagggccg gcctagtaga 16020
tttaaattgg ccttagtggc caagcttggc gtaatcatgg agcctgcttt tttgtacaaa 16080

```
cttgggtacc ggcctattag gccacggtcc gtacagtgtt taaacgattg acctgcagga  16140

tacaagtgcg cacagactag cggccgctaa tcccgggaat taccggtagt aggcgcctac  16200

tttggccggc ctagtagatt taaattggcc ttagtggcca agcttggcgt aatcatggca  16260

actttt                                                             16266


<210> SEQ ID NO 106
<211> LENGTH: 300
<212> TYPE: DNA
<213> ORGANISM: Brassica napus

<400> SEQUENCE: 106

atggccatga caacaaagcc aatttcttca ttcgccgtat ttttcatttt ctttttggtt     60

atctttgaaa tgcctgagac cgaagcgcag gatagagagt gcttgaaaga atacggtggt    120

gaggttggct tcagttattg tgcgcctttg atacgtccga cgttttgttt tagacgatgc    180

cgtgaggaca agggagctaa aggtggagaa tgccgttggg gagatgagtt taatgttaag    240

tgcttatgcg acttctgcag cgacaaagct tatgatcaga ttctaagtac tggtatttga    300


<210> SEQ ID NO 107
<211> LENGTH: 55
<212> TYPE: DNA
<213> ORGANISM: Artificial sequence
<220> FEATURE:
<223> OTHER INFORMATION: Primer

<400> SEQUENCE: 107

atacccggga tacctgcagg ttaggccggc cacttgcgcc gaagatatat ccgac          55


<210> SEQ ID NO 108
<211> LENGTH: 69
<212> TYPE: DNA
<213> ORGANISM: Artificial sequence
<220> FEATURE:
<223> OTHER INFORMATION: Primer

<400> SEQUENCE: 108

caatcaatta taggcctcgc atgctttaat taacgatcga gccatggctt ctctctatat     60

atctcttac                                                             69


<210> SEQ ID NO 109
<211> LENGTH: 71
<212> TYPE: DNA
<213> ORGANISM: Artificial sequence
<220> FEATURE:
<223> OTHER INFORMATION: Primer

<400> SEQUENCE: 109

ccatggctcg atcgttaatt aaagcatgcg aggcctataa ttgattgata cttcacaact     60

ttgcataagc c                                                          71


<210> SEQ ID NO 110
<211> LENGTH: 61
<212> TYPE: DNA
<213> ORGANISM: Artificial sequence
<220> FEATURE:
<223> OTHER INFORMATION: Primer

<400> SEQUENCE: 110

taagcggccg caatcggacc gataccggta ggcgccacca aatccgaaac cgaatccgaa     60

c                                                                     61
```

<210> SEQ ID NO 111
<211> LENGTH: 1335
<212> TYPE: DNA
<213> ORGANISM: Brassica napus

<400> SEQUENCE: 111
tattcactac ttatagagaa cacgagcttg aaaccttgta tgtatgcaaa tgaatcatct 60
ttcactaaag cctgtatatt gacttgtcgt gtacaagtgt agtaacaaga ttacaagaat 120
tgtaaaatgg accaaacttg tccaaagctt tcagttgcag aagagaagag aagacagttc 180
ataacatata tataagtctt aataacaaaa tgaaacacca aactccaatc gcagacaact 240
ctttcaccct ctttcttctg tttgtctcac aaatccttga ctctttgctt tgcaatattg 300
ccacaggaca cacgaaacac aaaatgattc tataaccctc tgtcgacaca gttaaaacaa 360
gagtaagcta caaagctaca cattttgttt tgtggataca aattaattaa tcctcacaac 420
ctgagatttt tgataagaag aaatcttgat agtcaatgaa aatcgtatgg taacatagac 480
ttctccccaa ctctaatcca atacttgtaa ctttccttgt cttacggaca cagttagcct 540
cgtgctgtga ctattgacta gagaccagac tgttcctgga agtagttgac tagaggcctg 600
ttcttttcgc aaacgcgcga ctagcagcgg caactgaaaa ttacctcttt accatcagaa 660
atatagcgct ggtgaaataa ccgaaacttc ctttttcagt cgcagcggca aaacgcagta 720
actaaatccg acgctgaaaa tatcagtggc agcatcatcc tctttttcca tcgttgcggc 780
aagctgcgat aattaagttt actttcaaga gcgttcatct tgactccgtc aaagtgtgat 840
tttgttgccg cgaccgctag tcgcagcggc aatgaaaaga acaggcctta ggtatcaaaa 900
gtgtagatac acatttcaaa actggttttg tcacataaac tatttgtttt gaatacaagc 960
ttaatctaga gaatgacatt ataacactaa ttgggtaagg aaaataaaca ttaacaacat 1020
ttacagaaaa tatgtctcta ccgagcatca tatgccaaat ctggatccaa aaagacactt 1080
gcaaacacaa tcttttgagg tgattagttt ggatctttga tactcatttc cacaatattt 1140
tctcagtatt attttcctat ggagacaaaa acttaacgtc gttctctctg ttttggcaaa 1200
gcaaagatat ctttgccaac tggcactata ccttacctca aatcctcctt tataaagagc 1260
aaggactaca tctgtgcaac atatcctctc tttcatataa gttattacta gagaaatacg 1320
ccaaactttt tcaca 1335

<210> SEQ ID NO 112
<211> LENGTH: 521
<212> TYPE: DNA
<213> ORGANISM: Brassica napus

<400> SEQUENCE: 112
aacaagaagc aacaaagcct aaactattgt atgaatcaaa aaaaaaaaag aagaactacg 60
catatcatca gtttcaatga agtccgacga cgagtttatg tttgtatttt tatttcccat 120
attttctcca gccttagagc agcattatcg ataacaaact gctatagttt tttttaaaaa 180
attatgttag tattataatt atctaagtac attctagctt tctagtatta attgaatcaa 240
taataaagtg acaggtgcta tatgaggttt tagaccgcat acaaaaagtg tttaaattgg 300
gttcttgact taatatatcc tcaactcttt aattttggca taattaagct ttacttttat 360
tttggcataa taaatattaa actctttcaa aaatctgcct aaatcctaaa atttctattt 420
ttttggctaa aaagagcttt ggttaactta cattgtaacc tcgtcacgta tccattacgt 480

-continued ctttctctct ttttttctg aacttcacga aaactcaaat c 521

<210> SEQ ID NO 113
<211> LENGTH: 15776
<212> TYPE: DNA
<213> ORGANISM: Artificial sequence
<220> FEATURE:
<223> OTHER INFORMATION: Plasmid

<400> SEQUENCE: 113
gagcaaaagg ccagcaaaag gccaggaacc gtaaaaaggc cgcgttgctg gcgtttttcc 60
ataggctccg cccccctgac gagcatcaca aaaatcgacg ctcaagtcag aggtggcgaa 120
acccgacagg actataaaga taccaggcgt ttccccctgg aagctccctc gtgcgctctc 180
ctgttccgac cctgccgctt accggatacc tgtccgcctt tctcccttcg ggaagcgtgg 240
cgctttctca tagctcacgc tgtaggtatc tcagttcggt gtaggtcgtt cgctccaagc 300
tgggctgtgt gcacgaaccc cccgttcagc ccgaccgctg cgccttatcc ggtaactatc 360
gtcttgagtc caacccggta agacacgact tatcgccact ggcagcagcc actggtaaca 420
ggattagcag agcgaggtat gtaggcggtg ctacagagtt cttgaagtgg tggcctaact 480
acggctacac tagaaggaca gtatttggta tctgcgctct gctgaagcca gttaccttcg 540
gaaaaagagt tggtagctct tgatccggca aacaaaccac cgctggtagc ggtggttttt 600
ttgtttgcaa gcagcagatt acgcgcagaa aaaaaggatc tcaagaagat cctttgatct 660
tttctacggg gtccttcaac tcatcgatag tttggctgtg agcaattatg tgcttagtgc 720
atctaacgct tgagttaagc cgcgccgcga agcggcgtcg gcttgaacga atttctagct 780
agacattatt tgccaacgac cttcgtgatc tcgcccttga catagtggac aaattcttcg 840
agctggtcgg cccgggacgc gagacggtct tcttcttggc ccagataggc ttggcgcgct 900
tcgaggatca cgggctggta ttgcgccgga aggcgctcca tcgcccagtc ggcggcgaca 960
tccttcggcg cgatcttgcc ggtaaccgcc gagtaccaaa tccggctcag cgtaaggacc 1020
acattgcgct catcgcccgc ccaatccggc ggggagttcc acagggtcag cgtctcgttc 1080
agtgcttcga acagatcctg ttccggcacc gggtcgaaaa gttcctcggc cgcggggccg 1140
acgagggcca cgctatgctc ccgggccttg gtgagcagga tcgccagatc aatgtcgatg 1200
gtggccggtt caaagatacc cgccagaata tcattacgct gccattcgcc gaactggagt 1260
tcgcgtttgg ccggatagcg ccaggggatg atgtcatcgt gcaccacaat cgtcacctca 1320
accgcgcgca ggatttcgct ctcgccgggg gaggcggacg tttccagaag gtcgttgata 1380
agcgcgcggc gcgtggtctc gtcgagacgg acggtaacgg tgacaagcag gtcgatgtcc 1440
gaatggggct taaggccgcc gtcaacggcg ctaccataca gatgcacggc gaggagggtc 1500
ggttcgaggt ggcgctcgat gacacccacg acttccgaca gctgggtgga cacctcggcg 1560
atgaccgctt cacccatgat gtttaacttt gttttagggc gactgccctg ctgcgtaaca 1620
tcgttgctgc tccataacat caaacatcga cccacggcgt aacgcgcttg ctgcttggat 1680
gcccgaggca tagactgtac cccaaaaaaa cagtcataac aagccatgaa aaccgccact 1740
gcgttccatg aatattcaaa caaacacata cagcgcgact tatcatggat attgacatac 1800
aaatggacga acggataaac cttttcacgc ccttttaaat atccgattat tctaataaac 1860
gctcttttct cttaggttta cccgccaata tatcctgtca aacactgata gtttaaactg 1920
aaggcgggaa acgacaatct gatcactgat tagtaactaa ggcctttaat taatctagag 1980
gcgcgccggg ccccctgcag ggagctcggc cggccaattt aaattgatat cggtacatcg 2040

```
attacgccaa gctatcaact ttgtatagaa aagttgccat gattacgcca agcttggcca   2100
ctaaggccaa tttaaatcta ctaggccggc caaagtaggc gcctactacc ggtaattccc   2160
gggattagcg gccgctagtc tgtgcgcact tgtatcctgc aggtcaatcg tttaaacact   2220
gtacggaccg tggcctaata ggccggtacc caagtttgta caaaaaagca ggctccatga   2280
ttacgccaag cttggccact aaggccaatt taaatctact aggccggcct attcactact   2340
tatagagaac acgagcttga aaccttgtat gtatgcaaat gaatcatctt tcactaaagc   2400
ctgtatattg acttgtcgtg tacaagtgta gtaacaagat tacaagaatt gtaaaatgga   2460
ccaaacttgt ccaaagcttt cagttgcaga agagaagaga agacagttca taacatatat   2520
ataagtctta ataacaaaat gaaacaccaa actccaatcg cagacaactc tttcaccctc   2580
tttcttctgt ttgtctcaca aatccttgac tctttgcttt gcaatattgc cacaggacac   2640
acgaaacaca aaatgattct ataaccctct gtcgacacag ttaaaacaag agtaagctac   2700
aaagctacac attttgtttt gtggatacaa atttattaat cctcacaacc tgagattttt   2760
gataagaaga aatcttgata gtcaatgaaa atcgtatggt aacatagact tctccccaac   2820
tctaatccaa tacttgtaac tttccttgtc ttacggacac agttagcctc gtgctgtgac   2880
tattgactag agaccagact gttcctggaa gtagttgact agaggcctgt tcttttcgca   2940
aacgcgcgac tagcagcggc aactgaaaat tacctcttta ccatcagaaa tatagcgctg   3000
gtgaaataac cgaaacttcc tttttcagtc gcagcggcaa aacgcagtaa ctaaatccga   3060
cgctgaaaat atcagtggca gcatcatcct ctttttccat cgttgcggca agctgcgata   3120
attaagttta ctttcaagag cgttcatctt gactccgtca aagtgtgatt ttgttgccgc   3180
gaccgctagt cgcagcggca atgaaaagaa caggccttag gtatcaaaag tgtagataca   3240
catttcaaaa ctggttttgt cacataaact atttgttttg aatacaagct taatctagag   3300
aatgacatta taacactaat tgggtaagga aaataaacat taacaacatt tacagaaaat   3360
atgtctctac cgagcatcat atgccaaatc tggatccaaa aagacacttg caaacacaat   3420
cttttgaggt gattagtttg gatctttgat actcatttcc acaatatttt ctcagtatta   3480
ttttcctatg gagacaaaaa cttaacgtcg ttctctctgt tttggcaaag caaagatatc   3540
tttgccaact ggcactatac cttacctcaa atcctccttt ataaagagca aggactacat   3600
ctgtgcaaca tatcctctct ttcatataag ttattactag agaaatacgc caaacttttt   3660
cacaccgcgc cggggcccaa aatggtggac ctcaagcctg gagtgaagcg cctggtgagc   3720
tggaaggaga tccgcgagca cgcgacgccc gcgaccgcgt ggatcgtgat tcaccacaag   3780
gtctacgaca tctccaagtg ggactcgcac ccgggtggct ccgtgatgct cacgcaggcc   3840
ggcgaggacg ccacggacgc cttcgcggtc ttccacccgt cctcggcgct caagctgctc   3900
gagcagttct acgtcggcga cgtggacgaa acctccaagg ccgagatcga gggggagccg   3960
gcgagcgacg aggagcgcgc gcgccgcgag cgcatcaacg agttcatcgc gtcctaccgc   4020
cgtctgcgcg tcaaggtcaa gggcatgggg ctctacgacg ccagcgcgct ctactacgcg   4080
tggaagctcg tgagcacgtt cggcatcgcg gtgctctcga tggcgatctg cttcttcttc   4140
aacagtttcg ccatgtacat ggtcgccggc gtgattatgg ggctcttcta ccagcagtcc   4200
ggatggctgg cgcacgactt cttgcacaac caggtgtgcg agaaccgcac gctcggcaac   4260
cttatcggct gcctcgtggg caacgcctgg cagggcttca gcatgcagtg gtggaagaac   4320
aagcacaacc tgcaccacgc ggtgccgaac ctgcacagcg ccaaggacga gggcttcatc   4380
```

-continued ggcgacccgg acatcgacac catgccgctg ctggcgtggt ctaaggagat ggcgcgcaag 4440
gcgttcgagt cggcgcacgg cccgttcttc atccgcaacc aggcgttcct atacttcccg 4500
ctgctgctgc tcgcgcgcct gagctggctc gcgcagtcgt tcttctacgt gttcaccgag 4560
ttctcgttcg gcatcttcga caaggtcgag ttcgacggac cggagaaggc gggtctgatc 4620
gtgcactaca tctggcagct cgcgatcccg tacttctgca acatgagcct gtttgagggc 4680
gtggcatact tcctcatggg ccaggcgtcc tgcggcttgc tcctggcgct ggtgttcagt 4740
attggccaca acggcatgtc ggtgtacgag cgcgaaacca agccggactt ctggcagctg 4800
caggtgacca cgacgcgcaa catccgcgcg tcggtattca tggactggtt caccggtggc 4860
ttgaactacc agatcgacca tcacctgttc ccgctcgtgc cgcgccacaa cttgccaaag 4920
gtcaacgtgc tcatcaagtc gctatgcaag gagttcgaca tcccgttcca cgagaccggc 4980
ttctgggagg gcatctacga ggtcgtggac cacctggcgg acatcagcaa ggaatttatc 5040
accgagttcc cagcgatgta agttaactta attaataatt gattgctgct ttaatgagat 5100
atgcgagacg cctatgatcg catgatattt gctttcaatt ctgttgtgca cgttgtaaaa 5160
aacctgagca tgtgtagctc agatccttac cgccggtttc ggttcattct aatgaatata 5220
tcacccgtta ctatcgtatt tttatgaata atattctccg ttcaatttac tgattgtggc 5280
gcctactacc ggtaattccc gggattagcg gccgctagtc tgtgcgcact tgtatcctgc 5340
aggtcaatcg tttaaacact gtacggaccg tggcctaata ggccggtacc acccagcttt 5400
cttgtacaaa gtggccatga ttacgccaag ctctccaccg cggtggcggc cgctctagcc 5460
caagctttaa ggatgaccta cccattcttg agacaaatgt tacattttag tatcagagta 5520
aaatgtgtac ctataactca aattcgattg acatgtatcc attcaacata aaattaaacc 5580
agcctgcacc tgcatccaca tttcaagtat tttcaaaccg ttcggctcct atccaccggg 5640
tgtaacaaga cggattccga atttggaaga ttttgactca aattcccaat ttatattgac 5700
cgtgactaaa tcaactttaa cttctataat tctgattaag ctcccaattt atattcccaa 5760
cggcactacc tccaaaattt atagactctc atcccctttt aaaccaactt agtaaacgtt 5820 tttttttttaa ttttatgaag ttaagttttt accttgtttt taaaaagaat cgttcataag 5880
atgccatgcc agaacattag ctacacgtta cacatagcat gcagccgcgg agaattgttt 5940
ttcttcgcca cttgtcactc ccttcaaaca cctaagagct tctctctcac agcacacaca 6000
tacaatcaca tgcgtgcatg cattattaca cgtgatcgcc atgcaaatct cctttatagc 6060
ctataaatta actcatcggc ttcactcttt actcaaacca aaactcatca atacaaacaa 6120
gattaaaaac ataaggcgcg ccaattgact agtaggccta tcgattagga gaataacaat 6180
ggtgcgctcc tccaagaacg tcatcaagga gttcatgcgc ttcaaggtgc gcatggaggg 6240
caccgtgaac ggccacgagt tcgagatcga gggcgagggc gagggccgcc cctacgaggg 6300
ccacaacacc gtgaagctga aggtgaccaa gggcggcccc ctgcccttcg cctgggacat 6360
cctgtccccc cagttccagt acggctccaa ggtgtacgtg aagcaccccg ccgacatccc 6420
cgactacaag aagctgtcct tccccgaggg cttcaagtgg gagcgcgtga tgaacttcga 6480
ggacggcggc gtggtgaccg tgacccagga ctcctccctg caggacggct gcttcatcta 6540
caaggtgaag ttcatcggcg tgaacttccc ctccgacggc cccgtaatgc agaagaagac 6600
catgggctgg gaggcctcca ccgagcgcct gtaccccccgc gacggcgtgc tgaagggcga 6660
gatccacaag gccctgaagc tgaaggacgg cggccactac ctggtggagt tcaagtccat 6720
ctacatggcc aagaagcccg tgcagctgcc cggctactac tacgtggact ccaagctgga 6780
catcacctcc cacaacgagg actacaccat cgtggagcag tacgagcgca ccgagggccg 6840
ccaccacctg ttcctgctcg agtctagagg taccggttgt taacgttagc cggctacgta 6900
tactccggaa tattaatagg cctaggatgc atatggcggc cgcctgcagc tggcgccatc 6960
gattaattaa ggccgcctcg agcatgcatc tagagggccc gctagcgtta accctgcttt 7020
aatgagatat gcgagacgcc tatgatcgca tgatatttgc tttcaattct gttgtgcacg 7080
ttgtaaaaaa cctgagcatg tgtagctcag atccttaccg ccggtttcgg ttcattctaa 7140
tgaatatatc acccgttact atcgtatttt tatgaataat attctccgtt caatttactg 7200
attgtccgtc gagcatatgc tagaggatcc ccgggtaccc aactttatta tacatagttg 7260
ataattcact ggccggatgt accgaattcg cggccgcaag cttgtacact agtacgcgtc 7320
aattggcgat cgcggatctg agatgaaacc ggtgattatc agaacctttt atggtctttg 7380
tatgcatatg gtaaaaaaac ttagtttgca atttcctgtt tgttttggta atttgagttt 7440
cttttagttg ttgatctgcc tgctttttgg tttacgtcag actactactg ctgttgttgt 7500
ttggtttcct ttctttcatt ttataaataa ataatccggt tcggtttact ccttgtgact 7560
ggctcagttt ggttattgcg aaatgcgaat ggtaaattga gtaattgaaa ttcgttatta 7620
gggttctaag ctgttttaac agtcactggg ttaatatctc tcgaatcttg catggaaaat 7680
gctcttacca ttggttttta attgaaatgt gctcatatgg gccgtggttt ccaaattaaa 7740
taaaactacg atgtcatcga gaagtaaaat caactgtgtc cacattatca gttttgtgta 7800
tacgatgaaa tagggtaatt caaaatctag cttgatatgc cttttggttc attttaacct 7860
tctgtaaaca tttttcaga ttttgaacaa gtaaatccaa aaaaaaaaaa aaaaaatctc 7920
aactcaacac taaattattt taatgtataa aagatgctta aaacatttgg cttaaaagaa 7980
agaagctaaa aacatagaga actcttgtaa attgaagtat gaaaatatac tgaattgggt 8040
attatatgaa tttttctgat ttaggattca catgatccaa aaaggaaatc cagaagcact 8100
aatcagacat tggaagtagg aatatttcaa aaagtttttt ttttttaagt aagtgacaaa 8160
agcttttaaa aaatagaaaa gaaactagta ttaaagttgt aaatttaata aacaaaagaa 8220
attttttata ttttttcatt tctttttcca gcatgaggtt atgatggcag gatgtggatt 8280
tcattttttt cctttttgata gccttttaat tgatctatta taattgacga aaaaatatta 8340
gttaattata gatatatttt aggtagtatt agcaatttac acttccaaaa gactatgtaa 8400
gttgtaaata tgatgcgttg atctcttcat cattcaatgg ttagtcaaaa aaataaaagc 8460
ttaactagta aactaaagta gtcaaaaatt gtactttagt ttaaaatatt acatgaataa 8520
tccaaaacga catttatgtg aaacaaaaac aatatagatc cattaccctg ttatccctag 8580
aggggaaaat tcgaatccaa aaattacgga tatgaatata ggcatatccg tatccgaatt 8640
atccgtttga cagctagcaa cgattgtaca attgcttctt taaaaaagga agaaagaaag 8700
aaagaaaaga atcaacatca gcgttaacaa acggccccgt tacggcccaa acggtcatat 8760
agagtaacgg cgttaagcgt tgaaagactc ctatcgaaat acgtaaccgc aaacgtgtca 8820
tagtcagatc ccctcttcct tcaccgcctc aaacacaaaa ataatcttct acagcctata 8880
tatacaaccc ccccttctat ctctcctttc tcacaattca tcatctttct ttctctaccc 8940
ccaattttaa gaaatcctct cttctcctct tcattttcaa ggtaaatctc tctctctctc 9000
tctctctctg ttattccttg ttttaattag gtatgtatta ttgctagttt gttaatctgc 9060
ttatcttatg tatgccttat gtgaatatct ttatcttgtt catctcatcc gtttagaagc 9120

-continued

```
tataaatttg ttgatttgac tgtgtatcta cacgtggtta tgtttatatc taatcagata   9180
tgaatttctt catattgttg cgtttgtgtg taccaatccg aaatcgttga tttttttcat   9240
ttaatcgtgt agctaattgt acgtatacat atggatctac gtatcaattg ttcatctgtt   9300
tgtgtttgta tgtatacaga tctgaaaaca tcacttctct catctgattg tgttgttaca   9360
tacatagata tagatctgtt atatcatttt ttttattaat tgtgtatata tatatgtgca   9420
tagatctgga ttacatgatt gtgattattt acatgatttt gttatttacg tatgtatata   9480
tgtagatctg gactttttgg agttgttgac ttgattgtat ttgtgtgtgt atatgtgtgt   9540
tctgatcttg atatgttatg tatgtgcagc tgaaccatgg cggcggcaac aacaacaaca   9600
acaacatctt cttcgatctc cttctccacc aaaccatctc cttcctcctc caaatcacca   9660
ttaccaatct ccagattctc cctcccattc tccctaaacc ccaacaaatc atcctcctcc   9720
tcccgccgcc gcggtatcaa atccagctct ccctcctcca tctccgccgt gctcaacaca   9780
accaccaatg tcacaaccac tccctctcca accaaaccta ccaaacccga aacattcatc   9840
tcccgattcg ctccagatca accccgcaaa ggcgctgata tcctcgtcga agctttagaa   9900
cgtcaaggcg tagaaaccgt attcgcttac cctggaggta catcaatgga gattcaccaa   9960
gccttaaccc gctcttcctc aatccgtaac gtccttcctc gtcacgaaca aggaggtgta  10020
ttcgcagcag aaggatacgc tcgatcctca ggtaaaccag gtatctgtat agccacttca  10080
ggtcccggag ctacaaatct cgttagcgga ttagccgatg cgttgttaga tagtgttcct  10140
cttgtagcaa tcacaggaca agtccctcgt cgtatgattg gtacagatgc gtttcaagag  10200
actccgattg ttgaggtaac gcgttcgatt acgaagcata actatcttgt gatggatgtt  10260
gaagatatcc ctaggattat tgaggaagct ttctttttag ctacttctgg tagacctgga  10320
cctgttttgg ttgatgttcc taaagatatt caacaacagc ttgcgattcc taattgggaa  10380
caggctatga gattacctgg ttatatgtct aggatgccta aacctccgga agattctcat  10440
ttggagcaga ttgttaggtt gatttctgag tctaagaagc ctgtgttgta tgttggtggt  10500
ggttgtttga attctagcga tgaattgggt aggtttgttg agcttacggg gatccctgtt  10560
gcgagtacgt tgatggggct gggatcttat ccttgtgatg atgagttgtc gttacatatg  10620
cttggaatgc atgggactgt gtatgcaaat tacgctgtgg agcatagtga tttgttgttg  10680
gcgtttgggg taaggtttga tgatcgtgtc acgggtaagc ttgaggcttt tgctagtagg  10740
gctaagattg ttcatattga tattgactcg gctgagattg ggaagaataa gactcctcat  10800
gtgtctgtgt gtggtgatgt taagctggct ttgcaaggga tgaataaggt tcttgagaac  10860
cgagcggagg agcttaagct tgattttgga gtttggagga atgagttgaa cgtacagaaa  10920
cagaagtttc cgttgagctt taagacgttt ggggaagcta ttcctccaca gtatgcgatt  10980
aaggtccttg atgagttgac tgatggaaaa gccataataa gtactggtgt cgggcaacat  11040
caaatgtggg cggcgcagtt ctacaattac aagaaaccaa ggcagtggct atcatcagga  11100
ggccttggag ctatgggatt tggacttcct gctgcgattg gagcgtctgt tgctaaccct  11160
gatgcgatag ttgtggatat tgacggagat ggaagcttta taatgaatgt gcaagagcta  11220
gccactattc gtgtagagaa tcttccagtg aaggtacttt tattaaacaa ccagcatctt  11280
ggcatggtta tgcaatggga agatcggttc tacaaagcta accgagctca cacatttctc  11340
ggggatccgg ctcaggagga cgagatattc ccgaacatgt tgctgtttgc agcagcttgc  11400
gggattccag cggcgagggt gacaaagaaa gcagatctcc gagaagctat tcagacaatg  11460
ctggatacac caggacctta cctgttggat gtgatttgtc cgcaccaaga acatgtgttg  11520
```

ccgatgatcc cgaatggtgg cactttcaac gatgtcataa cggaaggaga tggccggatt 11580
aaatactgat agggataaca gggtaatctc gacgagatga aaccggtgat tatcagaacc 11640
ttttatggtc tttgtatgca tatggtaaaa aaacttagtt tgcaatttcc tgtttgtttt 11700
ggtaatttga gtttctttta gttgttgatc tgcctgcttt ttggtttacg tcagactact 11760
actgctgttg ttgtttggtt tcctttcttt cattttataa ataaataatc cggttcggtt 11820
tactccttgt gactggctca gtttggttat tgcgaaatgc gaatggtaaa ttgagtaatt 11880
gaaattcgtt attagggttc taagctgttt taacagtcac tgggttaata tctctcgaat 11940
cttgcatgga aaatgctctt accattggtt tttaattgaa atgtgctcat atgggccgtg 12000
gtttccaaat taaataaaac tacgatgtca tcgagaagta aaatcaactg tgtccacatt 12060
atcagttttg tgtatacgat gaaatagggt aattcaaaat ctagcttgat atgccttttg 12120
gttcatttta accttctgta aacatttttt cagattttga acaagtaaat ccaaaaaaaa 12180
aaaaaaaaaa tctcaactca acactaaatt attttaatgt ataaaagatg cttaaaacat 12240
ttggcttaaa agaaagaagc taaaaacata gagaactctt gtaaattgaa gtatgaaaat 12300
atactgaatt gggtattata tgaatttttc tgatttagga ttcacatgat ccaaaaagga 12360
aatccagaag cactaatcag acattggaag taggaatatt tcaaaaagtt tttttttttt 12420
aagtaagtga caaaagcttt taaaaaatag aaaagaaact agtattaaag ttgtaaattt 12480
aataaacaaa agaaattttt tatatttttt catttctttt tccagcatga ggttatgatg 12540
gcaggatgtg gatttcattt ttttcctttt gatagccttt taattgatct attataattg 12600
acgaaaaaat attagttaat tatagatata ttttaggtag tattagcaat ttacacttcc 12660
aaaagactat gtaagttgta aatatgatgc gttgatctct tcatcattca atggttagtc 12720
aaaaaaataa aagcttaact agtaaactaa agtagtcaaa aattgtactt tagtttaaaa 12780
tattacatga ataatccaaa acgacattta tgtgaaacaa aaacaatatg tcgaggcgat 12840
cgcagtactt aatcagtgat cagtaactaa attcagtaca ttaaagacgt ccgcaatgtg 12900
ttattaagtt gtctaagcgt caatttgttt acaccacaat atatcctgcc accagccagc 12960
caacagctcc ccgaccggca gctcggcaca aaatcactga tcatctaaaa aggtgatgtg 13020
tatttgagta aaacagcttg cgtcatgcgg tcgctgcgta tatgatgcga tgagtaaata 13080
aacaaatacg caaggggaac gcatgaaggt tatcgctgta cttaaccaga aaggcgggtc 13140
aggcaagacg accatcgcaa cccatctagc ccgcgccctg caactcgccg gggccgatgt 13200
tctgttagtc gattccgatc cccagggcag tgcccgcgat tgggcggccg tgcgggaaga 13260
tcaaccgcta accgttgtcg gcatcgaccg cccgacgatt gaccgcgacg tgaaggccat 13320
cggccggcgc gacttcgtag tgatcgacgg agcgccccag gcggcggact tggctgtgtc 13380
cgcgatcaag gcagccgact tcgtgctgat tccggtgcag ccaagccctt acgacatttg 13440
ggccaccgcc gacctggtgg agctggttaa gcagcgcatt gaggtcacgg atggaaggct 13500
acaagcggcc tttgtcgtgt cgcgggcgat caaaggcacg cgcatcggcg gtgaggttgc 13560
cgaggcgctg gccgggtacg agctgcccat tcttgagtcc cgtatcacgc agcgcgtgag 13620
ctacccaggc actgccgccg ccggcacaac cgttcttgaa tcagaacccg agggcgacgc 13680
tgcccgcgag gtccaggcgc tggccgctga aattaaatca aaactcattt gagttaatga 13740
ggtaaagaga aaatgagcaa aagcacaaac acgctaagtg ccggccgtcc gagcgcacgc 13800
agcagcaagg ctgcaacgtt ggccagcctg gcagacacgc cagccatgaa gcgggtcaac 13860

-continued

```
tttcagttgc cggcggagga tcacaccaag ctgaagatgt acgcggtacg ccaaggcaag  13920

accattaccg agctgctatc tgaatacatc gcgcagctac cagagtaaat gagcaaatga  13980

ataaatgagt agatgaattt tagcggctaa aggaggcggc atggaaaatc aagaacaacc  14040

aggcaccgac gccgtggaat gccccatgtg tggaggaacg ggcggttggc caggcgtaag  14100

cggctgggtt gtctgccggc cctgcaatgg cactggaacc cccaagcccg aggaatcggc  14160

gtgagcggtc gcaaaccatc cggcccggta caaatcggcg cggcgctggg tgatgacctg  14220

gtggagaagt tgaaggccgc gcaggccgcc cagcggcaac gcatcgaggc agaagcacgc  14280

cccggtgaat cgtggcaagg ggccgctgat cgaatccgca aagaatcccg gcaaccgccg  14340

gcagccggtg cgccgtcgat taggaagccg cccaagggcg acgagcaacc agattttttc  14400

gttccgatgc tctatgacgt gggcacccgc gatagtcgca gcatcatgga cgtggccgtt  14460

ttccgtctgt cgaagcgtga ccgacgagct ggcgaggtga tccgctacga gcttccagac  14520

gggcacgtag aggtttccgc aggccccgcc ggcatggcca gtgtgtggga ttacgacctg  14580

gtactgatgg cggtttccca tctaaccgaa tccatgaacc gataccggga agggaaggga  14640

gacaagcccg gccgcgtgtt ccgtccacac gttgcggacg tactcaagtt ctgccggcga  14700

gccgatggcg gaaagcagaa agacgacctg gtagaaacct gcattcggtt aaacaccacg  14760

cacgttgcca tgcagcgtac caagaaggcc aagaacggcc gcctggtgac ggtatccgag  14820

ggtgaagcct tgattagccg ctacaagatc gtaaagagcg aaaccgggcg gccggagtac  14880

atcgagatcg agcttgctga ttggatgtac cgcgagatca cagaaggcaa gaacccggac  14940

gtgctgacgg ttcaccccga ttactttttg atcgaccccg gcatcggccg ttttctctac  15000

cgcctggcac gccgcgccgc aggcaaggca gaagccagat ggttgttcaa gacgatctac  15060

gaacgcagtg gcagcgccgg agagttcaag aagttctgtt tcaccgtgcg caagctgatc  15120

gggtcaaatg acctgccgga gtacgatttg aaggaggagg cggggcaggc tggcccgatc  15180

ctagtcatgc gctaccgcaa cctgatcgag ggcgaagcat ccgccggttc ctaatgtacg  15240

gagcagatgc tagggcaaat tgccctagca ggggaaaaag gtcgaaaagg tctctttcct  15300

gtggatagca cgtacattgg gaacccaaag ccgtacattg ggaaccggaa cccgtacatt  15360

gggaacccaa agccgtacat tgggaaccgg tcacacatgt aagtgactga tataaaagag  15420

aaaaaaggcg atttttccgc ctaaaactct ttaaaactta ttaaaactct taaaacccgc  15480

ctggcctgtg cataactgtc tggccagcgc acagccgaag agctgcaaaa agcgcctacc  15540

cttcggtcgc tgcgctccct acgccccgcc gcttcgcgtc ggcctatcgc ggcctatgcg  15600

gtgtgaaata ccgcacagat gcgtaaggag aaaataccgc atcaggcgct cttccgcttc  15660

ctcgctcact gactcgctgc gctcggtcgt tcggctgcgg cgagcggtat cagctcactc  15720

aaaggcggta atacggttat ccacagaatc aggggataac gcaggaaaga acatgt      15776
```

<210> SEQ ID NO 114
<211> LENGTH: 303
<212> TYPE: DNA
<213> ORGANISM: Brassica napus

<400> SEQUENCE: 114

```
atggcatcaa actcaatgtc ttcttatgga tctggctcat ggactgttaa gcagaacaaa     60

gtctttgagc gtgctctagc aacctatgac caagacactc ctgaccgttg gtataatgtt    120

gctagagctg ttggtggaac aacacctgat gaagctaaga gacaatatga ccttctcgta    180

cgtgacatcg aaatcatcga taatgggcat gtgccattcc ctaactacac gactactgga    240
```

ggcagaacca aaggcaggct gcgtgatgag gaaaaaagga tgagaaacat gaagctgcag 300
taa 303

<210> SEQ ID NO 115
<211> LENGTH: 55
<212> TYPE: DNA
<213> ORGANISM: Artificial sequence
<220> FEATURE:
<223> OTHER INFORMATION: Primer

<400> SEQUENCE: 115
atacccggga tacctgcagg ttaggccggc catattcact acttatagag aacac 55

<210> SEQ ID NO 116
<211> LENGTH: 70
<212> TYPE: DNA
<213> ORGANISM: Artificial sequence
<220> FEATURE:
<223> OTHER INFORMATION: Primer

<400> SEQUENCE: 116
caatcaatta taggcctcgc atgctttaat taacgatcga gccatggtgt gaaaaagttt 60
ggcgtatttc 70

<210> SEQ ID NO 117
<211> LENGTH: 74
<212> TYPE: DNA
<213> ORGANISM: Artificial sequence
<220> FEATURE:
<223> OTHER INFORMATION: Primer

<400> SEQUENCE: 117
ccatggctcg atcgttaatt aaagcatgcg aggcctataa ttgattgaac aagaagcaac 60
aaagcctaaa ctat 74

<210> SEQ ID NO 118
<211> LENGTH: 61
<212> TYPE: DNA
<213> ORGANISM: Artificial sequence
<220> FEATURE:
<223> OTHER INFORMATION: Primer

<400> SEQUENCE: 118
taagcggccg caatcggacc gataccggta ggcgccgatt tgagttttcg tgaagttcag 60
a 61

<210> SEQ ID NO 119
<211> LENGTH: 1565
<212> TYPE: DNA
<213> ORGANISM: Brassica napus

<400> SEQUENCE: 119
gagcattatg cttccaagcg gactaagttc gttatggctc atgattccag gattgcttgc 60
ttcgctctca cgcaggatgg gcatctgttg gcgacggcta gctctaaggg gactctggtt 120
cggatcttta atactgttga tggcaccttg cgacaagagg taactagtca tcgaaagcct 180
ttctctttta gctgatttgg tggtttagta gtcactttct tgaggatgaa tgaattatta 240
tgttattatg ttaggaaatc tcaaatgtag ttttgatcct ttatagtaat aatattttgc 300
gagtttggag tccatgggtt cagtaatggc aaaacgtgtg tatgtgaatg tacaggttag 360
gaggggtgca gatagagcag agatttatag tctggctttc tcttcaaatg ctcagtggtt 420
agctgtctca agtgacaaag gaaccgtcca tgtctttggc ctcaaaggca actccggtgc 480
tcaggtgaaa gacacaccca gaattgcatc tgatcttact cgtacttcct catccccatc 540
ctcgtctctg tcgttattca aaggtatata ttatcaccat ttagcagtct cttggttcag 600
taagcataag tctttttgct ctattaggag tgctgcccaa gtatttcagc tcggagtggt 660
cggtggctca gttccggttg gttgaaggaa ctcaatacat agtcgccttt ggtcaccaga 720
agaacactgt tgttattctt ggcatggatg ggaggtaagc agaacaaaac ttgtcaactc 780
ttagtgcaat gtgcttcgac gagtctgaat tatatattct ttgttgtgtt tgaacagctt 840
ctacagatgc cagtttgatc cggtgaatgg gggagaaatg tctcagcttg agtatcacaa 900
ctgtctaaaa cctccttctg ttttctagat gcaatctatt ctcttaagtt ccttcaatct 960
tttatctctg ctctacttga gtggtgagag ttggtgcaat ggtgttaatg tatatagttt 1020
gtgtgtataa taattacgaa tggttcttat aatttccaaa aaccttttat cgctacccaa 1080
aacagactcg ggctcttcca atttgtgtct tccctagaca ttccactaaa ccaacttgtt 1140
ttgttgtgta agaacagttc agtcaacatt gttccggtca aaggacgaga gaccacgtga 1200
gctagcagct gagtgccacg tgaacgctca cggatcctca tgcgcatagt aacgatggca 1260
ggtaaaaaaa aatatcgtat aacgagtttc gaggcacgag gaaaaggaat cctatttcaa 1320
actgtcaaat ttcaacgacc agtctctgaa agaactgcaa agattcgact gcttgcgtaa 1380
cctaattgtt agatttcata tttctatata gttgttaaaa gtccaagaaa cagtaggacc 1440
atgttcatct tggcttggtt gtacaggaca aaagcatatg ttatatatat agaagcagta 1500
gcaaaatgag atcacagctc agtctctgac tcactctctc ttccgagtta cgaagttaga 1560
gtgaa 1565

<210> SEQ ID NO 120
<211> LENGTH: 16007
<212> TYPE: DNA
<213> ORGANISM: Artificial sequence
<220> FEATURE:
<223> OTHER INFORMATION: Plasmid

<400> SEQUENCE: 120
tcaagatcag aacacacata tacacacaca aatacaatca agtcaacaac tccaaaaagt 60
ccagatctac atatatacat acgtaaataa caaaatcatg taaataatca caatcatgta 120
atccagatct atgcacatat atatatacac aattaataaa aaaaatgata taacagatct 180
atatctatgt atgtaacaac acaatcagat gagagaagtg atgttttcag atctgtatac 240
atacaaacac aaacagatga acaattgata cgtagatcca tatgtatacg tacaattagc 300
tacacgatta aatgaaaaaa atcaacgatt tcggattggt acacacaaac gcaacaatat 360
gaagaaattc atatctgatt agatataaac ataaccacgt gtagatacac agtcaaatca 420
acaaatttat agcttctaaa cggatgagat gaacaagata aagatattca cataaggcat 480
acataagata agcagattaa caaactagca ataatacata cctaattaaa acaaggaata 540
acagagagag agagagagag agagatttac cttgaaaatg aagaggagaa gagaggattt 600
cttaaaattg ggggtagaga aagaaagatg atgaattgtg agaaaggaga gatagaaggg 660
ggggttgtat atataggctg tagaagatta tttttgtgtt tgaggcggtg aaggaagagg 720
ggatctgact atgacacgtt tgcggttacg tatttcgata ggagtctttc aacgcttaac 780
gccgttactc tatatgaccg tttgggccgt aacggggccg tttgttaacg ctgatgttga 840

```
ttcttttctt tctttctttc ttcctttttt aaagaagcaa ttgtacaatc gttgctagct    900
gtcaaacgga taattcggat acggatatgc ctatattcat atccgtaatt tttggattcg    960
aattttcccc tctagggata acagggtaat ggatctatat tgtttttgtt tcacataaat   1020
gtcgttttgg attattcatg taatatttta aactaaagta caatttttga ctactttagt   1080
ttactagtta agcttttatt tttttgacta accattgaat gatgaagaga tcaacgcatc   1140
atatttacaa cttacatagt cttttggaag tgtaaattgc taatactacc taaaatatat   1200
ctataattaa ctaatatttt ttcgtcaatt ataatagatc aattaaaagg ctatcaaaag   1260
gaaaaaaatg aaatccacat cctgccatca taacctcatg ctggaaaaag aaatgaaaaa   1320
atataaaaaa tttcttttgt ttattaaatt tacaacttta atactagttt cttttctatt   1380
ttttaaaagc ttttgtcact tacttaaaaa aaaaaaactt tttgaaatat tcctacttcc   1440
aatgtctgat tagtgcttct ggatttcctt tttggatcat gtgaatccta aatcagaaaa   1500
attcatataa tacccaattc agtatatttt catacttcaa tttacaagag ttctctatgt   1560
ttttagcttc tttcttttaa gccaaatgtt ttaagcatct tttatacatt aaaataattt   1620
agtgttgagt tgagattttt tttttttttt tttggattta cttgttcaaa atctgaaaaa   1680
atgtttacag aaggttaaaa tgaaccaaaa ggcatatcaa gctagatttt gaattaccct   1740
atttcatcgt atacacaaaa ctgataatgt ggacacagtt gattttactt ctcgatgaca   1800
tcgtagtttt atttaatttg gaaaccacgg cccatatgag cacatttcaa ttaaaaacca   1860
atggtaagag cattttccat gcaagattcg agagatatta acccagtgac tgttaaaaca   1920
gcttagaacc ctaataacga atttcaatta ctcaatttac cattcgcatt tcgcaataac   1980
caaactgagc cagtcacaag gagtaaaccg aaccggatta tttatttata aaatgaaaga   2040
aaggaaacca aacaacaaca gcagtagtag tctgacgtaa accaaaaagc aggcagatca   2100
acaactaaaa gaaactcaaa ttaccaaaac aaacaggaaa ttgcaaacta agttttttta   2160
ccatatgcat acaaagacca taaaaggttc tgataatcac cggtttcatc tcagatccgc   2220
gatcgccaat tgacgcgtac tagtgtacaa gcttgcggcc gcgaattcgg tacatccggc   2280
cagtgaatta tcaactatgt ataataaagt tgggtacccg gggatcctct agcatatgct   2340
cgacggacaa tcagtaaatt gaacggagaa tattattcat aaaaatacga tagtaacggg   2400
tgatatattc attagaatga accgaaaccg gcggtaagga tctgagctac acatgctcag   2460
gtttttttaca acgtgcacaa cagaattgaa agcaaatatc atgcgatcat aggcgtctcg   2520
catatctcat taaagcaggg ttaacgctag cgggccctct agatgcatgc tcgaggcggc   2580
cttaattaat cgatggcgcc agctgcaggc ggccgccata tgcatcctag gcctattaat   2640
attccggagt atacgtagcc ggctaacgtt aacaaccggt acctctagac tcgagcagga   2700
acaggtggtg gcggccctcg gtgcgctcgt actgctccac gatggtgtag tcctcgttgt   2760
gggaggtgat gtccagcttg gagtccacgt agtagtagcc gggcagctgc acgggcttct   2820
tggccatgta gatggacttg aactccacca ggtagtggcc gccgtccttc agcttcaggg   2880
ccttgtggat ctcgcccttc agcacgccgt cgcgggggta caggcgctcg gtggaggcct   2940
cccagcccat ggtcttcttc tgcattacgg ggccgtcgga ggggaagttc acgccgatga   3000
acttcacctt gtagatgaag cagccgtcct gcagggagga gtcctgggtc acggtcacca   3060
cgccgccgtc ctcgaagttc atcacgcgct cccacttgaa gccctcgggg aaggacagct   3120
tcttgtagtc ggggatgtcg gcggggtgct tcacgtacac cttggagccg tactggaact   3180
```

-continued

```
gggggggacag gatgtcccag gcgaagggca gggggccgcc cttggtcacc ttcagcttca   3240
cggtgttgtg gccctcgtag gggcggccct cgccctcgcc ctcgatctcg aactcgtggc   3300
cgttcacggt gccctccatg cgcaccttga agcgcatgaa ctccttgatg acgttcttgg   3360
aggagcgcac cattgttatt ctcctaatcg ataggcctac tagtcaattg gcgcgcctta   3420
tgtttttaat cttgtttgta ttgatgagtt ttggtttgag taaagagtga agccgatgag   3480
ttaatttata ggctataaag gagatttgca tggcgatcac gtgtaataat gcatgcacgc   3540
atgtgattgt atgtgtgtgc tgtgagagag aagctcttag gtgtttgaag ggagtgacaa   3600
gtggcgaaga aaaacaattc tccgcggctg catgctatgt gtaacgtgta gctaatgttc   3660
tggcatggca tcttatgaac gattcttttt aaaaacaagg taaaaactta acttcataaa   3720
attaaaaaaa aaacgtttac taagttggtt taaaagggga tgagagtcta taaattttgg   3780
aggtagtgcc gttgggaata taaattggga gcttaatcag aattatagaa gttaaagttg   3840
atttagtcac ggtcaatata aattgggaat ttgagtcaaa atcttccaaa ttcggaatcc   3900
gtcttgttac acccggtgga taggagccga acggtttgaa aatacttgaa atgtggatgc   3960
aggtgcaggc tggtttaatt ttatgttgaa tggatacatg tcaatcgaat ttgagttata   4020
ggtacacatt ttactctgat actaaaatgt aacatttgtc tcaagaatgg gtaggtcatc   4080
cttaaagctt gggctagagc ggccgccacc gcggtggaga gcttggcgta atcatggcca   4140
ctttgtacaa gaaagctggg tggtaccggc ctattaggcc acggtccgta cagtgtttaa   4200
acgattgacc tgcaggatac aagtgcgcac agactagcgg ccgctaatcc cgggaattac   4260
cggtagtagg cgccacaatc agtaaattga acggagaata ttattcataa aaatacgata   4320
gtaacgggtg atatattcat tagaatgaac cgaaaccggc ggtaaggatc tgagctacac   4380
atgctcaggt tttttacaac gtgcacaaca gaattgaaag caaatatcat gcgatcatag   4440
gcgtctcgca tatctcatta aagcagcaat caattattaa ttaagttaac ttacatcgct   4500
gggaactcgg tgataaattc cttgctgatg tccgccaggt ggtccacgac ctcgtagatg   4560
ccctcccaga agccggtctc gtggaacggg atgtcgaact ccttgcatag cgacttgatg   4620
agcacgttga cctttggcaa gttgtggcgc ggcacgagcg ggaacaggtg atggtcgatc   4680
tggtagttca agccaccggt gaaccagtcc atgaataccg acgcgcggat gttgcgcgtc   4740
gtggtcacct gcagctgcca gaagtccggc ttggtttcgc gctcgtacac cgacatgccg   4800
ttgtggccaa tactgaacac cagcgccagg agcaagccgc aggacgcctg gcccatgagg   4860
aagtatgcca cgccctcaaa caggctcatg ttgcagaagt acgggatcgc gagctgccag   4920
atgtagtgca cgatcagacc cgccttctcc ggtccgtcga actcgacctt gtcgaagatg   4980
ccgaacgaga actcggtgaa cacgtagaag aacgactgcg cgagccagct caggcgcgcg   5040
agcagcagca gcgggaagta taggaacgcc tggttgcgga tgaagaacgg gccgtgcgcc   5100
gactcgaacg ccttgcgcgc catctcctta gaccacgcca gcagcggcat ggtgtcgatg   5160
tccgggtcgc cgatgaagcc ctcgtccttg gcgctgtgca ggttcggcac cgcgtggtgc   5220
aggttgtgct tgttcttcca ccactgcatg ctgaagccct gccaggcgtt gcccacgagg   5280
cagccgataa ggttgccgag cgtgcggttc tcgcacacct ggttgtgcaa gaagtcgtgc   5340
gccagccatc cggactgctg gtagaagagc cccataatca cgccggcgac catgtacatg   5400
gcgaaactgt tgaagaagaa gcagatcgcc atcgagagca ccgcgatgcc gaacgtgctc   5460
acgagcttcc acgcgtagta gagcgcgctg gcgtcgtaga gccccatgcc cttgaccttg   5520
acgcgcagac ggcggtagga cgcgatgaac tcgttgatgc gctcgcggcg cgcgcgctcc   5580
```

-continued

```
tcgtcgctcg ccggctcccc ctcgatctcg gccttggagg tttcgtccac gtcgccgacg   5640
tagaactgct cgagcagctt gagcgccgag gacgggtgga agaccgcgaa ggcgtccgtg   5700
gcgtcctcgc cggcctgcgt gagcatcacg gagccacccg ggtgcgagtc ccacttggag   5760
atgtcgtaga ccttgtggtg aatcacgatc cacgcggtcg cgggcgtcgc gtgctcgcgg   5820
atctccttcc agctcaccag gcgcttcact ccaggcttga ggtccaccat tttgggcccc   5880
ggcgcgcctt cactctaact tcgtaactcg gaagagagag tgagtcagag actgagctgt   5940
gatctcattt tgctactgct tctatatata taacatatgc ttttgtcctg tacaaccaag   6000
ccaagatgaa catggtccta ctgtttcttg gacttttaac aactatatag aaatatgaaa   6060
tctaacaatt aggttacgca agcagtcgaa tctttgcagt tctttcagag actggtcgtt   6120
gaaatttgac agtttgaaat aggattcctt ttcctcgtgc ctcgaaactc gttatacgat   6180
attttttttt acctgccatc gttactatgc gcatgaggat ccgtgagcgt tcacgtggca   6240
ctcagctgct agctcacgtg gtctctcgtc ctttgaccgg aacaatgttg actgaactgt   6300
tcttacacaa caaaacaagt tggtttagtg gaatgtctag ggaagacaca aattgaagag   6360
ccccgagtct gttttgggta gcgataaaag gtttttggaa attataagaa ccattcgtaa   6420
ttattataca cacaaactat atacattaac accattgcac caactctcac cactcaagta   6480
gagcagagat aaaagattga aggaacttaa gagaatagat tgcatctaga aaacagaagg   6540
aggttttaga cagttgtgat actcaagctg agacatttct cccccattca ccggatcaaa   6600
ctggcatctg tagaagctgt tcaaacacaa caaagaatat ataattcaga ctcgtcgaag   6660
cacattgcac taagagttga caagttttgt tctgcttacc tcccatccat gccaagaata   6720
acaacagtgt tcttctggtg accaaaggcg actatgtatt gagttccttc aaccaaccgg   6780
aactgagcca ccgaccactc cgagctgaaa tacttgggca gcactcctaa tagagcaaaa   6840
agacttatgc ttactgaacc aagagactgc taaatggtga taatatatac ctttgaataa   6900
cgacagagac gaggatgggg atgaggaagt acgagtaaga tcagatgcaa ttctgggtgt   6960
gtctttcacc tgagcaccgg agttgccttt gaggccaaag acatggacgg ttcctttgtc   7020
acttgagaca gctaaccact gagcatttga agagaaagcc agactataaa tctctgctct   7080
atctgcaccc ctcctaacct gtacattcac atacacacgt tttgccatta ctgaacccat   7140
ggactccaaa ctcgcaaaat attattacta taaaggatca aaactacatt tgagatttcc   7200
taacataata acataataat tcattcatcc tcaagaaagt gactactaaa ccaccaaatc   7260
agctaaaaga gaaaggcttt cgatgactag ttacctcttg tcgcaaggtg ccatcaacag   7320
tattaaagat ccgaaccaga gtccccttag agctagccgt cgccaacaga tgcccatcct   7380
gcgtgagagc gaagcaagca atcctggaat catgagccat aacgaactta gtccgcttgg   7440
aagcataatg ctcggccggc ctagtagatt taaattggcc ttagtggcca agcttggcgt   7500
aatcatggag cctgcttttt tgtacaaact tgggtaccgg cctattaggc cacggtccgt   7560
acagtgttta aacgattgac ctgcaggata caagtgcgca cagactagcg gccgctaatc   7620
ccgggaatta ccggtagtag gcgcctactt tggccggcct agtagattta aattggcctt   7680
agtggccaag cttggcgtaa tcatggcaac ttttctatac aaagttgata gcttggcgta   7740
atcgatgtac cgatatcaat ttaaattggc cggccgagct ccctgcaggg ggcccggcgc   7800
gcctctagat taattaaagg ccttagttac taatcagtga tcagattgtc gtttcccgcc   7860
ttcagtttaa actatcagtg tttgacagga tatattggcg ggtaaaccta agagaaaaga   7920
```

-continued

```
gcgtttatta gaataatcgg atatttaaaa gggcgtgaaa aggtttatcc gttcgtccat   7980
ttgtatgtca atatccatga taagtcgcgc tgtatgtgtt tgtttgaata ttcatggaac   8040
gcagtggcgg ttttcatggc ttgttatgac tgttttttttg gggtacagtc tatgcctcgg   8100
gcatccaagc agcaagcgcg ttacgccgtg ggtcgatgtt tgatgttatg gagcagcaac   8160
gatgttacgc agcagggcag tcgccctaaa acaaagttaa acatcatggg tgaagcggtc   8220
atcgccgagg tgtccaccca gctgtcggaa gtcgtgggtg tcatcgagcg ccacctcgaa   8280
ccgaccctcc tcgccgtgca tctgtatggt agcgccgttg acggcggcct taagccccat   8340
tcggacatcg acctgcttgt caccgttacc gtccgtctcg acgagaccac gcgccgcgcg   8400
cttatcaacg accttctgga aacgtccgcc tcccccggcg agagcgaaat cctgcgcgcg   8460
gttgaggtga cgattgtggt gcacgatgac atcatcccct ggcgctatcc ggccaaacgc   8520
gaactccagt tcggcgaatg gcagcgtaat gatattctgg cgggtatctt tgaaccggcc   8580
accatcgaca ttgatctggc gatcctgctc accaaggccc gggagcatag cgtggccctc   8640
gtcggccccg cggccgagga acttttcgac ccggtgccgg aacaggatct gttcgaagca   8700
ctgaacgaga cgctgaccct gtggaactcc ccgccggatt gggcgggcga tgagcgcaat   8760
gtggtcctta cgctgagccg gatttggtac tcggcggtta ccggcaagat cgcgccgaag   8820
gatgtcgccg ccgactgggc gatggagcgc cttccggcgc aataccagcc cgtgatcctc   8880
gaagcgcgcc aagcctatct gggccaagaa gaagaccgtc tcgcgtcccg ggccgaccag   8940
ctcgaagaat ttgtccacta tgtcaagggc gagatcacga aggtcgttgg caaataatgt   9000
ctagctagaa attcgttcaa gccgacgccg cttcgcggcg cggcttaact caagcgttag   9060
atgcactaag cacataattg ctcacagcca aactatcgat gagttgaagg accccgtaga   9120
aaagatcaaa ggatcttctt gagatccttt ttttctgcgc gtaatctgct gcttgcaaac   9180
aaaaaaacca ccgctaccag cggtggtttg tttgccggat caagagctac caactctttt   9240
tccgaaggta actggcttca gcagagcgca gataccaaat actgtccttc tagtgtagcc   9300
gtagttaggc caccacttca agaactctgt agcaccgcct acatacctcg ctctgctaat   9360
cctgttacca gtggctgctg ccagtggcga taagtcgtgt cttaccgggt tggactcaag   9420
acgatagtta ccggataagg cgcagcggtc gggctgaacg gggggttcgt gcacacagcc   9480
cagcttggag cgaacgacct acaccgaact gagataccta cagcgtgagc tatgagaaag   9540
cgccacgctt cccgaaggga gaaaggcgga caggtatccg gtaagcggca gggtcggaac   9600
aggagagcgc acgagggagc ttccaggggg aaacgcctgg tatctttata gtcctgtcgg   9660
gtttcgccac ctctgacttg agcgtcgatt tttgtgatgc tcgtcagggg ggcggagcct   9720
atggaaaaac gccagcaacg cggccttttt acggttcctg gccttttgct ggccttttgc   9780
tcacatgttc tttcctgcgt tatcccctga ttctgtggat aaccgtatta ccgcctttga   9840
gtgagctgat accgctcgcc gcagccgaac gaccgagcgc agcgagtcag tgagcgagga   9900
agcggaagag cgcctgatgc ggtattttct ccttacgcat ctgtgcggta tttcacaccg   9960
cataggccgc gataggccga cgcgaagcgg cggggcgtag ggagcgcagc gaccgaaggg   10020
taggcgcttt ttgcagctct tcggctgtgc gctggccaga cagttatgca caggccaggc   10080
gggttttaag agttttaata agttttaaag agttttaggc ggaaaaatcg cctttttttct   10140
cttttatatc agtcacttac atgtgtgacc ggttcccaat gtacggcttt gggttcccaa   10200
tgtacgggtt ccggttccca atgtacggct ttgggttccc aatgtacgtg ctatccacag   10260
gaaagagacc ttttcgacct tttcccctg ctagggcaat ttgccctagc atctgctccg   10320
```

tacattagga accggcggat gcttcgccct cgatcaggtt gcggtagcgc atgactagga 10380
tcgggccagc ctgccccgcc tcctccttca aatcgtactc cggcaggtca tttgacccga 10440
tcagcttgcg cacggtgaaa cagaacttct tgaactctcc ggcgctgcca ctgcgttcgt 10500
agatcgtctt gaacaaccat ctggcttctg ccttgcctgc ggcgcggcgt gccaggcggt 10560
agagaaaacg gccgatgccg gggtcgatca aaaagtaatc ggggtgaacc gtcagcacgt 10620
ccgggttctt gccttctgtg atctcgcggt acatccaatc agcaagctcg atctcgatgt 10680
actccggccg cccggtttcg ctctttacga tcttgtagcg gctaatcaag gcttcaccct 10740
cggataccgt caccaggcgg ccgttcttgg ccttcttggt acgctgcatg gcaacgtgcg 10800
tggtgtttaa ccgaatgcag gtttctacca ggtcgtcttt ctgctttccg ccatcggctc 10860
gccggcagaa cttgagtacg tccgcaacgt gtggacggaa cacgcggccg ggcttgtctc 10920
ccttcccttc ccggtatcgg ttcatggatt cggttagatg ggaaaccgcc atcagtacca 10980
ggtcgtaatc ccacacactg gccatgccgg cggggcctgc ggaaacctct acgtgcccgt 11040
ctggaagctc gtagcggatc acctcgccag ctcgtcggtc acgcttcgac agacggaaaa 11100
cggccacgtc catgatgctg cgactatcgc gggtgcccac gtcatagagc atcggaacga 11160
aaaaatctgg ttgctcgtcg cccttgggcg gcttcctaat cgacggcgca ccggctgccg 11220
gcggttgccg ggattctttg cggattcgat cagcggcccc ttgccacgat tcaccggggc 11280
gtgcttctgc ctcgatgcgt tgccgctggg cggcctgcgc ggccttcaac ttctccacca 11340
ggtcatcacc cagcgccgcg ccgatttgta ccgggccgga tggtttgcga ccgctcacgc 11400
cgattcctcg ggcttggggg ttccagtgcc attgcagggc cggcagacaa cccagccgct 11460
tacgcctggc caaccgcccg ttcctccaca catggggcat tccacggcgt cggtgcctgg 11520
ttgttcttga ttttccatgc cgcctccttt agccgctaaa attcatctac tcatttattc 11580
atttgctcat ttactctggt agctgcgcga tgtattcaga tagcagctcg gtaatggtct 11640
tgccttggcg taccgcgtac atcttcagct tggtgtgatc ctccgccggc aactgaaagt 11700
tgacccgctt catggctggc gtgtctgcca ggctggccaa cgttgcagcc ttgctgctgc 11760
gtgcgctcgg acggccggca cttagcgtgt ttgtgctttt gctcattttc tctttacctc 11820
attaactcaa atgagttttg atttaatttc agcggccagc gcctggacct cgcgggcagc 11880
gtcgccctcg ggttctgatt caagaacggt tgtgccggcg gcggcagtgc ctgggtagct 11940
cacgcgctgc gtgatacggg actcaagaat gggcagctcg tacccggcca gcgcctcggc 12000
aacctcaccg ccgatgcgcg tgcctttgat cgcccgcgac acgacaaagg ccgcttgtag 12060
ccttccatcc gtgacctcaa tgcgctgctt aaccagctcc accaggtcgg cggtggccca 12120
aatgtcgtaa gggcttggct gcaccggaat cagcacgaag tcggctgcct tgatcgcgga 12180
cacagccaag tccgccgcct ggggcgctcc gtcgatcact acgaagtcgc gccggccgat 12240
ggccttcacg tcgcggtcaa tcgtcgggcg gtcgatgccg acaacggtta gcggttgatc 12300
ttcccgcacg gccgcccaat cgcgggcact gccctgggga tcggaatcga ctaacagaac 12360
atcggccccg gcgagttgca gggcgcgggc tagatgggtt gcgatggtcg tcttgcctga 12420
cccgcctttc tggttaagta cagcgataac cttcatgcgt tccccttgcg tatttgttta 12480
tttactcatc gcatcatata cgcagcgacc gcatgacgca agctgtttta ctcaaataca 12540
catcaccttt ttagatgatc agtgattttg tgccgagctg ccggtcgggg agctgttggc 12600
tggctggtgg caggatatat tgtggtgtaa acaaattgac gcttagacaa cttaataaca 12660

-continued

```
cattgcggac gtctttaatg tactgaattt agttactgat cactgattaa gtactgcgat  12720
cgcctcgaca tattgttttt gtttcacata aatgtcgttt tggattattc atgtaatatt  12780
ttaaactaaa gtacaatttt tgactacttt agtttactag ttaagctttt atttttttga  12840
ctaaccattg aatgatgaag agatcaacgc atcatattta caacttacat agtcttttgg  12900
aagtgtaaat tgctaatact acctaaaata tatctataat taactaatat tttttcgtca  12960
attataatag atcaattaaa aggctatcaa aaggaaaaaa atgaaatcca catcctgcca  13020
tcataacctc atgctggaaa aagaaatgaa aaaatataaa aaatttcttt tgtttattaa  13080
atttacaact ttaatactag tttcttttct attttttaaa agcttttgtc acttacttaa  13140
aaaaaaaaaa ctttttgaaa tattcctact tccaatgtct gattagtgct tctggatttc  13200
ctttttggat catgtgaatc ctaaatcaga aaaattcata taataccca ttcagtatat  13260
tttcatactt caatttacaa gagttctcta tgtttttagc ttctttcttt taagccaaat  13320
gttttaagca tcttttatac attaaaataa tttagtgttg agttgagatt tttttttttt  13380
tttttggat ttacttgttc aaaatctgaa aaaatgttta cagaaggtta aaatgaacca  13440
aaaggcatat caagctagat tttgaattac cctatttcat cgtatacaca aaactgataa  13500
tgtggacaca gttgatttta cttctcgatg acatcgtagt tttatttaat ttggaaacca  13560
cggcccatat gagcacattt caattaaaaa ccaatggtaa gagcattttc catgcaagat  13620
tcgagagata ttaacccagt gactgttaaa acagcttaga accctaataa cgaatttcaa  13680
ttactcaatt taccattcgc atttcgcaat aaccaaactg agccagtcac aaggagtaaa  13740
ccgaaccgga ttatttattt ataaaatgaa agaaaggaaa ccaaacaaca acagcagtag  13800
tagtctgacg taaaccaaaa agcaggcaga tcaacaacta aaagaaactc aaattaccaa  13860
aacaaacagg aaattgcaaa ctaagttttt ttaccatatg catacaaaga ccataaaagg  13920
ttctgataat caccggtttc atctcgtcga gattaccctg ttatccctat cagtatttaa  13980
tccggccatc tccttccgtt atgacatcgt tgaaagtgcc accattcggg atcatcggca  14040
acacatgttc ttggtgcgga caaatcacat ccaacaggta aggtcctggt gtatccagca  14100
ttgtctgaat agcttctcgg agatctgctt tctttgtcac cctcgccgct ggaatcccgc  14160
aagctgctgc aaacagcaac atgttcggga atatctcgtc ctcctgagcc ggatccccga  14220
gaaatgtgtg agctcggtta gctttgtaga accgatcttc ccattgcata accatgccaa  14280
gatgctggtt gtttaataaa agtaccttca ctggaagatt ctctacacga atagtggcta  14340
gctcttgcac attcattata aagcttccat ctccgtcaat atccacaact atcgcatcag  14400
ggttagcaac agacgctcca atcgcagcag gaagtccaaa tcccatagct ccaaggcctc  14460
ctgatgatag ccactgcctt ggtttcttgt aattgtagaa ctgcgccgcc cacatttgat  14520
gttgcccgac accagtactt attatggctt ttccatcagt caactcatca aggaccttaa  14580
tcgcatactg tggaggaata gcttccccaa acgtcttaaa gctcaacgga aacttctgtt  14640
tctgtacgtt caactcattc ctccaaactc caaaatcaag cttaagctcc tccgctcggt  14700
tctcaagaac cttattcatc ccttgcaaag ccagcttaac atcaccacac acagacacat  14760
gaggagtctt attcttccca atctcagccg agtcaatatc aatatgaaca atcttagccc  14820
tactagcaaa agcctcaagc ttacccgtga cacgatcatc aaaccttacc ccaaacgcca  14880
acaacaaatc actatgctcc acagcgtaat ttgcatacac agtcccatgc attccaagca  14940
tatgtaacga caactcatca tcacaaggat aagatcccag ccccatcaac gtactcgcaa  15000
cagggatccc cgtaagctca acaaacctac ccaattcatc gctagaattc aaacaaccac  15060
```

caccaacata caacacaggc ttcttagact cagaaatcaa cctaacaatc tgctccaaat 15120
gagaatcttc cggaggttta ggcatcctag acatataacc aggtaatctc atagcctgtt 15180
cccaattagg aatcgcaagc tgttgttgaa tatctttagg aacatcaacc aaaacaggtc 15240
caggtctacc agaagtagct aaaaagaaag cttcctcaat aatcctaggg atatcttcaa 15300
catccatcac aagatagtta tgcttcgtaa tcgaacgcgt tacctcaaca atcggagtct 15360
cttgaaacgc atctgtacca atcatacgac gagggacttg tcctgtgatt gctacaagag 15420
gaacactatc taacaacgca tcggctaatc cgctaacgag atttgtagct ccgggacctg 15480
aagtggctat acagatacct ggtttacctg aggatcgagc gtatccttct gctgcgaata 15540
cacctccttg ttcgtgacga ggaaggacgt tacggattga ggaagagcgg gttaaggctt 15600
ggtgaatctc cattgatgta cctccagggt aagcgaatac ggtttctacg ccttgacgtt 15660
ctaaagcttc gacgaggata tcagcgcctt tgcggggttg atctggagcg aatcgggaga 15720
tgaatgtttc gggtttggta ggtttggttg gagagggagt ggttgtgaca ttggtggttg 15780
tgttgagcac ggcggagatg gaggagggag agctggattt gataccgcgg cggcgggagg 15840
aggaggatga tttgttgggg tttagggaga atgggaggga gaatctggag attggtaatg 15900
gtgatttgga ggaggaagga gatggtttgg tggagaagga gatcgaagaa gatgttgttg 15960
ttgttgttgt tgccgccgcc atggttcagc tgcacataca taacata 16007

<210> SEQ ID NO 121
<211> LENGTH: 660
<212> TYPE: DNA
<213> ORGANISM: Brassica napus

<400> SEQUENCE: 121
atggcgatga aggtatatgg aaatgggatg tcagtgtgcg tggcacgtgt gcttctatgc 60
cttcacgaga aggagactga gttcgagctt gtccccgtcg atctctttgc ttgccaccac 120
aagctccctt ctttcctctc catgaacccc tttggccaag ttccagttct acaagacgac 180
gaccttaccc tttttgagtc gagggcaatc acggcatata tagcagagaa acacaaagac 240
aaaggaacgg atctgacgag acatgcagac gctaaagaag cagccattgt gaagctgtgg 300
tcggaagtgg agtcccacca cttcaacccc gcgatctccg ccgtcatcca ccagcttata 360
gttgtgccgc ttcaaggcaa gactcctgat gcagccatcg tggaggagaa tctggagaag 420
ttagggaaag tgctcgatgt gtacgaagag aagctcggga agacaaaata cttggccgga 480
gattcttaca cactcgcgga tctccaccac gttccttaca cttactactt catgaagacg 540
ggtcatgctg gtttggtcaa cgaccgtcct aatgtcaagg cgtggtggga agacctttgt 600
tctcgtccgg ctttccttaa agtctctcct ggcttgaccg ttgctccggc aacgaactga 660

<210> SEQ ID NO 122
<211> LENGTH: 55
<212> TYPE: DNA
<213> ORGANISM: Artificial sequence
<220> FEATURE:
<223> OTHER INFORMATION: Primer

<400> SEQUENCE: 122
atacccggga tacctgcagg ttaggccggc cagagcatta tgcttccaag cggac 55

<210> SEQ ID NO 123
<211> LENGTH: 69
<212> TYPE: DNA

```
<213> ORGANISM: Artificial sequence
<220> FEATURE:
<223> OTHER INFORMATION: Primer

<400> SEQUENCE: 123

caatcaatta taggcctcgc atgctttaat taacgatcga gccatggttc actctaactt     60

cgtaactcg                                                             69


<210> SEQ ID NO 124
<211> LENGTH: 2447
<212> TYPE: DNA
<213> ORGANISM: Brassica napus

<400> SEQUENCE: 124

aacggcaatt gattctcgcc ctgtggtgga tacgtgtctt tgtatgattt attttacatc     60

aaaactttga tttaatttaa ataaattaga aaattaagaa aatacgattt ctttttttgca   120

aaagaaacat actatttgtg ataaatggtt tagtttaaga ttttagttat ttatattcag    180

ttacgatgtt actgttccac aaaatacaac aaaaatcaaa tgatctattt tgagtcatgc    240

agaaattatt tactatcttc ccacgaaaat taaagttatg aaattctata cgttcaaaat    300

atagaagttt ggtgtttcca atgaaagttt ttattttttt atcataaatt tattcatatt    360

aattaatata attattgaaa tagattaaac tcttttaaaa tatgatattg aaaggattaa    420

atttattttc aaatatataa atatccaaag ctcttgtctt gagagacaga aagagtatct    480

gattgtgtga cagaaactaa acagtatgag cttaattctc cataaaccgt gatcatcgct    540

ttaaaacttt gtgtacatat caaacctaaa atggtactaa tttctttact cttattattg    600

actgccagag atgattataa aattacttag attacagtaa ttattgatca agatagttga    660

cttcccagtt cacatattag acattattgt tagtgtttgg aaatacaaat aaaatatgaa    720

attatattta tattctatta gcgaatatct tcaaaatgta agagactctc accaaaaagt    780

tatttgaagg attttgaata attttctcac atttaaaata cttactaata caataataat    840

aacatttaag aaattgaata ttattatatt ttgtatttag aaaccttgat gaaatagggt    900

ttttagtaat taaccctcca actaaagatg aatcgtaaaa aaaccctcaa ctaaaaatcc    960

tgtgaaataa accctcaact ttaatttcgt taacatatgt taccctccgt ctaaaaaacc   1020

gtgacggagg gtaacatatg ttaactgttt ataattaagt tgaaggttta taatgttgaa   1080

aacttagttg agggtttttt tacgattcaa aaatagttaa acggttttat cactaaaagt   1140

cattaaatgc tattaaaata tttattatca tttatacatt gttttagatt gatttataag   1200

cctttaaaac taatttgtaa attttaatat attatttttt ataaattaat ttatacatcc   1260

aaaattaatt attttcaaca ctacttacaa cttattataa cttcaaaata ttaaattatt   1320

tgatatttga aaatagtgat ataaaatatt tgtgtgttta tatcgtcatt gtcaaatatc   1380

aaataattta aaatgtctaa gttatattaa gtcttaagta gtgtcgaaga taattcatca   1440

atgaagtcaa tctttctatt tagagcatga tgcacttttt cctattttca tgatttccgt   1500

catccagctc atactttcct cctatcccca aaaataatgc atgattattt gcattctcat   1560

taatttctaa ataaatatgt tatatttttc ttttcttaat cagtagtata tttgatatat   1620

tgttcttgat ttattgtatt actttctgtt tcaatataat gttggattat ttgatcctaa   1680

caagtagcag aaaatgtaaa aacttataaa atcattgtga aactgtatta atcatatgta   1740

aaagtattaa aatatttatg aagctttata aatcggttat aaagtaatgt attaaaattt   1800

ataaattatt tttaagggct tatatcaatc taaattaatg tataaatgat aataactttt   1860
```

agtgataaaa cccctcaact atttttgaat cataaaaaaa acttcaacta agttttcaac 1920
attataaacc cgcaacttat aaactgttaa cgtatgtcac cctccgttgc ggtttttttag 1980 atggacggta acatatgcta acagaattaa agttaagggt ttatttcaca aatttttttag 2040 ttgacgtttt tttttacaat tcatctttat ttgatgggtt taattactaa aattccaatg 2100
aaatactagc aatactaatg cttttctctc caacatttta attttaattt ttattcactg 2160
tctaaaatgt tgaaagatat agaacatcgt atattacttc tatacattga caaacagtca 2220
catattaaaa aaaatgtgat cacattttca aagtcatttg gaatataaaa taagtttatc 2280
aagataaagg gatgggtaaa gaatagattc actggaatat gtctcgaata aaccaagaaa 2340
caaagtttaa agtaaagaag ctttatcaaa agaaaaaaat taagaaaatt tattggcttt 2400
ttattggacg agtcatatta aaatgacgtg gtttcaataa cctctct 2447

<210> SEQ ID NO 125
<211> LENGTH: 865
<212> TYPE: DNA
<213> ORGANISM: Brassica napus

<400> SEQUENCE: 125
tttacatatt ggcccaagag gcataataaa aaatatgttg aaaaaaaaaa aaaaaatgac 60
gtggtttcac actaaactag agagtcgcat gaaccggtct gaccgtcgat ttaagacaat 120
aactccctgc cgttggatct gtcacttttg gaagagacct ttccttgttt tcgccatatt 180
tctctaggag aagggggttc gattattctg cttttgtcta tgcggaagta cgtatgtatt 240
tattcattgt caatgtatta aatccaacta atctgcttct ttttttata acaccatcca 300 acttatctgc ttattctgct tatttctttc gagtatttga accaaatcca actaatctcc 360
tttatcgtct aatgtctaat gaagattact aatgaatcat tttcgtctgg ttaaagacca 420
ctagaacact gtaaccctta gaacatctca gtaaactttt tgaacagtta tagtgaactt 480
tttttctttt tttttttgag aaccaacatt tatagtgaac ttcttctaat ggttaccaag 540
aacatttcct aatgcttata tttttctgaa agacactgca caaatatttg acgtaaatta 600
ttaggacatt tccaatagta tggttctcat ttgttaatga aaatattttt aaaatatttt 660
attattaata tttattgtta aagatttttt aattaatata ttaaatcaat tcaatccaaa 720
aatgagacta aagttctact cactcgcaca ctcaaaattt ttaatttaaa catttcttaa 780
ctagctttgt tcgaccaatc atcccaggca cgttccatta gtttgaatct gaaatctttg 840
gaaattcggt accgttttca ttaac 865

<210> SEQ ID NO 126
<211> LENGTH: 768
<212> TYPE: DNA
<213> ORGANISM: Brassica napus

<400> SEQUENCE: 126
ctcttccttt gttttctcta acctctctct aagtcttcgt taaaaaaaaa aaatcaatcc 60
tagtggccgg tgggttcacc accgccggtc accaacccct tttttgtttt tgtttgtaaa 120
tattttcgtt aggcgactct tttcttccgt ttatcggata aaaactttgc aaggtgactt 180
ttgttgtgtg ttttccaaac ccgatttctc tatcctttgc aaatcaatat cccgtttgat 240
tttgttagat tccagtcttc tagttaatca cactttttcc ttcccatata tggtattaat 300
cttagcgtgc agaattttat gacggagtat ccattgtgtg ttagagatta agttgtttga 360

-continued

```
ttaagcgtag agagaagaag caagctcaga ttagctggag tttctttatc agaaacgttt    420

tggcaaggcc cagctttcat ccctttgaag ctattcaccg gagttcactt gtaacgagcg    480

gatgaagaat cgagcataat tgacggcgaa cagcgatacg aggaacagtc aagtagattc    540

aactagtcga agaaagttac tgaaagttcc cgttccggca tgtctccggc gagactgaca    600

gtgctatttc tttgactcta gaaacatcgt gacccatcta actgtacacg tgtcgttcat    660

gctttagagt ttttatatta gcgaacacgt ggttttaatc ttatcttttg ttcggttggg    720

tttcgatatg gactgaatat atattaggat ggctgttgta tctacttg                 768


<210> SEQ ID NO 127
<211> LENGTH: 55
<212> TYPE: DNA
<213> ORGANISM: Artificial sequence
<220> FEATURE:
<223> OTHER INFORMATION: Primer

<400> SEQUENCE: 127

atacccggga tacctgcagg ttaggccggc caaacggcaa ttgattctcg ccctg          55


<210> SEQ ID NO 128
<211> LENGTH: 69
<212> TYPE: DNA
<213> ORGANISM: Artificial sequence
<220> FEATURE:
<223> OTHER INFORMATION: Primer

<400> SEQUENCE: 128

caatcaatta taggcctcgc atgctttaat taacgatcga gccatggaga gaggttattg     60

aaaccacgt                                                             69


<210> SEQ ID NO 129
<211> LENGTH: 74
<212> TYPE: DNA
<213> ORGANISM: Artificial sequence
<220> FEATURE:
<223> OTHER INFORMATION: Primer

<400> SEQUENCE: 129

ccatggctcg atcgttaatt aaagcatgcg aggcctataa ttgattgttt acatattggc     60

ccaagaggca taat                                                       74


<210> SEQ ID NO 130
<211> LENGTH: 61
<212> TYPE: DNA
<213> ORGANISM: Artificial sequence
<220> FEATURE:
<223> OTHER INFORMATION: Primer

<400> SEQUENCE: 130

taagcggccg caatcggacc gataccggta ggcgccgtta atgaaaacgg taccgaattt     60

c                                                                     61


<210> SEQ ID NO 131
<211> LENGTH: 1593
<212> TYPE: DNA
<213> ORGANISM: Brassica napus

<400> SEQUENCE: 131

aatagtcaag tttatgaatc acagattagc catctagaat caaaggtgat gcaggtttca     60

tctcccaaca agaactataa tccatgaaaa catagaacaa cataaactca tgaagctttt    120
```

```
attcttatag gcatcaagaa aatttggtga agcaatggaa attaaacatg aaaacaagtt    180
tccgagggta agtcactgat attgtatatg ttggttcttg aaactgaaac tattattatg    240
gaccatgtga tatatgtaga tggagaacca ccgttgtttt agttcactga aggaatttga    300
agctccaaag gttacgaact cccaagatga acattctatt gaatctctca gaaaagtaag    360
tgagcatttt atcatattca gcttgtatta aatttgtgtt ttcttatgaa attaacaata    420
ttaacttttt cctacagcta tgtctcactt ccgatactga tttagttgct ccttgtatct    480
catctacata gagaattttc aagatattat tttgcttgta caaattagac atggctatga    540
agagatttga gagttttaat gcgcgggagg gatcatgcac aggtatttga aacctagtgc    600
cttgctctgt ctcatcattt acttgttata tttggaccaa acaacacatc tccatcaaat    660
catatttctt aaacgagttt gaatttgcag gacattcatc aggaagtgcc caatcgctcc    720
ttgagtttca cagttctctt aaagcatatt atatatgtgc tcttattaga tggtagaagt    780
ttcataaatt tgcaatgctt gtgtttgatc atcaatgaat aatgtaaaaa atttatacat    840
tgtgatagaa gtagagacct taatggatgt gtgtgcttta aagaggagac tgaaatactt    900
ttatcagtgt tgcgaaaaaa aaaaagactt ttatctaact cgtgaaatgg gttgttttgg    960
aaagacattt tccacaattt tgacaatgaa cctccagaca tatctggttt cttacgtaaa   1020
acataaattg acctaactta attatttcgt actgttattg aaatgttctt gagaattaaa   1080
ataaatcatt catggagttt gtttggtagt agtaggtgga gctcatggga aaagtggcgc   1140
cacgtaactg actcatgttg ctatttttct gcttcacttg tttactctcc ccttaataca   1200
aatttgtttt cttttgaagg ctctctactt gaacgtgtcc ttacactaga atcagcacca   1260
aacatattaa aacaccttca cggatacgtt gtgaactgta tattcttttt gaaatattta   1320
ttatttatta gttttgaacg gggtattcat tgtattcttt tttttttttt ttcaatgggg   1380
tattcattgt attcatatta gtttttcatc attatatttg acctaactcg gttaaccccg   1440
aagagaaaaa cttgttattt aatttgtttt tgtaaaacat aaatgtgttt gtgacatgtg   1500
gcttatttca ttgatgcaag gtttgacacg ttgagttctt tgctatttat cttccttggt   1560
atcccgcagg cagtaatgtc aagaagttca aga                                1593
```

<210> SEQ ID NO 132
<211> LENGTH: 16034
<212> TYPE: DNA
<213> ORGANISM: Artificial sequence
<220> FEATURE:
<223> OTHER INFORMATION: Plasmid

<400> SEQUENCE: 132

```
ctatacaaag ttgatagctt ggcgtaatcg atgtaccgat atcaatttaa attggccggc     60
cgagctccct gcagggggcc cggcgcgcct ctagattaat taaaggcctt agttactaat    120
cagtgatcag attgtcgttt cccgccttca gtttaaacta tcagtgtttg acaggatata    180
ttggcgggta aacctaagag aaaagagcgt ttattagaat aatcggatat ttaaaagggc    240
gtgaaaaggt ttatccgttc gtccatttgt atgtcaatat ccatgataag tcgcgctgta    300
tgtgtttgtt tgaatattca tggaacgcag tggcggtttt catggcttgt tatgactgtt    360
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
```

-continued

```
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
```

ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc accttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980
actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280
aaaaaaatga aatccacatc ctgccatcat aacctcatgc tggaaaaaga aatgaaaaaa 5340
tataaaaaat ttcttttgtt tattaaattt acaactttaa tactagtttc ttttctattt 5400
tttaaaagct tttgtcactt acttaaaaaa aaaaaacttt ttgaaatatt cctacttcca 5460
atgtctgatt agtgcttctg gatttccttt ttggatcatg tgaatcctaa atcagaaaaa 5520
ttcatataat acccaattca gtatattttc atacttcaat ttacaagagt tctctatgtt 5580
tttagcttct ttcttttaag ccaaatgttt taagcatctt ttatacatta aaataattta 5640
gtgttgagtt gagatttttt tttttttttt ttggatttac ttgttcaaaa tctgaaaaaa 5700
tgtttacaga aggttaaaat gaaccaaaag gcatatcaag ctagattttg aattacccta 5760
tttcatcgta tacacaaaac tgataatgtg gacacagttg attttacttc tcgatgacat 5820
cgtagtttta tttaatttgg aaaccacggc ccatatgagc acatttcaat taaaaaccaa 5880
tggtaagagc attttccatg caagattcga gagatattaa cccagtgact gttaaaacag 5940
cttagaaccc taataacgaa tttcaattac tcaatttacc attcgcattt cgcaataacc 6000
aaactgagcc agtcacaagg agtaaaccga accggattat ttatttataa aatgaaagaa 6060
aggaaaccaa acaacaacag cagtagtagt ctgacgtaaa ccaaaaagca ggcagatcaa 6120
caactaaaag aaactcaaat taccaaaaca aacaggaaat tgcaaactaa gtttttttac 6180
catatgcata caaagaccat aaaaggttct gataatcacc ggtttcatct cgtcgagatt 6240
accctgttat ccctatcagt atttaatccg gccatctcct tccgttatga catcgttgaa 6300
agtgccacca ttcgggatca tcggcaacac atgttcttgg tgcggacaaa tcacatccaa 6360
caggtaaggt cctggtgtat ccagcattgt ctgaatagct tctcggagat ctgctttctt 6420
tgtcaccctc gccgctggaa tcccgcaagc tgctgcaaac agcaacatgt tcgggaatat 6480
ctcgtcctcc tgagccggat ccccgagaaa tgtgtgagct cggttagctt tgtagaaccg 6540
atcttcccat tgcataacca tgccaagatg ctggttgttt aataaaagta ccttcactgg 6600
aagattctct acacgaatag tggctagctc ttgcacattc attataaagc ttccatctcc 6660
gtcaatatcc acaactatcg catcagggtt agcaacagac gctccaatcg cagcaggaag 6720
tccaaatccc atagctccaa ggcctcctga tgatagccac tgccttggtt tcttgtaatt 6780
gtagaactgc gccgcccaca tttgatgttg cccgacacca gtacttatta tggcttttcc 6840
atcagtcaac tcatcaagga ccttaatcgc atactgtgga ggaatagctt ccccaaacgt 6900
cttaaagctc aacggaaact tctgtttctg tacgttcaac tcattcctcc aaactccaaa 6960
atcaagctta agctcctccg ctcggttctc aagaacctta ttcatccctt gcaaagccag 7020
cttaacatca ccacacacag acacatgagg agtcttattc ttcccaatct cagccgagtc 7080
aatatcaata tgaacaatct tagccctact agcaaaagcc tcaagcttac ccgtgacacg 7140
atcatcaaac cttaccccaa acgccaacaa caaatcacta tgctccacag cgtaatttgc 7200
atacacagtc ccatgcattc caagcatatg taacgacaac tcatcatcac aaggataaga 7260
tcccagcccc atcaacgtac tcgcaacagg gatccccgta agctcaacaa acctacccaa 7320
ttcatcgcta gaattcaaac aaccaccacc aacatacaac acaggcttct tagactcaga 7380
aatcaaccta acaatctgct ccaaatgaga atcttccgga ggtttaggca tcctagacat 7440
ataaccaggt aatctcatag cctgttccca attaggaatc gcaagctgtt gttgaatatc 7500
tttaggaaca tcaaccaaaa caggtccagg tctaccagaa gtagctaaaa agaaagcttc 7560
ctcaataatc ctagggatat cttcaacatc catcacaaga tagttatgct tcgtaatcga 7620
acgcgttacc tcaacaatcg gagtctcttg aaacgcatct gtaccaatca tacgacgagg 7680

```
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa gggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
```

-continued

```
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
```

gtaatcatgg ccactttgta caagaaagct gggtggtacc ggcctattag gccacggtcc 12480
gtacagtgtt taaacgattg acctgcagga tacaagtgcg cacagactag cggccgctaa 12540
tcccgggaat taccggtagt aggcgccaca atcagtaaat tgaacggaga atattattca 12600
taaaaatacg atagtaacgg gtgatatatt cattagaatg aaccgaaacc ggcggtaagg 12660
atctgagcta cacatgctca ggttttttac aacgtgcaca acagaattga aagcaaatat 12720
catgcgatca taggcgtctc gcatatctca ttaaagcagc aatcaattat taattaagtt 12780
aacttacatc gctgggaact cggtgataaa ttccttgctg atgtccgcca ggtggtccac 12840
gacctcgtag atgccctccc agaagccggt ctcgtggaac gggatgtcga actccttgca 12900
tagcgacttg atgagcacgt tgacctttgg caagttgtgg cgcggcacga gcgggaacag 12960
gtgatggtcg atctggtagt tcaagccacc ggtgaaccag tccatgaata ccgacgcgcg 13020
gatgttgcgc gtcgtggtca cctgcagctg ccagaagtcc ggcttggttt cgcgctcgta 13080
caccgacatg ccgttgtggc caatactgaa caccagcgcc aggagcaagc cgcaggacgc 13140
ctggcccatg aggaagtatg ccacgccctc aaacaggctc atgttgcaga agtacgggat 13200
cgcgagctgc cagatgtagt gcacgatcag acccgccttc tccggtccgt cgaactcgac 13260
cttgtcgaag atgccgaacg agaactcggt gaacacgtag aagaacgact gcgcgagcca 13320
gctcaggcgc gcgagcagca gcagcgggaa gtataggaac gcctggttgc ggatgaagaa 13380
cgggccgtgc gccgactcga acgccttgcg cgccatctcc ttagaccacg ccagcagcgg 13440
catggtgtcg atgtccgggt cgccgatgaa gccctcgtcc ttggcgctgt gcaggttcgg 13500
caccgcgtgg tgcaggttgt gcttgttctt ccaccactgc atgctgaagc cctgccaggc 13560
gttgcccacg aggcagccga taaggttgcc gagcgtgcgg ttctcgcaca cctggttgtg 13620
caagaagtcg tgcgccagcc atccggactg ctggtagaag agccccataa tcacgccggc 13680
gaccatgtac atggcgaaac tgttgaagaa gaagcagatc gccatcgaga gcaccgcgat 13740
gccgaacgtg ctcacgagct tccacgcgta gtagagcgcg ctggcgtcgt agagccccat 13800
gcccttgacc ttgacgcgca gacggcggta ggacgcgatg aactcgttga tgcgctcgcg 13860
gcgcgcgcgc tcctcgtcgc tcgccggctc cccctcgatc tcggccttgg aggtttcgtc 13920
cacgtcgccg acgtagaact gctcgagcag cttgagcgcc gaggacgggt ggaagaccgc 13980
gaaggcgtcc gtggcgtcct cgccggcctg cgtgagcatc acggagccac ccgggtgcga 14040
gtcccacttg gagatgtcgt agaccttgtg gtgaatcacg atccacgcgg tcgcgggcgt 14100
cgcgtgctcg cggatctcct tccagctcac caggcgcttc actccaggct tgaggtccac 14160
cattttgggc cccggcgcgg tcttgaactt cttgacatta ctgcctgcgg gataccaagg 14220
aagataaata gcaaagaact caacgtgtca aaccttgcat caatgaaata agccacatgt 14280
cacaaacaca tttatgtttt acaaaaacaa attaaataac aagtttttct cttcggggtt 14340
aaccgagtta ggtcaaatat aatgatgaaa aactaatatg aatacaatga ataccccatt 14400
gaaaaaaaaa aaaaaagaat acaatgaata ccccgttcaa aactaataaa taataaatat 14460
ttcaaaaaga atatacagtt cacaacgtat ccgtgaaggt gttttaatat gtttggtgct 14520
gattctagtg taaggacacg ttcaagtaga gagccttcaa aagaaaacaa atttgtatta 14580
aggggagagt aaacaagtga agcagaaaaa tagcaacatg agtcagttac gtggcgccac 14640
ttttcccatg agctccacct actactacca aacaaactcc atgaatgatt tattttaatt 14700
ctcaagaaca tttcaataac agtacgaaat aattaagtta ggtcaattta tgttttacgt 14760

-continued

```
aagaaaccag atatgtctgg aggttcattg tcaaaattgt ggaaaatgtc tttccaaaac  14820

aacccatttc acgagttaga taaaagtctt ttttttttc gcaacactga taaaagtatt  14880

tcagtctcct ctttaaagca cacacatcca ttaaggtctc tacttctatc acaatgtata  14940

aattttttac attattcatt gatgatcaaa cacaagcatt gcaaatttat gaaacttcta  15000

ccatctaata agagcacata tataatatgc tttaagagaa ctgtgaaact caaggagcga  15060

ttgggcactt cctgatgaat gtcctgcaaa ttcaaactcg tttaagaaat atgatttgat  15120

ggagatgtgt tgtttggtcc aaatataaca agtaaatgat gagacagagc aaggcactag  15180

gtttcaaata cctgtgcatg atccctcccg cgcattaaaa ctctcaaatc tcttcatagc  15240

catgtctaat ttgtacaagc aaaataatat cttgaaaatt ctctatgtag atgagataca  15300

aggagcaact aaatcagtat cggaagtgag acatagctgt aggaaaaagt taatattgtt  15360

aatttcataa gaaaacacaa atttaataca agctgaatat gataaaatgc tcacttactt  15420

ttctgagaga ttcaatagaa tgttcatctt gggagttcgt aacctttgga gcttcaaatt  15480

ccttcagtga actaaaacaa cggtggttct ccatctacat atatcacatg gtccataata  15540

atagtttcag tttcaagaac caacatatac aatatcagtg acttaccctc ggaaacttgt  15600

tttcatgttt aatttccatt gcttcaccaa attttcttga tgcctataag aataaaagct  15660

tcatgagttt atgttgttct atgttttcat ggattatagt tcttgttggg agatgaaacc  15720

tgcatcacct ttgattctag atggctaatc tgtgattcat aaacttgact attggccggc  15780

ctagtagatt taaattggcc ttagtggcca agcttggcgt aatcatggag cctgcttttt  15840

tgtacaaact tgggtaccgg cctattaggc cacggtccgt acagtgttta aacgattgac  15900

ctgcaggata caagtgcgca cagactagcg gccgctaatc ccgggaatta ccggtagtag  15960

gcgcctactt tggccggcct agtagattta aattggcctt agtggccaag cttggcgtaa  16020

tcatggcaac tttt                                                    16034
```

```
<210> SEQ ID NO 133
<211> LENGTH: 574
<212> TYPE: DNA
<213> ORGANISM: Brassica napus

<400> SEQUENCE: 133

atggcgtctt tgcaactcct cacactcctc tttttcttct tcttcttctt cttcttcttc     60

actgtttcaa aatccatcga tgtctcgaag cctcatgcag cagaatcact tgatatcaat    120

ctcattcaga atttcggaag ctgtaggtac acggtgatca tcaggacgag ttgttcctca    180

cctaggtaca cgagagacca gatcagcctc tctttcgggg atggctacag aaaccaggta    240

tacgcaccta ggcttgacga cccagggtcg agagcatttg agcgatgttc atcagataca    300

tatgagataa atggaccatg tgtacgccag atctgctatg tatatgttca caggtctggt    360

ccagatggtt gggttccaga gagtgttcaa atattcagtc atagctccaa agcagtcact    420

ttcactttca acacgcatgt ccctgaaagc atatggtttg gtcataatta ctgcaacacc    480

atctaaccct accttccggt ctcatcaaac tcctaatact tgaaaggctt gctacgttgc    540

ttaaatgtct ctcttatgta aattaaatgt ctag                                574
```

```
<210> SEQ ID NO 134
<211> LENGTH: 56
<212> TYPE: DNA
<213> ORGANISM: Artificial sequence
<220> FEATURE:
<223> OTHER INFORMATION: Primer
```

<400> SEQUENCE: 134
atacccggga tacctgcagg ttaggccggc caaatagtca agtttatgaa tcacag 56

<210> SEQ ID NO 135
<211> LENGTH: 69
<212> TYPE: DNA
<213> ORGANISM: Artificial sequence
<220> FEATURE:
<223> OTHER INFORMATION: Primer

<400> SEQUENCE: 135
caatcaatta taggcctcgc atgctttaat taacgatcga gccatggtct tgaacttctt 60
gacattact 69

<210> SEQ ID NO 136
<211> LENGTH: 664
<212> TYPE: DNA
<213> ORGANISM: Brassica napus

<400> SEQUENCE: 136
taaggatgac ctacccattc ttgagacaaa tgttacattt tagtatcaga gtaaaatgtg 60
tacctataac tcaaattcga ttgacatgta tccattcaac ataaaattaa accagcctgc 120
acctgcatcc acatttcaag tattttcaaa ccgttcggct cctatccacc gggtgtaaca 180
agacggattc cgaatttgga agattttgac tcaaattccc aatttatatt gaccgtgact 240
aaatcaactt taacttctat aattctgatt aagctcccaa tttatattcc caacggcact 300
acctccaaaa tttatagact ctcatcccct tttaaaccaa cttagtaaac gttttttttt 360
taattttatg aagttaagtt tttaccttgt ttttaaaaag aatcgttcat aagatgccat 420
gccagaacat tagctacacg ttacacatag catgcagccg cggagaattg tttttcttcg 480
ccacttgtca ctcccttcaa acacctaaga gcttctctct cacagcacac acatacaatc 540
acatgcgtgc atgcattatt acacgtgatc gccatgcaaa tctcctttat agcctataaa 600
ttaactcatc ggcttcactc tttactcaaa ccaaaactca tcaatacaaa caagattaaa 660
aaca 664

<210> SEQ ID NO 137
<211> LENGTH: 15441
<212> TYPE: DNA
<213> ORGANISM: Artificial sequence
<220> FEATURE:
<223> OTHER INFORMATION: Plasmid

<400> SEQUENCE: 137
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540

-continued

```
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta tcaacgacct tctggaaacg tccgcctccc    720
ccggcgagag cgaaatcctg cgcgcggttg aggtgacgat tgtggtgcac gatgacatca    780
tcccctggcg ctatccggcc aaacgcgaac tccagttcgg cgaatggcag cgtaatgata    840
ttctggcggg tatctttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
```

-continued ccaatcagca agctcgatct cgatgtactc cggccgcccg gtttcgctct ttacgatctt 3000
gtagcggcta atcaaggctt caccctcgga taccgtcacc aggcggccgt tcttggcctt 3060
cttggtacgc tgcatggcaa cgtgcgtggt gtttaaccga atgcaggttt ctaccaggtc 3120
gtctttctgc tttccgccat cggctcgccg gcagaacttg agtacgtccg caacgtgtgg 3180
acggaacacg cggccgggct tgtctccctt cccttcccgg tatcggttca tggattcggt 3240
tagatgggaa accgccatca gtaccaggtc gtaatcccac acactggcca tgccggcggg 3300
gcctgcggaa acctctacgt gcccgtctgg aagctcgtag cggatcacct cgccagctcg 3360
tcggtcacgc ttcgacagac ggaaaacggc cacgtccatg atgctgcgac tatcgcgggt 3420
gcccacgtca tagagcatcg gaacgaaaaa atctggttgc tcgtcgccct tgggcggctt 3480
cctaatcgac ggcgcaccgg ctgccggcgg ttgccgggat tctttgcgga ttcgatcagc 3540
ggccccttgc cacgattcac cggggcgtgc ttctgcctcg atgcgttgcc gctgggcggc 3600
ctgcgcggcc ttcaacttct ccaccaggtc atcacccagc gccgcgccga tttgtaccgg 3660
gccggatggt ttgcgaccgc tcacgccgat tcctcgggct tgggggttcc agtgccattg 3720
cagggccggc agacaaccca gccgcttacg cctggccaac cgcccgttcc tccacacatg 3780
gggcattcca cggcgtcggt gcctggttgt tcttgatttt ccatgccgcc tcctttagcc 3840
gctaaaattc atctactcat ttattcattt gctcatttac tctggtagct gcgcgatgta 3900
ttcagatagc agctcggtaa tggtcttgcc ttggcgtacc gcgtacatct tcagcttggt 3960
gtgatcctcc gccggcaact gaaagttgac ccgcttcatg gctggcgtgt ctgccaggct 4020
ggccaacgtt gcagccttgc tgctgcgtgc gctcggacgg ccggcactta gcgtgtttgt 4080
gcttttgctc attttctctt tacctcatta actcaaatga gttttgattt aatttcagcg 4140
gccagcgcct ggacctcgcg ggcagcgtcg ccctcgggtt ctgattcaag aacggttgtg 4200
ccggcggcgg cagtgcctgg gtagctcacg cgctgcgtga tacgggactc aagaatgggc 4260
agctcgtacc cggccagcgc ctcggcaacc tcaccgccga tgcgcgtgcc tttgatcgcc 4320
cgcgacacga caaaggccgc ttgtagcctt ccatccgtga cctcaatgcg ctgcttaacc 4380
agctccacca ggtcggcggt ggcccaaatg tcgtaagggc ttggctgcac cggaatcagc 4440
acgaagtcgg ctgccttgat cgcggacaca gccaagtccg ccgcctgggg cgctccgtcg 4500
atcactacga agtcgcgccg gccgatggcc ttcacgtcgc ggtcaatcgt cgggcggtcg 4560
atgccgacaa cggttagcgg ttgatcttcc cgcacggccg cccaatcgcg ggcactgccc 4620
tggggatcgg aatcgactaa cagaacatcg gccccggcga gttgcagggc gcgggctaga 4680
tgggttgcga tggtcgtctt gcctgacccg cctttctggt taagtacagc gataaccttc 4740
atgcgttccc cttgcgtatt tgtttattta ctcatcgcat catatacgca gcgaccgcat 4800
gacgcaagct gttttactca aatacacatc accttttag atgatcagtg attttgtgcc 4860
gagctgccgg tcggggagct gttggctggc tggtggcagg atatattgtg gtgtaaacaa 4920
attgacgctt agacaactta ataacacatt gcggacgtct ttaatgtact gaatttagtt 4980
actgatcact gattaagtac tgcgatcgcc tcgacatatt gtttttgttt cacataaatg 5040
tcgttttgga ttattcatgt aatattttaa actaaagtac aatttttgac tactttagtt 5100
tactagttaa gcttttattt ttttgactaa ccattgaatg atgaagagat caacgcatca 5160
tatttacaac ttacatagtc ttttggaagt gtaaattgct aatactacct aaaatatatc 5220
tataattaac taatattttt tcgtcaatta taatagatca attaaaaggc tatcaaaagg 5280

-continued

```
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gttttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
```

-continued

```
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa gggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt atttttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
```

-continued

```
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
```

gtaatcatgg ccactttgta caagaaagct gggtccatga ttacgccaag cttgcatgcc 12480
catatgctcg aggcggccgc agatatctgc agaattcgcc ctttaagcgg ccgcaatcgg 12540
accgataccg gtaggcgcca ttgatgcatg ttgtcaatca attggcaagt cataaaatgc 12600
attaaaaaat attttcatac tcaactacaa atccatgagt ataactataa ttataaagca 12660
atgattagaa tctgacaagg attctggaaa attacataaa ggaaagttca taaatgtcta 12720
aaacacaaga ggacatactt gtattcagta acatttgcag cttttctagg tctgaaaata 12780
tatttgttgc ctagtgaata agcataatgg tacaactaca agtgttttac tcctcatatt 12840
aacttcggtc attagaggcc acgatttgac acatttttac tcaaaacaaa atgtttgcat 12900
atctcttata atttcaaatt caacacacaa caaataagag aaaaaacaaa taatattaat 12960
ttgagaatga acaaaaggac catatcattc attaactctt ctccatccat ttccatttca 13020
cagttcgata gcgaaaaccg aataaaaaac acagtaaatt acaagcacaa caaatggtac 13080
aagaaaaaca gttttcccaa tgccataata ctcgaaccaa tcaattatta attaagttaa 13140
cttacatcgc tgggaactcg gtgataaatt ccttgctgat gtccgccagg tggtccacga 13200
cctcgtagat gccctcccag aagccggtct cgtggaacgg gatgtcgaac tccttgcata 13260
gcgacttgat gagcacgttg acctttggca agttgtggcg cggcacgagc gggaacaggt 13320
gatggtcgat ctggtagttc aagccaccgg tgaaccagtc catgaatacc gacgcgcgga 13380
tgttgcgcgt cgtggtcacc tgcagctgcc agaagtccgg cttggtttcg cgctcgtaca 13440
ccgacatgcc gttgtggcca atactgaaca ccagcgccag gagcaagccg caggacgcct 13500
ggcccatgag gaagtatgcc acgccctcaa acaggctcat gttgcagaag tacgggatcg 13560
cgagctgcca gatgtagtgc acgatcagac ccgccttctc cggtccgtcg aactcgacct 13620
tgtcgaagat gccgaacgag aactcggtga acacgtagaa gaacgactgc gcgagccagc 13680
tcaggcgcgc gagcagcagc agcgggaagt ataggaacgc ctggttgcgg atgaagaacg 13740
ggccgtgcgc cgactcgaac gccttgcgcg ccatctcctt agaccacgcc agcagcggca 13800
tggtgtcgat gtccgggtcg ccgatgaagc cctcgtcctt ggcgctgtgc aggttcggca 13860
ccgcgtggtg caggttgtgc ttgttcttcc accactgcat gctgaagccc tgccaggcgt 13920
tgcccacgag gcagccgata aggttgccga gcgtgcggtt ctcgcacacc tggttgtgca 13980
agaagtcgtg cgccagccat ccggactgct ggtagaagag ccccataatc acgccggcga 14040
ccatgtacat ggcgaaactg ttgaagaaga agcagatcgc catcgagagc accgcgatgc 14100
cgaacgtgct cacgagcttc cacgcgtagt agagcgcgct ggcgtcgtag agccccatgc 14160
ccttgacctt gacgcgcaga cggcggtagg acgcgatgaa ctcgttgatg cgctcgcggc 14220
gcgcgcgctc ctcgtcgctc gccggctccc cctcgatctc ggccttggag gtttcgtcca 14280
cgtcgccgac gtagaactgc tcgagcagct tgagcgccga ggacgggtgg aagaccgcga 14340
aggcgtccgt ggcgtcctcg ccggcctgcg tgagcatcac ggagccaccc gggtgcgagt 14400
cccacttgga gatgtcgtag accttgtggt gaatcacgat ccacgcggtc gcgggcgtcg 14460
cgtgctcgcg gatctccttc cagctcacca ggcgcttcac tccaggcttg aggtccacca 14520
ttttgggccc cggcgcggtg tttttaatct tgtttgtatt gatgagtttt ggtttgagta 14580
aagagtgaag ccgatgagtt aatttatagg ctataaagga gatttgcatg gcgatcacgt 14640
gtaataatgc atgcacgcat gtgattgtat gtgtgtgctg tgagagagaa gctcttaggt 14700
gtttgaaggg agtgacaagt ggcgaagaaa aacaattctc cgcggctgca tgctatgtgt 14760

-continued

```
aacgtgtagc taatgttctg gcatggcatc ttatgaacga ttctttttaa aaacaaggta  14820

aaaacttaac ttcataaaat taaaaaaaaa acgtttacta agttggttta aaaggggatg  14880

agagtctata aattttggag gtagtgccgt tgggaatata aattgggagc ttaatcagaa  14940

ttatagaagt taaagttgat ttagtcacgg tcaatataaa ttgggaattt gagtcaaaat  15000

cttccaaatt cggaatccgt cttgttacac ccggtggata ggagccgaac ggtttgaaaa  15060

tacttgaaat gtggatgcag gtgcaggctg gtttaatttt atgttgaatg gatacatgtc  15120

aatcgaattt gagttatagg tacacatttt actctgatac taaaatgtaa catttgtctc  15180

aagaatgggt aggtcatcct tatggccggc ctaacctgca ggtatcccgg gtaccagcct  15240

gctttttttgt acaaacttgg gtaccggcct attaggccac ggtccgtaca gtgtttaaac  15300

gattgacctg caggatacaa gtgcgcacag actagcggcc gctaatcccg ggaattaccg  15360

gtagtaggcg cctactttgg ccggcctagt agatttaaat tggccttagt ggccaagctt  15420

ggcgtaatca tggcaacttt t                                            15441
```

```
<210> SEQ ID NO 138
<211> LENGTH: 56
<212> TYPE: DNA
<213> ORGANISM: Artificial sequence
<220> FEATURE:
<223> OTHER INFORMATION: Primer

<400> SEQUENCE: 138

atacccggga tacctgcagg ttaggccggc cataaggatg acctacccat tcttga        56
```

```
<210> SEQ ID NO 139
<211> LENGTH: 69
<212> TYPE: DNA
<213> ORGANISM: Artificial sequence
<220> FEATURE:
<223> OTHER INFORMATION: Primer

<400> SEQUENCE: 139

caatcaatta taggcctcgc atgctttaat taacgatcga gccatggtgt ttttaatctt     60

gtttgtatt                                                             69
```

```
<210> SEQ ID NO 140
<211> LENGTH: 1727
<212> TYPE: DNA
<213> ORGANISM: Linum usitatissimum

<400> SEQUENCE: 140

cacgggcagg acatagggac tactacaagc atagtatgct tcagacaaag agctaggaaa     60

gaactcttga tggaggttaa gagaaaaaag tgctagaggg gcatagtaat caaacttgtc    120

aaaaccgtca tcatgatgag ggatgacata atataaaaag ttgactaagg tcttggtagt    180

actctttgat tagtattata tattggtgag aacatgagtc aagaggagac aagaaaccga    240

ggaaccatag tttagcaaca agatggaagt tgcaaagttg agctagccgc tcgattagtt    300

acatctccta agcagtacta caaggaatgg tctctatact ttcatgttta gcacatggta    360

gtgcggattg acaagttaga aacagtgctt aggagacaaa gagtcagtaa aggtattgaa    420

agagtgaagt tgatgctcga caggtcagga gaagtccctc cgccagatgg tgactaccaa    480

ggggttggta tcagctgaga cccaaataag attcttcggt tgaaccagtg gttcgaccga    540

gactcttagg gtgggatttc actgtaagat ttgtgcattt tgttgaatat aaattgacaa    600

ttttttttat ttaattatag attatttaga atgaattaca tatttagttt ctaacaagga    660
```

tagcaatgga tgggtatggg tacaggttaa acatatctat tacccaccca tctagtcgtc 720
gggttttaca cgtacccacc cgtttacata aaccagaccg gaattttaaa ccgtacccgt 780
ccgttagcgg gtttcagatt tacccgttta atcgggtaaa acctgattac taaatatata 840
tttttatttt gataaacaaa acaaaaatgt taatattttc atattggatg caattttaag 900
aaacacatat tcataaattt ccatatttgt aggaaaataa aaagaaaaat atattcaaga 960
acacaaattt caccgacatg acttttatta cagagttgga attagatcta acaattgaaa 1020
aattaaaatt aagatagaat atgttgagga acatgacata gtataatgct gggttacccg 1080
tcgggtaggt atcgaggcgg atactactaa atccatccca ctcgctatcc gataatcact 1140
ggtttcgggt atacccattc ccgtcaacag gccttttaa ccggataatt tcaacttata 1200
gtgaatgaat tttgaataaa tagttagaat accaaaatcc tggattgcat ttgcaatcaa 1260
attttgtgaa ccgttaaatt ttgcatgtac ttgggataga tataatagaa ccgaattttc 1320
attagtttaa tttataactt actttgttca aagaaaaaaa atatctatcc aatttactta 1380
taataaaaaa taatctatcc aagttactta ttataatcaa cttgtaaaaa ggtaagaata 1440
caaatgtggt agcgtacgtg tgattatatg tgacgaaatg ttatatctaa caaaagtcca 1500
aattcccatg gtaaaaaaaa tcaaaatgca tggcaggctg tttgtaacct tggaataaga 1560
tgttggccaa ttctggagcc gccacgtacg caagactcag ggccacgttc tcttcatgca 1620
aggatagtag aacaccactc cacccacctc ctatattaga cctttgccca accctcccca 1680
actttcccat cccatccaca aagaaaccga catttttatc ataaatc 1727

<210> SEQ ID NO 141
<211> LENGTH: 16281
<212> TYPE: DNA
<213> ORGANISM: Artificial sequence
<220> FEATURE:
<223> OTHER INFORMATION: Plasmid

<400> SEQUENCE: 141
ctatacaaag ttgatagctt ggcgtaatcg atgtaccgat atcaatttaa attggccggc 60
cgagctccct gcagggggcc cggcgcgcct ctagattaat taaaggcctt agttactaat 120
cagtgatcag attgtcgttt cccgccttca gtttaaacta tcagtgtttg acaggatata 180
ttggcgggta aacctaagag aaaagagcgt ttattagaat aatcggatat ttaaaagggc 240
gtgaaaaggt ttatccgttc gtccatttgt atgtcaatat ccatgataag tcgcgctgta 300
tgtgtttgtt tgaatattca tggaacgcag tggcggtttt catggcttgt tatgactgtt 360
tttttggggt acagtctatg cctcgggcat ccaagcagca agcgcgttac gccgtgggtc 420
gatgtttgat gttatggagc agcaacgatg ttacgcagca gggcagtcgc cctaaaacaa 480
agttaaacat catgggtgaa gcggtcatcg ccgaggtgtc cacccagctg tcggaagtcg 540
tgggtgtcat cgagcgccac ctcgaaccga ccctcctcgc cgtgcatctg tatggtagcg 600
ccgttgacgg cggccttaag ccccattcgg acatcgacct gcttgtcacc gttaccgtcc 660
gtctcgacga gaccacgcgc cgcgcgctta tcaacgacct tctggaaacg tccgcctccc 720
ccggcgagag cgaaatcctg cgcgcggttg aggtgacgat tgtggtgcac gatgacatca 780
tcccctggcg ctatccggcc aaacgcgaac tccagttcgg cgaatggcag cgtaatgata 840
ttctggcggg tatctttgaa ccggccacca tcgacattga tctggcgatc ctgctcacca 900
aggcccggga gcatagcgtg gccctcgtcg gccccgcggc cgaggaactt ttcgacccgg 960

-continued

```
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaaccaccgc taccagcggt ggtttgtttg   1500
ccggatcaag agctaccaac tctttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa gcggcagggt cggaacagga gagcgcacga gggagcttcc agggggaaac   1920
gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgctttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctccctt cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
```

-continued

```
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
gcttttgctc attttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
agctcgtacc cggccagcgc ctcggcaacc tcaccgccga tgcgcgtgcc tttgatcgcc   4320
cgcgacacga caaaggccgc ttgtagcctt ccatccgtga cctcaatgcg ctgcttaacc   4380
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cgggcggtcg   4560
atgccgacaa cggttagcgg ttgatcttcc cgcacggccg cccaatcgcg ggcactgccc   4620
tggggatcgg aatcgactaa cagaacatcg gccccggcga gttgcagggc gcgggctaga   4680
tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc accttttag atgatcagtg attttgtgcc    4860
gagctgccgg tcggggagct gttggctggc tggtggcagg atatattgtg gtgtaaacaa   4920
attgacgctt agacaactta ataacacatt gcggacgtct ttaatgtact gaatttagtt   4980
actgatcact gattaagtac tgcgatcgcc tcgacatatt gtttttgttt cacataaatg   5040
tcgttttgga ttattcatgt aatattttaa actaaagtac aatttttgac tactttagtt   5100
tactagttaa gcttttattt ttttgactaa ccattgaatg atgaagagat caacgcatca   5160
tatttacaac ttacatagtc ttttggaagt gtaaattgct aatactacct aaaatatatc   5220
tataattaac taatattttt tcgtcaatta taatagatca attaaaaggc tatcaaaagg   5280
aaaaaaatga aatccacatc ctgccatcat aacctcatgc tggaaaaaga aatgaaaaaa   5340
tataaaaaat ttcttttgtt tattaaattt acaactttaa tactagtttc ttttctattt   5400
tttaaaagct tttgtcactt acttaaaaaa aaaaaacttt ttgaaatatt cctacttcca   5460
atgtctgatt agtgcttctg gatttccttt ttggatcatg tgaatcctaa atcagaaaaa   5520
ttcatataat acccaattca gtatattttc atacttcaat ttacaagagt tctctatgtt   5580
tttagcttct ttcttttaag ccaaatgttt taagcatctt ttatacatta aaataattta   5640
gtgttgagtt gagatttttt tttttttttt ttggatttac ttgttcaaaa tctgaaaaaa   5700
```

-continued

```
tgtttacaga aggttaaaat gaaccaaaag gcatatcaag ctagattttg aattacccta   5760
tttcatcgta tacacaaaac tgataatgtg gacacagttg attttacttc tcgatgacat   5820
cgtagtttta tttaatttgg aaaccacggc ccatatgagc acatttcaat taaaaaccaa   5880
tggtaagagc attttccatg caagattcga gagatattaa cccagtgact gttaaaacag   5940
cttagaaccc taataacgaa tttcaattac tcaatttacc attcgcattt cgcaataacc   6000
aaactgagcc agtcacaagg agtaaaccga accggattat ttatttataa aatgaaagaa   6060
aggaaaccaa acaacaacag cagtagtagt ctgacgtaaa ccaaaaagca ggcagatcaa   6120
caactaaaag aaactcaaat taccaaaaca aacaggaaat tgcaaactaa gtttttttac   6180
catatgcata caaagaccat aaaaggttct gataatcacc ggtttcatct cgtcgagatt   6240
accctgttat ccctatcagt atttaatccg gccatctcct tccgttatga catcgttgaa   6300
agtgccacca ttcgggatca tcggcaacac atgttcttgg tgcggacaaa tcacatccaa   6360
caggtaaggt cctggtgtat ccagcattgt ctgaatagct tctcggagat ctgctttctt   6420
tgtcaccctc gccgctggaa tcccgcaagc tgctgcaaac agcaacatgt tcgggaatat   6480
ctcgtcctcc tgagccggat ccccgagaaa tgtgtgagct cggttagctt tgtagaaccg   6540
atcttcccat tgcataacca tgccaagatg ctggttgttt aataaaagta ccttcactgg   6600
aagattctct acacgaatag tggctagctc ttgcacattc attataaagc ttccatctcc   6660
gtcaatatcc acaactatcg catcagggtt agcaacagac gctccaatcg cagcaggaag   6720
tccaaatccc atagctccaa ggcctcctga tgatagccac tgccttggtt tcttgtaatt   6780
gtagaactgc gccgcccaca tttgatgttg cccgacacca gtacttatta tggcttttcc   6840
atcagtcaac tcatcaagga ccttaatcgc atactgtgga ggaatagctt ccccaaacgt   6900
cttaaagctc aacggaaact tctgtttctg tacgttcaac tcattcctcc aaactccaaa   6960
atcaagctta agctcctccg ctcggttctc aagaacctta ttcatccctt gcaaagccag   7020
cttaacatca ccacacacag acacatgagg agtcttattc ttcccaatct cagccgagtc   7080
aatatcaata tgaacaatct tagccctact agcaaaagcc tcaagcttac ccgtgacacg   7140
atcatcaaac cttaccccaa acgccaacaa caaatcacta tgctccacag cgtaatttgc   7200
atacacagtc ccatgcattc caagcatatg taacgacaac tcatcatcac aaggataaga   7260
tcccagcccc atcaacgtac tcgcaacagg gatccccgta agctcaacaa acctacccaa   7320
ttcatcgcta gaattcaaac aaccaccacc aacatacaac acaggcttct tagactcaga   7380
aatcaaccta acaatctgct ccaaatgaga atcttccgga ggtttaggca tcctagacat   7440
ataaccaggt aatctcatag cctgttccca attaggaatc gcaagctgtt gttgaatatc   7500
tttaggaaca tcaaccaaaa caggtccagg tctaccagaa gtagctaaaa agaaagcttc   7560
ctcaataatc ctagggatat cttcaacatc catcacaaga tagttatgct tcgtaatcga   7620
acgcgttacc tcaacaatcg gagtctcttg aaacgcatct gtaccaatca tacgacgagg   7680
gacttgtcct gtgattgcta caagaggaac actatctaac aacgcatcgg ctaatccgct   7740
aacgagattt gtagctccgg gacctgaagt ggctatacag atacctggtt tacctgagga   7800
tcgagcgtat ccttctgctg cgaatacacc tccttgttcg tgacgaggaa ggacgttacg   7860
gattgaggaa gagcgggtta aggcttggtg aatctccatt gatgtacctc cagggtaagc   7920
gaatacggtt tctacgcctt gacgttctaa agcttcgacg aggatatcag cgcctttgcg   7980
gggttgatct ggagcgaatc gggagatgaa tgtttcgggt ttggtaggtt tggttggaga   8040
gggagtggtt gtgacattgg tggttgtgtt gagcacggcg gagatggagg agggagagct   8100
```

-continued

```
ggatttgata ccgcggcggc gggaggagga ggatgatttg ttggggttta gggagaatgg   8160
gagggagaat ctggagattg gtaatggtga tttggaggag gaaggagatg gtttggtgga   8220
gaaggagatc gaagaagatg ttgttgttgt tgttgttgcc gccgccatgg ttcagctgca   8280
catacataac atatcaagat cagaacacac atatacacac acaaatacaa tcaagtcaac   8340
aactccaaaa agtccagatc tacatatata catacgtaaa taacaaaatc atgtaaataa   8400
tcacaatcat gtaatccaga tctatgcaca tatatatata cacaattaat aaaaaaaatg   8460
atataacaga tctatatcta tgtatgtaac aacacaatca gatgagagaa gtgatgtttt   8520
cagatctgta tacatacaaa cacaaacaga tgaacaattg atacgtagat ccatatgtat   8580
acgtacaatt agctacacga ttaaatgaaa aaaatcaacg atttcggatt ggtacacaca   8640
aacgcaacaa tatgaagaaa ttcatatctg attagatata aacataacca cgtgtagata   8700
cacagtcaaa tcaacaaatt tatagcttct aaacggatga gatgaacaag ataaagatat   8760
tcacataagg catacataag ataagcagat taacaaacta gcaataatac atacctaatt   8820
aaaacaagga ataacagaga gagagagaga gagagagatt taccttgaaa atgaagagga   8880
gaagagagga tttcttaaaa ttgggggtag agaaagaaag atgatgaatt gtgagaaagg   8940
agagatagaa ggggggggttg tatatatagg ctgtagaaga ttatttttgt gtttgaggcg   9000
gtgaaggaag aggggatctg actatgacac gtttgcggtt acgtatttcg ataggagtct   9060
ttcaacgctt aacgccgtta ctctatatga ccgtttgggc cgtaacgggg ccgtttgtta   9120
acgctgatgt tgattctttt ctttctttct ttcttccttt tttaaagaag caattgtaca   9180
atcgttgcta gctgtcaaac ggataattcg gatacggata tgcctatatt catatccgta   9240
atttttggat tcgaattttc ccctctaggg ataacagggt aatggatcta tattgttttt   9300
gtttcacata aatgtcgttt tggattattc atgtaatatt ttaaactaaa gtacaatttt   9360
tgactacttt agtttactag ttaagctttt attttttga ctaaccattg aatgatgaag   9420
agatcaacgc atcatattta caacttacat agtcttttgg aagtgtaaat tgctaatact   9480
acctaaaata tatctataat taactaatat tttttcgtca attataatag atcaattaaa   9540
aggctatcaa aaggaaaaaa atgaaatcca catcctgcca tcataacctc atgctggaaa   9600
aagaaatgaa aaaatataaa aaatttcttt tgtttattaa atttacaact ttaatactag   9660
tttcttttct attttttaaa agcttttgtc acttacttaa aaaaaaaaaa ctttttgaaa   9720
tattcctact tccaatgtct gattagtgct tctggatttc ctttttggat catgtgaatc   9780
ctaaatcaga aaaattcata taatacccaa ttcagtatat tttcatactt caatttacaa   9840
gagttctcta tgtttttagc ttctttcttt taagccaaat gttttaagca tcttttatac   9900
attaaaataa tttagtgttg agttgagatt tttttttttt ttttttggat ttacttgttc   9960
aaaatctgaa aaaatgttta cagaaggtta aaatgaacca aaaggcatat caagctagat  10020
tttgaattac cctatttcat cgtatacaca aaactgataa tgtggacaca gttgatttta  10080
cttctcgatg acatcgtagt tttatttaat ttggaaacca cggcccatat gagcacattt  10140
caattaaaaa ccaatggtaa gagcattttc catgcaagat tcgagagata ttaacccagt  10200
gactgttaaa acagcttaga accctaataa cgaatttcaa ttactcaatt taccattcgc  10260
atttcgcaat aaccaaactg agccagtcac aaggagtaaa ccgaaccgga ttatttattt  10320
ataaaatgaa agaaaggaaa ccaaacaaca acagcagtag tagtctgacg taaaccaaaa  10380
agcaggcaga tcaacaacta aaagaaactc aaattaccaa aacaaacagg aaattgcaaa  10440
```

-continued

```
ctaagttttt ttaccatatg catacaaaga ccataaaagg ttctgataat caccggtttc  10500
atctcagatc cgcgatcgcc aattgacgcg tactagtgta caagcttgcg gccgcgaatt  10560
cggtacatcc ggccagtgaa ttatcaacta tgtataataa agttgggtac ccggggatcc  10620
tctagcatat gctcgacgga caatcagtaa attgaacgga gaatattatt cataaaaata  10680
cgatagtaac gggtgatata ttcattagaa tgaaccgaaa ccggcggtaa ggatctgagc  10740
tacacatgct caggtttttt acaacgtgca caacagaatt gaaagcaaat atcatgcgat  10800
cataggcgtc tcgcatatct cattaaagca gggttaacgc tagcgggccc tctagatgca  10860
tgctcgaggc ggccttaatt aatcgatggc gccagctgca ggcggccgcc atatgcatcc  10920
taggcctatt aatattccgg agtatacgta gccggctaac gttaacaacc ggtacctcta  10980
gactcgagca ggaacaggtg gtggcggccc tcggtgcgct cgtactgctc cacgatggtg  11040
tagtcctcgt tgtgggaggt gatgtccagc ttggagtcca cgtagtagta gccgggcagc  11100
tgcacgggct tcttggccat gtagatggac ttgaactcca ccaggtagtg gccgccgtcc  11160
ttcagcttca gggccttgtg gatctcgccc ttcagcacgc cgtcgcgggg gtacaggcgc  11220
tcggtggagg cctcccagcc catggtcttc ttctgcatta cggggccgtc ggaggggaag  11280
ttcacgccga tgaacttcac cttgtagatg aagcagccgt cctgcaggga ggagtcctgg  11340
gtcacggtca ccacgccgcc gtcctcgaag ttcatcacgc gctcccactt gaagccctcg  11400
gggaaggaca gcttcttgta gtcggggatg tcggcggggt gcttcacgta caccttggag  11460
ccgtactgga actgggggga caggatgtcc caggcgaagg gcagggggcc gcccttggtc  11520
accttcagct tcacggtgtt gtggccctcg taggggcggc cctcgccctc gccctcgatc  11580
tcgaactcgt ggccgttcac ggtgccctcc atgcgcacct tgaagcgcat gaactccttg  11640
atgacgttct tggaggagcg caccattgtt attctcctaa tcgataggcc tactagtcaa  11700
ttggcgcgcc ttatgttttt aatcttgttt gtattgatga gttttggttt gagtaaagag  11760
tgaagccgat gagttaattt ataggctata aaggagattt gcatggcgat cacgtgtaat  11820
aatgcatgca cgcatgtgat tgtatgtgtg tgctgtgaga gagaagctct taggtgtttg  11880
aagggagtga caagtggcga agaaaaacaa ttctccgcgg ctgcatgcta tgtgtaacgt  11940
gtagctaatg ttctggcatg gcatcttatg aacgattctt tttaaaaaca aggtaaaaac  12000
ttaacttcat aaaattaaaa aaaaaacgtt tactaagttg gtttaaaagg ggatgagagt  12060
ctataaattt tggaggtagt gccgttggga atataaattg ggagcttaat cagaattata  12120
gaagttaaag ttgatttagt cacggtcaat ataaattggg aatttgagtc aaaatcttcc  12180
aaattcggaa tccgtcttgt tacacccggt ggataggagc cgaacggttt gaaaatactt  12240
gaaatgtgga tgcaggtgca ggctggttta attttatgtt gaatggatac atgtcaatcg  12300
aatttgagtt ataggtacac attttactct gatactaaaa tgtaacattt gtctcaagaa  12360
tgggtaggtc atccttaaag cttgggctag agcggccgcc accgcggtgg agagcttggc  12420
gtaatcatgg ccactttgta caagaaagct gggtggtacc cgatctatcg gtttcattcg  12480
gtttgatgcg atattcccct tttgtcactt ttaagttcgg ttttaaagtc acttttccat  12540
acagatgaga gtattagcat tttcataagc tcaatacgtt tttcaaatat atcaactttt  12600
acatttgatt cggtttcaat tcttgatcaa aagcaaggat tgaagaattc ggttctctat  12660
tccaatccga ctagtaaata aatcgtcgta ctaaaccact ctatatagaa caaacttctt  12720
tttattaata caaggcctac acctagtgca ccacatcatc accatacgtt acaaacgtaa  12780
ttatttttgt ttacacgtac gtaaaaacat taatatcata caatacttgc atgtacgtta  12840
```

tatagtaggc ttttgttatt atctttgcgg ccggggatcc tctaggtcga ccagatctga 12900
tatctgcggc cttaattaag ttaacttaca tcgctgggaa ctcggtgata aattccttgc 12960
tgatgtccgc caggtggtcc acgacctcgt agatgccctc ccagaagccg gtctcgtgga 13020
acgggatgtc gaactccttg catagcgact tgatgagcac gttgaccttt ggcaagttgt 13080
ggcgcggcac gagcgggaac aggtgatggt cgatctggta gttcaagcca ccggtgaacc 13140
agtccatgaa taccgacgcg cggatgttgc gcgtcgtggt cacctgcagc tgccagaagt 13200
ccggcttggt ttcgcgctcg tacaccgaca tgccgttgtg gccaatactg aacaccagcg 13260
ccaggagcaa gccgcaggac gcctggccca tgaggaagta tgccacgccc tcaaacaggc 13320
tcatgttgca gaagtacggg atcgcgagct gccagatgta gtgcacgatc agacccgcct 13380
tctccggtcc gtcgaactcg accttgtcga agatgccgaa cgagaactcg gtgaacacgt 13440
agaagaacga ctgcgcgagc cagctcaggc gcgcgagcag cagcagcggg aagtatagga 13500
acgcctggtt gcggatgaag aacgggccgt gcgccgactc gaacgccttg cgcgccatct 13560
ccttagacca cgccagcagc ggcatggtgt cgatgtccgg gtcgccgatg aagccctcgt 13620
ccttggcgct gtgcaggttc ggcaccgcgt ggtgcaggtt gtgcttgttc ttccaccact 13680
gcatgctgaa gccctgccag gcgttgccca cgaggcagcc gataaggttg ccgagcgtgc 13740
ggttctcgca cacctggttg tgcaagaagt cgtgcgccag ccatccggac tgctggtaga 13800
agagccccat aatcacgccg gcgaccatgt acatggcgaa actgttgaag aagaagcaga 13860
tcgccatcga gagcaccgcg atgccgaacg tgctcacgag cttccacgcg tagtagagcg 13920
cgctggcgtc gtagagcccc atgcccttga ccttgacgcg cagacggcgg taggacgcga 13980
tgaactcgtt gatgcgctcg cggcgcgcgc gctcctcgtc gctcgccggc tccccctcga 14040
tctcggcctt ggaggtttcg tccacgtcgc cgacgtagaa ctgctcgagc agcttgagcg 14100
ccgaggacgg gtggaagacc gcgaaggcgt ccgtggcgtc ctcgccggcc tgcgtgagca 14160
tcacggagcc acccgggtgc gagtcccact tggagatgtc gtagaccttg tggtgaatca 14220
cgatccacgc ggtcgcgggc gtcgcgtgct cgcggatctc cttccagctc accaggcgct 14280
tcactccagg cttgaggtcc accattttgg gccccggcgc gccgatttat gataaaaatg 14340
tcggtttctt tgtggatggg atgggaaagt tggggagggt tgggcaaagg tctaatatag 14400
gaggtgggtg gagtggtgtt ctactatcct tgcatgaaga gaacgtggcc ctgagtcttg 14460
cgtacgtggc ggctccagaa ttggccaaca tcttattcca aggttacaaa cagcctgcca 14520
tgcattttga ttttttttac catgggaatt tggacttttg ttagatataa catttcgtca 14580
catataatca cacgtacgct accacatttg tattcttacc tttttacaag ttgattataa 14640
taagtaactt ggatagatta ttttttatta taagtaaatt ggatagatat ttttttttctt 14700
tgaacaaagt aagttataaa ttaaactaat gaaaattcgg ttctattata tctatcccaa 14760
gtacatgcaa aatttaacgg ttcacaaaat ttgattgcaa atgcaatcca ggattttggt 14820
attctaacta tttattcaaa attcattcac tataagttga aattatccgg ttaaaaaggc 14880
ctgttgacgg gaatgggtat acccgaaacc agtgattatc ggatagcgag tgggatggat 14940
ttagtagtat ccgcctcgat acctacccga cgggtaaccc agcattatac tatgtcatgt 15000
tcctcaacat attctatctt aattttaatt tttcaattgt tagatctaat tccaactctg 15060
taataaaagt catgtcggtg aaatttgtgt tcttgaatat atttttcttt ttattttcct 15120
acaaatatgg aaatttatga atatgtgttt cttaaaattg catccaatat gaaaatatta 15180

-continued

```
acatttttgt tttgtttatc aaataaaaaa tatatattta gtaatcaggt tttacccgat  15240

taaacgggta aatctgaaac ccgctaacgg acgggtacgg tttaaaattc cggtctggtt  15300

tatgtaaacg ggtgggtacg tgtaaaaccc gacgactaga tgggtgggta atagatatgt  15360

ttaacctgta cccataccca tccattgcta tccttgttag aaactaaata tgtaattcat  15420

tctaaataat ctataattaa ataaaaaaaa ttgtcaattt atattcaaca aaatgcacaa  15480

atcttacagt gaaatcccac cctaagagtc tcggtcgaac cactggttca accgaagaat  15540

cttatttggg tctcagctga taccaacccc ttggtagtca ccatctggcg gagggacttc  15600

tcctgacctg tcgagcatca acttcactct ttcaatacct ttactgactc tttgtctcct  15660

aagcactgtt tctaacttgt caatccgcac taccatgtgc taaacatgaa agtatagaga  15720

ccattccttg tagtactgct taggagatgt aactaatcga gcggctagct caactttgca  15780

acttccatct tgttgctaaa ctatggttcc tcggtttctt gtctcctctt gactcatgtt  15840

ctcaccaata tataatacta atcaaagagt actaccaaga ccttagtcaa ctttttatat  15900

tatgtcatcc ctcatcatga tgacggtttt gacaagtttg attactatgc ccctctagca  15960

ctttttctc ttaacctcca tcaagagttc tttcctagct ctttgtctga agcatactat  16020

gcttgtagta gtccctatgt cctgcccgtg cccgggaagc ttggcgtaat catggagcct  16080

gctttttgt acaaacttgg gtaccggcct attaggccac ggtccgtaca gtgtttaaac  16140

gattgacctg caggatacaa gtgcgcacag actagcggcc gctaatcccg ggaattaccg  16200

gtagtaggcg cctactttgg ccggcctagt agatttaaat tggccttagt ggccaagctt  16260

ggcgtaatca tggcaacttt t                                          16281
```

```
<210> SEQ ID NO 142
<211> LENGTH: 56
<212> TYPE: DNA
<213> ORGANISM: Artificial sequence
<220> FEATURE:
<223> OTHER INFORMATION: Primer

<400> SEQUENCE: 142

atacccggga tacctgcagg ttaggccggc cacacgggca ggacataggg actact      56


<210> SEQ ID NO 143
<211> LENGTH: 69
<212> TYPE: DNA
<213> ORGANISM: Artificial sequence
<220> FEATURE:
<223> OTHER INFORMATION: Primer

<400> SEQUENCE: 143

caatcaatta taggcctcgc atgctttaat taacgatcga gccatgggat ttatgataaa  60

aatgtcggt                                                        69
```